(12) United States Patent
Brown et al.

(10) Patent No.: US 12,233,111 B2
(45) Date of Patent: Feb. 25, 2025

(54) COMPOSITIONS COMPRISING PHARMACEUTICALLY ACCEPTABLE SALTS OF GLUCAGON-LIKE PEPTIDE-1 ANALOGS AND USES THEREOF

(71) Applicant: i2O Therapeutics, Inc., Cambridge, MA (US)

(72) Inventors: Tyler Brown, Cambridge, MA (US); Kelly Ibsen, Boston, MA (US)

(73) Assignee: I2O THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 18/444,463

(22) Filed: Feb. 16, 2024

(65) Prior Publication Data

US 2024/0277814 A1 Aug. 22, 2024

Related U.S. Application Data

(63) Continuation of application No. PCT/US2022/049585, filed on Nov. 10, 2022.

(60) Provisional application No. 63/380,125, filed on Oct. 19, 2022, provisional application No. 63/334,410, filed on Apr. 25, 2022, provisional application No. 63/295,197, filed on Dec. 30, 2021, provisional application No. 63/277,878, filed on Nov. 10, 2021.

(51) Int. Cl.
| | |
|---|---|
| *A61K 38/26* | (2006.01) |
| *A61K 9/08* | (2006.01) |
| *A61K 31/14* | (2006.01) |
| *A61K 47/12* | (2006.01) |
| *A61K 47/18* | (2017.01) |
| *A61K 47/54* | (2017.01) |
| *A61K 47/68* | (2017.01) |
| *C07K 14/575* | (2006.01) |
| *C07K 14/605* | (2006.01) |
| *C07K 16/24* | (2006.01) |
| *A61K 38/00* | (2006.01) |

(52) U.S. Cl.
CPC ........... *A61K 38/26* (2013.01); *A61K 9/08* (2013.01); *A61K 31/14* (2013.01); *A61K 47/12* (2013.01); *A61K 47/18* (2013.01); *A61K 47/183* (2013.01); *A61K 47/186* (2013.01); *A61K 47/542* (2017.08); *A61K 47/6845* (2017.08); *C07K 14/575* (2013.01); *C07K 14/605* (2013.01); *C07K 16/241* (2013.01); *A61K 38/00* (2013.01); *C07K 2317/24* (2013.01)

(58) Field of Classification Search
CPC ........ A61K 38/26; A61K 47/12; A61K 47/542
See application file for complete search history.

(56) References Cited

U.S. PATENT DOCUMENTS

| | | | |
|---|---|---|---|
| 3,536,809 | A | 10/1970 | Applezweig et al. |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,124,061 | A | 6/1992 | Geary, Sr. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis |
| 6,114,304 | A | 9/2000 | Kolterman et al. |
| 6,365,185 | B1 | 4/2002 | Ritschel et al. |
| 7,762,994 | B2 | 7/2010 | Klint et al. |
| 8,114,833 | B2 | 2/2012 | Pedersen et al. |
| 8,129,343 | B2 | 3/2012 | Lau et al. |
| 8,536,122 | B2 | 9/2013 | Lau et al. |
| 8,575,090 | B2 | 11/2013 | Schaeffer et al. |
| 8,579,869 | B2 | 11/2013 | Klint et al. |
| 8,684,969 | B2 | 4/2014 | Moller et al. |
| 8,920,383 | B2 | 12/2014 | Enggaard et al. |
| 9,108,002 | B2 | 8/2015 | Markussen |
| 9,132,239 | B2 | 9/2015 | Møller et al. |
| 9,278,123 | B2 | 3/2016 | Sauerberg et al. |
| 9,457,154 | B2 | 10/2016 | Moller et al. |
| RE46,363 | E | 4/2017 | Moeller et al. |
| 9,616,180 | B2 | 4/2017 | Markussen |

(Continued)

FOREIGN PATENT DOCUMENTS

| | | |
|---|---|---|
| AU | 2015249035 A1 | 6/2016 |
| CA | 2202520 A1 | 4/1996 |

(Continued)

OTHER PUBLICATIONS

Abbott et al., Deep eutectic solvents formed between choline chloride and carboxylic acids: versatile alternatives to ionic liquids. Journal of the American Chemical Society 126(29):9142-9147 (2004).

(Continued)

*Primary Examiner* — Gyan Chandra
(74) *Attorney, Agent, or Firm* — WILSON SONSINI GOODRICH & ROSATI

(57) ABSTRACT

Provided herein are compounds having the structure of Formula Ia, wherein the compounds comprise a therapeutic agent having the sequence of SEQ ID NO: 35, and the compounds have an anion:cation molar ratio of from about 1:1 to about 1:7, and methods of using thereof for the treatment of metabolic diseases or disorders, including type 1 diabetes, type 2 diabetes, obesity, overweight, and nonalcoholic steatohepatitis, and for reducing weight in a subject in need thereof.

28 Claims, 55 Drawing Sheets

Specification includes a Sequence Listing.

(56) References Cited

U.S. PATENT DOCUMENTS

| | | |
|---|---|---|
| 9,687,611 B2 | 6/2017 | Moeller et al. |
| 9,764,003 B2 | 9/2017 | Jensen |
| 9,775,953 B2 | 10/2017 | Enggaard et al. |
| 9,861,757 B2 | 1/2018 | Moller et al. |
| 10,086,047 B2 | 10/2018 | Sauerberg et al. |
| 10,220,155 B2 | 3/2019 | Eiland et al. |
| 10,278,923 B2 | 5/2019 | Nielsen et al. |
| 10,335,462 B2 | 7/2019 | Jensen |
| 10,357,616 B2 | 7/2019 | Moller et al. |
| 10,376,652 B2 | 8/2019 | Markussen |
| 10,463,733 B1 | 11/2019 | Slocik et al. |
| 10,888,605 B2 | 1/2021 | Moeller et al. |
| 10,933,120 B2 | 3/2021 | Vilhelmsen et al. |
| 10,960,052 B2 | 3/2021 | Sauerberg et al. |
| 11,097,063 B2 | 8/2021 | Eiland et al. |
| 11,311,679 B2 | 4/2022 | Markussen |
| 11,318,191 B2 | 5/2022 | Engelund et al. |
| 11,382,957 B2 | 7/2022 | Sauerberg et al. |
| 11,446,253 B2 | 9/2022 | Mitragotri et al. |
| 11,446,443 B2 | 9/2022 | Moeller et al. |
| 11,752,198 B2 | 9/2023 | Moeller et al. |
| 11,759,501 B2 | 9/2023 | Vilhelmsen et al. |
| 11,759,502 B2 | 9/2023 | Vilhelmsen et al. |
| 11,759,503 B2 | 9/2023 | Vilhelmsen et al. |
| 2004/0258747 A1 | 12/2004 | Ponzoni et al. |
| 2006/0239955 A1 | 10/2006 | Chandar et al. |
| 2009/0181912 A1 | 7/2009 | Wang et al. |
| 2013/0058999 A1 | 3/2013 | Foeger |
| 2013/0274181 A1 | 10/2013 | Walewski et al. |
| 2014/0221282 A1 | 8/2014 | Sun et al. |
| 2015/0071922 A1 | 3/2015 | Larson et al. |
| 2015/0164828 A1 | 6/2015 | Golini |
| 2015/0328113 A1 | 11/2015 | Patel et al. |
| 2016/0115478 A1 | 4/2016 | Schmidts et al. |
| 2016/0263225 A1 | 9/2016 | Zakrewsky et al. |
| 2018/0093011 A1 | 4/2018 | Kellar et al. |
| 2019/0309040 A1 | 10/2019 | Thennati et al. |
| 2020/0071352 A1 | 3/2020 | Jezek et al. |
| 2020/0323799 A1 | 10/2020 | Koppisch et al. |
| 2021/0030871 A1 | 2/2021 | Rinaldi et al. |
| 2021/0353565 A1 | 11/2021 | Mitragotri et al. |
| 2022/0144914 A1 | 5/2022 | Mitragotri et al. |
| 2022/0257767 A1 | 8/2022 | Mitragotri et al. |
| 2023/0040805 A1 | 2/2023 | Mitragotri et al. |
| 2023/0082544 A1 | 3/2023 | Sander et al. |
| 2023/0093875 A1 | 3/2023 | Mitragotri et al. |
| 2023/0102247 A1 | 3/2023 | Mitragotri et al. |
| 2023/0310350 A1 | 10/2023 | Mitragotri et al. |
| 2024/0016735 A1 | 1/2024 | Mitragotri et al. |
| 2024/0067716 A1 | 2/2024 | Brown et al. |
| 2024/0130994 A1 | 4/2024 | Brown et al. |
| 2024/0293552 A1 | 9/2024 | Brown et al. |
| 2024/0307499 A1 | 9/2024 | Brown et al. |
| 2024/0325323 A1 | 10/2024 | Brown et al. |
| 2024/0336668 A1 | 10/2024 | Brown et al. |

FOREIGN PATENT DOCUMENTS

| | | |
|---|---|---|
| CN | 106420610 A | 2/2017 |
| CN | 109464661 A | 3/2019 |
| CN | 111588846 A | 8/2020 |
| EP | 3811962 A1 | 4/2021 |
| KR | 20170052278 A | 5/2017 |
| KR | 20170109377 A | 9/2017 |
| WO | WO-9804290 A2 | 2/1998 |
| WO | WO-2004014387 A1 | 2/2004 |
| WO | WO-2004052340 A1 | 6/2004 |
| WO | WO-2007044693 A2 | 4/2007 |
| WO | WO-2007104789 A2 | 9/2007 |
| WO | WO-2010118384 A2 | 10/2010 |
| WO | WO-2011080103 A1 | 7/2011 |
| WO | WO-2011138421 A1 | 11/2011 |
| WO | WO-2012098187 A1 | 7/2012 |
| WO | WO-2012162542 A1 | 11/2012 |
| WO | WO-2015066647 A2 | 5/2015 |
| WO | WO-2016034604 A1 | 3/2016 |
| WO | WO-2016054259 A1 | 4/2016 |
| WO | WO-2017060500 A1 | 4/2017 |
| WO | WO-2017164627 A2 | 9/2017 |
| WO | WO-2018044920 A1 | 3/2018 |
| WO | WO-2018065634 A1 | 4/2018 |
| WO | WO-2018222924 A1 | 12/2018 |
| WO | WO-2019099837 A1 | 5/2019 |
| WO | WO-2019122329 A1 | 6/2019 |
| WO | WO-2019099837 A9 | 9/2019 |
| WO | WO-2019183142 A1 | 9/2019 |
| WO | WO-2019193204 A1 | 10/2019 |
| WO | WO-2019201894 A1 | 10/2019 |
| WO | WO-2019217854 A1 | 11/2019 |
| WO | WO-2020180534 A1 | 9/2020 |
| WO | WO-2020205409 A1 | 10/2020 |
| WO | WO-2021092522 A1 | 5/2021 |
| WO | WO-2021102084 A1 | 5/2021 |
| WO | WO-2021144476 A1 | 7/2021 |
| WO | WO-2021214762 A1 | 10/2021 |
| WO | WO-2021222196 A1 | 11/2021 |
| WO | WO-2022036309 A2 | 2/2022 |
| WO | WO-2022049310 A1 | 3/2022 |
| WO | WO-2022051304 A1 | 3/2022 |
| WO | WO-2022235882 A1 | 11/2022 |
| WO | WO-2022254209 A1 | 12/2022 |
| WO | WO-2022256291 A1 | 12/2022 |
| WO | WO-2022265880 A1 | 12/2022 |
| WO | WO-2023059846 A1 | 4/2023 |
| WO | WO-2023086499 A1 | 5/2023 |
| WO | WO-2023110833 A1 | 6/2023 |
| WO | WO-2023166179 A1 | 9/2023 |
| WO | WO-2023187067 A1 | 10/2023 |
| WO | WO-2023227133 A1 | 11/2023 |
| WO | WO-2024076715 A1 | 4/2024 |

OTHER PUBLICATIONS

Adawiyah et al., Ionic liquids as a potential tool for drug delivery systems. MedChemComm 7(10):1881-1897 (2016).

Agatemor, Christian, et al. Choline-Geranate Deep Eutectic Solvent Improves Stability and Half-Life of Glucagon-Like Peptide-1. Advanced therapeutics 4(3):2000180 (2021).

Agatemor et al., Ionic liquids for addressing unmet needs in healthcare. Bioengineering & Translational Medicine 3(1):7-25 (2018).

Aguirre et al. Current status of selected oral peptide technologies in advanced preclinical development and in clinical trials. Advanced Drug Delivery Reviews 106(Part B):223-241 (2016).

Albadawi, Hassan, et al., Percutaneous Liquid Ablation Agent for Tumor Treatment and Drug Delivery. Science Translational Medicine 13(580):eabe3889, 12pages (2021).

Ammendola et al. 10-Undecanhydroxamic acid, a hydroxamate derivative of the undecanoic acid, has strong antimicrobial activity through a mechanism that limits iron availability. FEMS Microbiology Letters 294(1):61-67 (2009).

Angsantikul, Pavimol et al. Ionic Liquids and Deep Eutectic Solvents for Enhanced Delivery of Antibodies in the Gastrointestinal Tract. Advanced Functional Materials 31:2002912 (2021).

Angsantikul, Pavimol et al. Ionic Liquids and Deep Eutectic Solvents for Enhanced Delivery of Antibodies in the Gastrointestinal Tract. Advanced Functional Materials 31:2002912 (2021) Supplemental Information.

Araki et al. Ionic liquid-mediated transcutaneous protein delivery with solid-in-oil nanodispersions. MedChemComm 3(12): 2124-2128 (2015).

Arbit et al. Oral Insulin Delivery in a Physiologic Context: Review. J Diabetes Sci Technol 11(4):825-832 (Jul. 2017) Epub Feb. 2, 2017.

Baah et al., Antibody-drug conjugates—a tutorial review. Molecules 26(2943):1-19 (2021).

Baekdal, Tine A. et al. Effect of Various Dosing Conditions on the Pharmacokinetics of Oral Semaglutide, a Human Glucagon-Like Peptide-1 Analogue in a Tablet Formulation. Diabetes Ther 12(7):1915-1927 (2021).

(56) References Cited

OTHER PUBLICATIONS

Baekdal, Tine A. et al. Pharmacokinetics, Safety, and Tolerability of Oral Semaglutide in Subjects With Hepatic Impairment. J Clin Pharmacol 58(10):1314-1323 (2018).
Banerjee et al. Ionic liquids for oral insulin delivery. PNAS USA 115(28):7296-7301 (2018).
Banerjee et al. Ionic liquids for oral insulin delivery. PNAS USA 115(28):7296-7301 (2018) Supplementary Information.
Banerjee et al., Transdermal protein delivery using choline and geranate (CAGE) deep eutectic solvent. Advanced Healthcare Materials 6(15):1601411 (2017).
Benhabbour, Rahima S, et al., Ultra-long-acting Tunable Biodegradable and Removable Controlled Release Implants for Drug Delivery. Nature Communications 10(1):4324, 1-12 (2019).
Bergsson et al. in vitro killing of Candida albicans by fatty acids and monoglycerides. Antimicrobial Agents and Chemotherapy 45(11):3209-3212 (2001).
Berton et al. Transdermal Bioavailability in Rats of Lidocaine in the Forms of Ionic Liquids, Salts, and Deep Eutectic. ACS Med Chem Lett 8(5):498-503 (2017).
Brichtova, Eva Prada et al. Glucagon-like peptide 1 aggregates into low-molecular-weight oligomers off-pathway to fibrillation. Biophys J 122(12):2475-2488 (2023).
Brown, Tyler D. et al. Materials for oral delivery of proteins and peptides. Nature Reviews Materials 5(2):127-148 (2020).
Buckley et al. Chemically modified peptides and proteins—critical considerations for oral delivery. Tissue Barriers 4(2):e1156805 (2016).
Buckley et al. Transcellular stomach absorption of a derivatized glucagon-like peptide-1 receptor agonist. Sci Transl Med 10(467):eaar7047 (2018).
Cagrilintide acetate. Available at https://www.medchemexpress.com/cagrilintide-acetate.html (2013-2024).
Carrillo-Conde et al. Complexation hydrogels as oral delivery vehicles of therapeutic antibodies: an in vitro and ex vivo evaluation of antibody stability and bioactivity. Industrial & engineering chemistry research 54(42):10197-10205 (2015).
CAS1450806-98-0. GLP-1(7-37) acetate Cat. No. M13967. Available at https://www.abmole.com/products/glp-1-7-37-acetate.html ((2010-2023).
Cassie Lane Aesthetics—Semaglutide FAQ—Available at https://www.cassielaneaesthetics.com/wp-content/uploads/2023/06/weight-loss-semaglutide-no-bleed.pdf (2023).
Chaubet, Guilhem et al. Investigating Ugi/Passerini Multicomponent Reactions for the Site-Selective Conjugation of Native Trastuzumab. Chemistry: A European Journal vol. 26,61: pp. 13797-13805 (2020).
Chen et al. Enhanced paracellular delivery of vaccine by hydrogel microparticles-mediated reversible tight junction 3pening for effective oral immunization. Journal of Controlled Release 311-312:50-64 (2019).
Co-pending U.S. Appl. No. 18/444,443, inventor Brown; Tyler, filed Feb. 16, 2024.
Co-pending U.S. Appl. No. 18/444,471, inventor Brown; Tyler, filed Feb. 16, 2024.
Co-pending U.S. Appl. No. 18/444,485, inventor Brown; Tyler, filed Feb. 16, 2024.
Co-pending U.S. Appl. No. 18/444,501, inventor Brown; Tyler, filed Feb. 16, 2024.
Demurtas et al., Cholinium-based ionic liquids from hydroxycinnamic acids as new promising bioactive agents: A combined experimental and theoretical investigation. ACS Sustainable Chemistry & Engineering 9:2975-2986 (2021).
Dharamdasani et al. Topical delivery of siRNA into skin using ionic liquids. Journal of Controlled Release 323:475-482 (2020).
Dobler et al. Ionic liquids as ingredients in topical drug delivery systems. International Journal of Pharmaceutics 441(1-2):620-627 (2013).
Domingues, Ines et al. Effects of semaglutide-loaded lipid nanocapsules on metabolic dysfunction-associated steatotic liver disease. Drug Deliv Transl Res doi: 10.1007/s13346-024-01576-z. Online ahead of print (Apr. 2024).
Eaimtrakarn et al. Absorption enhancing effect of labrasol on the intestinal absorption of insulin in rats. J Drug Target 10(3):255-260 (2002).
Egorova et al., Biological activity of ionic liquids and their application in pharmaceutics and medicine. Chemical Reviews 117(10):7132-7189 (2017).
Esteban-Fernandez de Avila et al. Micromotor-enabled active drug delivery for in vivo treatment of stomach infection. Nature communications 8(1):272 (2017).
Esteban-Fernandez de Avila et al. Micromotors go in vivo: from test tubes to live animals. Advanced Functional Materials 28(25):1705640 (2018).
Fan et al. Functional nanoparticles exploit the bile acid pathway to overcome multiple barriers of the intestinal 3pithelium for oral insulin delivery. Biomaterials 151:13-23 (2018).
Fiebig et al., Quantitative evaluation of myoglobin unfolding in the presence of guanidinium hydrochloride and ionic liquids in solution. The Journal of Physical Chemistry B 118(2):406-412 (2013).
Fletcher, Madeleine M. et al. AM833 Is a Novel Agonist of Calcitonin Family G Protein-Coupled Receptors: Pharmacological Comparison with Six Selective and Nonselective Agonists. J Pharmacol Exp Ther 377(3):417-440 (2021).
Fonte et al. Oral insulin delivery: How far are we? J Diabetes Sci Technol 7(2):520-531 (2013).
Garber. Long-acting glucagon-like peptide 1 receptor agonists: a review of their efficacy and tolerability. Diabetes Care 34 Supp 2(Supp 2):S279-84 (2011).
GLP-1(7-37) acetate. Cat. No. HY-P0055A. Available at https://www.medchemexpress.com/GLP-1_7-37_acetate.html(2010-2023).
Goindi et al. Development of novel ionic liquid-based microemulsion formulation for dermal delivery of 5-fluorouracil. AAPS PharmSciTech 15(4):810-821 (2014).
Gupta et al. Delivery of exenatide and insulin using mucoadhesive intestinal devices. Annals of Biomedical Engineering 44(6):1993-2007 (2016).
Gupta. Glucagon-like peptide-1 analogues: An overview. Indian J Endocrinol Metab. 17(3):413-421 (2013).
Haidari et al., Development of topical delivery systems for flightless neutralizing antibody. Journal of Pharmaceutical Sciences 106(7):1795-1804 (2017).
Hamadani, Christine M. et al., Protein-avoidant ionic liquid (PAIL)-coated nanoparticles to increase bloodstream circulation and drive biodistribution. Science Advances 6(48):eabd7563 (2020).
Hansen, Benworth B, et al., Deep Eutectic Solvents: A Review of Fundamentals and Applications. Chemical Reviews 121(3):1232-1285 (2021).
Hattori, Tadashi et al. Transdermal delivery of nobiletin using ionic liquids. Sci Rep 9(1):20191 (2019).
Hough et al., The Third Evolution of Ionic Liquids: Active Pharmaceutical Ingredients. New Journal of Chemistry 31(8):1429-1436 (2007).
Hsu et al. Delivery of siRNA and other macromolecules into skin and cells using a peptide enhancer. PNAS USA 108(38):15816-15821 (2011).
Ibsen et al. Mechanism of antibacterial activity of choline-based ionic liquids (CAGE). ACS Biomaterials Science & Engineering 4(7):2370-2379 (2018).
Jain et al. Effect of trehalose on protein structure. Protein Science 18(1):24-36 (2009).
Jean. Esters et sels de la choline et de quelues acides derives du phosphore. Bulletin de la Societe Chimique de France 5:783-786 (1957).
Johansen et al. IκBζ is a key driver in the development of psoriasis. PNAS USA 112(43):E5825-E5833 (2015).
Kandimalla et al. Effect of fatty acids on the permeation of melatonin across rat and pig skin in-vitro and on the Transepidermal water loss in rats in-vivo. J Pharm Pharmacol 51(7):783-790 (2010).

(56) References Cited

OTHER PUBLICATIONS

Karande et al., Design principles of chemical penetration enhancers for transdermal drug delivery. PNAS USA 102(13):4688-4693 (2005).

Karande et al. Discovery of transdermal penetration enhancers by high-throughput screening. Nature Biotechnology 22(2):192-197 (2004).

Kelley et al., Understanding the effects of ionicity in salts, solvates, co-crystals, ionic co-crystals, and ionic liquids, rather than nomenclature, is critical to understanding their behavior. Crystal Growth and Design. 13(3):965-975 (2013).

Khan et al., Key interactions of surfactants in therapeutic protein formulations: A review. European Journal of Pharmaceutics and Biopharmaceutics 97 97(Pt A):60-67 (2015).

Kharroubi et al., Diabetes mellitus: The epidemic of the century. World Journal of Diabetes 6(6):850-867 (2015).

Kim, Jayoung, et al., A Deep Eutectic Solvent-based Approach to Intravenous Formulation. Advanced Healthcare Materials 10(18):e2100585, 8pages (2021).

Kim, Jayoung et al. A deep eutectic-based, self-emulsifying subcutaneous depot system for apomorphine therapy in Parkinson's disease. PNAS USA 119(9):e2110450119 (2022).

Ko, Justin, et al., Clinical Translation of Choline and Geranic Acid Deep Eutectic Solvent. Bioengineering & Translational Medicine 6(2):e10191,11pages (2020).

Kommineni, Nagavendra et al. SNAC for Enhanced Oral Bioavailability: An Updated Review. Pharm Res. 40(3):633-650 (2023) (Epub Dec. 20, 2022).

Kopecki et al., Topically applied flightless I neutralizing antibodies improve healing of blistered skin in in a murine model of epidermolysis bullosa acquisita. Journal of Investigative Dermatology 133(4):1008-1016 (2013).

Korkmaz et al., Therapeutic intradermal delivery of tumor necrosis factor-alpha antibodies using tip-loaded dissolvable microneedle arrays. Acta Biomaterialia 24:96-105 (2015).

Krug et al. Sodium caprate as an enhancer of macromolecule permeation across tricellular tight junctions of intestinal cells. Biomaterials 34(1):275-282 (2013).

Kruse, Thomas et al. Development of Cagrilintide, a Long-Acting Amylin Analogue. J Med Chem 64(15):11183-11194 (2021).

Kumar et al. Peptides as skin penetration enhancers: mechanisms of action. Journal of Controlled Release 199:168-178 (2015).

Kumar. Prevention of insulin self-aggregation by a protic ionic liquid. Royal Society of Chemistry Advances 3:362-367 (2013).

Lane. Skin penetration enhancers. International Journal of Pharmaceutics 447(1-2):12-21 (2013).

Lau et al., Discovery of the once-weekly glucagon-like peptide-1 (GLP-1) analogue semaglutide. Journal of Medicinal Chemistry 58:7370-7380 (2015).

Lee et al. Development of pH-responsive organic-inorganic hybrid nanocomposites as an effective oral delivery system of protein drugs. Journal of Controlled Release 311-312:74-84 (2019).

Lee, Jeongmi, et al., Applications of Deep Eutectic Solvents to Quantitative Analyses of Pharmaceuticals and Pesticides in Various Matrices: A Brief Review. Archives of Pharmacal Research 43(9):900-919 (2020).

Lei et al., Introduction: ionic liquids. Chem Rev 117(10):6633-6635 (2017).

Lesch et al., Peptides in the presence of aqueous ionic liquids-tunable co-solutes as denaturants or protectants? Physical Chemistry Chemical Physics 17(39):26049-26053 (2015).

Li et al., Insights into the deactivation of bovine serum albumin with a thermo-responsive ionic liquid. Soft Matter 10(33):6161-6171 (2014).

Li et al. Micromotors Spontaneously Neutralize Gastric Acid for pH-Responsive Payload Release. Angewandte Shemie International Edition 56(8):2156-2161 (2017).

Lovshin, Julie et al. Incretin-based therapies for type 2 diabetes mellitus. Nat Rev Endocrinol 5(5):262-269 (2009).

Madsbad, S. et al. An overview of once-weekly glucagon-like peptide-1 receptor agonists—available efficacy and safety data and perspectives for the future. Diabetes Obes Metab 13(5):394-407 (2011).

Mandal et al. Treatment of psoriasis with NFKBIZ siRNA using topical ionic liquid formulations. Science Advances 6:1-9 (2020).

Marrucho et al., Ionic liquids in pharmaceutical applications. Annual Review of Chemical and Biomolecular Engineering 5:527-546 (2014).

Matteucci et al. Insulin administration: Present strategies and future directions for a noninvasive (possibly more physiological) delivery. Drug Des Devel Ther 9:3109-3118 (2015).

Mechanism of action of RYBELSUS® (semaglutide), the first type 2 diabetes pill in its class (GLP-1 RA). Available at https://www.novomedlink.com/diabetes/products/treatments/rybelsus/about/mechanism-of-action.html (2024).

Medical Weight Loss. Available at https://prestigerm.com/weight-loss/ (retrieved 2024).

Meyers, Eugene W et al. Optimal Alignments in Linear Space. Computer Applications in the Biosciences vol. 4,1: pp. 11-17 (1988).

Micaelo et al. Protein structure and dynamics in ionic liquids. insights from molecular dynamics simulation studies. J Phys Chem B 112(9):2566-2572 (2008).

Miyasaka, Kota. [New drug for type 2 diabetes: introduction of oral Semaglutide (Rybelsus® tablets), an oral GLP-1 receptor agonist]. Nihon Yakurigaku Zasshi 157(2):146-154 (2022) (English Abstract).

Müller et al. IκBζ is a key transcriptional regulator of IL-36—driven psoriasis-related gene expression in keratinocytes. PNAS USA 115(40):10088-10093 (2018).

Moniruzzaman et al. Ionic liquid based microemulsion with pharmaceutically accepted components: Formulation and potential applications. Journal of Colloid and Interface Science 352(1):136-142 (2010).

Monti et al. Ionic liquids as potential enhancers for transdermal drug delivery. Int J Pharm 516(1-2):45-51 (2017).

Muheem et al. A review on the strategies for oral delivery of proteins and peptides and their clinical perspectives. Saudi Pharmaceutical Journal 24(4):413-428 (2016).

NCT04817644. A Trial Investigating Semaglutide and SNAC Concentrations in Breastmilk Following Administration of Multiple Doses of Oral Semaglutide in Healthy, Lactating Females Available at https://classic.clinicaltrials.gov/ct2/show/NCT04817644 (Start Date Sep. 10, 2021).

Needleman, Saul B et al. A General Method Applicable to the Search for Similarities in the Amino Acid Sequence of Two Proteins. Journal of Molecular Biology vol. 48,3: pp. 444-453 (1970).

Niu, Shu et al. Semaglutide ameliorates metabolism and hepatic outcomes in an NAFLD mouse model. Frontiers in Endocrinology 13:1046130 (2022).

Nurunnabi et al. Oral ionic liquid for the treatment of diet-induced obesity. PNAS USA 116(50):25042-25047 (2019).

Nurunnabi et al. Oral ionic liquid for the treatment of diet-induced obesity. PNAS USA 116(50):25042-25047 (2019) Supplementary Information.

Oleck et al. Commentary: Why was inhaled insulin a failure in the market? Diabetes Spectr 29(3):180-184 (2016).

Olokoba et al. Type 2 diabetes mellitus: A review of current trends. Oman Med J 27(4):269-273 (2012).

O'Toole et al. Diphosphonium ionic liquids as broad spectrum antimicrobial agents. Cornea 31(7):810-816 (2012).

Park et al. Lidocaine-ibuprofen ionic liquid for dermal anesthesia. AIChE Journal 61(9):2732-2738 (2015).

Patel et al., Recent advances in the applications of ionic liquids in protein stability and activity: a review. Applied 3iochemistry and Biotechnology 172(8):3701-3720 (2014).

Paul et al., Deciphering the interaction of a model transport protein with a prototypical imidazolium room temperature ionic liquid: effect on the conformation and activity of the protein. Journal of Photochemistry and Photobiology B 133:99-107 (2014).

PCT/US2018/061532 International Search Report and Written Opinion dated Mar. 25, 2019.

(56) References Cited

OTHER PUBLICATIONS

PCT/US2020/019639 International Search Report and Written Opinion dated May 29, 2020.
PCT/US2020/024866 International Search Report and Written Opinion dated Jun. 24, 2020.
PCT/US2020/061185 International Search Report and Written Opinion dated Mar. 11, 2021.
PCT/US2021/048537 International Invitation to Pay Additional Fees dated Nov. 3, 2021.
PCT/US2021/048537 International Search Report and Written Opinion dated Jan. 18, 2022.
PCT/US2022/027794 International Search Report and Written Opinion dated Aug. 17, 2022.
PCT/US2022/049585 International Search Report and Written Opinion dated Mar. 31, 2023.
Petkovic et al. Novel biocompatible cholinium-based ionic liquids-toxicity and biodegradability. Green Chemistry 12(4):643-649 (2010).
Prausnitz et al. Transdermal drug delivery. Nature Biotechnology 26(11):1261-1268 (2008).
PubChem SID 56843331. Semaglutide (Compound) Available at https://pubchem.ncbi.nlm.nih.gov/compound/Semaglutide. (retrieved May 2024).
Qi et al. Mechanistic study of transdermal delivery of macromolecules assisted by ionic liquids. J Control Release 311-312:162-169 (2019).
Qi, Qin M., et al. Comparison of ionic liquids and chemical permeation enhancers for transdermal drug delivery. Advanced Functional Materials 30(45):2004257 (2020).
Ren, Qingjuan et al. An Effective Glucagon-Like Peptide-1 Receptor Agonists, Semaglutide, Improves Sarcopenic Obesity in Obese Mice by Modulating Skeletal Muscle Metabolism. Drug Des Devel Ther 16:3723-3735 (2022).
Rogers et al., Ionic liquids-solvents of the future? Science 302(5646):792-793 (2003).
Sahbaz et al., Transformation of poorly water-soluble drugs into lipophilic ionic liquids enhances oral drug exposure rom lipid based formulations. Molecular Pharmaceutics 12(6):1980-1991 (2015).
Sano et al. Stat3 links activated keratinocytes and immunocytes required for development of psoriasis in a novel transgenic mouse model. Nature Medicine 11(1):43-49 (2005).
Schröder. Proteins in ionic liquids: Current status of experiments and simulations. Top Curr Chem (Cham) 375(2):25-017-0110-2 (2017).
Scott-Moncrief et al. Enhancement of intestinal insulin absorption by bile Salt-Fatty acid mixed micelles in dogs. J Pharm Sci 83(10):1465-1469 (1994).
Search Result for "Nursing Skills". https://open.umn.edu/opentextbooks/textbooks?term=nursing+skills&commit=Go (retrieved May 2024).
Semaglutide in Charlottesville—Natural, Rapid Weight Loss. Available at https://neroli-spa.com/services/semaglutide-in-charlottesville/# (2024).
Semaglutide TFA. Available at https://www.medchemexpress.com/Semaglutide_TFA.html (2013-2024).
Semaglutide Weight Loss Injection. Available at https://progressmd.com/semaglutide-injections (2024).
Semaglutide Weight Loss Plan. Available at https://www.awesomechiropractic.com/medical-services-professional-chiropractic-services-semaglutide-weight-loss-plan/ (2023).
Semaglutide Weight Loss Program. Available at https://mensvitalitycenter.com/service/semaglutide-weight-loss-program/#what-is-semaglutide (2024).
Shaji, et al. Protein and Peptide drug delivery: oral approaches. Indian J Pharm Sci. May-Jun.;70(3):269-77 (2008).
Shamshina et al., Ionic liquids in drug delivery. Expert Opinion on Drug Delivery 10(10):1367-1381 (2013).
Shao On the influence of hydrated imidazolium-based ionic liquid on protein structure stability: a molecular dynamics simulation study. The Journal of Chemical Physics 139(11):115102 (2013).
Sharma et al. High concentration DNA solubility in bio-ionic liquids with long-lasting chemical and structural stability at room temperature. RSC Advances 5:40546-40551 (2015).
Shi et al. Oral delivery of sorafenib through spontaneous formation of ionic liquid nanocomplexes. Journal of Controlled Release 322:602-609 (2020).
Shi, Yujie et al. Enhancement of Anticancer Efficacy and Tumor Penetration of Sorafenib by Ionic Liquids. Adv Healthc Mater 10(2):e2001455 (2020).
Singh et al., Dynamics of ionic liquid-assisted refolding of denatured cytochrome c: a study of preferential interactions toward renaturation. Molecular Pharmaceutics 15(7):2648-2697 (2018).
Singh et al., Effect of polysorbate 20 and polysorbate 80 on the higher-order structure of a monoclonal antibody and its Fab and Fc fragments probed using 2D nuclear magnetic resonance spectroscopy. Journal of Pharmaceutical Sciences 106(12):3486-3498 (2017).
Sivapragasam et al., Recent advances in exploiting ionic liquids for biomolecules: solubility, stability and applications. Biotechnology Journal 11(8):1000-1013 (2016).
Smith et al. Deep Eutectic Solvents (DESs) and Their Applications. Chemical Reviews 114(21):11060-11082 (2014).
Startzel. Arginine as an excipient for protein freeze-drying: A mini review. Journal of Pharmaceutical Sciences 107(4):960-967 (2018).
Streit et al., Topical application of the tumour necrosis factor—α antibody infliximab improves healing of chronic wounds. International Wound Journal 3(3):171-179 (2006).
Tanner, Eden EL et al. The Influence of Water on Choline-Based Ionic Liquids. ACS Biomater SCI Eng 5(7):3645-3653 (2019).
Tanner et al. Design Principles of Ionic Liquids for Transdermal Drug Delivery. Advanced Materials 31(27):1901103 (2019).
Tanner et al. Transdermal insulin delivery using choline-based ionic liquids (Cage). J Control Release 286:137-144 (2018).
Tiwari, Gaurav et al. Drug delivery systems: An updated review. Int J Pharm Investig 2(1):2-11 (2012).
Ukidve, Anvay, et al., Ionic-liquid-based Safe Adjuvants. Advanced Materials 32(46):e2002990, 5pages (2020).
UniProt Acession No. P01375. TNFA_Human 16 pages. Retrieved Jun. 3, 2024 at URL: https://www.uniprot.org/uniprotkb/P01375/entry.
UniProt Acession No. P05556. ITB1_HUMAN, 30 pages. Retrieved Jun. 3, 2024 at URL: https://www.uniprot.org/uniprotkb/P05556/entry.
UniProt Acession No. P10997. IAPP_Human, 8 pages. Retrieved Jun. 3, 2024 at URL: https://www.uniprot.org/uniprotkb/P10997/entry.
UniProt Acession No. P13612. ITA4_HUMAN 13 pages. Retrieved Jun. 3, 2024 at URL: https://www.uniprot.org/uniprotkb/P13612/entry.
UniProt Acession No. P26010. ITB7_HUMAN, 11 pages. Retrieved Jun. 3, 2024 at URL: https://www.uniprot.org/uniprotkb/P26010/entry.
UniProt Acession No. P29459 IL12A_HUMAN, 6 pages. Retrieved Jun. 3, 2024 at URL: https://uniprot.org/uniprotkb/P29459/entry.
UniProt Acession No. P29460 IL12B_HUMAN, 09 pages. Retrieved Jun. 3, 2024 at URL: https://www.uniprot.org/uniprotkb/P29460/entry.
UniProt Acession No. Q9NPF7. IL23A_HUMAN, 7 pages. Retrieved Jun. 3, 2024 at URL: https://www.uniprot.org/uniprotkb/Q9NPF7/entry.
Uralcan et al. A computational study of the ionic liquid-induced destabilization of the miniprotein, Trp-Cage. The Journal of Physical Chemistry B 122(21):5707-5715 (2018).
US Food and Drug Administration. Medications containing semaglutide marketed for type 2 diabetes or weight loss. Available at https://www.fda.gov/drugs/postmarket-drug-safety-information-patients-and-providers/medications-containing-semaglutide-marketed-type-2-diabetes-or-weight-loss (2023).
U.S. Appl. No. 16/762,361 Office Action dated Nov. 23, 2021.
Vaidya, Amogh et al. Ionic liquid-mediated delivery of insulin to buccal mucosa. J Control Release 327:26-34 (2020).
Vereshchagin, Anatoly N, et al., Quaternary Ammonium Compounds (QACs) and Ionic Liquids (ILs) as Biocides: From Simple

(56) References Cited

OTHER PUBLICATIONS

Antiseptics to Tunable Antimicrobials. International Journal of Molecular Sciences 22(13):6793, 82pages (2021).
Veselinovic et al., Topical gel formulation of broadly neutralizing anti-HIV-1 monoclonal antibody VRC01 confers protection against HIV-1 vaginal challenge in a humanized mouse model. Virology 432(2):505-510 (2012).
Vllasaliu et al. Recent advances in oral delivery of biologics: Nanomedicine and physical modes of delivery. Expert opinion on drug delivery 15(8):759-770 (2018).
Wang et al., Stabilizing two IgG1 monoclonal antibodies by surfactants: Balance between aggregation prevention and structure perturbation. European Journal of Pharmaceutics and Biopharmaceutics 114:263-277 (2017).
Wei et al. Biomimetic Micromotor Enables Active Delivery of Antigens for Oral Vaccination. Nano letters 19(3):1914-1921 (2019).
Williams et al., Ionic liquids provide unique opportunities for oral drug delivery: structure optimization and in vivo evidence of utility. Chemical Communications 50(14):1688-1690 (2014).
Wong et al. Oral delivery of insulin for treatment of diabetes: Status quo, challenges and opportunities. J Pharm Pharmacol 68(9):1093-1108 (2016).
Wu et al., An improved synthesis of a fluorescent gabapentin-choline conjugate for single molecule detection. Tetrahedron Letters 50:2100-2102 (2009).
Wu et al. Improved transdermal permeability of ibuprofen by ionic liquid technology: Correlation between counterion structure and the physiochemical and biological properties. Journal of Molecular Liquids 283:399-409 (2019).
Wu et al. Improving dermal delivery of hydrophilic macromolecules by biocompatible ionic liquid based on choline and nalic acid. Int J Pharm 558:380-387 (2019).
Xu et al. Ionic Liquids: Ion Mobilities, Glass Temperatures, and Fragilities. J Phys Chem B 107(25):6170-6178 (2003).
Yang et al., Using ionic liquids in whole-cell biocatalysis for the nucleoside acylation. Microbial Cell Factories 13 (1):143 (2014).
Zakrewsky et al., Choline and geranate deep eutectic solvent as a broad-spectrum antiseptic agent for preventive and therapeutic applications. Advanced Healthcare Materials 5(11):1282-1289 (2016).
Zakrewsky et al., Ionic liquids as a class of materials for transdermal delivery and pathogen neutralization. PNAS 111(37):13313-13318 (2014).
Zeisel. Choline: Human requirements and effects on human performance. In Food Components to Enhance Performance: An Evaluation of Potential Performance-Enhancing Food Components for Operational Rations. Institute of Medicine. Committee on Military Nutritional Research Food and Nutrition Board, B. M. Marriott. Ed. National Academies Press, Washington DC. Chapter 19:381-406 (1994).
Zeisel et al. Choline: An essential nutrient for public health. Nutr Rev 67(11):615-623 (2009).
Zhang et al. A hydrophobic deep eutectic solvent-based vortex-assisted dispersive liquid-liquid microextraction combined with HPLC for the determination of nitrite in water and biological samples. J Sep Sci 42(2):574-581 (2019) (Epub Nov. 19, 2018.).
Zhang et al. Evaluations of imidazolium ionic liquids as novel skin permeation enhancers for drug transdermal Delivery. Pharm Dev Technol 22(4):511-520 (2017).
Zhang et al., Impact of the alkyl chain length on binding of imidazolium-based ionic liquids to bovine serum albumin. Spectrochim Acta Part A: Molecular and Biomolecular Spectroscopy 196:323-333 (2018).
Zijlstra et al. Oral insulin reloaded: A structured approach. J Diabetes Sci Technol 8(3):458-465 (2014).
Myers, et al. Optimal Alignments in Linear Space. Computer Applications in the Biosciences 4(1):11-17 (1988).
Needleman, et al. A General Method Applicable to the Search for Similarities in the Amino Acid Sequence of Two Proteins. Journal of Molecular Biology 48(3):443-453 (1970).

Tang et al. "Modern Pharmacology" 1st Edition, China Medical Science and Technology Press. p. 974 (1997).
American Diabetes Association. Insulin Administration. Diabetes Care 27(1):S106-S109 (2004).
Bormel, Frances Gail. Semaglutide Letter. Federation of State Medical Boards, Oct. 10, 2023, pp. 1-3.
Bormel, Frances Gail. Semaglutide Letter. National Association of Boards of Pharmacy, Oct. 10, 2023, pp. 1-3.
Bristol-Myers Squibb Company. Taxol® (paclitaxel) Injection. Retrieved from the internet at https://www.accessdata.fda.gov/drugsatfda_docs/label/2011/020262s049lbl.pdf (2011).
Comer, Ben. Novo Nordisk Returns To Growth, With Growing Pains. Life Science Leader, Aug. 1, 2023; [retrieved on Oct. 8, 2024].Available at URL:https://www.qgdigitalpublishing.com/publication/?m=53489&i=797050&view=articleBrowser&article_id=4610792&ver=html5 pp. 1-3.
Enebo, Lone B. et al. Safety, tolerability, pharmacokinetics, and pharmacodynamics of concomitant administration of multiple doses of cagrilintide with semaglutide 2•4 mg for weight management: a randomised, controlled, phase 1b trial. Lancet 397(10286):1736-1748 (2021).
Ernst, Diana. FDA Concerned Over Compounded Semaglutide Following Reports of Adverse Events. Medical Professionals Reference, May 31, 2023; [retrieved on Oct. 4, 2024]. Available at URL:https://www.empr.com/home/news/safety-alerts-and-recalls/fda-concerned-over-compounded-semaglutide-following-reports-of-adverse-events/ pp. 1-3.
Fakhari et al. Engineered in-situ depot-forming hydrogels for intratumoral drug delivery. Journal of controlled 220:465-475 (2015).
FDA's Concerns with Unapproved GLP-1 Drugs Used for Weight Loss. Food and Drug Administration, [retrieved on Oct. 4, 2024]. Available at URL:https://www.fda.gov/drugs/postmarket-drug-safety-information-patients-and-providers/fdas-concerns-unapproved-glp-1-drugs-used-weight-loss pp. 1-3.
Lima, Luis Mauricio T. R. et al. Amyloidogenicity of peptides targeting diabetes and obesity. Colloids and Surfaces B: Biointerfaces 209(Pt 1):112157, 1-11 (2022).
MedChemExpress. Product data sheet for cagrilintide acetate (2013-2024). Cat No. HY-P3462A. Retrieved from the internet at https://www.medchemexpress.com/cagrilintide-acetate.html.
MedChemExpress. Product data sheet for GLP-1(7-37) acetate (2010-2023). Cat No. HY-P0055A. Retrieved from the internet at https://www.medchemexpress.com/GLP-1_7-37acetate.html.
MedChemExpress. Product data sheet for Semaglutide TFA (2013-2024). Cat No. HY-114118A. Retrieved from https://www.medchemexpress.com/Semaglutide_TFA.html.
Novo Nordisk successfully completes phase 2 trial with CagriSema in people with type 2 diabetes. Company Announcement: Novo Nordisk, Aug. 22, 2022; [retrieved on Oct. 8, 2024].Available at URL:https://www.novonordisk.com/news-and-media/news-and-ir-materials/news-details.htmlid=131155#:~:text=Novo%20Nordisk%20successfully%20completes%20phase,a%20novel%20amylin%20analogue%2C%20cagrilintide pp. 1-2.
PubChem. Semaglutide summary page. PubChem CID 56843331. Retrieved from the internet at https://pubchem.ncbi.nlm.nih.gov/compound/Semaglutide (created Mar. 21, 2012).
Staby, Arne. et al. Influence of production process and scale on quality of polypeptide drugs: a case study on GLP-1 analogs. Pharmaceutical Research 37:120, 1-18 (2020).
UniProt. IAPP_HUMAN, Accession No. P10997. Retrieved from the internet at https://www.uniprot.org/uniprotkb/P10997/entry (Retrieved Jun. 2024).
UniProt. IL12A_HUMAN, Accession No. P29459. Retrieved from the internet at https://www.uniprot.org/uniprotkb/P29459/entry (retrieved Jun. 2024).
UniProt. IL12B_HUMAN, Accession No. P29460. Retrieved from the internet at https://www.uniprot.org/uniprotkb/P29460/entry (retrieved Jun. 2024).
UniProt. IL23A_HUMAN, Accession No. Q9NPF7. Retrieved from the internet at https://www.uniprot.org/uniprotkb/Q9NPF7/entry (retrieved Jun. 2024).

(56) References Cited

OTHER PUBLICATIONS

UniProt. ITA4_HUMAN, Accession No. P13612. Retrieved from the internet at https://www.uniprot.org/uniprotkb/P13612/entry (retrieved Jun. 2024).
UniProt. ITB1_HUMAN, Accession No. P05556. Retrieved from the internet at https://www.uniprot.org/uniprotkb/P05556/entry (retrieved Jun. 2024).
UniProt. ITB7_HUMAN, Accession No. P26010. Retrieved from the internet at https://www.uniprot.org/uniprotkb/P26010/entry (retrieved Jun. 2024).
UniProt. TFA_HUMAN, Accession No. P01375. Retrieved from the internet at https://www.uniprot.org/uniprotkb/P01375/entry (retrieved Jun. 2024).
U.S. Appl. No. 18/444,443 Ex Parte Quayle dated Oct. 23, 2024.
U.S. Appl. No. 18/444,443 Office Action dated Aug. 16, 2024.
U.S. Appl. No. 18/444,471 Office Action dated Jul. 25, 2024.

Non-cleavable linkers maleimide alkane linker maleimide cyclohexane linker "MCC"

Chemically cleavable linkers hydrazone linker disulfide linker "SPP"

| Ratio x:1 | GLP Analog (mg) | Choline Bicarb (μl) | Mol Choline Bicarb | Mass of Choline Bicarb (mg) | Mass of Choline (mg) | Mass of Bicarb (before rxn) (mg) | Mol of Bicarb (post rxn) | Mass of Bicarb (post rxn) (mg) | Total Mass of GLP Analog (mg) | Total Mass of Choline (mg) | Total Mass of Bicarb (mg) | Total Mass (mg) | % GLP Analog | % Choline | % Bicarb |
|---|---|---|---|---|---|---|---|---|---|---|---|---|---|---|---|
| 0 | 60 | 0 | 0.0000 | 0.0 | 0.0 | 0.0 | 0.000 | 0.0 | 60.0 | 0.0 | 0.0 | 60.0 | 100% | 0% | 0% |
| 1 | 60 | 3.1 | 0.0145 | 2.4 | 1.5 | 0.9 | 0.000 | 0.0 | 60.0 | 1.5 | 0.0 | 61.5 | 98% | 2% | 0% |
| 7 | 60 | 21.7 | 0.1015 | 16.8 | 10.6 | 6.2 | 0.000 | 0.0 | 60.0 | 10.6 | 0.0 | 70.6 | 85% | 15% | 0% |
| 28 | 60 | 86.8 | 0.4059 | 67.1 | 42.3 | 24.8 | 0.304 | 18.6 | 60.0 | 42.3 | 18.6 | 120.9 | 50% | 35% | 15% |

FIG. 21

SEQUENCE LISTING

```
Sequence total quantity: 42
SEQ ID NO: 1            moltype = AA  length = 450
FEATURE                 Location/Qualifiers
source                  1..450
                        mol_type = protein
                        organism = synthetic construct
SEQUENCE: 1
EVKLEESGGG LVQPGGSMKL SCVASGFIFS NHWMNWVRQS PEKGLEWVAE IRSKSINSAT   60
HYAESVKGRF TISRDDSKSA VYLQMTDLRT EDTGVYYCSR NYYGSTYDYW GQGTTLTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 2            moltype = AA  length = 214
FEATURE                 Location/Qualifiers
source                  1..214
                        mol_type = protein
                        organism = synthetic construct
SEQUENCE: 2
DILLTQSPAI LSVSPGERVS FSCRASQFVG SSIHWYQQRT NGSPRLLIKY ASESMSGIPS   60
RFSGSGSGTD FTLSINTVES EDIADYYCQQ SHSWPFTFGS GTNLEVKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 3            moltype = AA  length = 224
FEATURE                 Location/Qualifiers
source                  1..224
                        mol_type = protein
                        organism = synthetic construct
SEQUENCE: 3
```

```
EVQLVESGGG LVQPGRSLRL SCAASGFTFD DYAMHWVRQA PGKGLEWVSA ITWNSGHIDY    60
ADSVEGRFTI SRDNAKNSLY LQMNSLRAED TAVYYCAKVS YLSTASSLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSC                    224

SEQ ID NO: 4            moltype = AA  length = 219
FEATURE                 Location/Qualifiers
source                  1..219
                        mol_type = protein
                        organism = synthetic construct
SEQUENCE: 4
EVQLVESGGG LVQPGRSLRL SCAASGFTFD DYAMHWVRQA PGKGLEWVSA ITWNSGHIDY    60
ADSVEGRFTI SRDNAKNSLY LDMNSLRAED TAVYYCAKVS YLSTASSLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKI                          219

SEQ ID NO: 5            moltype = AA  length = 451
FEATURE                 Location/Qualifiers
source                  1..451
                        mol_type = protein
                        organism = synthetic construct
SEQUENCE: 5
EVQLVESGGG LVQPGRSLRL SCAASGFTFD DYAMHWVRQA PGKGLEWVSA ITWNSGHIDY    60
ADSVEGRFTI SRDNAKNSLY LQMNSLRAED TAVYYCAKVS YLSTASSLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 6            moltype = AA  length = 214
FEATURE                 Location/Qualifiers
source                  1..214
                        mol_type = protein
                        organism = synthetic construct
SEQUENCE: 6
DIQMTQSPSS LSASVGDRVT ITCRASQGIR NYLAWYQQKP GKAPKLLIYA ASTLQSGVPS    60
RFSGSGSGTD FTLTISSLQP EDVATYYCQR YNRAPYTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 7            moltype = AA  length = 211
FEATURE                 Location/Qualifiers
source                  1..211
                        mol_type = protein
                        organism = synthetic construct
SEQUENCE: 7
DIQMTQSPSS LSASVGDRVT ITCRASQGIR NYLAWYQQKP GKAPKLLIYA ASTLQSGVPS    60
RFSGSGSGTD FTLTISSLQP EDVATYYCQR YNRAPYTFGQ GTKVEIKRTV AAPTVKILQS   120
SCDGGGHFPP TIQLLCLVSG YTPGTIQITW LEDGQVMDVD LSTASTTQEG ELASTQSELT   180
LSQKHWLSDR TYTCQVTYQG HTFEDSGKKC A                                  211

SEQ ID NO: 8            moltype = AA  length = 226
FEATURE                 Location/Qualifiers
source                  1..226
                        mol_type = protein
                        organism = synthetic construct
SEQUENCE: 8
EVQLVQSGAE VKKPGESLKI SCKGSGYSFT TYWLGWVRQM PGKGLDWIGI MSPVDSDIRY    60
SPSFQGQVTM SVDKSITTAY LQWNSLKASD TAMYYCARRR PGQGYFDFWG QGTLVTVSSS   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTH                  226

SEQ ID NO: 9            moltype = AA  length = 214
FEATURE                 Location/Qualifiers
source                  1..214
                        mol_type = protein
                        organism = synthetic construct
SEQUENCE: 9
DIQMTQSPSS LSASVGDRVT ITCRASQGIS SWLAWYQQKP EKAPKSLIYA ASSLQSGVPS    60
RFSGSGSGTD FTLTISSLQP EDFATYYCQQ YNIYPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 10           moltype = AA  length = 129
FEATURE                 Location/Qualifiers
source                  1..129
                        mol_type = protein
```

```
                        organism = synthetic construct
SEQUENCE: 10
SKLQVQLVES GGGVVQPGRS LRLSCAASGF IFSSYAMHWV RQAPGNGLEW VAFMSYDGSN    60
KKYADSVKGR FTISRDNSKN TLYLQMNSLR AEDTAVYYCA RDRGIAAGGN YYYYGMDVWG   120
QGTTVTVSS                                                          129

SEQ ID NO: 11           moltype = AA  length = 119
FEATURE                 Location/Qualifiers
source                  1..119
                        mol_type = protein
                        organism = synthetic construct
SEQUENCE: 11
AGSEIVLTQS PATLSLSPGE RATLSCRASQ SVYSYLAWYQ QKPGQAPRLL IYDASNRATG    60
IPARFSGSGS GTDFTLTISS LEPEDFAVYY CQQRSNWPPF TFGPGTKVDI KTSENLYFQ   119

SEQ ID NO: 12           moltype = AA  length = 222
FEATURE                 Location/Qualifiers
source                  1..222
                        mol_type = protein
                        organism = synthetic construct
SEQUENCE: 12
QVQLVQSGAE VKKPGASVKV SCKASGFNIK DTYIHWVRQA PGQRLEWMGR IDPANGYTKY    60
DPKFQGRVTI TADTSASTAY MELSSLRSED EAVYYCAREG YYGNYGVYAM DYWGQGTLVT   120
VSSASTKGPS VFPLAPCSRS TSESTAALGC LVKDYFPEPV TVSWNSGALT SGVHTFPAVL   180
QSSGLYSLSS VVTVPSSSLG TKTYTCNVDH KPSNTKVDKR VE                     222

SEQ ID NO: 13           moltype = AA  length = 234
FEATURE                 Location/Qualifiers
source                  1..234
                        mol_type = protein
                        organism = synthetic construct
SEQUENCE: 13
QVQLVQSGAE VKKPGASVKV SCKASGFNIK DTYIHWVRQA PGQRLEWMGR IDPANGYTKY    60
DPKFQGRVTI TADTSASTAY MELSSLRSED EAVYYCAREG YYGNYGVYAM DYWGQGTLVT   120
VSSASTKGPS VFPLAPCSRS TSESTAALGC LVKDYFPEPV TVSWNSGALT SGVHTFPAVL   180
QSSGLYSLSS VVTVPSSSLG TKTYTCNVDH KPSNTKVDKR VESKYGPPEN LYFQ         234

SEQ ID NO: 14           moltype = AA  length = 210
FEATURE                 Location/Qualifiers
source                  1..210
                        mol_type = protein
                        organism = synthetic construct
SEQUENCE: 14
DIQMTQSPSS LSASVGDRVT ITCKTSQDIN KYMAWYQQTP GKAPRLLIHY TSALQPGIPS    60
RFSGSGSGRD YTFTISSLQP EDIATYYCLQ YDNLWTFGQG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR                                   210

SEQ ID NO: 15           moltype = AA  length = 211
FEATURE                 Location/Qualifiers
source                  1..211
                        mol_type = protein
                        organism = synthetic construct
SEQUENCE: 15
DIQMTQSPSS LSASVGDRVT ITCKTSQDIN KYMAWYQQTP GKAPRLLIHY TSALQPGIPS    60
RFSGSGSGRD YTFTISSLQP EDIATYYCLQ YDNLWTFGQG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR G                                 211

SEQ ID NO: 16           moltype = AA  length = 451
FEATURE                 Location/Qualifiers
source                  1..451
                        mol_type = protein
                        organism = synthetic construct
SEQUENCE: 16
QVQLVQSGAE VKKPGASVKV SCKGSGYTFT SYWMHWVRQA PGQRLEWIGE IDPSESNTNY    60
NQKFKGRVTL TVDISASTAY MELSSLRSED TAVYYCARGG YDGWDYAIDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELAG   240
APSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                 451

SEQ ID NO: 17           moltype = AA  length = 219
FEATURE                 Location/Qualifiers
source                  1..219
                        mol_type = protein
                        organism = synthetic construct
```

```
SEQUENCE: 17
DVVMTQSPLS LPVTPGEPAS ISCRSSQSLA KSYGNTYLSW YLQKPGQSPQ LLIYGISNRF   60
SGVPDRFSGS GSGTDFTLKI SRVEAEDVGV YYCLQGTHQP YTFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 18           moltype = AA   length = 229
FEATURE                 Location/Qualifiers
source                  1..229
                        mol_type = protein
                        organism = synthetic construct
SEQUENCE: 18
EVQLVESGGG LVQPGGSLRL SCAASGYVFT DYGMNWVRQA PGKGLEWMGW INTYIGEPIY   60
ADSVKGRFTF SLDTSKSTAY LQMNSLRAED TAVYYCARGY RSYAMDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCAA             229

SEQ ID NO: 19           moltype = AA   length = 214
FEATURE                 Location/Qualifiers
source                  1..214
                        mol_type = protein
                        organism = synthetic construct
SEQUENCE: 19
DIQMTQSPSS LSASVGDRVT ITCKASQNVG TNVAWYQQKP GKAPKALIYS ASFLYSGVPY   60
RFSGSGSGTD FTLTISSLQP EDFATYYCQQ YNIYPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 20           moltype = AA   length = 37
FEATURE                 Location/Qualifiers
source                  1..37
                        mol_type = protein
                        organism = synthetic construct
SITE                    37
                        note = Amidated residue
SEQUENCE: 20
KCNTATCATQ RLANFLVHSS NNFGPILPPT NVGSNTY                           37

SEQ ID NO: 21           moltype = AA   length = 37
FEATURE                 Location/Qualifiers
source                  1..37
                        mol_type = protein
                        organism = synthetic construct
SITE                    37
                        note = Amidated residue
SEQUENCE: 21
KCNTATCATQ RLANFLVHSS NNFGPILPPT NVGSNTY                           37

SEQ ID NO: 22           moltype = AA   length = 31
FEATURE                 Location/Qualifiers
source                  1..31
                        mol_type = protein
                        organism = synthetic construct
SITE                    31
                        note = Hydroxylated residue
SEQUENCE: 22
HAEGTFTSDV SSYLEGEAAK EFIAWLVKGR G                                 31

SEQ ID NO: 23           moltype = AA   length = 36
FEATURE                 Location/Qualifiers
source                  1..36
                        mol_type = protein
                        organism = synthetic construct
SITE                    36
                        note = Amidated residue
SEQUENCE: 23
HGEGTFTSDL SKQMEEAVRL FIEWKNGGPS SGAPPS                            36

SEQ ID NO: 24           moltype = AA   length = 226
FEATURE                 Location/Qualifiers
source                  1..226
                        mol_type = protein
                        organism = synthetic construct
SEQUENCE: 24
EVKLEESGGG LVQPGGSMKL SCVASGFIFS NHWMNWVRQS PEKGLEWVAE IRSKSINSAT   60
HYAESVKGRF TISRDDSKSA VYLQMTDLRT EDTGVYYCSR NYYGSTYDYW GQGTTLTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKT                226
```

```
SEQ ID NO: 25              moltype = AA  length = 39
FEATURE                    Location/Qualifiers
source                     1..39
                           mol_type = protein
                           organism = synthetic construct
SITE                       2
                           note = alpha-amino isobutyric acid
SITE                       13
                           note = alpha-amino isobutyric acid
SEQUENCE: 25
YXEGTFTSDY SIXLDKIAQK AFVQWLIAGG PSSGAPPPS                                  39

SEQ ID NO: 26              moltype = AA  length = 37
FEATURE                    Location/Qualifiers
source                     1..37
                           mol_type = protein
                           organism = synthetic construct
DISULFID                   2..7
                           note = Intrachain disulfide bond
SITE                       37
                           note = Amidated tyrosine
SEQUENCE: 26
KCNTATCATQ RLANFLVHSS NNFGPILPPT NVGSNTY                                    37

SEQ ID NO: 27              moltype = AA  length = 37
FEATURE                    Location/Qualifiers
source                     1..37
                           mol_type = protein
                           organism = synthetic construct
SITE                       1
                           note = alpha-amino group of lysine residue conjugated to
                             20-((1-carboxy-4-oxobutyl)amino)-20-oxoicosanoic acid
DISULFID                   2..7
                           note = Intrachain disulfide bond
SITE                       37
                           note = Amidated tyrosine
SEQUENCE: 27
KCNTATCATQ RLANFLVHSS NNFGPILPPT NVGSNTY                                    37

SEQ ID NO: 28              moltype = AA  length = 37
FEATURE                    Location/Qualifiers
source                     1..37
                           mol_type = protein
                           organism = synthetic construct
SITE                       1
                           note = alpha-amino group of lysine residue conjugated to
                             20-((1-carboxy-4-oxobutyl)amino)-20-oxoicosanoate,
                             ionically bound to (2-hydroxyethyl)trimethylazanium
DISULFID                   2..7
                           note = Intrachain disulfide bond
SITE                       37
                           note = Amidated tyrosine
SEQUENCE: 28
KCNTATCATQ RLANFLVHSS NNFGPILPPT NVGSNTY                                    37

SEQ ID NO: 29              moltype = AA  length = 37
FEATURE                    Location/Qualifiers
source                     1..37
                           mol_type = protein
                           organism = synthetic construct
SITE                       1
                           note = alpha-amino group of lysine residue conjugated to
                             2-((20-((1-carboxy-4-oxobutyl)amino)-20-oxoicosanoyl)oxy)-N
                             ,N,N-trimethylethan-1-aminium
DISULFID                   2..7
                           note = Intrachain disulfide bond
SITE                       37
                           note = Amidated tyrosine
SEQUENCE: 29
KCNTATCATQ RLANFLVHSS NNFGPILPPT NVGSNTY                                    37

SEQ ID NO: 30              moltype = AA  length = 39
FEATURE                    Location/Qualifiers
source                     1..39
                           mol_type = protein
                           organism = synthetic construct
MOD_RES                    2
                           note = Aminoisobutyric acid (Aib)
MOD_RES                    13
```

```
                               note = Aminoisobutyric acid (Aib)
SITE                           20
                               note = Lysine residue conjugated to
                                 22-carboxy-1,10,19,24-tetraoxo-3,6,12,15-tetraoxa-9,18,23-t
                                 riazatritetracontan-43-oic acid
SITE                           39
                               note = Amidated serine
SEQUENCE: 30
YXEGTFTSDY SIXLDKIAQK AFVQWLIAGG PSSGAPPPS                                  39

SEQ ID NO: 31                  moltype = AA   length = 39
FEATURE                        Location/Qualifiers
source                         1..39
                               mol_type = protein
                               organism = synthetic construct
MOD_RES                        2
                               note = Aminoisobutyric acid (Aib)
MOD_RES                        13
                               note = Aminoisobutyric acid (Aib)
SITE                           20
                               note = C20 fatty diacid moiety (eicosanedioic acid) linked
                                 via hydrophilic linkers (gamma-Glu-2xAdo, gamma glutamate
                                 and bis-aminodiethoxyacetyl) connected to lysine residue
SITE                           39
                               note = Amidated serine
SEQUENCE: 31
YXEGTFTSDY SIXLDKIAQK AFVQWLIAGG PSSGAPPPS                                  39

SEQ ID NO: 32                  moltype = AA   length = 39
FEATURE                        Location/Qualifiers
source                         1..39
                               mol_type = protein
                               organism = synthetic construct
MOD_RES                        2
                               note = Aminoisobutyric acid (Aib)
MOD_RES                        13
                               note = Aminoisobutyric acid (Aib)
SITE                           20
                               note = Lysine residue side chain conjugated to
                                 22-carboxy-1,10,19,24-tetraoxo-3,6,12,15-tetraoxa-9,18,23-t
                                 riazatritetracontan-43-oate, ionically bound to
                                 (2-hydroxyethyl)trimethylazanium
SITE                           39
                               note = Amidated serine
SEQUENCE: 32
YXEGTFTSDY SIXLDKIAQK AFVQWLIAGG PSSGAPPPS                                  39

SEQ ID NO: 33                  moltype = AA   length = 39
FEATURE                        Location/Qualifiers
source                         1..39
                               mol_type = protein
                               organism = synthetic construct
MOD_RES                        2
                               note = Aminoisobutyric acid (Aib)
MOD_RES                        13
                               note = Aminoisobutyric acid (Aib)
SITE                           20
                               note = Lysine residue side chain conjugated to
                                 22-carboxy-N,N,N-trimethyl-1,10,19,24,43-pentaoxo-3,6,12,15
                                 ,44-pentaoxa-9,18,23-triazahexatetracontan-46-aminium
SITE                           39
                               note = Amidated serine
SEQUENCE: 33
YXEGTFTSDY SIXLDKIAQK AFVQWLIAGG PSSGAPPPS                                  39

SEQ ID NO: 34                  moltype = AA   length = 31
FEATURE                        Location/Qualifiers
source                         1..31
                               mol_type = protein
                               organism = synthetic construct
SITE                           20
                               note = Lysine side chain linked via an amide linkage to
                                 gamma-glutamate-palmitic acid (gammaGlu-C16 fatty acid)
SEQUENCE: 34
HAEGTFTSDV SSYLEGQAAK EFIAWLVRGR G                                          31

SEQ ID NO: 35                  moltype = AA   length = 31
FEATURE                        Location/Qualifiers
source                         1..31
```

```
                                        mol_type = protein
                                        organism = synthetic construct
MOD_RES                                 2
                                        note = aminoisobutyric acid (Aib)
SITE                                    20
                                        note = Lysine residue side chain conjugated to
                                        22-carboxy-1,10,19,24-tetraoxo-3,6,12,15-tetraoxa-9,18,23-t
                                        riazahentetracontan-41-oic acid
SEQUENCE: 35
HXEGTFTSDV SSYLEGQAAK EFIAWLVRGR G                                                  31

SEQ ID NO: 36                           moltype = AA   length = 31
FEATURE                                 Location/Qualifiers
source                                  1..31
                                        mol_type = protein
                                        organism = synthetic construct
MOD_RES                                 2
                                        note = Aminoisobutyric acid (Aib)
SITE                                    20
                                        note = Lysine residue side chain conjugated to
                                        22-carboxy-1,10,19,24-tetraoxo-3,6,12,15-tetraoxa-9,18,23-t
                                        riazahentetracontan-41-oate, ionically bound to
                                        (2-hydroxyethyl)trimethylazanium
SEQUENCE: 36
HXEGTFTSDV SSYLEGQAAK EFIAWLVRGR G                                                  31

SEQ ID NO: 37                           moltype = AA   length = 31
FEATURE                                 Location/Qualifiers
source                                  1..31
                                        mol_type = protein
                                        organism = synthetic construct
MOD_RES                                 2
                                        note = Aminoisobutyric acid (Aib)
SITE                                    20
                                        note = Lysine residue side chain conjugated to
                                        22-carboxy-N,N,N-trimethyl-1,10,19,24,41-pentaoxo-3,6,12,15
                                        ,42-pentaoxa-9,18,23-triazatetratetracontan-44-aminium
SEQUENCE: 37
HXEGTFTSDV SSYLEGQAAK EFIAWLVRGR G                                                  31

SEQ ID NO: 38                           moltype = AA   length = 31
FEATURE                                 Location/Qualifiers
source                                  1..31
                                        mol_type = protein
                                        organism = synthetic construct
MOD_RES                                 2
                                        note = Aminoisobutyric acid (Aib)
SITE                                    20
                                        note = Lysine residue side chain conjugated to
                                        22-carboxy-1,10,19,24-tetraoxo-3,6,12,15-tetraoxa-9,18,23-t
                                        riazahentetracontan-41-oic acid
SEQUENCE: 38
HXEGTFTSDV SSYLEGQAAK EFIAWLVRGR G                                                  31

SEQ ID NO: 39                           moltype = AA   length = 31
FEATURE                                 Location/Qualifiers
source                                  1..31
                                        mol_type = protein
                                        organism = synthetic construct
MOD_RES                                 2
                                        note = Aminoisobutyric acid (Aib)
SITE                                    20
                                        note = Lysine residue side chain conjugated to
                                        22-carboxyl-1,10,19,24-tetraoxo-3,6,12,15-tetraoxa-9,18,23-
                                        triazahentetracontan-41-oate, ionically bound to
                                        (2-hydroxyethyl)trimethylazanium
SEQUENCE: 39
HXEGTFTSDV SSYLEGQAAK EFIAWLVRGR G                                                  31

SEQ ID NO: 40                           moltype = AA   length = 31
FEATURE                                 Location/Qualifiers
source                                  1..31
                                        mol_type = protein
                                        organism = synthetic construct
MOD_RES                                 2
                                        note = Aminoisobutyric acid (Aib)
SITE                                    3
                                        note = (2-hydroxyethyl)trimethylazanium ionically bound to
                                        Glutamate residue at a ratio of 1:1
```

| | | |
|---|---|---|
| SITE | 9 | |
| | note = (2-hydroxyethyl)trimethylazanium ionically bound to Aspartate residue at a ratio of 1:1 | |
| SITE | 15 | |
| | note = (2-hydroxyethyl)trimethylazanium ionically bound to Glutamate residue at a ratio of 1:1 | |
| SITE | 20 | |
| | note = Lysine residue side chain conjugated to 22-carboxyl-1,10,19,24-tetraoxo-3,6,12,15-tetraoxa-9,18,23-triazahentetracontan-41-oate, ionically bound to (2-hydroxyethyl)trimethylazanium | |
| SITE | 21 | |
| | note = (2-hydroxyethyl)trimethylazanium ionically bound to Glutamate residue at a ratio of 1:1 | |
| SITE | 31 | |
| | note = (2-hydroxyethyl)trimethylazanium ionically bound to Glycinate residue at a ratio of 1:1 | |
| SEQUENCE: 40 | | |
| HXEGTFTSDV SSYLEGQAAK EFIAWLVRGR G | | 31 |
| | | |
| SEQ ID NO: 41 | moltype = AA   length = 31 | |
| FEATURE | Location/Qualifiers | |
| source | 1..31 | |
| | mol_type = protein | |
| | organism = synthetic construct | |
| MOD_RES | 2 | |
| | note = Aminoisobutyric acid (Aib) | |
| SITE | 3 | |
| | note = (2-hydroxyethyl)trimethylazanium ionically bound to Glutamate residue at a ratio of 4:1 | |
| SITE | 9 | |
| | note = (2-hydroxyethyl)trimethylazanium ionically bound to Aspartate residue at a ratio of 4:1 | |
| SITE | 15 | |
| | note = (2-hydroxyethyl)trimethylazanium ionically bound to Glutamate residue at a ratio of 4:1 | |
| SITE | 20 | |
| | note = Lysine residue side chain conjugated to 22-carboxyl-1,10,19,24-tetraoxo-3,6,12,15-tetraoxa-9,18,23-triazahentetracontan-41-oate, ionically bound to (2-hydroxyethyl)trimethylazanium | |
| SITE | 21 | |
| | note = (2-hydroxyethyl)trimethylazanium ionically bound to Glutamate residue at a ratio of 4:1 | |
| SITE | 31 | |
| | note = (2-hydroxyethyl)trimethylazanium ionically bound to Glycinate residue at a ratio of 4:1 | |
| SEQUENCE: 41 | | |
| HXEGTFTSDV SSYLEGQAAK EFIAWLVRGR G | | 31 |
| | | |
| SEQ ID NO: 42 | moltype = AA   length = 31 | |
| FEATURE | Location/Qualifiers | |
| source | 1..31 | |
| | mol_type = protein | |
| | organism = synthetic construct | |
| MOD_RES | 2 | |
| | note = aminoisobutyric acid (Aib) | |
| SITE | 20 | |
| | note = Lysine residue side chain conjugated to 22-((cinnamyloxy)carbonyl)-1,10,19,24-tetraoxo-3,6,12,15-tetraoxa-9,18,23-triazahentetracontan-41-oic acid | |
| SEQUENCE: 42 | | |
| HXEGTFTSDV SSYLEGQAAK EFIAWLVRGR G | | 31 |

COMPOSITIONS COMPRISING PHARMACEUTICALLY ACCEPTABLE SALTS OF GLUCAGON-LIKE PEPTIDE-1 ANALOGS AND USES THEREOF

CROSS-REFERENCE

This application is a continuation of International Application No. PCT/US2022/049585, filed Nov. 10, 2022, which claims the benefit of U.S. Provisional Application No. 63/380,125, filed Oct. 19, 2022, U.S. Provisional Application No. 63/334,410, filed Apr. 25, 2022, U.S. Provisional Application No. 63/295,197, filed Dec. 30, 2021, and U.S. Provisional Application No. 63/277,878, filed Nov. 10, 2021, each of which is incorporated herein by reference in its entirety.

SEQUENCE LISTING

The instant application contains a Sequence Listing which has been submitted electronically in XML file format and is hereby incorporated by reference in its entirety. Said XML copy, created on Feb. 15, 2024, is named 56017_712_302_SL.xml and is 66,348 bytes in size.

TECHNICAL FIELD

The technology described herein relates to ionic liquids and deep eutectic liquids for the treatment of diseases including obesity, metabolic disorders and gastro-intestinal inflammation.

SUMMARY

Provided herein are compositions of matter and methods of use for the treatment of diseases or disorders.

The inventors have found that certain modifications to proteins surprisingly improve their use with ionic liquid compositions for formulation and delivery. These formulations can be delivered orally to a patient for the purpose of treating the patient.

In one embodiment, described herein is a composition wherein a protein or a peptide is non-covalently attached to one or more ions wherein such ions are also present in the said ionic liquid that is present in the formulation.

In one embodiment, described herein is a composition wherein a protein or a peptide is covalently attached to one or more ions wherein such ions are also present in the said ionic liquid that is present in the formulation.

In an aspect, provided herein is, inter alia, a compound having the structure of Formula Ia:

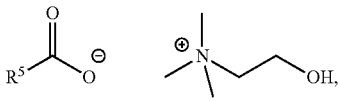

Formula Ia wherein:

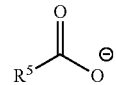

is a therapeutic agent,
wherein the therapeutic agent is an GLP-1 analog or functional variant thereof, and comprises the sequence of SEQ ID NO: 35.

In some embodiments, the sequence of SEQ ID NO: 35 comprises the following structure:

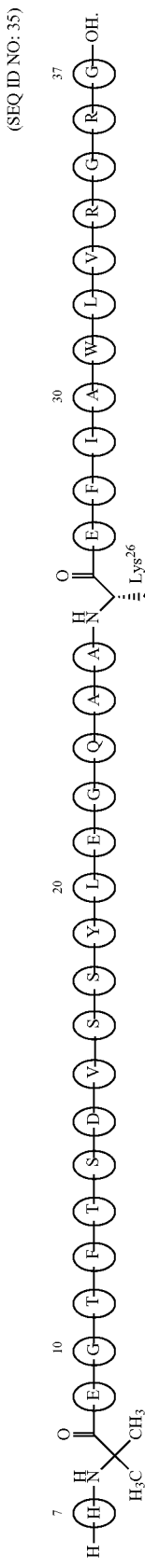
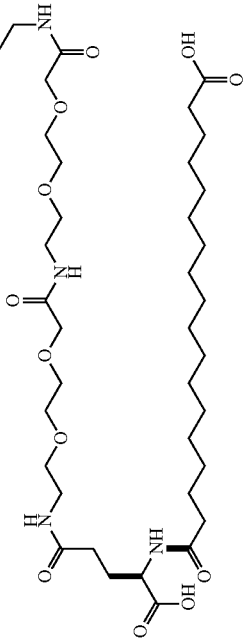
(SEQ ID NO: 35)

In some embodiments, the compound comprises the following structure:

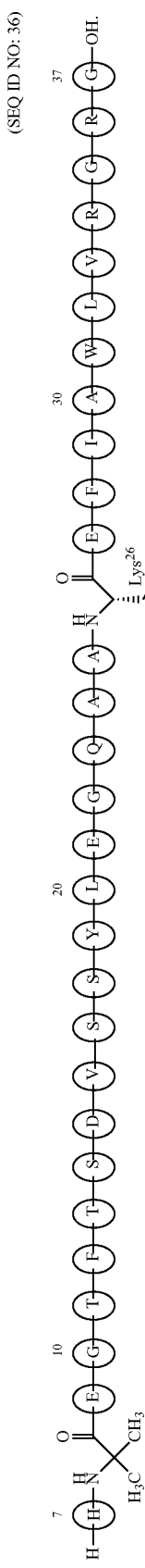
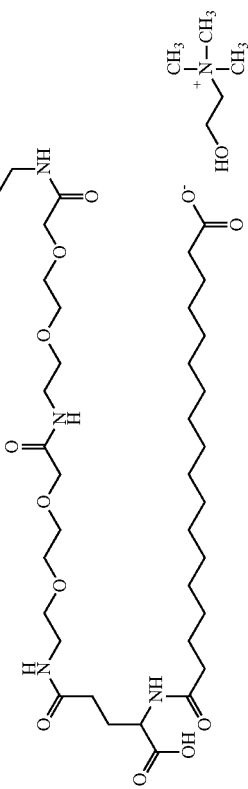
(SEQ ID NO: 36)

In some embodiments, the compound comprises a

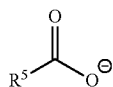

to

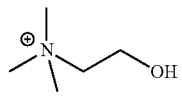

molar ratio of from about 1:1 to about 1:12.

In some embodiments, the compound comprises a

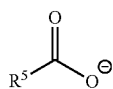

to

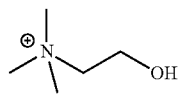

molar ratio of about 1:4.

In some embodiments, the compound further comprises one or more additional salts.

In some embodiments, the compound comprises one or more additional salts formed between one or more additional

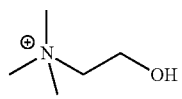

and one or more carboxylic acids of the therapeutic agent.

In another aspect, provided herein is a pharmaceutical composition comprising the compound as provided herein, and a pharmaceutically acceptable excipient.

In some embodiments, the pharmaceutical composition as provided herein further comprises at least one permeation enhancer.

In some embodiments, the at least one permeation enhancer is selected from the group consisting of salcaprozate sodium (SNAC), sodium caprylate, sodium caprate, a bile salt, ethylenediaminetetraacetic acid (EDTA), ethylene glycol-bis-(2-aminoethylether)-N,N,N',N'-tetraacetic acid (EGTA), and 3-[N,N-Dimethyl(3-palmitoylaminopropyl)-ammonio]-propanesulfonate (PPS), and any combination thereof.

In some embodiments, the at least one permeation enhancer comprises salcaprozate sodium (SNAC).

In some embodiments, the pharmaceutical composition as provided herein further comprises one or more ionic liquids, wherein each of the one or more ionic liquids independently comprises an anion and a cation.

In some embodiments, each of the one or more ionic liquids independently comprise a cation selected from the group consisting of aminoguanidine, choline or choline derivative, carnitine, acetylcholine, ammonium, tetramethyl ammonium, tetraethyl ammonium, tetrabutyl ammonium, and guanidine derivatives.

In some embodiments, each of the one or more ionic liquids independently comprise a cation selected from the group consisting of choline or a choline derivative, carnitine, or acetylcholine.

In some embodiments, each of the one or more ionic liquids independently comprise an anion selected from the group consisting of (R)-α-lipoic acid, 12-hydroxystearic acid, 2-(4-isobutylphenyl)propionic acid, 2-(4,4-dimethyl-2-pentanyl)-5,7,7-trimethyloctanoic acid, 2-aminoethanesulfonic acid (taurine acid), 2-hexyldecanoic acid, 2-hydroxyhippuric acid, 3-(4-hydroxyphenyl)propionic acid, 3-methylcrotonic acid, 3,3-diphenylpropionic acid, 3,4-dihydroxbenzoic acid (protocatechuic acid), 3,7-dimethyloctanoic acid, 4-hydroxybenzenesulfonic acid, 4-hydroxybenzoic acid, 4-methylhexanoic acid, 4-methyloctanoic acid, 4-methylvaleric acid, 5-norbornene-2-carboxylic acid, 8-[(2-hydroxybenzoyl)amino]octanoic acid, abietic acid, acetic acid, acetylcysteine, aconitic acid, arachidonic acid, behenic acid, benzoic acid, caffeic acid, chenodeoxycholic acid, cinnamic acid, citric acid, citronellic acid, crotonic acid, D-(+)-galactonic acid, decanoic acid, deoxycholic acid, dihydrocaffeic acid, DL-2-phenylpropionic (hydratropic) acid, DL-tartaric acid, DL-tropic acid, eicosanedioic acid, eicosapentanoic acid (EPA), elaidic acid, ellagic acid, erucic acid, ethylenediaminetetraacetic acid (EDTA), formic acid, fumaric acid, geranic acid, glutaric acid, glycolic acid, heptanoic acid, hexanoic acid, hydrocinnamic acid (3-phenylpropionic acid), isobutyric acid, isovaleric acid, L-(+)-tartaric acid, L-ascorbic acid, L-aspartic acid, L-glutamic acid, L-glutathione reduced, lactic acid, lauric acid, levulinic acid, linoleic acid, linolenic acid, lithocholic acid, maleic acid, malic acid, malonic acid, mandelic acid, mesaconic acid, nicotinic acid, nonanoic acid, octanoic acid, oleic acid, oxalic acid, p-coumaric acid, p-toluenesulfonic acid, palmitic acid, perillic acid, phosphoric acid, pimelic acid, pivalic acid, propionic acid, pyroglutamic acid, pyruvic acid, ricinoleic acid, salicylic acid (2-hydroxybenzoic acid), sinapinic acid (3,5-dimethoxy-4-hydroxycinnamic acid), sorbic acid, stearic acid, succinic acid, syringic acid, tiglic acid, trans-2-decenoic acid, trans-2-hexenoic acid, trans-2-octenoic acid, trans-3-octenoic acid, trans-γ-octenoic acid, trans-ferulic acid, undecanoic acid, valeric acid, vanillic acid, and β-ketoglutaric acid.

In some embodiments, each of the one or more ionic liquids independently comprise an anion selected from the group consisting of cinnamic acid, mandelic acid, citric acid, ricinoleic acid, linoleic acid, and tiglic acid.

In some embodiments, the one or more ionic liquids comprise:
(i) choline or a choline derivative-cinnamic acid, choline or a choline derivative-mandelic acid, choline or a choline derivative-citric acid, choline or a choline derivative-ricinoleic acid, choline or a choline derivative-linoleic acid, or choline or a choline derivative-tiglic acid;
(ii) carnitine-cinnamic acid, carnitine-mandelic acid, carnitine-citric acid, carnitine-ricinoleic acid, carnitine-linoleic acid, or carnitine-tiglic acid;
(iii) acetylcholine-cinnamic acid, acetylcholine-mandelic acid, acetylcholine-citric acid, acetylcholine-ricinoleic acid, acetylcholine-linoleic acid, or acetylcholine-tiglic acid; or
(iv) any combination thereof.

In some embodiments, the one or more ionic liquids comprise a choline-cinnamic acid ionic liquid.

In some embodiments, the pharmaceutical composition as provided herein further comprises one or more ionic liquids, wherein each of the one or more ionic liquids independently comprises an anion and a cation.

In some embodiments, the at least one permeation enhancer comprises salcaprozate sodium (SNAC) and the one or more ionic liquids comprise a choline-cinnamic acid ionic liquid.

In another aspect, provided herein is a method of treating a disease or disorder in a subject in need thereof, comprising administering to the subject a therapeutically effective amount of the compound as provided herein, wherein the administering is effective to treat the disease or disorder in the subject, and wherein the disease or disorder is a metabolic disease or disorder.

In some embodiments, the metabolic disease or disorder is selected from the group consisting of type 1 diabetes, type 2 diabetes, obesity, overweight, and nonalcoholic steatohepatitis (NASH).

In some embodiments, the metabolic disease or disorder is type 2 diabetes.

In some embodiments, the metabolic disease or disorder is obesity.

In some embodiments, the metabolic disease or disorder is overweight.

In some embodiments, the metabolic disease or disorder is nonalcoholic steatohepatitis (NASH).

In some embodiments, the compound is administered via subcutaneous administration or intravenous administration.

In some embodiments, the compound is administered via oral administration.

In another aspect, provided herein is a method of reducing weight in a subject in need thereof, comprising administering to the subject a therapeutically effective amount of the compound as provided herein, wherein the administering is effective to reduce weight in the subject.

BRIEF DESCRIPTION OF THE DRAWINGS

FIG. 1B, continued from FIG. 1A. FIG. 1 and FIG. 1B disclose SEQ ID NO: 26.

FIG. 2B, continued from FIG. 2A; and FIG. 2C, continued from FIG. 2B. FIGS. 2A, 2B, and 2C disclose SEQ ID NO: 27.

FIG. 3B, continued from FIG. 3A. FIG. 3A and FIG. 3B disclose SEQ ID NO: 28.

FIG. 4B, continued from FIG. 4A. FIG. 4A and FIG. 4B disclose SEQ ID NO: 29.

FIG. 11B, continued from FIG. 11A; and FIG. 11C, continued from FIG. 11B. FIGS. 11A, 11B, and 11C disclose SEQ ID NO: 30.

FIG. 12 discloses SEQ ID NO: 31.

FIG. 13B, continued from FIG. 13A; and FIG. 13C, continued from FIG. 13B. FIGS. 13A, 13B, and 13C disclose SEQ ID NO: 32.

FIG. 14B, continued from FIG. 14A; and FIG. 14C, continued from FIG. 14B. FIGS. 14A, 14B, and 14C disclose SEQ ID NO: 33.

FIG. 15A discloses SEQ ID NO: 34.

FIG. 15B discloses SEQ ID NO: 35.

FIG. 16 discloses SEQ ID NO: 36.

FIG. 17B discloses SEQ ID NO: 37.

FIG. 20A and FIG. 20B depict a chemical structure of an exemplary GLP-1 analog or functional variant thereof or mimetic thereof. FIG. 20B, continued from FIG. 20A. FIG. 20A and FIG. 20B disclose SEQ ID NO: 38. FIG. 20C and FIG. 20D depict an exemplary structure of choline-an exemplary GLP-1 analog or functional variant thereof or mimetic thereof at the 1:1 ratio. In some embodiments, choline ionization could occur at any of the —COOH sites. FIG. 20D, continued from FIG. 20C. FIG. 20C and FIG. 20D disclose SEQ ID NO: 39. FIG. 20E and FIG. 20F depict an exemplary structure of choline-an exemplary GLP-1 analog or functional variant thereof or mimetic thereof at the 7:1 ratio. FIG. 20F, continued from FIG. 20E. FIG. 20E and FIG. 20F disclose SEQ ID NO: 40. FIG. 20G and FIG. 20H depict an exemplary structure of choline-an exemplary GLP-1 analog or functional variant thereof or mimetic thereof at the 28:1 ratio. In some embodiments, excess bicarbonate is also present in the 28:1 ratio. FIG. 20H, continued from FIG. 20G. FIG. 20G and FIG. 20H disclose SEQ ID NO: 41.

FIG. 21 depicts Table 3 showing an exemplary GLP-1 analog or functional variant thereof or mimetic thereof ("GLP-1 analog") mass normalization calculation.

FIG. 23A depicts exemplary analytical characterization results of an exemplary GLP-1 analog or functional variant thereof or mimetic thereof ("GLP-1 analog") based on pH using 2 mg/mL solutions in water. The results are not normalized to an exemplary GLP-1 analog or functional variant thereof or mimetic thereof Mass. FIG. 23B depicts exemplary analytical characterization results of an exemplary GLP-1 analog or functional variant thereof or mimetic thereof ("GLP-1 analog") based on pH using 2 mg/mL solutions in water. The results of the choline-the exemplary GLP-1 analog or functional variant thereof or mimetic thereof are normalized to the exemplary GLP-1 analog or functional variant thereof or mimetic thereof Mass. FIG. 23C depicts exemplary analytical characterization results of an exemplary GLP-1 analog or functional variant thereof or mimetic thereof ("GLP-1 analog") based on pH using 2 mg/mL solutions in water, wherein the exemplary reaction using choline bicarbonate as shown above the graph was used. The results of the choline-the exemplary GLP-1 analog or functional variant thereof or mimetic thereof are normalized to the exemplary GLP-1 analog or functional variant thereof or mimetic thereof Mass. FIG. 23D depicts exemplary analytical characterization results of the negative control of an exemplary GLP-1 analog or functional variant thereof or mimetic thereof ("GLP-1 analog") based on pH using 2 mg/mL solutions in water, wherein the exemplary reaction using choline chloride as shown above the graph was used. The results of the choline-Cl-the exemplary GLP-1 analog or functional variant thereof or mimetic thereof are normalized to the exemplary GLP-1 analog or functional variant thereof or mimetic thereof Mass.

FIG. 24A depicts exemplary analytical characterization results of an exemplary GLP-1 analog or functional variant thereof or mimetic thereof ("GLP-1 analog") based on conductivity using 2 mg/mL solutions in water. The results are not normalized to an exemplary GLP-1 analog or functional variant thereof or mimetic thereof Mass. FIG. 24B depicts exemplary analytical characterization results of an exemplary GLP-1 analog or functional variant thereof or mimetic thereof ("GLP-1 analog") based on conductivity using 2 mg/mL solutions in water. The results of the choline-the exemplary GLP-1 analog or functional variant thereof or mimetic thereof are normalized to the exemplary GLP-1 analog or functional variant thereof or mimetic thereof Mass. FIG. 24C depicts exemplary analytical characterization results of an exemplary GLP-1 analog or functional variant thereof or mimetic thereof ("GLP-1 analog") based on conductivity using 2 mg/mL solutions in water, wherein the exemplary reaction using choline bicarbonate as shown above the graph was used. The results of the choline-the exemplary GLP-1 analog or functional variant thereof or mimetic thereof are normalized to the exemplary GLP-1 analog or functional variant thereof or mimetic thereof Mass. FIG. 24D depicts exemplary analytical characterization results of the negative control of an exemplary GLP-1 analog or functional variant thereof or mimetic thereof ("GLP-1 analog") based on conductivity using 2 mg/mL solutions in water, wherein the exemplary reaction using choline chloride as shown above the graph was used. The results of the choline-Cl-the exemplary GLP-1 analog or functional variant thereof or mimetic thereof are normalized to the exemplary GLP-1 analog or functional variant thereof or mimetic thereof Mass.

FIG. 25A depicts exemplary analytical characterization results based on NMR of choline-an exemplary GLP-1 analog or functional variant thereof or mimetic thereof ("GLP-1 analog") ratios. FIG. 25B depicts exemplary analytical characterization results based on NMR of choline-an exemplary GLP-1 analog or functional variant thereof or mimetic thereof ("GLP-1 analog") ratios in a larger view.

FIG. 27B, continued from FIG. 27A. FIG. 27A and FIG. 27B disclose SEQ ID NO: 42.

DETAILED DESCRIPTION

Figure 1A:
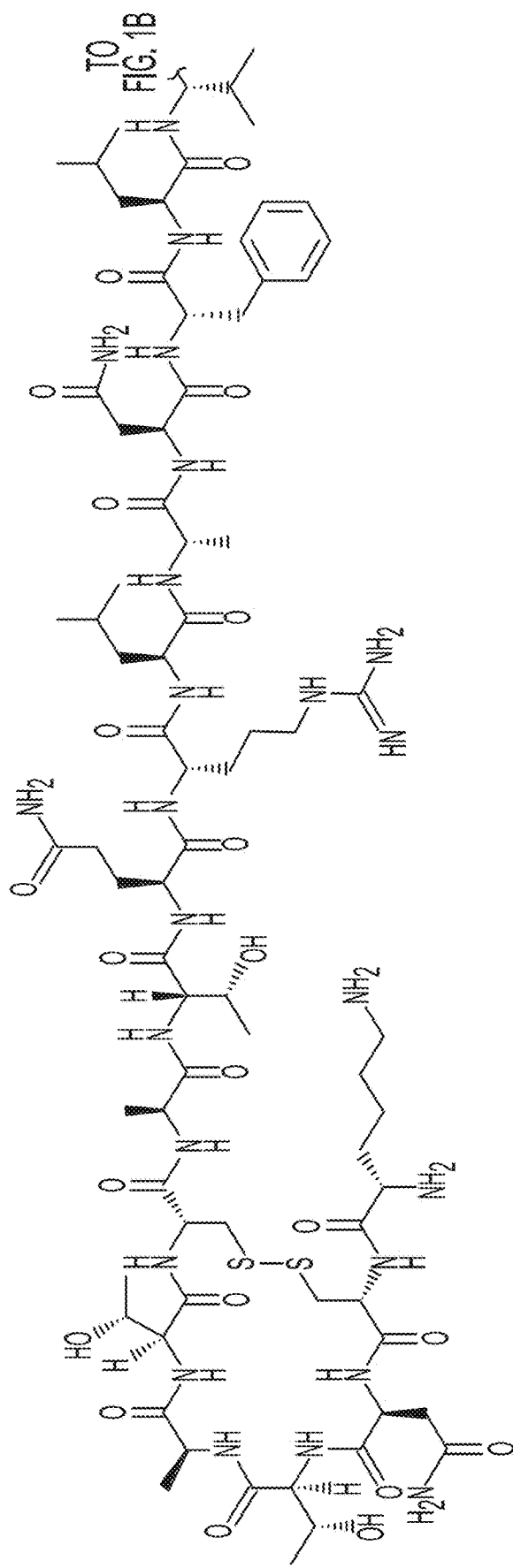
FIG. 1A and FIG. 1B depict the structure of an exemplary amylin analog or functional variant thereof or mimetic thereof.

The invention describes modification of drugs with ions to improve their formulation with ionic liquids for treating patients by oral administration. Oral administration can be achieved in any one of the dosing forms including pills, caplets, capsules, aerosol sprays, or liquids. The ionic liquid or the drug to be delivered with the ionic liquid can be encapsulated in a capsule. The ionic liquid with the dosing form may be present in any of the physical forms including a clear neat ionic liquid, a homogenous mixture of an ionic liquid with a pharmaceutically acceptable diluent, an emulsion, or a suspension. The oral dose can also be given as a syrup or a spray or an aerosol. The composition of any oral dose disclosed herein may contain a predetermined amount of ionic liquid and optionally one drug, and may be prepared by methods of pharmacy well known to those skilled in the art.

In one embodiment, described herein is a method of treatment of patients comprising orally administering an oral formulation of insulin in combination with an ionic liquid.

In one embodiment, described herein is a method of treatment of diabetes comprising orally administering an oral formulation of an amylin analog or functional variant thereof or mimetic thereof or a GLP-1 polypeptide or mimetic or analog thereof in combination with ionic liquid.

As described elsewhere herein, ionic liquid is able to safely carry active compounds across the mucus membranes encountered during oral administration.

As described in the examples herein, ionic liquids provide solubilization of the drug and enhanced delivery into systemic circulation. Accordingly, they are particularly suitable as a delivery vehicle to/across mucus membranes.

In one embodiment, the ionic liquid can be combined with another solvent to enhance solubility and/or delivery. The solvent may be aqueous or non-aqueous. In one embodiment, the purpose of the solvent is to control the dose of the ionic liquid experienced by the mucus membrane or the gastrointestinal tract. Dilution of the ionic liquid by the solvent can serve the purpose of delivering a safe dose to the subject. In another embodiment, the purpose of the solvent is to improve solubility of the drug. Such improvement may come from the ability of the solvent to control the physicochemical environment of the ionic liquid to match the chemical properties of the drug. In one embodiment, the solvent may serve the purpose of improving the delivery across the mucosal membrane.

The solvents used in any of the embodiments include without limitation: sterile water, saline solution, glycerin, propylene glycol, ethanol, oils, ethyl oleate, isopropyl myristate, benzyl benzoate, or surfactants.

In one embodiment, the solvent is chosen so as to not adversely impact the compatibility of the ionic liquid with the capsule.

The term "ionic liquids" as used herein refers to organic salts or mixtures of organic salts which are in liquid state at room temperature. Ionic liquids have been shown to be useful in a variety of fields, including in industrial processing, catalysis, pharmaceuticals, and electrochemistry. The ionic liquids contain at least one anionic and at least one cationic component. Ionic liquids can comprise an additional hydrogen bond donor (i.e. any molecule that can provide an —OH or an —NH group), examples include but are not limited to alcohols, fatty acids, and amines. The anionic and the cationic component may be present in any molar ratio. Exemplary molar ratios (cation:anion) include but are not limited to 1:1, 1:2, 2:1, and ranges between these ratios. In some embodiments, the ionic liquid or solvent exists as a liquid below 100° C. In some embodiments, the ionic liquid or solvent exists as a liquid at room temperature. In some embodiments, the ionic liquids comprise more than one anionic components and one cationic component. In some embodiments, comprise choline or choline derivative, and cinnamic acid and mandelic acid.

In some embodiments, the ionic liquid is dominated by the ionic interactions between the anion and the cation. In some embodiments, the ionic liquid is dominated by the hydrogen bonding interactions between the anion and cation. The relative dominance of ionic and hydrogen bonding interactions may vary depending on the nature of the ions.

As used herein, "in combination with" refers to two or more substances being present in the same dose administered to a subject in any form.

In some embodiments, the drug(s) may form micelles or other self-assembled structures. In some embodiments, such structure may occur only in the presence of ionic liquids.

As used herein, the terms "therapeutic agent" and "drug" are interchangeably used. A therapeutic agent or a drug is any agent which will exert an effect on a target cell or organism. A drug can be selected from a group comprising: chemicals; small organic or inorganic molecules; peptide; protein; or nucleic acid. Non-limiting examples of active compounds contemplated for use in the methods described herein include small molecules, polypeptides, nucleic acids, antibodies, vaccines, an antibody or an antibody fragment thereof, a GLP-1 polypeptide or mimetic or analog thereof, amylin, an amylin analog or functional variant thereof or mimetic thereof, PYY, pramlintide, and insulin.

In some embodiments, the terms "mimetic," "functional variant," "functional analog," or "functional homolog thereof" may be used interchangeably.

Dual GIP/GLP-1 Receptor Agonist or Functional Variant Thereof or Mimetic or Functional Analog Thereof or Functional Homolog Thereof In some embodiments, a dual GIP (glucose-dependent insulinotropic polypeptide)/GLP-1 (Glucagon-like peptide-1) receptor agonist or functional variant thereof is Tirzepatide or functional variant thereof or mimetic or functional analog thereof or functional homolog thereof. As used herein, the term "Tirzepatide," also known as LY3298176 and GIP/GLP-1 RA, refers to a fatty acid modified peptide with dual glucose-dependent insulinotropic polypeptide (GIP) and Glucagon-like peptide-1 (GLP-1) receptor agonist activity. In some embodiments, Tirzepatide is a dual GIP and GLP-1 receptor agonist.

In some embodiments, a dual GIP/GLP-1 receptor agonist or functional variant thereof is a GIP-based dual Incretin receptor agonist. In some embodiments, GIP and GLP-1 are hormones involved in blood sugar control. In some embodiments, a dual GIP/GLP-1 receptor agonist or functional variant thereof activates both the GLP-1 and GIP receptors. In some embodiments, a dual GIP/GLP-1 receptor agonist or functional variant thereof activates both GIP and GLP-1 receptor signaling. In some embodiments, a dual GIP/GLP-1 receptor agonist or functional variant thereof shows glucose-dependent insulin secretion and improved glucose tolerance by acting on both GIP and GLP-1 receptors. In some embodiments, a dual GIP/GLP-1 receptor agonist or functional variant thereof leads to improved blood sugar control. In some embodiments, a dual GIP/GLP-1 receptor agonist or functional variant thereof decreases body weight and food intake. In some embodiments, a dual GIP/GLP-1 receptor agonist or functional variant thereof shows that the metabolic action of GIP adds to the established clinical benefits of selective GLP-1 receptor agonists in type 2 diabetes mellitus (T2DM). In some embodiments, a dual GIP/GLP-1 receptor agonist or functional variant thereof reduces fasting serum glucose. In some embodiments, a dual GIP/GLP-1 receptor agonist or functional variant thereof results in reductions in body weight. In some embodiments, a dual GIP/GLP-1 receptor agonist or functional variant thereof is used to treat diabetes mellitus. In some embodiments, a dual GIP/GLP-1 receptor agonist or functional variant thereof is used to treat type 2 diabetes mellitus. In some embodiments, a dual GIP/GLP-1 receptor agonist or functional variant thereof is used to treat T2DM patients. In some embodiments, a dual GIP/GLP-1 receptor agonist or functional variant thereof is used to deliver clinically meaningful improvement in glycaemic control and body weight. In some embodiments, a dual GIP/GLP-1 receptor agonist or functional variant thereof is used to deliver clinically meaningful improvement in glycaemic control. In some embodiments, a dual GIP/GLP-1 receptor agonist or functional variant thereof is used to deliver clinically meaningful improvement in body weight. In some embodiments, a dual GIP/GLP-1 receptor agonist or functional variant thereof is used for the treatment of T2DM and obesity. In some embodiments, a dual GIP/GLP-1 receptor agonist or functional variant thereof is used for the treatment of obesity. In some embodiments, a dual GIP/GLP-1 receptor agonist or functional variant thereof is designed for once-weekly subcutaneous administration. In some embodiments, a dual GIP/GLP-1 receptor agonist or functional variant thereof is designed for oral administration. In some embodiments, a dual GIP/GLP-1 receptor agonist or functional variant thereof is designed for chronic administration.

In some embodiments, a dual GIP/GLP-1 receptor agonist or functional variant thereof is an analog of Glucose-dependent insulinotropic polypeptide (GIP), a human hormone that stimulates the release of insulin from the pancreas. In some embodiments, a dual GIP/GLP-1 receptor agonist or functional variant thereof is a linear polypeptide of 39 amino acids that has been chemically modified by lipidation. In some embodiments, a dual GIP/GLP-1 receptor agonist or functional variant thereof is a linear polypeptide of 39 amino acids that has been chemically modified by lipidation to improve its uptake into cells and its stability to metabolism. In some embodiments, a dual GIP/GLP-1 receptor agonist or functional variant thereof is the compound as show in FIGS. 11A, 11B, and 11C, or FIG. 12, In some embodiments, a dual GIP/GLP-1 receptor agonist or functional variant thereof comprises a sequence having at least 50%, 55%, 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of sequence identity to the sequence of: YAibEGTFTSDYSIAibLDKI-AQKAFVQWLIAGGPSSGAPPPS, wherein Aib refers to α-amino isobutyric acid (SEQ ID NO: 25).

In some embodiments, a dual GIP/GLP-1 receptor agonist or functional variant thereof comprises the sequence of: YAibEGTFTSDYSIAibLDKI-AQKAFVQWLIAGGPSSGAPPPS, wherein Aib refers to α-amino isobutyric acid (SEQ ID NO: 25).

In some embodiments, a dual GIP/GLP-1 receptor agonist or functional variant thereof comprises C20 diacid-γ-Glu-(AEEA)$_2$ attached to a residue of a sequence having at least 50%, 55%, 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 25. In some embodiments, a dual GIP/GLP-1 receptor agonist or functional variant thereof comprises C20 diacid-γ-Glu-(AEEA)$_2$ attached to a residue of the sequence of SEQ ID NO: 25.

In some embodiments, a dual GIP/GLP-1 receptor agonist or functional variant thereof comprises C20 diacid-γ-Glu-(AEEA)$_2$ attached to a Lys residue of a sequence having at least 50%, 55%, 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 25. In some embodiments, a dual GIP/GLP-1 receptor agonist or functional variant thereof comprises C20 diacid-γ-Glu-(AEEA)$_2$ attached to a Lys residue of the sequence of SEQ ID NO: 25.

In some embodiments, a dual GIP/GLP-1 receptor agonist or functional variant thereof comprises C20 diacid-γ-Glu-(AEEA)$_2$ attached to the Lys residue at the position 20 (from the N-terminus) of a sequence having at least 50%, 55%, 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 25. In some embodiments, a dual GIP/GLP-1 receptor agonist or functional variant thereof comprises C20 diacid-γ-Glu-(AEEA)$_2$ attached to the Lys residue at the position 20 (from the N-terminus) of the sequence of SEQ ID NO: 25.

In some embodiments, a dual GIP/GLP-1 receptor agonist or functional variant thereof comprises C20 diacid-γ-Glu-(AEEA)$_2$ attached to the residue at the position 20 (from the N-terminus) of a sequence having at least 50%, 55%, 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 25. In some embodiments, a dual GIP/GLP-1 receptor agonist or functional variant thereof comprises C20 diacid-γ-Glu-(AEEA)$_2$ attached to the residue at the position 20 (from the N-terminus) of the sequence of SEQ ID NO: 25.

As used herein, "glucose-dependent insulinotropic polypeptide," also known as gastric inhibitory polypeptide, GIP, or gastric inhibitory peptide, refers to an inhibiting hormone of the secretin family of hormones. In some embodiments, glucose-dependent insulinotropic polypeptide is a weak inhibitor of gastric acid secretion. In some embodiments, the main role of glucose-dependent insulinotropic polypeptide is to stimulate insulin secretion. Glucose-dependent insulinotropic polypeptide, as used herein, includes any of the recombinant or naturally-occurring forms of glucose-dependent insulinotropic polypeptide or variants or homologs thereof that have or maintain glucose-dependent insulinotropic polypeptide activity (e.g., at least 40% 50%, 60%, 70%, 80%, 90%, 95%, 96%, 97%, 98%, 99% or 100% activity). In some aspects, the variants or homologs have at least 40%, 45%, 50%, 55%, 60%, 65%, 70%, 75%, 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring glucose-dependent insulinotropic polypeptide.

As used herein, "glucagon-like peptide-1," also known as GLP-1, refers to a 30- or 31-amino-acid-long peptide hormone deriving from the tissue-specific posttranslational processing of the proglucagon peptide. In some embodiments, glucagon-like peptide-1 is produced and secreted by intestinal enteroendocrine L-cells and certain neurons within the nucleus of the solitary tract in the brainstem upon food consumption. Glucagon-like peptide-1, as used herein, includes any of the recombinant or naturally-occurring forms of glucagon-like peptide-1 or variants or homologs thereof that have or maintain glucagon-like peptide-1 activity (e.g., at least 40% 50%, 60%, 70%, 80%, 90%, 95%, 96%, 97%, 98%, 99% or 100% activity). In some aspects, the variants or homologs have at least 40%, 45%, 50%, 55%, 60%, 65%, 70%, 75%, 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring glucagon-like peptide-1.

Figure 13A:
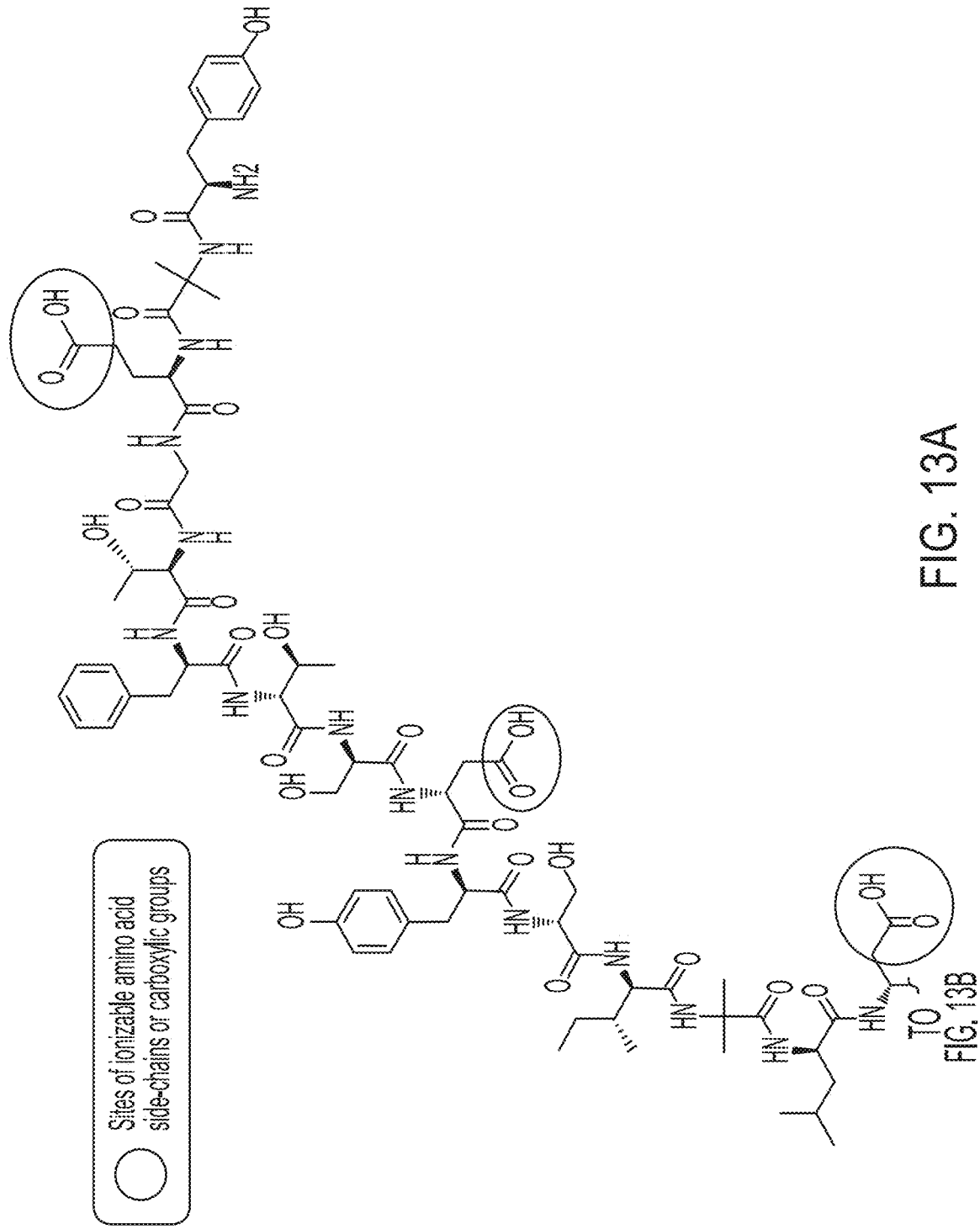
FIGS. 13A, 13B, and 13C depict an exemplary embodiment of a choline-modified dual GIP/GLP-1 receptor agonist ionic derivative structure using an exemplary dual GIP/GLP-1 receptor agonist backbone. The circles indicate the exemplary sites of ionizable amino acid side-chains or carboxylic groups.
Figure 13B:
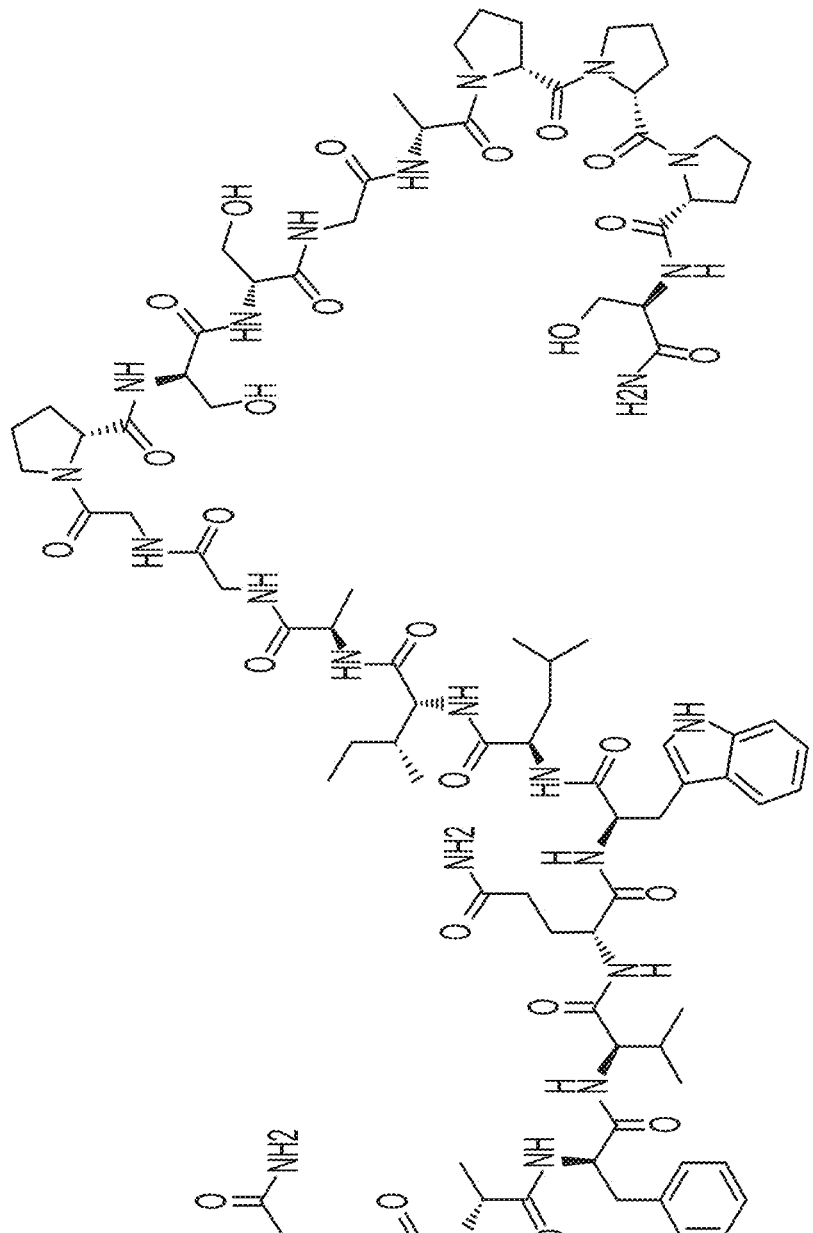
Figure 13B:
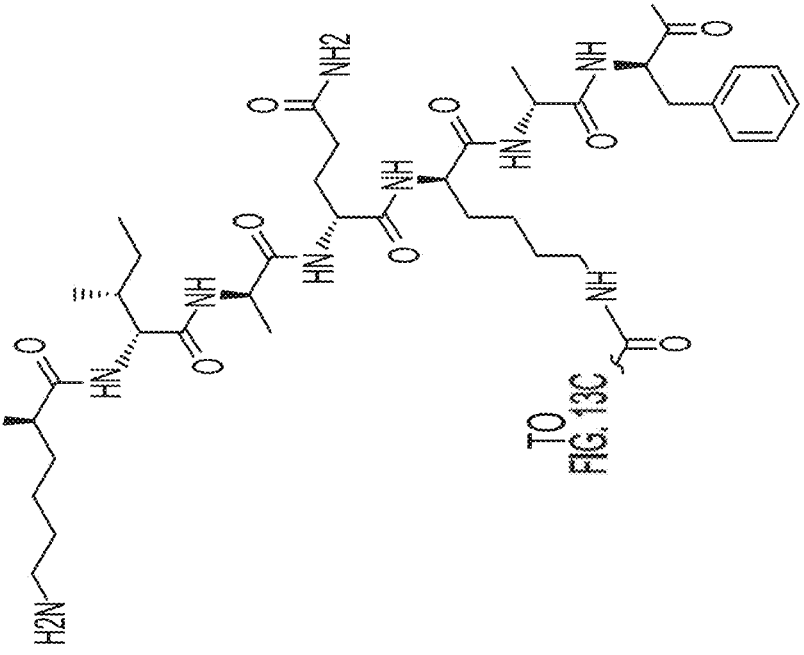
Figure 13B:
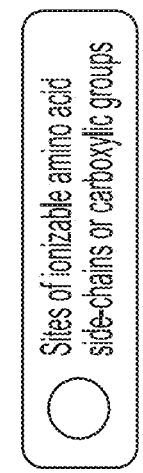
Figure 13C:
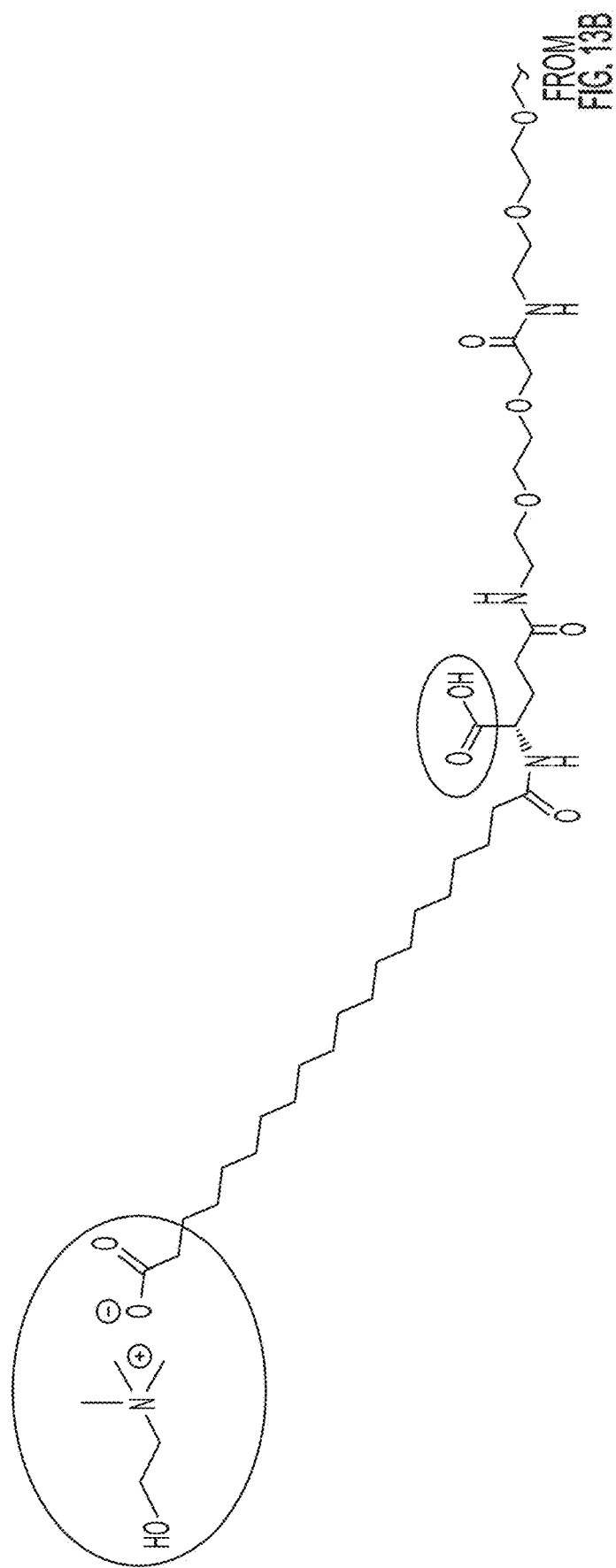

In some embodiments, there are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 ionizable groups present on a dual GIP/GLP-1 receptor agonist or functional variant thereof with a cation (e.g., FIGS. 13A, 13B, and 13C). In some embodiments, the choline:a dual GIP/GLP-1 receptor agonist or functional variant thereof ratio of the choline-a dual GIP/GLP-1 receptor agonist or functional variant thereof ionic derivatives is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, or 100:1.

Figure 14A:
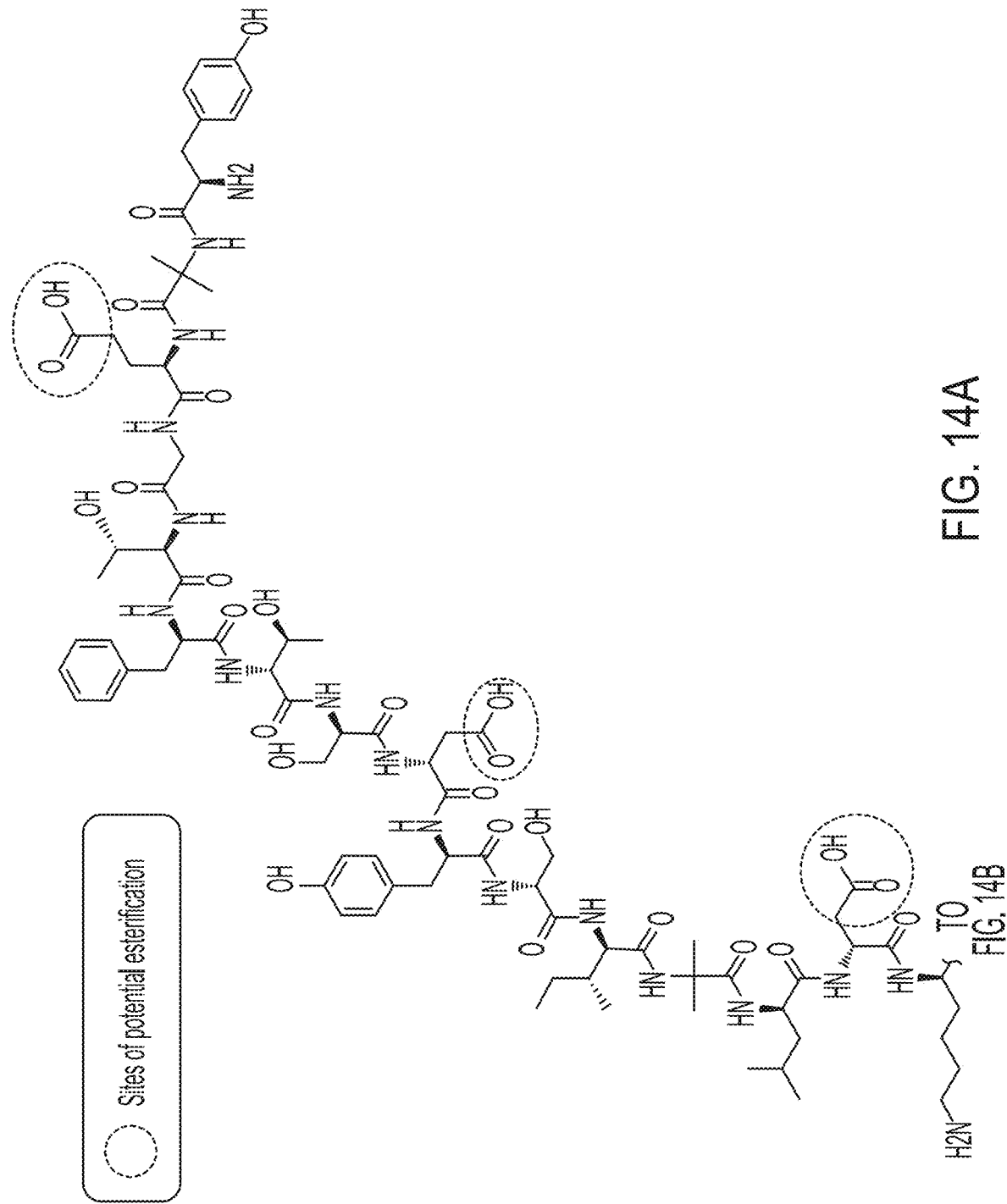
FIGS. 14A, 14B, and 14C depict an exemplary embodiment of a choline-modified a dual GIP/GLP-1 receptor agonist ester structure using an exemplary dual GIP/GLP-1 receptor agonist backbone. The circles indicate the exemplary sites of potential esterification.
Figure 14B:
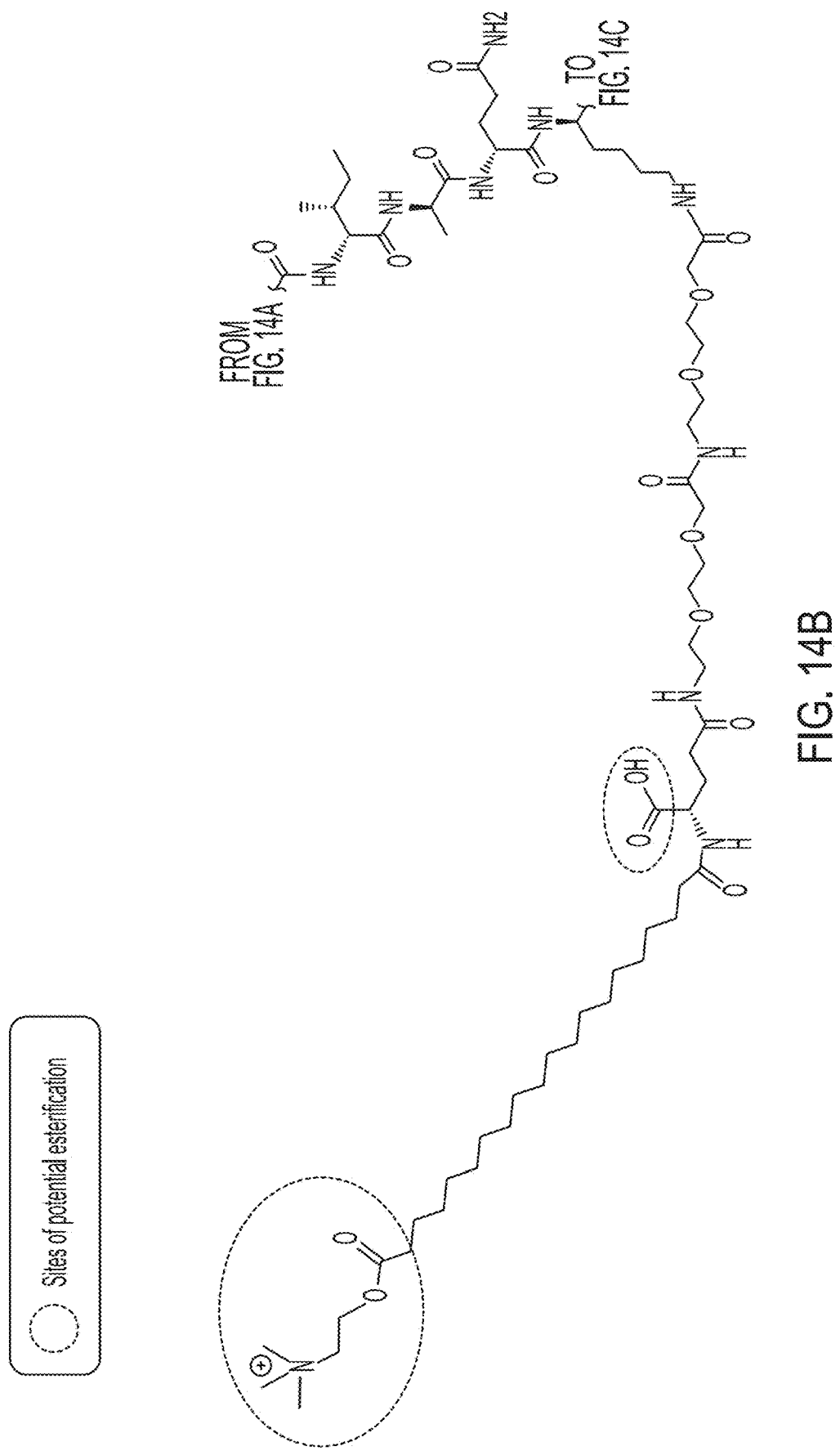
Figure 14C:
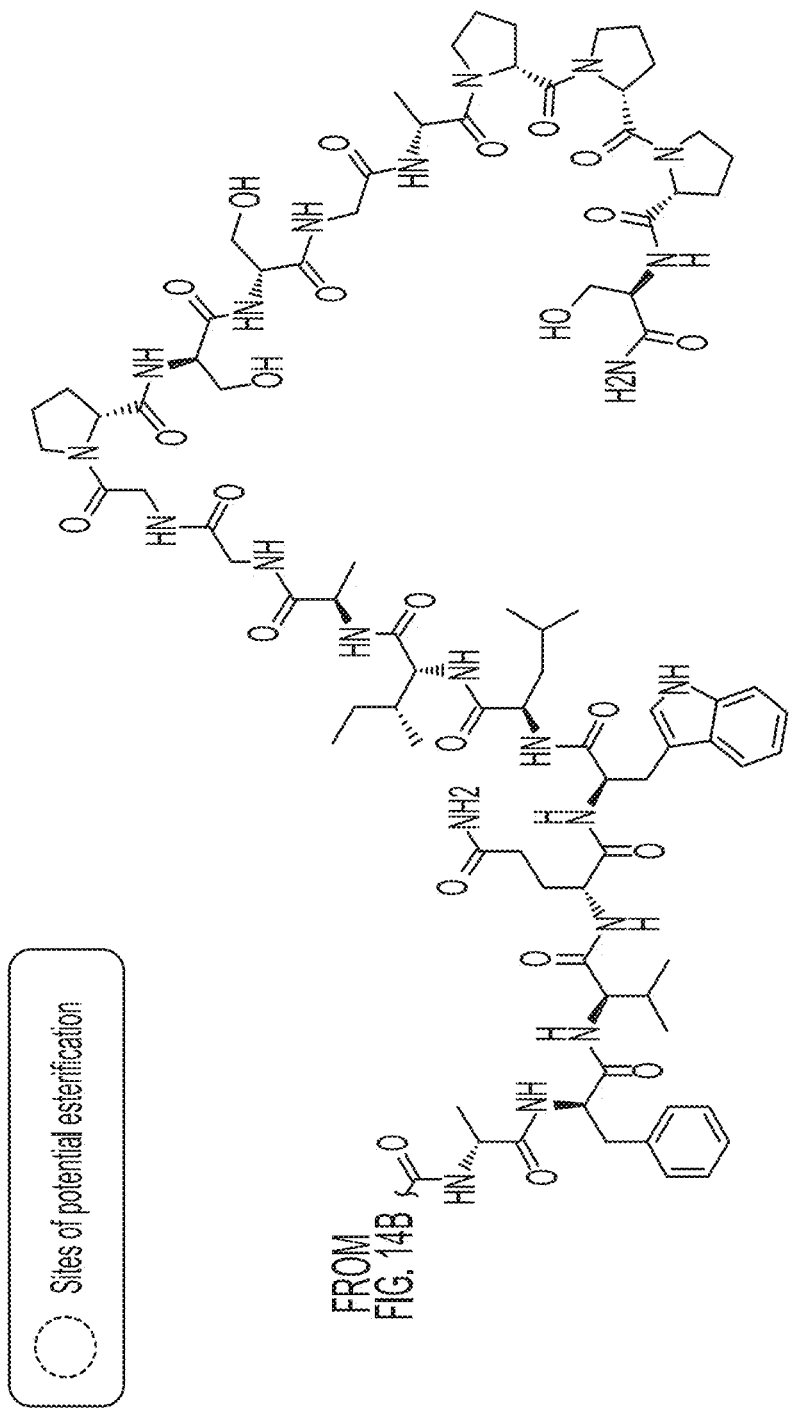

In some embodiments, there are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 potential sites of esterification on a dual GIP/GLP-1 receptor agonist or functional variant thereof with a cation (e.g., FIGS. 14A, 14B, and 14C). In some embodiments, choline-a dual GIP/GLP-1 receptor agonist or functional variant thereof ester derivatives can be formed by conjugating a cation (e.g., choline) to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 sites on the a dual GIP/GLP-1 receptor agonist or functional variant thereof structure.

In some embodiments, the composition comprises a

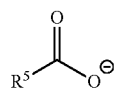

to

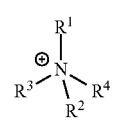

molar ratio of from about 1:1 to about 1:20. In some embodiments, the composition comprises a

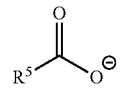

to

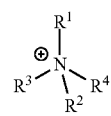

molar ratio of from about 1:1 to about 1:200, from about 1:1 to about 1:199, from about 1:1 to about 1:198, from about 1:1 to about 1:197, from about 1:1 to about 1:196, from about 1:1 to about 1:195, from about 1:1 to about 1:194, from about 1:1 to about 1:193, from about 1:1 to about 1:192, from about 1:1 to about 1:191, from about 1:1 to about 1:190, from about 1:1 to about 1:189, from about 1:1 to about 1:188, from about 1:1 to about 1:187, from about 1:1 to about 1:186, from about 1:1 to about 1:185, from about 1:1 to about 1:184, from about 1:1 to about 1:183, from about 1:1 to about 1:182, from about 1:1 to about 1:181, from about 1:1 to about 1:180, from about 1:1 to about 1:179, from about 1:1 to about 1:178, from about 1:1 to about 1:177, from about 1:1 to about 1:176, from about 1:1 to about 1:175, from about 1:1 to about 1:174, from about 1:1 to about 1:173, from about 1:1 to about 1:172, from about 1:1 to about 1:171, from about 1:1 to about 1:170, from about 1:1 to about 1:169, from about 1:1 to about 1:168, from about 1:1 to about 1:167, from about 1:1 to about 1:166, from about 1:1 to about 1:165, from about 1:1 to about 1:164, from about 1:1 to about 1:163, from about 1:1 to about 1:162, from about 1:1 to about 1:161, from about 1:1 to about 1:160, from about 1:1 to about 1:159, from about 1:1 to about 1:158, from about 1:1 to about 1:157, from about 1:1 to about 1:156, from about 1:1 to about 1:155, from about 1:1 to about 1:154, from about 1:1 to about 1:153, from about 1:1 to about 1:152, from about 1:1 to about 1:151, from about 1:1 to about 1:150, from about 1:1 to about 1:149, from about 1:1 to about 1:148, from about 1:1 to about 1:147, from about 1:1 to about 1:146, from about 1:1 to about 1:145, from about 1:1 to about 1:144, from about 1:1 to about 1:143, from about 1:1 to about 1:142, from about 1:1 to about 1:141, from about 1:1 to about 1:140, from about 1:1 to about 1:139, from about 1:1 to about 1:138, from about 1:1 to about 1:137, from about 1:1 to about 1:136, from about 1:1 to about 1:135, from about 1:1 to about 1:134, from about 1:1 to about 1:133, from about 1:1 to about 1:132, from about 1:1 to about 1:131, from about 1:1 to about 1:130, from about 1:1 to about 1:129, from about 1:1 to about 1:128, from about 1:1 to about 1:127, from about 1:1 to about 1:126, from about 1:1 to about 1:125, from about 1:1 to about 1:124, from about 1:1 to about 1:123, from about 1:1 to about 1:122, from about 1:1 to about 1:121, from about 1:1 to about 1:120, from about 1:1 to about 1:119, from about 1:1 to about 1:118, from about 1:1 to about 1:117, from about 1:1 to about 1:116, from about 1:1 to about 1:115, from about 1:1 to about 1:114, from about 1:1 to about 1:113, from about 1:1 to about 1:112, from about 1:1 to about 1:111, from about 1:1 to about 1:110, from about 1:1 to about 1:109, from about 1:1 to about 1:108, from about 1:1 to about 1:107, from about 1:1 to about 1:106, from about 1:1 to about 1:105, from about 1:1 to about 1:104, from about 1:1 to about 1:103, from about 1:1 to about 1:102, from about 1:1 to about 1:101, from about 1:1 to about 1:100, from about 1:1 to about 1:99, from about 1:1 to about 1:98, from about 1:1 to about 1:97, from about 1:1 to about 1:96, from about 1:1 to about 1:95, from about 1:1 to about 1:94, from about 1:1 to about 1:93, from about 1:1 to about 1:92, from about 1:1 to about 1:91, from about 1:1 to about 1:90, from about 1:1 to about 1:89, from about 1:1 to about 1:88, from about 1:1 to about 1:87, from about 1:1 to about 1:86, from about 1:1 to about 1:85, from about 1:1 to about 1:84, from about 1:1 to about 1:83, from about 1:1 to about 1:82, from about 1:1 to about 1:81, from about 1:1 to about 1:80, from about 1:1 to about 1:79, from about 1:1 to about 1:78, from about 1:1 to about 1:77, from about 1:1 to about 1:76, from about 1:1 to about 1:75, from about 1:1 to about 1:74, from about 1:1 to about 1:73, from about 1:1 to about 1:72, from about 1:1 to about 1:71, from about 1:1 to about 1:70, from about 1:1 to about 1:69, from about 1:1 to about 1:68, from about 1:1 to about 1:67, from about 1:1 to about 1:66, from about 1:1 to about 1:65, from about 1:1 to about 1:64, from about 1:1 to about 1:63, from about 1:1 to about 1:62, from about 1:1 to about 1:61, from about 1:1 to about 1:60, from about 1:1 to about 1:59, from about 1:1 to about 1:58, from about 1:1 to about 1:57, from about 1:1 to about 1:56, from about 1:1 to about 1:55, from about 1:1 to about 1:54, from about 1:1 to about 1:53, from about 1:1 to about 1:52, from about 1:1 to about 1:51, from about 1:1 to about 1:50, from about 1:1 to about 1:49, from about 1:1 to about 1:48, from about 1:1 to about 1:47, from about 1:1 to about 1:46, from about 1:1 to about 1:45, from about 1:1 to about 1:44, from about 1:1 to about 1:43, from about 1:1 to about 1:42, from about 1:1 to about 1:41, from about 1:1 to about 1:40, from about 1:1 to about 1:39, from about 1:1 to about 1:38, from about 1:1 to about 1:37, from about 1:1 to about 1:36, from about 1:1 to about 1:35, from about 1:1 to about 1:34, from about 1:1 to about 1:33, from about 1:1 to about 1:32, from about 1:1 to about 1:31, from about 1:1 to about 1:30, from about 1:1 to about 1:29, from about 1:1 to about 1:28, from about 1:1 to about 1:27, from about 1:1 to about 1:26, from about 1:1 to about 1:25, from about 1:1 to about 1:24, from about 1:1 to about 1:23, from about 1:1 to about 1:22, from about 1:1 to about 1:21, from about 1:1 to about 1:20, from about 1:1 to about 1:19, from about 1:1 to about 1:18, from about 1:1 to about 1:17, from about 1:1 to about 1:16, from about 1:1 to about 1:15, from about 1:1 to about 1:14, from about 1:1 to about 1:13, from about 1:1 to about 1:12, from about 1:1 to about 1:11, from about 1:1 to about 1:10, from about 1:1 to about 1:9, from about 1:1 to about 1:8, from about 1:1 to about 1:7, from about 1:1 to about 1:6, from about 1:1 to about 1:5, from about 1:1 to about 1:4, from about 1:1 to about 1:3, or from about 1:1 to about 1:2.

In some embodiments, the composition comprises a

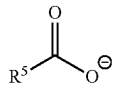

to

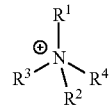

molar ratio of about 1:200, about 1:199, about 1:198, about 1:197, about 1:196, about 1:195, about 1:194, about 1:193, about 1:192, about 1:191, about 1:190, about 1:189, about 1:188, about 1:187, about 1:186, about 1:185, about 1:184, about 1:183, about 1:182, about 1:181, about 1:180, about 1:179, about 1:178, about 1:177, about 1:176, about 1:175, about 1:174, about 1:173, about 1:172, about 1:171, about 1:170, about 1:169, about 1:168, about 1:167, about 1:166, about 1:165, about 1:164, about 1:163, about 1:162, about 1:161, about 1:160, about 1:159, about 1:158, about 1:157, about 1:156, about 1:155, about 1:154, about 1:153, about 1:152, about 1:151, about 1:150, about 1:149, about 1:148, about 1:147, about 1:146, about 1:145, about 1:144, about 1:143, about 1:142, about 1:141, about 1:140, about 1:139, about 1:138, about 1:137, about 1:136, about 1:135, about 1:134, about 1:133, about 1:132, about 1:131, about 1:130, about 1:129, about 1:128, about 1:127, about 1:126, about 1:125, about 1:124, about 1:123, about 1:122, about 1:121, about 1:120, about 1:119, about 1:118, about 1:117, about 1:116, about 1:115, about 1:114, about 1:113, about 1:112, about 1:111, about 1:110, about 1:109, about 1:108, about 1:107, about 1:106, about 1:105, about 1:104, about 1:103, about 1:102, about 1:101, about 1:100, about 1:99, about 1:98, about 1:97, about 1:96, about 1:95, about 1:94, about 1:93, about 1:92, about 1:91, about 1:90, about 1:89, about 1:88, about 1:87, about 1:86, about 1:85, about 1:84, about 1:83, about 1:82, about 1:81, about 1:80, about 1:79, about 1:78, about 1:77, about 1:76, about 1:75, about 1:74, about 1:73, about 1:72, about 1:71, about 1:70, about 1:69, about 1:68, about 1:67, about 1:66, about 1:65, about 1:64, about 1:63, about 1:62, about 1:61, about 1:60, about 1:59, about 1:58, about 1:57, about 1:56, about 1:55, about 1:54, about 1:53, about 1:52, about 1:51, about 1:50, about 1:49, about 1:48, about 1:47, about 1:46, about 1:45, about 1:44, about 1:43, about 1:42, about 1:41, about 1:40, about 1:39, about 1:38, about 1:37, about 1:36, about 1:35, about 1:34, about 1:33, about 1:32, about 1:31, about 1:30, about 1:29, about 1:28, about 1:27, about 1:26, about 1:25, about 1:24, about 1:23, about 1:22, about 1:21, about 1:20, about 1:19, about 1:18, about 1:17, about 1:16, about 1:15, about 1:14, about 1:13, about 1:12, about 1:11, about 1:10, about 1:9, about 1:8, about 1:7, about 1:6, about 1:5, about 1:4, about 1:3, about 1:2 or about 1:1.

In some aspects, provided herein, inter alia, is a compound according to Formula I:

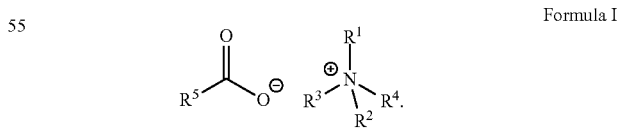

Formula I

In some embodiments, $R^1$, $R^2$, and $R^3$ are independently $C_1$-$C_5$ alkyl. In some embodiments, $R^1$ is $C_1$-$C_5$ alkyl. In some embodiments, $R^2$ is $C_1$-$C_5$ alkyl. In some embodiments, $R^3$ is $C_1$-$C_5$ alkyl.

In some embodiments, $R^1$, $R^2$, and $R^3$ are independently $C_1$-$C_{20}$ alkyl. In some embodiments, $R^1$ is $C_1$-$C_{20}$ alkyl. In some embodiments, $R^1$ is $C_1$-$C_{19}$ alkyl. In some embodiments, $R^1$ is $C_1$-$C_{18}$ alkyl. In some embodiments, $R^1$ is $C_1$-$C_{17}$ alkyl. In some embodiments, $R^1$ is $C_1$-$C_{16}$ alkyl. In some embodiments, $R^1$ is $C_1$-$C_{15}$ alkyl. In some embodiments, $R^1$ is $C_1$-$C_{14}$ alkyl. In some embodiments, $R^1$ is $C_1$-$C_{13}$ alkyl. In some embodiments, $R^1$ is $C_1$-$C_{12}$ alkyl. In some embodiments, $R^1$ is $C_1$-$C_{11}$ alkyl. In some embodiments, $R^1$ is $C_1$-$C_{10}$ alkyl. In some embodiments, $R^1$ is $C_1$-$C_9$ alkyl. In some embodiments, $R^1$ is $C_1$-$C_8$ alkyl. In some embodiments, $R^1$ is $C_1$-$C_7$ alkyl. In some embodiments, $R^1$ is $C_1$-$C_6$ alkyl. In some embodiments, $R^1$ is $C_1$-$C_5$ alkyl. In some embodiments, $R^1$ is $C_1$-$C_4$ alkyl. In some embodiments, $R^1$ is $C_1$-$C_3$ alkyl. In some embodiments, $R^1$ is $C_1$-$C_2$ alkyl. In some embodiments, $R^2$ is $C_1$-$C_{20}$ alkyl. In some embodiments, $R^2$ is $C_1$-$C_{19}$ alkyl. In some embodiments, $R^2$ is $C_1$-$C_{18}$ alkyl. In some embodiments, $R^2$ is $C_1$-$C_{17}$ alkyl. In some embodiments, $R^2$ is $C_1$-$C_{16}$ alkyl. In some embodiments, $R^2$ is $C_1$-$C_{15}$ alkyl. In some embodiments, $R^2$ is $C_1$-$C_{14}$ alkyl. In some embodiments, $R^2$ is $C_1$-$C_{13}$ alkyl. In some embodiments, $R^2$ is $C_1$-$C_{12}$ alkyl. In some embodiments, $R^2$ is $C_1$-$C_{11}$ alkyl. In some embodiments, $R^2$ is $C_1$-$C_{10}$ alkyl. In some embodiments, $R^2$ is $C_1$-$C_9$ alkyl. In some embodiments, $R^2$ is $C_1$-$C_8$ alkyl. In some embodiments, $R^2$ is $C_1$-$C_7$ alkyl. In some embodiments, $R^2$ is $C_1$-$C_6$ alkyl. In some embodiments, $R^2$ is $C_1$-$C_5$ alkyl. In some embodiments, $R^2$ is $C_1$-$C_4$ alkyl. In some embodiments, $R^2$ is $C_1$-$C_3$ alkyl. In some embodiments, $R^2$ is $C_1$-$C_2$ alkyl. In some embodiments, $R^3$ is $C_1$-$C_{20}$ alkyl. In some embodiments, $R^3$ is $C_1$-$C_{19}$ alkyl. In some embodiments, $R^3$ is $C_1$-$C_{18}$ alkyl. In some embodiments, $R^3$ is $C_1$-$C_{17}$ alkyl. In some embodiments, $R^3$ is $C_1$-$C_{16}$ alkyl. In some embodiments, $R^3$ is $C_1$-$C_{15}$ alkyl. In some embodiments, $R^3$ is $C_1$-$C_{14}$ alkyl. In some embodiments, $R^3$ is $C_1$-$C_{13}$ alkyl. In some embodiments, $R^3$ is $C_1$-$C_{12}$ alkyl. In some embodiments, $R^3$ is $C_1$-$C_{11}$ alkyl. In some embodiments, $R^3$ is $C_1$-$C_{10}$ alkyl. In some embodiments, $R^3$ is $C_1$-$C_9$ alkyl. In some embodiments, $R^3$ is $C_1$-$C_5$ alkyl. In some embodiments, $R^3$ is $C_1$-$C_7$ alkyl. In some embodiments, $R^3$ is $C_1$-$C_6$ alkyl. In some embodiments, $R^3$ is $C_1$-$C_5$ alkyl. In some embodiments, $R^3$ is $C_1$-$C_4$ alkyl. In some embodiments, $R^3$ is $C_1$-$C_3$ alkyl. In some embodiments, $R^3$ is $C_1$-$C_2$ alkyl.

In some embodiments, $R^1$ is $C_1$ alkyl. In some embodiments, $R^1$ is $C_2$ alkyl. In some embodiments, $R^1$ is $C_3$ alkyl. In some embodiments, $R^1$ is $C_4$ alkyl. In some embodiments, $R^1$ is $C_5$ alkyl. In some embodiments, $R^1$ is $C_6$ alkyl. In some embodiments, $R^1$ is $C_7$ alkyl. In some embodiments, $R^1$ is $C_8$ alkyl. In some embodiments, $R^1$ is $C_9$ alkyl. In some embodiments, $R^1$ is $C_{10}$ alkyl. In some embodiments, $R^1$ is $C_{11}$ alkyl. In some embodiments, $R^1$ is $C_{12}$ alkyl. In some embodiments, $R^1$ is $C_{13}$ alkyl. In some embodiments, $R^1$ is $C_{14}$ alkyl. In some embodiments, $R^1$ is $C_{15}$ alkyl. In some embodiments, $R^1$ is $C_{16}$ alkyl. In some embodiments, $R^1$ is $C_{17}$ alkyl. In some embodiments, $R^1$ is $C_{18}$ alkyl. In some embodiments, $R^1$ is $C_{19}$ alkyl. In some embodiments, $R^1$ is $C_{20}$ alkyl. In some embodiments, $R^2$ is $C_1$ alkyl. In some embodiments, $R^2$ is $C_2$ alkyl. In some embodiments, $R^2$ is $C_3$ alkyl. In some embodiments, $R^2$ is $C_4$ alkyl. In some embodiments, $R^2$ is $C_5$ alkyl. In some embodiments, $R^2$ is $C_6$ alkyl. In some embodiments, $R^2$ is $C_7$ alkyl. In some embodiments, $R^2$ is $C_8$ alkyl. In some embodiments, $R^2$ is $C_9$ alkyl. In some embodiments, $R^2$ is $C_{10}$ alkyl. In some embodiments, $R^2$ is $C_{11}$ alkyl. In some embodiments, $R^2$ is $C_{12}$ alkyl. In some embodiments, $R^2$ is $C_{13}$ alkyl. In some embodiments, $R^2$ is $C_{14}$ alkyl. In some embodiments, $R^2$ is $C_{15}$ alkyl. In some embodiments, $R^2$ is $C_{16}$ alkyl. In some embodiments, $R^2$ is $C_{17}$ alkyl. In some embodiments, $R^2$ is $C_{18}$ alkyl. In some embodiments, $R^2$ is $C_{19}$ alkyl. In some embodiments, $R^2$ is $C_{20}$ alkyl. In some embodiments, $R^3$ is $C_1$ alkyl. In some embodiments, $R^3$ is $C_2$ alkyl. In some embodiments, $R^3$ is $C_3$ alkyl. In some embodiments, $R^3$ is $C_4$ alkyl. In some embodiments, $R^3$ is $C_5$ alkyl. In some embodiments, $R^3$ is $C_6$ alkyl. In some embodiments, $R^3$ is $C_7$ alkyl. In some embodiments, $R^3$ is $C_8$ alkyl. In some embodiments, $R^3$ is $C_9$ alkyl. In some embodiments, $R^3$ is $C_{10}$ alkyl. In some embodiments, $R^3$ is $C_{11}$ alkyl. In some embodiments, $R^3$ is $C_{12}$ alkyl. In some embodiments, $R^3$ is $C_{13}$ alkyl. In some embodiments, $R^3$ is $C_{14}$ alkyl. In some embodiments, $R^3$ is $C_{15}$ alkyl. In some embodiments, $R^3$ is $C_{16}$ alkyl. In some embodiments, $R^3$ is $C_{17}$ alkyl. In some embodiments, $R^3$ is $C_{18}$ alkyl. In some embodiments, $R^3$ is $C_{19}$ alkyl. In some embodiments, $R^3$ is $C_{20}$ alkyl.

In some embodiments, $R^4$ is $C_2$-$C_5$ alkyl, wherein the $C_2$-$C_5$ alkyl is unsubstituted or substituted with 1 or more hydroxyl. In some embodiments, $R^4$ is $C_2$-$C_{20}$ alkyl, wherein the $C_2$-$C_5$ alkyl is unsubstituted or substituted with 1 or more hydroxyl. In some embodiments, $R^4$ is $C_2$-$C_{19}$ alkyl, wherein the $C_2$-$C_5$ alkyl is unsubstituted or substituted with 1 or more hydroxyl. In some embodiments, $R^4$ is $C_2$-$C_{18}$ alkyl, wherein the $C_2$-$C_5$ alkyl is unsubstituted or substituted with 1 or more hydroxyl. In some embodiments, $R^4$ is $C_2$-$C_{17}$ alkyl, wherein the $C_2$-$C_5$ alkyl is unsubstituted or substituted with 1 or more hydroxyl. In some embodiments, $R^4$ is $C_2$-$C_{16}$ alkyl, wherein the $C_2$-$C_5$ alkyl is unsubstituted or substituted with 1 or more hydroxyl. In some embodiments, $R^4$ is $C_2$-$C_{15}$ alkyl, wherein the $C_2$-$C_5$ alkyl is unsubstituted or substituted with 1 or more hydroxyl. In some embodiments, $R^4$ is $C_2$-$C_{14}$ alkyl, wherein the $C_2$-$C_5$ alkyl is unsubstituted or substituted with 1 or more hydroxyl. In some embodiments, $R^4$ is $C_2$-$C_{13}$ alkyl, wherein the $C_2$-$C_5$ alkyl is unsubstituted or substituted with 1 or more hydroxyl. In some embodiments, $R^4$ is $C_2$-$C_{12}$ alkyl, wherein the $C_2$-$C_5$ alkyl is unsubstituted or substituted with 1 or more hydroxyl. In some embodiments, $R^4$ is $C_2$-$C_{11}$ alkyl, wherein the $C_2$-$C_5$ alkyl is unsubstituted or substituted with 1 or more hydroxyl. In some embodiments, $R^4$ is $C_2$-$C_{10}$ alkyl, wherein the $C_2$-$C_5$ alkyl is unsubstituted or substituted with 1 or more hydroxyl. In some embodiments, $R^4$ is $C_2$-$C_9$ alkyl, wherein the $C_2$-$C_5$ alkyl is unsubstituted or substituted with 1 or more hydroxyl. In some embodiments, $R^4$ is $C_2$-$C_5$ alkyl, wherein the $C_2$-$C_5$ alkyl is unsubstituted or substituted with 1 or more hydroxyl. In some embodiments, $R^4$ is $C_2$-$C_7$ alkyl, wherein the $C_2$-$C_5$ alkyl is unsubstituted or substituted with 1 or more hydroxyl. In some embodiments, $R^4$ is $C_2$-$C_6$ alkyl, wherein the $C_2$-$C_5$ alkyl is unsubstituted or substituted with 1 or more hydroxyl. In some embodiments, $R^4$ is $C_2$-$C_5$ alkyl, wherein the $C_2$-$C_5$ alkyl is unsubstituted or substituted with 1 or more hydroxyl. In some embodiments, $R^4$ is $C_2$-$C_4$ alkyl, wherein the $C_2$-$C_5$ alkyl is unsubstituted or substituted with 1 or more hydroxyl. In some embodiments, $R^4$ is $C_2$-$C_3$ alkyl, wherein the $C_2$-$C_5$ alkyl is unsubstituted or substituted with 1 or more hydroxyl. In some embodiments, $R^4$ is $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl, wherein the $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl is unsubstituted or substituted with 1 or more hydroxyl.

In some embodiments, $R^5$ is a dual GIP/GLP-1 receptor agonist or functional variant thereof.

In some embodiments, $R^5$ is a therapeutic agent that comprises a sequence with at least 40%, 45%, 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, or 99.9 sequence identity to the sequence of SEQ ID NO: 25. In some embodiments, $R^5$ is a therapeutic agent that comprises the sequence of SEQ ID NO: 25.

In some embodiments, the therapeutic agent comprises C20 diacid-γ-Glu-(AEEA)2 attached to a residue of a sequence with at least 40%, 45%, 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, or 99.9 sequence identity to the sequence of SEQ ID NO: 25. In some embodiments, the therapeutic agent comprises C20 diacid-γ-Glu-(AEEA)2 attached to a residue of the sequence of SEQ ID NO: 25. In some embodiments, the therapeutic agent comprises C20 diacid-γ-Glu-(AEEA)2 attached to the Lys residue at the position 20 from the N-terminus of the sequence of SEQ ID NO: 25.

In the compound comprises a dual GIP/GLP-1 receptor agonist or functional variant thereof comprising a diacid consisting of 18 or 20 carbons in length. In some embodiments, the compound comprises a dual GIP/GLP-1 receptor agonist or functional variant thereof comprising a diacid consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 carbons in length.

In some embodiments, the diacid comprises a $C_{20}$ fatty diacid. In some embodiments, the diacid comprises a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ fatty diacid.

In some aspects, provided herein is a compound according to Formula II:

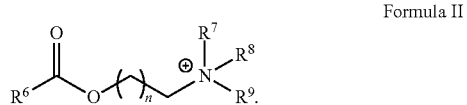

Formula II

In some embodiments, $R^7$, $R^8$, and $R^9$ are independently unsubstituted or substituted $C_1$-$C_5$ alkyl. In some embodiments, $R^7$ is unsubstituted or substituted $C_1$-$C_5$ alkyl. In some embodiments, $R^8$ is unsubstituted or substituted $C_1$-$C_5$ alkyl. In some embodiments, $R^9$ is unsubstituted or substituted $C_1$-$C_5$ alkyl.

In some embodiments, $R^7$, $R^8$, and $R^9$ are independently unsubstituted or substituted $C_1$-$C_{20}$ alkyl. In some embodiments, $R^7$ is unsubstituted or substituted $C_1$-$C_{20}$ alkyl. In some embodiments, $R^7$ is unsubstituted or substituted $C_1$-$C_{19}$ alkyl. In some embodiments, $R^7$ is unsubstituted or substituted $C_1$-$C_{18}$ alkyl. In some embodiments, $R^7$ is unsubstituted or substituted $C_1$-$C_{17}$ alkyl. In some embodiments, $R^7$ is unsubstituted or substituted $C_1$-$C_{16}$ alkyl. In some embodiments, $R^7$ is unsubstituted or substituted $C_1$-$C_{15}$ alkyl. In some embodiments, $R^7$ is unsubstituted or substituted $C_1$-$C_{14}$ alkyl. In some embodiments, $R^7$ is unsubstituted or substituted $C_1$-$C_{13}$ alkyl. In some embodiments, $R^7$ is unsubstituted or substituted $C_1$-$C_{12}$ alkyl. In some embodiments, $R^7$ is unsubstituted or substituted $C_1$-$C_{11}$ alkyl. In some embodiments, $R^7$ is unsubstituted or substituted $C_1$-$C_{10}$ alkyl. In some embodiments, $R^7$ is unsubstituted or substituted $C_1$-$C_9$ alkyl. In some embodiments, $R^7$ is unsubstituted or substituted $C_1$-$C_8$ alkyl. In some embodiments, $R^7$ is unsubstituted or substituted $C_1$-$C_7$ alkyl. In some embodiments, $R^7$ is unsubstituted or substituted $C_1$-$C_6$ alkyl. In some embodiments, $R^7$ is unsubstituted or substituted $C_1$-$C_5$ alkyl. In some embodiments, $R^7$ is unsubstituted or substituted $C_1$-$C_4$ alkyl. In some embodiments, $R^7$ is unsubstituted or substituted $C_1$-$C_3$ alkyl. In some embodiments, $R^7$ is unsubstituted or substituted $C_1$-$C_2$ alkyl. In some embodiments, $R^8$ is unsubstituted or substituted $C_1$-$C_{20}$ alkyl. In some embodiments, $R^8$ is unsubstituted or substituted $C_1$-$C_{19}$ alkyl. In some embodiments, $R^8$ is unsubstituted or substituted $C_1$-$C_{18}$ alkyl. In some embodiments, $R^8$ is unsubstituted or substituted $C_1$-$C_{17}$ alkyl. In some embodiments, $R^8$ is unsubstituted or substituted $C_1$-$C_{16}$ alkyl. In some embodiments, $R^8$ is unsubstituted or substituted $C_1$-$C_{15}$ alkyl. In some embodiments, $R^8$ is unsubstituted or substituted $C_1$-$C_{14}$ alkyl. In some embodiments, $R^8$ is unsubstituted or substituted $C_1$-$C_{13}$ alkyl. In some embodiments, $R^8$ is unsubstituted or substituted $C_1$-$C_{12}$ alkyl. In some embodiments, $R^8$ is unsubstituted or substituted $C_1$-$C_{11}$ alkyl. In some embodiments, $R^8$ is unsubstituted or substituted $C_1$-$C_{10}$ alkyl. In some embodiments, $R^8$ is unsubstituted or substituted $C_1$-$C_9$ alkyl. In some embodiments, $R^8$ is unsubstituted or substituted $C_1$-$C_8$ alkyl. In some embodiments, $R^8$ is unsubstituted or substituted $C_1$-$C_7$ alkyl. In some embodiments, $R^8$ is unsubstituted or substituted $C_1$-$C_6$ alkyl. In some embodiments, $R^8$ is unsubstituted or substituted $C_1$-$C_5$ alkyl. In some embodiments, $R^8$ is unsubstituted or substituted $C_1$-$C_4$ alkyl. In some embodiments, $R^8$ is unsubstituted or substituted $C_1$-$C_3$ alkyl. In some embodiments, $R^8$ is unsubstituted or substituted $C_1$-$C_2$ alkyl. In some embodiments, $R^9$ is unsubstituted or substituted $C_1$-$C_{20}$ alkyl. In some embodiments, $R^9$ is unsubstituted or substituted $C_1$-$C_{19}$ alkyl. In some embodiments, $R^9$ is unsubstituted or substituted $C_1$-$C_{18}$ alkyl. In some embodiments, $R^9$ is unsubstituted or substituted $C_1$-$C_{17}$ alkyl. In some embodiments, $R^9$ is unsubstituted or substituted $C_1$-$C_{16}$ alkyl. In some embodiments, $R^9$ is unsubstituted or substituted $C_1$-$C_{15}$ alkyl. In some embodiments, $R^9$ is unsubstituted or substituted $C_1$-$C_{14}$ alkyl. In some embodiments, $R^9$ is unsubstituted or substituted $C_1$-$C_{13}$ alkyl. In some embodiments, $R^9$ is unsubstituted or substituted $C_1$-$C_{12}$ alkyl. In some embodiments, $R^9$ is unsubstituted or substituted $C_1$-$C_{11}$ alkyl. In some embodiments, $R^9$ is unsubstituted or substituted $C_1$-$C_{10}$ alkyl. In some embodiments, $R^9$ is unsubstituted or substituted $C_1$-$C_9$ alkyl. In some embodiments, $R^9$ is unsubstituted or substituted $C_1$-$C_8$ alkyl. In some embodiments, $R^9$ is unsubstituted or substituted $C_1$-$C_7$ alkyl. In some embodiments, $R^9$ is unsubstituted or substituted $C_1$-$C_6$ alkyl. In some embodiments, $R^9$ is unsubstituted or substituted $C_1$-$C_5$ alkyl. In some embodiments, $R^9$ is unsubstituted or substituted $C_1$-$C_4$ alkyl. In some embodiments, $R^9$ is unsubstituted or substituted $C_1$-$C_3$ alkyl. In some embodiments, $R^9$ is unsubstituted or substituted $C_1$-$C_2$ alkyl.

In some embodiments, $R^7$ is unsubstituted or substituted $C_1$ alkyl. In some embodiments, $R^7$ is unsubstituted or substituted $C_2$ alkyl. In some embodiments, $R^7$ is unsubstituted or substituted $C_3$ alkyl. In some embodiments, $R^7$ is unsubstituted or substituted $C_4$ alkyl. In some embodiments, $R^7$ is unsubstituted or substituted $C_5$ alkyl. In some embodiments, $R^7$ is unsubstituted or substituted $C_6$ alkyl. In some embodiments, $R^7$ is unsubstituted or substituted $C_7$ alkyl. In some embodiments, $R^7$ is unsubstituted or substituted $C_8$ alkyl. In some embodiments, $R^7$ is unsubstituted or substituted $C_9$ alkyl. In some embodiments, $R^7$ is unsubstituted or substituted $C_{10}$ alkyl. In some embodiments, $R^7$ is unsubstituted or substituted $C_{11}$ alkyl. In some embodiments, $R^7$ is unsubstituted or substituted $C_{12}$ alkyl. In some embodiments, $R^7$ is unsubstituted or substituted $C_{13}$ alkyl. In some embodiments, $R^7$ is unsubstituted or substituted $C_{14}$ alkyl. In some embodiments, $R^7$ is unsubstituted or substituted $C_{15}$ alkyl. In some embodiments, $R^7$ is unsubstituted or substituted $C_{16}$ alkyl. In some embodiments, $R^7$ is unsubstituted or substituted $C_{17}$ alkyl. In some embodiments, $R^7$ is unsubstituted or substituted $C_{18}$ alkyl. In some embodiments, $R^7$ is unsubstituted or substituted $C_{19}$ alkyl. In some embodiments, $R^7$ is unsubstituted or substituted $C_{20}$ alkyl. In some embodiments, $R^8$ is unsubstituted or substituted $C_1$ alkyl. In some embodiments, $R^8$ is unsubstituted or substituted $C_2$ alkyl. In some embodiments, $R^8$ is unsubstituted or substituted $C_3$ alkyl. In some embodiments, $R^8$ is unsubstituted or substituted $C_4$ alkyl. In some embodiments, $R^8$ is unsubstituted or substituted $C_5$ alkyl. In some embodiments, $R^8$ is unsubstituted or substituted $C_6$ alkyl. In some embodiments, $R^8$ is unsubstituted or substituted $C_7$ alkyl. In some embodiments, $R^8$ is unsubstituted or substituted $C_8$ alkyl. In some embodiments, $R^8$ is unsubstituted or substituted $C_9$ alkyl. In some embodiments, $R^8$ is unsubstituted or substituted $C_{10}$ alkyl. In some embodiments, $R^8$ is unsubstituted or substituted $C_{11}$ alkyl. In some embodiments, $R^8$ is unsubstituted or substituted $C_{12}$ alkyl. In some embodiments, $R^8$ is unsubstituted or substituted $C_{13}$ alkyl. In some embodiments, $R^8$ is unsubstituted or substituted $C_{14}$ alkyl. In some embodiments, $R^8$ is unsubstituted or substituted $C_{15}$ alkyl. In some embodiments, $R^8$ is unsubstituted or substituted $C_{16}$ alkyl. In some embodiments, $R^8$ is unsubstituted or substituted $C_{17}$ alkyl. In some embodiments, $R^8$ is unsubstituted or substituted $C_{18}$ alkyl. In some embodiments, $R^8$ is unsubstituted or substituted $C_{19}$ alkyl. In some embodiments, $R^8$ is unsubstituted or substituted $C_{20}$ alkyl. In some embodiments, $R^9$ is unsubstituted or substituted $C_1$ alkyl. In some embodiments, $R^9$ is unsubstituted or substituted $C_2$ alkyl. In some embodiments, $R^9$ is unsubstituted or substituted $C_3$ alkyl. In some embodiments, $R^9$ is unsubstituted or substituted $C_4$ alkyl. In some embodiments, $R^9$ is unsubstituted or substituted $C_5$ alkyl. In some embodiments, $R^9$ is unsubstituted or substituted $C_6$ alkyl. In some embodiments, $R^9$ is unsubstituted or substituted $C_7$ alkyl. In some embodiments, $R^9$ is unsubstituted or substituted $C_8$ alkyl. In some embodiments, $R^9$ is unsubstituted or substituted $C_9$ alkyl. In some embodiments, $R^9$ is unsubstituted or substituted $C_{10}$ alkyl. In some embodiments, $R^9$ is unsubstituted or substituted $C_{11}$ alkyl. In some embodiments, $R^9$ is unsubstituted or substituted $C_{12}$ alkyl. In some embodiments, $R^9$ is unsubstituted or substituted $C_{13}$ alkyl. In some embodiments, $R^9$ is unsubstituted or substituted $C_{14}$ alkyl. In some embodiments, $R^9$ is unsubstituted or substituted $C_{15}$ alkyl. In some embodiments, $R^9$ is unsubstituted or substituted $C_{16}$ alkyl. In some embodiments, $R^9$ is unsubstituted or substituted $C_{17}$ alkyl. In some embodiments, $R^9$ is unsubstituted or substituted $C_{18}$ alkyl. In some embodiments, $R^9$ is unsubstituted or substituted $C_{19}$ alkyl. In some embodiments, $R^9$ is unsubstituted or substituted $C_{20}$ alkyl.

In some embodiments, n is 1, 2, 3, 4, or 5. In some embodiments, n is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In some embodiments, $R^6$ is a dual GIP/GLP-1 receptor agonist or functional variant thereof.

In some embodiments, $R^6$ is a therapeutic agent that comprises a sequence with at least 40%, 45%, 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, or 99.9 sequence identity to the sequence of SEQ ID NO: 25. In some embodiments, $R^6$ is a therapeutic agent that comprises the sequence of SEQ ID NO: 25.

In some embodiments, the therapeutic agent comprises C20 diacid-γ-Glu-(AEEA)2 attached to a residue of a sequence with at least 40%, 45%, 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, or 99.9 sequence identity to the sequence of SEQ ID NO: 25. In some embodiments, the therapeutic agent comprises C20 diacid-γ-Glu-(AEEA)2 attached to a residue of the sequence of SEQ ID NO: 25. In some embodiments, the therapeutic agent comprises C20 diacid-γ-Glu-(AEEA)2 attached to the Lys residue at the position 20 from the N-terminus of the sequence of SEQ ID NO: 25.

In some embodiments, the compound comprises a dual GIP/GLP-1 receptor agonist or functional variant thereof having a cation moiety comprising a choline or choline derivative-like residue.

In some embodiments, the compound comprises a dual GIP/GLP-1 receptor agonist or functional variant thereof comprising one or more choline or choline derivative-peptide ester formed on a Cys residue, a Lys residue, or any combination thereof.

In some embodiments, the one or more choline or choline derivative-peptide ester formed on the Cys residue comprises a linker-to-a dual GIP/GLP-1 receptor agonist or functional variant thereof ratio of 2-8, the one or more choline or choline derivative-peptide ester formed on the Lys residue comprises a linker-to-a dual GIP/GLP-1 receptor agonist or functional variant thereof ratio of 2-4, or a combination thereof.

In some embodiments, the one or more choline or choline derivative-peptide ester formed on the Cys residue comprises a linker-to-a dual GIP/GLP-1 receptor agonist or functional variant thereof ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, the one or more choline or choline derivative-peptide ester formed on the Cys residue comprises a linker-to-a dual GIP/GLP-1 receptor agonist or functional variant thereof ratio of 1-50, 1-49, 1-48, 1-47, 1-46, 1-45, 1-44, 1-43, 1-42, 1-41, 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, the one or more choline or choline derivative-peptide ester formed on the Cys residue comprises a linker-to-a dual GIP/GLP-1 receptor agonist or functional variant thereof ratio of 2-50, 3-50, 4-50, 5-50, 6-50, 7-50, 8-50, 9-50, 10-50, 11-50, 12-50, 13-50, 14-50, 15-50, 16-50, 17-50, 18-50, 19-50, 20-50, 21-50, 22-50, 23-50, 24-50, 25-50, 26-50, 27-50, 28-50, 29-50, 30-50, 31-50, 32-50, 33-50, 34-50, 35-50, 36-50, 37-50, 38-50, 39-50, 40-50, 41-50, 42-50, 43-50, 44-50, 45-50, 46-50, 47-50, 48-50, or 49-50. In some embodiments, the one or more choline or choline derivative-peptide ester formed on the Cys residue comprises a linker-to-a dual GIP/GLP-1 receptor agonist or functional variant thereof ratio of 1-7, 2-8, 3-9, 4-10, 5-11, 6-12, 7-13, 8-14, 9-15, 10-16, 11-17, 12-18, 13-19, 14-20, 15-21, 16-22, 17-23, 18-24, 19-25, 20-26, 21-27, 22-28, 23-29, 24-30, 25-31, 26-32, 27-33, 28-34, 29-35, 30-36, 31-37, 32-38, 33-39, 34-40, 35-41, 36-42, 37-43, 38-44, 39-45, 40-46, 41-47, 42-48, 43-49, or 44-50.

In some embodiments, the one or more choline or choline derivative-peptide ester formed on the Lys residue comprises a linker-to-a dual GIP/GLP-1 receptor agonist or functional variant thereof ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, the one or more choline or choline derivative-peptide ester formed on the Lys residue comprises a linker-to-a dual GIP/GLP-1 receptor agonist or functional variant thereof ratio of 1-50, 1-49, 1-48, 1-47, 1-46, 1-45, 1-44, 1-43, 1-42, 1-41, 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, the one or more choline or choline derivative-peptide ester formed on the Lys residue comprises a linker-to-a dual GIP/GLP-1 receptor agonist or functional variant thereof ratio of 2-50, 3-50, 4-50, 5-50, 6-50, 7-50, 8-50, 9-50, 10-50, 11-50, 12-50, 13-50, 14-50, 15-50, 16-50, 17-50, 18-50, 19-50, 20-50, 21-50, 22-50, 23-50, 24-50, 25-50, 26-50, 27-50, 28-50, 29-50, 30-50, 31-50, 32-50, 33-50, 34-50, 35-50, 36-50, 37-50, 38-50, 39-50, 40-50, 41-50, 42-50, 43-50, 44-50, 45-50, 46-50, 47-50, 48-50, or 49-50. In some embodiments, the one or more choline or choline derivative-peptide ester formed on the Lys residue comprises a linker-to-a dual GIP/GLP-1 receptor agonist or functional variant thereof ratio of 1-3, 2-4, 3-5, 4-6, 5-7, 6-8, 7-9, 8-10, 9-11, 10-12, 11-13, 12-14, 13-15, 14-16, 15-17, 16-18, 17-19, 18-20, 19-21, 20-22, 21-23, 22-24, 23-25, 24-26, 25-27, 26-28, 27-29, 28-30, 29-31, 30-32, 31-33, 32-34, 33-35, 34-36, 35-37, 36-38, 37-39, 38-40, 39-41, 40-42, 41-43, 42-44, 43-45, 44-46, 45-47, 46-48, 47-49, or 48-50.

In some embodiments, the compound comprises a dual GIP/GLP-1 receptor agonist or functional variant thereof comprising a diacid consisting of 18 or 20 carbons in length. In some embodiments, the compound comprises a dual GIP/GLP-1 receptor agonist or functional variant thereof comprising a diacid consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 carbons in length.

In some embodiments, the diacid comprises a $C_{20}$ fatty diacid. In some embodiments, the diacid comprises a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ fatty diacid.

In some aspects, provided herein is a compound according to Formula III:

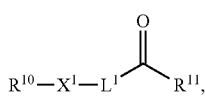

Formula III wherein:
$R^{10}$ is a therapeutic agent;
$R^{11}$ is substituted or unsubstituted $C_5$-$C_{10}$;
$X^1$ is

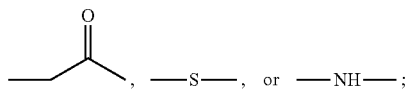

, —S—, or —NH—;

and
$L^1$ is a covalent bond or a linker.

In some embodiments, the compound comprises a dual GIP/GLP-1 receptor agonist or functional variant thereof comprising one or more $R^{11}$ linked to a Lys residue, a Cys residue, or any combination thereof.

In some embodiments, $R^{11}$ is linked to the Lys residue with a linker-to-a dual GIP/GLP-1 receptor agonist or functional variant thereof ratio of 2-4, $R^{11}$ is linked to the Cys residue with a linker-to-a dual GIP/GLP-1 receptor agonist or functional variant thereof ratio of 2-8 or with a linker-to-a dual GIP/GLP-1 receptor agonist or functional variant thereof ratio of 4, or a combination thereof.

In some embodiments, $R^{11}$ is linked to the Lys residue with a linker-to-a dual GIP/GLP-1 receptor agonist or functional variant thereof ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, $R^{11}$ is linked to the Lys residue with a linker-to-a dual GIP/GLP-1 receptor agonist or functional variant thereof ratio of 1-50, 1-49, 1-48, 1-47, 1-46, 1-45, 1-44, 1-43, 1-42, 1-41, 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, $R^{11}$ is linked to the Lys residue with a linker-to-a dual GIP/GLP-1 receptor agonist or functional variant thereof ratio of 2-50, 3-50, 4-50, 5-50, 6-50, 7-50, 8-50, 9-50, 10-50, 11-50, 12-50, 13-50, 14-50, 15-50, 16-50, 17-50, 18-50, 19-50, 20-50, 21-50, 22-50, 23-50, 24-50, 25-50, 26-50, 27-50, 28-50, 29-50, 30-50, 31-50, 32-50, 33-50, 34-50, 35-50, 36-50, 37-50, 38-50, 39-50, 40-50, 41-50, 42-50, 43-50, 44-50, 45-50, 46-50, 47-50, 48-50, or 49-50. In some embodiments, $R^{11}$ is linked to the Lys residue with a linker-to-a dual GIP/GLP-1 receptor agonist or functional variant thereof ratio of 1-3, 2-4, 3-5, 4-6, 5-7, 6-8, 7-9, 8-10, 9-11, 10-12, 11-13, 12-14, 13-15, 14-16, 15-17, 16-18, 17-19, 18-20, 19-21, 20-22, 21-23, 22-24, 23-25, 24-26, 25-27, 26-28, 27-29, 28-30, 29-31, 30-32, 31-33, 32-34, 33-35, 34-36, 35-37, 36-38, 37-39, 38-40, 39-41, 40-42, 41-43, 42-44, 43-45, 44-46, 45-47, 46-48, 47-49, or 48-50.

In some embodiments, $R^{11}$ is linked to the Cys residue with a linker-to-a dual GIP/GLP-1 receptor agonist or functional variant thereof ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, $R^{11}$ is linked to the Cys residue with a linker-to-a dual GIP/GLP-1 receptor agonist or functional variant thereof ratio of 1-50, 1-49, 1-48, 1-47, 1-46, 1-45, 1-44, 1-43, 1-42, 1-41, 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, $R^{11}$ is linked to the Cys residue with a linker-to-a dual GIP/GLP-1 receptor agonist or functional variant thereof ratio of 2-50, 3-50, 4-50, 5-50, 6-50, 7-50, 8-50, 9-50, 10-50, 11-50, 12-50, 13-50, 14-50, 15-50, 16-50, 17-50, 18-50, 19-50, 20-50, 21-50, 22-50, 23-50, 24-50, 25-50, 26-50, 27-50, 28-50, 29-50, 30-50, 31-50, 32-50, 33-50, 34-50, 35-50, 36-50, 37-50, 38-50, 39-50, 40-50, 41-50, 42-50, 43-50, 44-50, 45-50, 46-50, 47-50, 48-50, or 49-50. In some embodiments, $R^{11}$ is linked to the Cys residue with a linker-to-a dual GIP/GLP-1 receptor agonist or functional variant thereof ratio of 1-7, 2-8, 3-9, 4-10, 5-11, 6-12, 7-13, 8-14, 9-15, 10-16, 11-17, 12-18, 13-19, 14-20, 15-21, 16-22, 17-23, 18-24, 19-25, 20-26, 21-27, 22-28, 23-29, 24-30, 25-31, 26-32, 27-33, 28-34, 29-35, 30-36, 31-37, 32-38, 33-39, 34-40, 35-41, 36-42, 37-43, 38-44, 39-45, 40-46, 41-47, 42-48, 43-49, or 44-50.

In some embodiments, $R^{11}$ is linked to a dual GIP/GLP-1 receptor agonist or functional variant thereof with a linker-to-a dual GIP/GLP-1 receptor agonist or functional variant thereof ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In some embodiments, the compound comprises a dual GIP/GLP-1 receptor agonist or functional variant thereof comprising a dual conjugation. In some embodiments, the dual conjugation comprises a linker-to-a dual GIP/GLP-1 receptor agonist or functional variant thereof ratio of 1-2.

In some embodiments, the dual conjugation comprises a linker-to-a dual GIP/GLP-1 receptor agonist or functional variant thereof ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, the dual conjugation comprises a linker-to-a dual GIP/GLP-1 receptor agonist or functional variant thereof ratio of 1-50, 1-49, 1-48, 1-47, 1-46, 1-45, 1-44, 1-43, 1-42, 1-41, 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, the dual conjugation comprises a linker-to-a dual GIP/GLP-1 receptor agonist or functional variant thereof ratio of 2-50, 3-50, 4-50, 5-50, 6-50, 7-50, 8-50, 9-50, 10-50, 11-50, 12-50, 13-50, 14-50, 15-50, 16-50, 17-50, 18-50, 19-50, 20-50, 21-50, 22-50, 23-50, 24-50, 25-50, 26-50, 27-50, 28-50, 29-50, 30-50, 31-50, 32-50, 33-50, 34-50, 35-50, 36-50, 37-50, 38-50, 39-50, 40-50, 41-50, 42-50, 43-50, 44-50, 45-50, 46-50, 47-50, 48-50, or 49-50. In some embodiments, the dual conjugation comprises a linker-to-a dual GIP/GLP-1 receptor agonist or functional variant thereof ratio of 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, or 49-50.

In some embodiments, the therapeutic agent is a dual GIP/GLP-1 receptor agonist or functional variant thereof.

In some embodiments, the therapeutic agent comprises a sequence with at least 40%, 45%, 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, or 99.9 sequence identity to the sequence of SEQ ID NO: 25. In some embodiments, the therapeutic agent comprises the sequence of SEQ ID NO: 25.

In some embodiments, the therapeutic agent comprises C20 diacid-γ-Glu-(AEEA)2 attached to a residue of a sequence with at least 40%, 45%, 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, or 99.9 sequence identity to the sequence of SEQ ID NO: 25. In some embodiments, the therapeutic agent comprises C20 diacid-γ-Glu-(AEEA)2 attached to a residue of the sequence of SEQ ID NO: 25. In some embodiments, the therapeutic agent comprises C20 diacid-γ-Glu-(AEEA)2 attached to the Lys residue at the position 20 from the N-terminus of the sequence of SEQ ID NO: 25.

In some embodiments, the concentration of the compound as described herein is at least 0.1% weight per volume.

In some embodiments, the concentration of the compound as described herein is at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or 99% weight per volume.

In some embodiments, the concentration of the compound as described herein is at least 0.05M. In some embodiments, the concentration of the compound as described herein is at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or 100 M.

In some embodiments, the one or more ionic liquid independently comprises a cation selected from the group of the cations listed in Table 2. In some embodiments, the one or more ionic liquid independently comprises an anion selected from the group of the anions listed in Table 1. In some embodiments, the one or more ionic liquid independently comprises an ionic liquid selected from the group of the ionic liquids listed in Table 2.

In some embodiments, the composition or the pharmaceutical composition as provided herein comprises the composition as provided herein or the compound as provided herein, and the first, the second, the third, the fourth, the fifth, the sixth, the eighth, the ninth, the tenth, or more ionic liquids.

In some embodiments, the first, the second, the third, the fourth, the fifth, the sixth, the eighth, the ninth, the tenth, or more ionic liquids independently comprises a cation selected from the group consisting of aminoguanidine, choline or choline derivative, carnitine, acetylcholine, ammonium, tetramethyl ammonium, tetraethyl ammonium, tetrabutyl ammonium, and guanidine derivatives. In some embodiments, the first, the second, the third, the fourth, the fifth, the sixth, the eighth, the ninth, the tenth, or more ionic liquids independently comprises choline or choline derivative, carnitine, or acetylcholine.

In some embodiments, the first, the second, the third, the fourth, the fifth, the sixth, the eighth, the ninth, the tenth, or more ionic liquids independently comprises an anion selected from the group consisting of (R)-α-Lipoic Acid, 12-Hydroxystearic Acid, 2-(4-Isobutylphenyl)propionic Acid, 2-(4,4-Dimethyl-2-pentanyl)-5,7,7-trimethyloctanoic Acid, 2-Aminoethanesulfonic Acid (Taurine Acid), 2-Hexyldecanoic Acid, 2-Hydroxyhippuric Acid, 3-(4-Hydroxyphenyl)propionic Acid, 3-Methylcrotonic Acid, 3,3-Diphenylpropionic Acid, 3,4-Dihydroxbenzoic Acid (Protocatechuic Acid), 3,7-Dimethyloctanoic Acid, 4-Hydroxybenzenesulfonic Acid, 4-Hydroxybenzoic Acid, 4-Methylhexanoic Acid, 4-Methyloctanoic Acid, 4-Methylvaleric Acid, 5-Norbornene-2-carboxylic Acid, 8-[(2-hydroxybenzoyl)amino]octanoic acid, Abietic Acid, Acetic Acid, Acetylcysteine, Aconitic Acid, Arachidonic Acid, Behenic Acid, Benzoic Acid, Caffeic Acid, Chenodeoxycholic Acid, Cis-Cinnamic acid, Citric Acid, Citronellic Acid, Crotonic Acid, D-(+)-Galactonic Acid, Decanoic Acid, Deoxycholic Acid, Dihydrocaffeic Acid, DL-2-Phenylpropionic (Hydratropic) Acid, DL-Tartaric Acid, DL-Tropic Acid, Eicosanedioic Acid, Eicosapentanoic Acid (EPA), Elaidic Acid, Ellagic Acid, Erucic Acid, Ethylenediaminetetraacetic Acid (EDTA), Formic Acid, Fumaric Acid, Geranic Acid, Glutaric Acid, Glycolic Acid, Heptanoic Acid, Hexanoic Acid, Hydrocinnamic Acid (3-Phenylpropionic Acid), Isobutyric Acid, Isovaleric Acid, L-(+)-Tartaric Acid, L-Ascorbic Acid, L-Aspartic Acid, L-Glutamic Acid, L-Glutathione reduced, Lactic Acid, Lauric Acid, Levulinic Acid, Linoleic Acid, Linolenic Acid, Lithocholic Acid, Maleic Acid, Malic Acid, Malonic Acid, Mandelic acid, Mesaconic Acid, Nicotinic Acid, Nonanoic Acid, Octanoic Acid, Oleic Acid, Oxalic Acid, p-Coumaric Acid, p-Toluenesulfonic Acid, Palmitic Acid, Perillic Acid, Phosphoric Acid, Pimelic Acid, Pivalic Acid, Propionic Acid, Pyroglutamic Acid, Pyruvic Acid, Ricinoleic Acid, Salicylic Acid (2-Hydroxybenzoic Acid), Sinapinic Acid (3,5-Dimethoxy-4-Hydroxycinnamic Acid), Sorbic Acid, Stearic acid, Succinic Acid, Syringic Acid, Tiglic Acid, Trans-2-Decenoic Acid, Trans-2-Hexenoic Acid, Trans-2-Octenoic Acid, Trans-3-Octenoic Acid, Trans-γ-Octenoic Acid, Trans-Cinnamic Acid, Trans-Ferulic Acid, Undecanoic Acid, Valeric Acid, Vanillic Acid, and α-Ketoglutaric Acid.

In some embodiments, the first, the second, the third, the fourth, the fifth, the sixth, the eighth, the ninth, the tenth, or more ionic liquids independently comprises an anion selected from the group consisting of (R)-α-lipoic acid, 2-(4-isobutylphenyl)propionic acid, 2-(4,4-dimethyl-2-pentanyl)-5,7,7-trimethyloctanoic acid, 2-hexyldecanoic acid, 2-hydroxyhippuric acid, 3,7-dimethyloctanoic acid, 4-methylhexanoic acid, 4-methyloctanoic acid, 4-methylvaleric acid, 5-norbornene-2-carboxylic acid, abietic acid, acetic acid, acetylcysteine, arachidonic acid, caffeic acid, cinnamic acid, citric acid, citronellic acid, crotonic acid, D-(+)-galactonic acid, decanoic acid, deoxycholic acid, eicosapentanoic acid, fumaric acid, geranic acid, glutaric acid, glycolic acid, hexanoic acid, 3-phenylpropionic acid, isovaleric acid, L-(+)-tartaric acid, L-ascorbic acid, L-glutathione reduced, lactic acid, lauric acid, levulinic acid, linoleic acid, linolenic acid, maleic acid, malonic acid, mesaconic acid, mandelic acid, nonanoic acid, octanoic acid, oleic acid, p-toluenesulfonic acid, perillic acid, phosphoric acid, pimelic acid, propionic acid, pyroglutamic acid, pyruvic acid, ricinoleic acid, sorbic acid, syringic acid, trans-2-decenoic acid, trans-2-hexenoic acid, trans-2-octenoic acid, trans-3-octenoic acid, trans-γ-octenoic acid, trans-ferulic acid, undecanoic acid, vanillic acid, α-ketoglutaric acid, 3,3-diphenylpropionic acid, 3,4-dihydroxbenzoic acid (protocatechuic acid), 3-(4-hydroxyphenyl)propionic acid, 3-methylcrotonic acid, 4-hydroxybenzenesulfonic acid, 4-hydroxybenzoic acid, aconitic acid, benzoic acid, chenodeoxycholic acid, dihydrocaffeic acid, DL-2-phenylpropionic (hydratropic) acid, DL-tropic acid, eicosanedioic acid, ellagic acid, formic acid, heptanoic acid, isobutyric acid, DL-tartaric acid, lithocholic acid, malic acid, nicotinic acid, p-coumaric acid, palmitic acid, pivalic acid, salicylic acid (2-hydroxybenzoic acid), sinapinic acid (3,5-dimethoxy-4-hydroxycinnamic acid), succinic acid, tiglic acid, valeric acid, stearic acid, and 8-[(2-hydroxybenzoyl)amino]octanoic acid. In some embodiments, the first, the second, the third, the fourth, the fifth, the sixth, the eighth, the ninth, the tenth, or more ionic liquids independently comprises an anion selected from the group consisting of glycolic acid, tartaric acid, malic acid, hydrocinnamic acid, citric acid, cinnamic acid, mandelic acid, mesaconic acid, ricinoleic acid, linoleic acid, and tiglic acid. In some embodiments, the first, the second, the third, the fourth, the fifth, the sixth, the eighth, the ninth, the tenth, or more ionic liquids independently comprises an anion selected from the group consisting of cinnamic acid, mandelic acid, citric acid, ricinoleic acid, linoleic acid, and tiglic acid.

In some embodiments, the first, the second, the third, the fourth, the fifth, the sixth, the eighth, the ninth, the tenth, or more ionic liquids independently comprises choline or choline derivative-cinnamic acid, choline or choline derivative-mandelic acid, choline or choline derivative-citric acid, choline or choline derivative-ricinoleic acid, choline or choline derivative-linoleic acid, or choline or choline derivative-tiglic acid.

In some embodiments, the one or more ionic liquid independently comprises carnitine-cinnamic acid, carnitine-mandelic acid, carnitine-citric acid, carnitine-ricinoleic acid, carnitine-linoleic acid, or carnitine-tiglic acid.

In some embodiments, the one or more ionic liquid independently comprises acetylcholine-cinnamic acid, acetylcholine-mandelic acid, acetylcholine-citric acid, acetylcholine-ricinoleic acid, acetylcholine-linoleic acid, or acetylcholine-tiglic acid.

In some embodiments, the first, the second, the third, the fourth, the fifth, the sixth, the eighth, the ninth, the tenth, or more ionic liquids independently comprises a cation selected from the group of the cations listed in Table 2. In some embodiments, the first, the second, the third, the fourth, the fifth, the sixth, the eighth, the ninth, the tenth, or more ionic liquids independently comprises an anion selected from the group of the anions listed in Table 1. In some embodiments, some embodiments, the first, the second, the third, the fourth, the fifth, the sixth, the eighth, the ninth, the tenth, or more ionic liquids independently comprises an ionic liquid selected from the group of the ionic liquids listed in Table 2.

In some embodiments, to enhance the hydrophobicity of a dual GIP/GLP-1 receptor agonist or functional variant thereof, a dual GIP/GLP-1 receptor agonist or functional variant thereof is linked to one or more fatty acids or carboxylic acid-containing molecules. In some embodiments, one or more fatty acids or carboxylic acid-containing molecules are linked to a dual GIP/GLP-1 receptor agonist or functional variant thereof via a dual conjugation (or dual covalent conjugation). In some embodiments, one or more fatty acids or carboxylic acid-containing molecules comprise cinnamic acid. In some embodiments, one or more fatty acids or carboxylic acid-containing molecules are cinnamic acid.

In some embodiments, one or more fatty acids or carboxylic acid-containing molecules are non-covalently associated with a free amine of a dual GIP/GLP-1 receptor agonist or functional variant thereof. In some embodiments, one or more fatty acids or carboxylic acid-containing molecules are non-covalently associated with the N-terminal amine in the peptide backbone of a dual GIP/GLP-1 receptor agonist or functional variant thereof. In some embodiments, one or more fatty acids or carboxylic acid-containing molecules are non-covalently associated with the amine group of a Gln residue, the amine group of an Asn residue, the amine group of an Arg residue, the amine group of a Lys residue, the amine group of a His residue, or a combination thereof of a dual GIP/GLP-1 receptor agonist or functional variant thereof.

In some embodiments, one or more fatty acids or carboxylic acid-containing molecules are covalently conjugated to a free amine of a dual GIP/GLP-1 receptor agonist or functional variant thereof. In some embodiments, one or more fatty acids or carboxylic acid-containing molecules are covalently conjugated to the N-terminal amine in the peptide backbone of a dual GIP/GLP-1 receptor agonist or functional variant thereof. In some embodiments, one or more fatty acids or carboxylic acid-containing molecules are covalently conjugated to the amine group of a Gln residue, the amine group of an Asn residue, the amine group of an Arg residue, the amine group of a Lys residue, the amine group of a His residue, or a combination thereof of a dual GIP/GLP-1 receptor agonist or functional variant thereof.

In an aspect, provided herein, inter alia, is a compound according to Formula I:

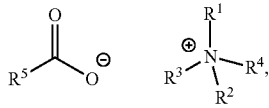

Formula I wherein:

$R^1$, $R^2$, and $R^3$ are independently $C_1$-$C_5$ alkyl;

$R^4$ is $C_2$-$C_5$ alkyl, wherein the $C_2$-$C_5$ alkyl is unsubstituted or substituted with 1 or more hydroxyl;

$R^5$ is a therapeutic agent.

In some embodiments, $R^1$, $R^2$, and $R^3$ are methyl.

In some embodiments, $R^1$, $R^2$, and $R^3$ are ethyl.

In some embodiments, $R^1$, $R^2$, and $R^3$ are propyl.

In some embodiments, $R^1$ and $R^2$ are methyl, and $R^3$ is ethyl.

In some embodiments, $R^1$ and $R^3$ are methyl, and $R^2$ is ethyl.

In some embodiments, $R^1$ and $R^2$ are ethyl, and $R^3$ is methyl.

In some embodiments, $R^1$ and $R^3$ are ethyl, and $R^2$ is methyl.

In some embodiments, $R^1$ and $R^2$ are propyl, and $R^3$ is methyl.

In some embodiments, $R^1$ and $R^3$ are propyl, and $R^2$ is methyl.

In some embodiments, $R^4$ is $C_2$-$C_5$ alkyl substituted with a hydroxyl.

In some embodiments, $R^4$ is

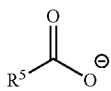

In some embodiments, the compound is according to Formula Ia:

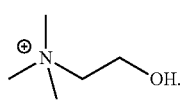

Formula Ia

In some embodiments, the compound is according to Formula Ib:

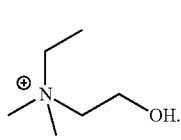

Formula Ib

In some embodiments, the compound is according to Formula Ic:

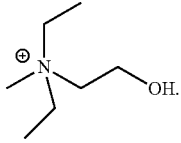

Formula Ic

In some embodiments, the therapeutic agent is a dual GIP (glucose-dependent insulinotropic polypeptide)/GLP-1 (Glucagon-like peptide-1) receptor agonist or functional variant thereof.

In some embodiments, the therapeutic agent comprises a sequence with at least 75% sequence identity to the sequence of SEQ ID NO: 25.

In some embodiments, the therapeutic agent comprises the sequence of SEQ ID NO: 25.

In some embodiments, the therapeutic agent comprises C20 diacid-γ-Glu-(AEEA)2 attached to a residue of a sequence with at least 75% sequence identity to the sequence of SEQ ID NO: 25.

In some embodiments, the therapeutic agent comprises C20 diacid-γ-Glu-(AEEA)2 attached to a residue of the sequence of SEQ ID NO: 25.

In some embodiments, the therapeutic agent comprises C20 diacid-γ-Glu-(AEEA)2 attached to the Lys residue at the position 20 from the N-terminus of the sequence of SEQ ID NO: 25.

In some embodiments, the compound comprises a

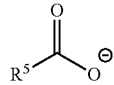

to

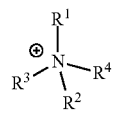

molar ratio of from about 1:1 to about 1:20.

In some embodiments, the compound comprises a

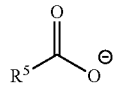

to

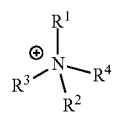

molar ratio of about 1:1.

In some embodiments, the compound comprises a

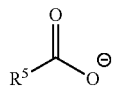

to

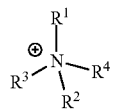

molar ratio of about 1:2.

In some embodiments, the compound comprises a

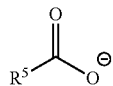

to

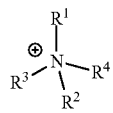

molar ratio of about 1:3.

In some embodiments, the compound comprises a

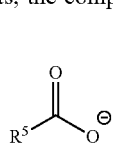

to

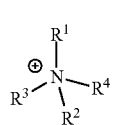

molar ratio of about 1:4.

In some embodiments, the compound comprises a

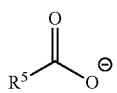

to

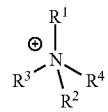

molar ratio of about 1:5.

In some embodiments, the compound comprises a

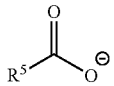

to

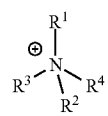

molar ratio of about 1:10.

In some embodiments, the compound comprises a

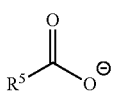

to

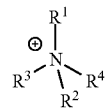

molar ratio of about 1:20.

In some embodiments, the compound comprises a dual GIP/GLP-1 receptor agonist or functional variant thereof having a modified structure.

In some embodiments, the compound comprises a dual GIP/GLP-1 receptor agonist or functional variant thereof having a choline or choline derivative-modified structure.

In some embodiments, the compound comprises a dual GIP/GLP-1 receptor agonist or functional variant thereof having a cation moiety comprising choline or choline derivative.

In some embodiments, the compound comprises a dual GIP/GLP-1 receptor agonist or functional variant thereof having a cation moiety comprising a choline or choline derivative-like residue.

In some embodiments, the compound comprises a dual GIP/GLP-1 receptor agonist or functional variant thereof comprising one or more choline or choline derivative-peptide derivative formed on a Glu residue, an Asp residue, or a combination thereof.

In some embodiments, the compound comprises a dual GIP/GLP-1 receptor agonist or functional variant thereof comprising a linker comprising one or more gamma glutamate (γGlu) residues, one or more 8-amino-3,6-dioxaoctanoic acid (OEG) residues, or a combination thereof.

In some embodiments, the compound comprises a dual GIP/GLP-1 receptor agonist or functional variant thereof comprising a linker comprising one or more gamma glutamate (γGlu) residues.

In some embodiments, the compound comprises a dual GIP/GLP-1 receptor agonist or functional variant thereof comprising a choline or choline derivative-peptide ester that is formed on the carboxylic acid of the one or more gamma glutamate residues of the linker.

In some embodiments, the compound comprises a dual GIP/GLP-1 receptor agonist or functional variant thereof comprising a choline or choline derivative-peptide derivative that is formed on the carboxylic acid of the one or more gamma glutamate residues of the linker.

In some embodiments, the compound comprises a dual GIP/GLP-1 receptor agonist or functional variant thereof comprising a diacid consisting of 18 or 20 carbons in length.

In some embodiments, the diacid comprises a $C_{20}$ fatty diacid.

In some embodiments, the diacid comprises 1,20-icosanedioic acid.

In another aspect, provided herein is a compound according to Formula II:

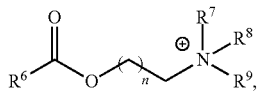

Formula II wherein:

$R^6$ is a therapeutic agent.

$R^7$, $R^8$, and $R^9$ are independently $C_1$-$C_5$ alkyl; and n is 1, 2, 3, 4, or 5.

In some embodiments, $R^7$, $R^8$, and $R^9$ are methyl.

In some embodiments, $R^7$, $R^8$, and $R^9$ are ethyl.

In some embodiments, $R^7$, $R^8$, and $R^9$ are propyl.

In some embodiments, $R^7$ and $R^8$ are methyl, and $R^9$ is ethyl.

In some embodiments, $R^7$ and $R^9$ are methyl, and $R^8$ is ethyl.

In some embodiments, $R^7$ and $R^8$ are ethyl, and $R^9$ is methyl.

In some embodiments, $R^7$ and $R^9$ are ethyl, and $R^8$ is methyl.

In some embodiments, $R^7$ and $R^8$ are propyl, and $R^9$ is methyl.

In some embodiments, $R^7$ and $R^9$ are propyl, and $R^8$ is methyl.

In some embodiments, n is 1.

In some embodiments, the compound is according to Formula IIa:

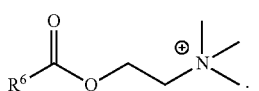

Formula IIa

In some embodiments, the compound is according to Formula IIb:

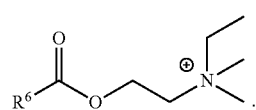

Formula IIb

In some embodiments, the compound is according to Formula IIc:

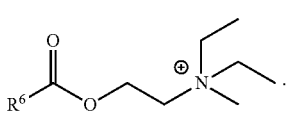

Formula IIc

In some embodiments, the therapeutic agent is a dual GIP/GLP-1 receptor agonist or functional variant thereof.

In some embodiments, the therapeutic agent comprises a sequence with at least 75% sequence identity to the sequence of SEQ ID NO: 25.

In some embodiments, the therapeutic agent comprises the sequence of SEQ ID NO: 25.

In some embodiments, the therapeutic agent comprises $C_{20}$ diacid-γ-Glu-(AEEA)2 attached to a residue of a sequence with at least 75% sequence identity to the sequence of SEQ ID NO: 25.

In some embodiments, the therapeutic agent comprises $C_{20}$ diacid-γ-Glu-(AEEA)2 attached to a residue of the sequence of SEQ ID NO: 25.

In some embodiments, the therapeutic agent comprises $C_{20}$ diacid-γ-Glu-(AEEA)2 attached to the Lys residue at the position 20 from the N-terminus of the sequence of SEQ ID NO: 25.

In some embodiments, the compound comprises a dual GIP/GLP-1 receptor agonist or functional variant thereof having a choline or choline derivative-modified structure.

In some embodiments, the compound comprises a dual GIP/GLP-1 receptor agonist or functional variant thereof having a cation moiety comprising choline or choline derivative.

In some embodiments, the compound comprises a dual GIP/GLP-1 receptor agonist or functional variant thereof having a choline or choline derivative-modified ester structure.

In some embodiments, the compound comprises a dual GIP/GLP-1 receptor agonist or functional variant thereof having a cation moiety comprising a choline or choline derivative-like residue.

In some embodiments, the compound comprises a dual GIP/GLP-1 receptor agonist or functional variant thereof comprising one or more choline or choline derivative-peptide ester formed on a Cys residue, a Lys residue, or any combination thereof.

In some embodiments, the one or more choline or choline derivative-peptide ester formed on the Cys residue comprises a linker-to-the dual GIP/GLP-1 receptor agonist or functional variant thereof ratio of 2-8, the one or more choline or choline derivative-peptide ester formed on the Lys residue comprises a linker-to-the dual GIP/GLP-1 receptor agonist or functional variant thereof ratio of 2-4, or a combination thereof.

In some embodiments, the compound comprises a dual GIP/GLP-1 receptor agonist or functional variant thereof comprising a linker comprising one or more gamma glutamate (γGlu) residues, one or more 8-amino-3,6-dioxaoctanoic acid (OEG) residues, or a combination thereof.

In some embodiments, the compound comprises a dual GIP/GLP-1 receptor agonist or functional variant thereof comprising a linker comprising one or more gamma glutamate (γGlu) residues.

In some embodiments, the compound comprises a dual GIP/GLP-1 receptor agonist or functional variant thereof comprising a choline or choline derivative-peptide derivative that is formed on the carboxylic acid of the one or more gamma glutamate residues of the linker.

In some embodiments, the compound comprises a dual GIP/GLP-1 receptor agonist or functional variant thereof comprising a choline or choline derivative-peptide ester that is formed on the carboxylic acid of the one or more gamma glutamate residues of the linker.

In some embodiments, the compound comprises a dual GIP/GLP-1 receptor agonist or functional variant thereof comprising a diacid consisting of 18 or 20 carbons in length.

In some embodiments, the diacid comprises a $C_{20}$ fatty diacid.

In some embodiments, the diacid comprises 1,20-icosanedioic acid.

In another aspect, provided herein is a compound according to Formula III:

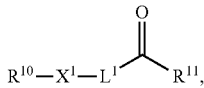

Formula III wherein:
$R^{10}$ is a therapeutic agent;
$R^{11}$ is substituted or unsubstituted $C_5$-$C_{10}$;
$X^1$ is

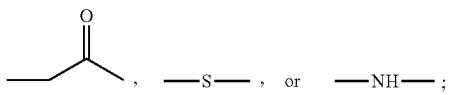

and
$L^1$ is a covalent bond or a linker.

In some embodiments, $L^1$ is a non-cleavable linker.
In some embodiments, $L^1$ comprises a maleimide alkane linker or a maleimide cyclohexane linker.
In some embodiments, $L^1$ comprises

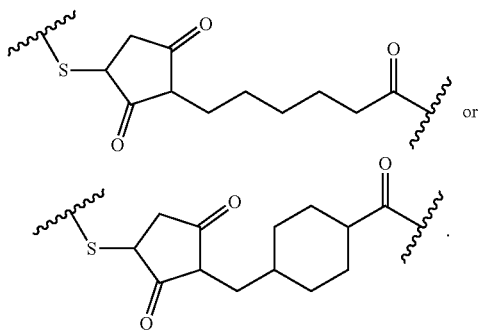

In some embodiments, $L^1$ is a chemically cleavable linker.
In some embodiments, $L^1$ comprises a hydrazone linker or a disulfide linker.
In some embodiments, $L^1$ comprises or

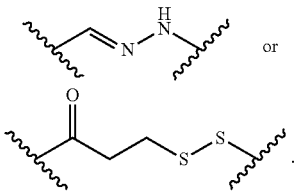

In some embodiments, $R^{11}$ is substituted or unsubstituted $C_{10}$.

In some embodiments, the therapeutic agent is a dual GIP/GLP-1 receptor agonist or functional variant thereof.

In some embodiments, the therapeutic agent comprises a sequence with at least 75% sequence identity to the sequence of SEQ ID NO: 25.

In some embodiments, the therapeutic agent comprises the sequence of SEQ ID NO: 25.

In some embodiments, the therapeutic agent comprises C20 diacid-γ-Glu-(AEEA)2 attached to a residue of a sequence with at least 75% sequence identity to the sequence of SEQ ID NO: 25.

In some embodiments, the therapeutic agent comprises C20 diacid-γ-Glu-(AEEA)2 attached to a residue of the sequence of SEQ ID NO: 25.

In some embodiments, the therapeutic agent comprises C20 diacid-γ-Glu-(AEEA)2 attached to the Lys residue at the position 20 from the N-terminus of the sequence of SEQ ID NO: 25.

In some embodiments, the compound comprises a dual GIP/GLP-1 receptor agonist or functional variant thereof having a choline or choline derivative-modified structure.

In some embodiments, the compound comprises a dual GIP/GLP-1 receptor agonist or functional variant thereof having a cation moiety comprising choline or choline derivative.

In some embodiments, the compound comprises a dual GIP/GLP-1 receptor agonist or functional variant thereof having a choline or choline derivative-modified ester structure.

In some embodiments, the compound comprises a dual GIP/GLP-1 receptor agonist or functional variant thereof having a cation moiety comprising a choline or choline derivative-like residue.

In some embodiments, the compound comprises a dual GIP/GLP-1 receptor agonist or functional variant thereof comprising one or more $R^{11}$ linked to a Lys residue, a Cys residue, or any combination thereof.

In some embodiments, $R^{11}$ is linked to the Lys residue with a linker-to-the dual GIP/GLP-1 receptor agonist or functional variant thereof ratio of 2-4, $R^{11}$ is linked to the Cys residue with a linker-to-the dual GIP/GLP-1 receptor agonist or functional variant thereof ratio of 2-8 or with a linker-to-the dual GIP/GLP-1 receptor agonist or functional variant thereof ratio of 4, or a combination thereof.

In some embodiments, the compound comprises a dual GIP/GLP-1 receptor agonist or functional variant thereof comprising a dual conjugation.

In some embodiments, the dual conjugation comprises a linker-to-the dual GIP/GLP-1 receptor agonist or functional variant thereof ratio of 1-2.

In some embodiments, the compound comprises a dual GIP/GLP-1 receptor agonist or functional variant thereof comprising a linker comprising one or more gamma glutamate (γGlu) residues, one or more 8-amino-3,6-dioxaoctanoic acid (OEG) residues, or a combination thereof.

In some embodiments, the compound comprises a dual GIP/GLP-1 receptor agonist or functional variant thereof comprising a linker comprising one or more gamma glutamate (γGlu) residues.

In some embodiments, the compound comprises a dual GIP/GLP-1 receptor agonist or functional variant thereof comprising a choline or choline derivative-peptide derivative that is formed on the carboxylic acid of the one or more gamma glutamate residues of the linker.

In some embodiments, the compound comprises a dual GIP/GLP-1 receptor agonist or functional variant thereof comprising a choline or choline derivative-peptide ester that is formed on the carboxylic acid of the one or more gamma glutamate residues of the linker.

In some embodiments, the compound comprises a dual GIP/GLP-1 receptor agonist or functional variant thereof comprising a diacid consisting of 18 or 20 carbons in length.

In some embodiments, the diacid comprises a $C_{20}$ fatty diacid.

In some embodiments, the diacid comprises 1,20-icosanedioic acid.

In another aspect, provided herein is a composition comprising the compound as described herein, and one or more ionic liquid.

In some embodiments, the one or more ionic liquid independently comprises a cation selected from the group consisting of aminoguanidine, choline or choline derivative, carnitine, acetylcholine, ammonium, tetramethyl ammonium, tetraethyl ammonium, tetrabutyl ammonium, and guanidine derivatives.

In some embodiments, the one or more ionic liquid independently comprises choline or choline derivative, carnitine, or acetylcholine.

In some embodiments, the one or more ionic liquid independently comprises an anion selected from the group consisting of (R)-α-Lipoic Acid, 12-Hydroxystearic Acid, 2-(4-Isobutylphenyl)propionic Acid, 2-(4,4-Dimethyl-2-pentanyl)-5,7,7-trimethyloctanoic Acid, 2-Aminoethanesulfonic Acid (Taurine Acid), 2-Hexyldecanoic Acid, 2-Hydroxyhippuric Acid, 3-(4-Hydroxyphenyl)propionic Acid, 3-Methylcrotonic Acid, 3,3-Diphenylpropionic Acid, 3,4-Dihydroxybenzoic Acid (Protocatechuic Acid), 3,7-Dimethyloctanoic Acid, 4-Hydroxybenzenesulfonic Acid, 4-Hydroxybenzoic Acid, 4-Methylhexanoic Acid, 4-Methyloctanoic Acid, 4-Methylvaleric Acid, 5-Norbornene-2-carboxylic Acid, 8-[(2-hydroxybenzoyl)amino] octanoic acid, Abietic Acid, Acetic Acid, Acetylcysteine, Aconitic Acid, Arachidonic Acid, Behenic Acid, Benzoic Acid, Caffeic Acid, Chenodeoxycholic Acid, Cis-Cinnamic acid, Citric Acid, Citronellic Acid, Crotonic Acid, D-(+)-Galactonic Acid, Decanoic Acid, Deoxycholic Acid, Dihydrocaffeic Acid, DL-2-Phenylpropionic (Hydratropic) Acid, DL-Tartaric Acid, DL-Tropic Acid, Eicosanedioic Acid, Eicosapentanoic Acid (EPA), Elaidic Acid, Ellagic Acid, Erucic Acid, Ethylenediaminetetraacetic Acid (EDTA), Formic Acid, Fumaric Acid, Geranic Acid, Glutaric Acid, Glycolic Acid, Heptanoic Acid, Hexanoic Acid, Hydrocinnamic Acid (3-Phenylpropionic Acid), Isobutyric Acid, Isovaleric Acid, L-(+)-Tartaric Acid, L-Ascorbic Acid, L-Aspartic Acid, L-Glutamic Acid, L-Glutathione reduced, Lactic Acid, Lauric Acid, Levulinic Acid, Linoleic Acid, Linolenic Acid, Lithocholic Acid, Maleic Acid, Malic Acid, Malonic Acid, Mandelic acid, Mesaconic Acid, Nicotinic Acid, Nonanoic Acid, Octanoic Acid, Oleic Acid, Oxalic Acid, p-Coumaric Acid, p-Toluenesulfonic Acid, Palmitic Acid, Perillic Acid, Phosphoric Acid, Pimelic Acid, Pivalic Acid, Propionic Acid, Pyroglutamic Acid, Pyruvic Acid, Ricinoleic Acid, Salicylic Acid (2-Hydroxybenzoic Acid), Sinapinic Acid (3,5-Dimethoxy-4-Hydroxycinnamic Acid), Sorbic Acid, Stearic acid, Succinic Acid, Syringic Acid, Tiglic Acid, Trans-2-Decenoic Acid, Trans-2-Hexenoic Acid, Trans-2-Octenoic Acid, Trans-3-Octenoic Acid, Trans-γ-Octenoic Acid, Trans-Cinnamic Acid, Trans-Ferulic Acid, Undecanoic Acid, Valeric Acid, Vanillic Acid, and α-Ketoglutaric Acid.

In some embodiments, the one or more ionic liquid independently comprises an anion selected from the group consisting of glycolic acid, tartaric acid, malic acid, hydrocinnamic acid, citric acid, cinnamic acid, mandelic acid, mesaconic acid, ricinoleic acid, linoleic acid, and tiglic acid.

In some embodiments, the one or more ionic liquid independently comprises an anion selected from the group consisting of cinnamic acid, mandelic acid, citric acid, ricinoleic acid, linoleic acid, and tiglic acid.

In some embodiments, the one or more ionic liquid independently comprises choline or choline derivative-cinnamic acid, choline or choline derivative-mandelic acid, choline or choline derivative-citric acid, choline or choline derivative-ricinoleic acid, choline or choline derivative-linoleic acid, or choline or choline derivative-tiglic acid.

In some embodiments, the one or more ionic liquid independently comprises carnitine-cinnamic acid, carnitine-mandelic acid, carnitine-citric acid, carnitine-ricinoleic acid, carnitine-linoleic acid, or carnitine-tiglic acid.

In some embodiments, the one or more ionic liquid independently comprises acetylcholine-cinnamic acid, acetylcholine-mandelic acid, acetylcholine-citric acid, acetylcholine-ricinoleic acid, acetylcholine-linoleic acid, or acetylcholine-tiglic acid.

In some embodiments, the composition as described herein further comprises at least one permeation enhancer.

In some embodiments, the at least one permeation enhancer is selected from the group consisting of salcaprozate sodium (SNAC), sodium caprylate, sodium caprate, a bile salt, ethylenediaminetetraacetic acid (EDTA), ethylene glycol-bis-(2-aminoethylether)-N,N,N',N'-tetraacetic acid (EGTA), and 3-[N,N-Dimethyl(3-palmitoylaminopropyl)-ammonio]-propanesulfonate (PPS), and any combination thereof.

In some embodiments, the bile salt is selected from the group consisting of sodium deoxycholate, sodium chenodeoxycholate, sodium taurodeoxycholate, and a combination thereof.

In some embodiments, the composition as described herein further comprises at least one pharmaceutically acceptable excipient.

In another aspect, provided herein is a composition comprising a dual GIP/GLP-1 receptor agonist or functional variant thereof and one or more ionic liquid.

In some embodiments, the one or more ionic liquid independently comprises a cation selected from the group consisting of aminoguanidine, choline or choline derivative, carnitine, acetylcholine, ammonium, tetramethyl ammonium, tetraethyl ammonium, tetrabutyl ammonium, and guanidine derivatives.

In some embodiments, the one or more ionic liquid independently comprises choline or choline derivative, carnitine, or acetylcholine.

In some embodiments, the one or more ionic liquid independently comprises an anion selected from the group consisting of (R)-α-Lipoic Acid, 12-Hydroxystearic Acid, 2-(4-Isobutylphenyl)propionic Acid, 2-(4,4-Dimethyl-2-pentanyl)-5,7,7-trimethyloctanoic Acid, 2-Aminoethanesulfonic Acid (Taurine Acid), 2-Hexyldecanoic Acid, 2-Hydroxyhippuric Acid, 3-(4-Hydroxyphenyl)propionic Acid, 3-Methylcrotonic Acid, 3,3-Diphenylpropionic Acid, 3,4-Dihydroxbenzoic Acid (Protocatechuic Acid), 3,7-Dimethyloctanoic Acid, 4-Hydroxybenzenesulfonic Acid, 4-Hydroxybenzoic Acid, 4-Methylhexanoic Acid, 4-Methyloctanoic Acid, 4-Methylvaleric Acid, 5-Norbornene-2-carboxylic Acid, 8-[(2-hydroxybenzoyl)amino]octanoic acid, Abietic Acid, Acetic Acid, Acetylcysteine, Aconitic Acid, Arachidonic Acid, Behenic Acid, Benzoic Acid, Caffeic Acid, Chenodeoxycholic Acid, Cis-Cinnamic acid, Citric Acid, Citronellic Acid, Crotonic Acid, D-(+)-Galactonic Acid, Decanoic Acid, Deoxycholic Acid, Dihydrocaffeic Acid, DL-2-Phenylpropionic (Hydratropic) Acid, DL-Tartaric Acid, DL-Tropic Acid, Eicosanedioic Acid, Eicosapentanoic Acid (EPA), Elaidic Acid, Ellagic Acid, Erucic Acid, Ethylenediaminetetraacetic Acid (EDTA), Formic Acid, Fumaric Acid, Geranic Acid, Glutaric Acid, Glycolic Acid, Heptanoic Acid, Hexanoic Acid, Hydrocinnamic Acid (3-Phenylpropionic Acid), Isobutyric Acid, Isovaleric Acid, L-(+)-Tartaric Acid, L-Ascorbic Acid, L-Aspartic Acid, L-Glutamic Acid, L-Glutathione reduced, Lactic Acid, Lauric Acid, Levulinic Acid, Linoleic Acid, Linolenic Acid, Lithocholic Acid, Maleic Acid, Malic Acid, Malonic Acid, Mandelic acid, Mesaconic Acid, Nicotinic Acid, Nonanoic Acid, Octanoic Acid, Oleic Acid, Oxalic Acid, p-Coumaric Acid, p-Toluenesulfonic Acid, Palmitic Acid, Perillic Acid, Phosphoric Acid, Pimelic Acid, Pivalic Acid, Propionic Acid, Pyroglutamic Acid, Pyruvic Acid, Ricinoleic Acid, Salicylic Acid (2-Hydroxybenzoic Acid), Sinapinic Acid (3,5-Dimethoxy-4-Hydroxycinnamic Acid), Sorbic Acid, Stearic acid, Succinic Acid, Syringic Acid, Tiglic Acid, Trans-2-Decenoic Acid, Trans-2-Hexenoic Acid, Trans-2-Octenoic Acid, Trans-3-Octenoic Acid, Trans-γ-Octenoic Acid, Trans-Cinnamic Acid, Trans-Ferulic Acid, Undecanoic Acid, Valeric Acid, Vanillic Acid, and α-Ketoglutaric Acid.

In some embodiments, the one or more ionic liquid independently comprises an anion selected from the group consisting of glycolic acid, tartaric acid, malic acid, hydrocinnamic acid, citric acid, cinnamic acid, mandelic acid, mesaconic acid, ricinoleic acid, linoleic acid, and tiglic acid.

In some embodiments, the one or more ionic liquid independently comprises an anion selected from the group consisting of cinnamic acid, mandelic acid, citric acid, ricinoleic acid, linoleic acid, and tiglic acid.

In some embodiments, the one or more ionic liquid independently comprises choline or choline derivative-cinnamic acid, choline or choline derivative-mandelic acid, choline or choline derivative-citric acid, choline or choline derivative-ricinoleic acid, choline or choline derivative-linoleic acid, or choline or choline derivative-tiglic acid.

In some embodiments, the one or more ionic liquid independently comprises carnitine-cinnamic acid, carnitine-mandelic acid, carnitine-citric acid, carnitine-ricinoleic acid, carnitine-linoleic acid, or carnitine-tiglic acid.

In some embodiments, the one or more ionic liquid independently comprises acetylcholine-cinnamic acid, acetylcholine-mandelic acid, acetylcholine-citric acid, acetylcholine-ricinoleic acid, acetylcholine-linoleic acid, or acetylcholine-tiglic acid.

In some embodiments, the solubility of a dual GIP/GLP-1 receptor agonist or functional variant thereof is increased relative to a dual GIP/GLP-1 receptor agonist or functional variant thereof in a composition without a ionic liquid.

In some embodiments, the delivery efficiency of a dual GIP/GLP-1 receptor agonist or functional variant thereof in a subject in need thereof is enhanced or improved when administered to the subject, relative to a dual GIP/GLP-1 receptor agonist or functional variant thereof in a composition without a ionic liquid.

In some embodiments, the composition further comprises at least one permeation enhancer.

In some embodiments, the at least one permeation enhancer is selected from the group consisting of salcaprozate sodium (SNAC), sodium caprylate, sodium caprate, a bile salt, ethylenediaminetetraacetic acid (EDTA), ethylene glycol-bis-(2-aminoethylether)-N,N,N',N'-tetraacetic acid (EGTA), and 3-[N,N-Dimethyl(3-palmitoylaminopropyl)-ammonio]-propanesulfonate (PPS), and any combination thereof.

In some embodiments, the bile salt is selected from the group consisting of sodium deoxycholate, sodium chenodeoxycholate, sodium taurodeoxycholate, and a combination thereof.

In another aspect, provided herein is a pharmaceutical composition comprising the compound as described herein or the composition as described herein, and at least one pharmaceutically acceptable excipient.

In some embodiments, the pharmaceutical composition further comprises at least one permeation enhancer.

In some embodiments, the at least one permeation enhancer is selected from the group consisting of salcaprozate sodium (SNAC), sodium caprylate, sodium caprate, a bile salt, ethylenediaminetetraacetic acid (EDTA), ethylene glycol-bis-(2-aminoethylether)-N,N,N',N'-tetraacetic acid (EGTA), and 3-[N,N-Dimethyl(3-palmitoylaminopropyl)-ammonio]-propanesulfonate (PPS), and any combination thereof.

In some embodiments, the bile salt is selected from the group consisting of sodium deoxycholate, sodium chenodeoxycholate, sodium taurodeoxycholate, and a combination thereof.

In another aspect, provided herein is a method of treating a disease or disorder in a subject in need thereof, comprising administering to the subject a therapeutically effective amount of the compound as described herein, the composition as described herein, or the pharmaceutical composition as described herein, wherein the administering is effective to treat the disease or disorder in the subject.

In some embodiments, the disease or disorder is a metabolic disease or disorder.

In some embodiments, the disease or disorder is diabetes mellitus.

In some embodiments, the disease or disorder is type 2 diabetes mellitus (T2DM).

In some embodiments, the disease or disorder is obesity or overweight.

In some embodiments, the administration activates GIP receptor signaling, GLP-1 receptor signaling, or a combination thereof.

In some embodiments, the administration increases or improves glucose-dependent insulin secretion, improves glucose tolerance, or a combination thereof.

In some embodiments, the administration increases or improves blood sugar control.

In some embodiments, the administration decreases or reduces fasting serum glucose.

In some embodiments, the administration decreases or reduces body weight, decreases or reduces food intake, or a combination thereof.

In some embodiments, the administration delivers improvement in glycaemic control, body weight, or a combination thereof.

In some embodiments, the composition, the compound, or the pharmaceutical composition is administered via subcutaneous, intravenous, or oral administration.

In some embodiments, the composition, the compound, or the pharmaceutical composition is administered orally.

In some embodiments, the composition, the compound, or the pharmaceutical composition is administered as a liquid-filled capsule.

In some embodiments, the composition, the compound, or the pharmaceutical composition is administered in multiple doses.

In some embodiments, the composition, the compound, or the pharmaceutical composition is administered in a single dose.

In some embodiments, the composition, the compound, or the pharmaceutical composition is administered to a mucus membrane.

In some embodiments, the composition, the compound, or the pharmaceutical composition is administered via subcutaneous, intravenous, or oral administration.

In some embodiments, the concentration of the compound as described herein is at least 0.1% weight per volume.

In some embodiments, the concentration of the compound as described herein is at least 0.05M.

In some embodiments, the composition further comprises one or more additional agents.

In some embodiments, the one or more additional agent is selected from the group consisting of a nucleic acid, a small molecule, and a polypeptide.

In some embodiments, the one or more additional agent is a nucleic acid.

In some embodiments, the one or more additional agent is a small molecule.

In some embodiments, the one or more additional agent is a polypeptide.

In some embodiments, the one or more additional agent is a polypeptide.

In some embodiments, the one or more additional agents is a therapeutic that treats a metabolic disease or disorder.

In some embodiments, the one or more additional agents is a therapeutic that treats diabetes mellitus.

In some embodiments, the one or more additional agents is a therapeutic that treats type 2 diabetes mellitus (T2DM).

In some embodiments, the one or more additional agents is a therapeutic that treats obesity or overweight.

In another aspect, provided herein is a method of increasing the solubility of a dual GIP/GLP-1 receptor agonist or functional variant thereof comprising preparing a composition comprising a compound according to Formula I:

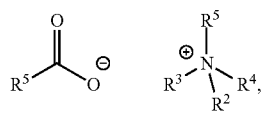

Formula I wherein:
$R^1$, $R^2$, and $R^3$ are independently $C_1$-$C_5$ alkyl;
$R^4$ is $C_2$-$C_5$ alkyl, wherein the $C_2$-$C_5$ alkyl is unsubstituted or substituted with 1 or more hydroxyl; and
$R^5$ is a dual GIP/GLP-1 receptor agonist or functional variant thereof.

In another aspect, provided herein is a method of enhancing or improving the delivery efficiency of a dual GIP/GLP-1 receptor agonist or functional variant thereof in a subject in need thereof comprising preparing a composition comprising a compound according to Formula I:

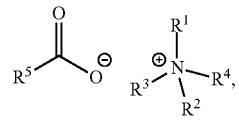

Formula I wherein:
$R^1$, $R^2$, and $R^3$ are independently $C_1$-$C_5$ alkyl;
$R^4$ is $C_2$-$C_5$ alkyl, wherein the $C_2$-$C_5$ alkyl is unsubstituted or substituted with 1 or more hydroxyl; and
$R^5$ is a dual GIP/GLP-1 receptor agonist or functional variant thereof; and administering the composition to the subject.

In some embodiments, $R^1$, $R^2$, and $R^3$ are methyl.
In some embodiments, $R^1$, $R^2$, and $R^3$ are ethyl.
In some embodiments, $R^1$, $R^2$, and $R^3$ are propyl.
In some embodiments, $R^1$ and $R^2$ are methyl, and $R^3$ is ethyl.
In some embodiments, $R^1$ and $R^3$ are methyl, and $R^2$ is ethyl.
In some embodiments, $R^1$ and $R^2$ are ethyl, and $R^3$ is methyl.
In some embodiments, $R^1$ and $R^3$ are ethyl, and $R^2$ is methyl.
In some embodiments, $R^1$ and $R^2$ are propyl, and $R^3$ is methyl.
In some embodiments, $R^1$ and $R^3$ are propyl, and $R^2$ is methyl.
In some embodiments, $R^4$ is $C_2$-$C_5$ alkyl substituted with a hydroxyl.
In some embodiments, $R^4$ is

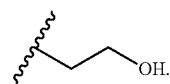

In some embodiments, the compound is according to Formula Ia:

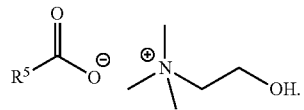

Formula Ia

In some embodiments, the compound is according to Formula Ib:

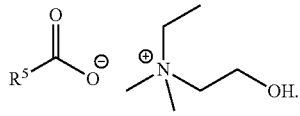

Formula Ib

In some embodiments, the compound is according to Formula Ic:

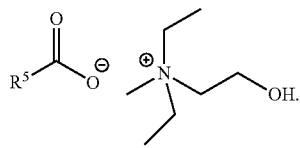

Formula Ic

In some embodiments, $R^5$ comprises a sequence with at least 75% sequence identity to the sequence of SEQ ID NO: 25.

In some embodiments, $R^5$ comprises the sequence of SEQ ID NO: 25.

In some embodiments, $R^5$ comprises C20 diacid-γ-Glu-(AEEA)2 attached to a residue of a sequence with at least 75% sequence identity to the sequence of SEQ ID NO: 25.

In some embodiments, $R^5$ comprises C20 diacid-γ-Glu-(AEEA)2 attached to a residue of the sequence of SEQ ID NO: 25.

In some embodiments, $R^5$ comprises C20 diacid-γ-Glu-(AEEA)2 attached to the Lys residue at the position 20 from the N-terminus of the sequence of SEQ ID NO: 25.

In some embodiments, the compound comprises a

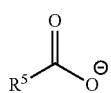

to

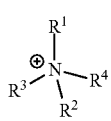

molar ratio of from about 1:1 to about 1:20.

In some embodiments, the compound comprises a

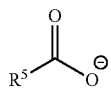

to

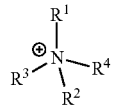

molar ratio of about 1:1.

In some embodiments, the compound comprises a

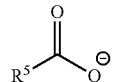

to

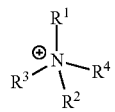

molar ratio of about 1:2.

In some embodiments, the compound comprises a

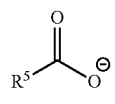

to

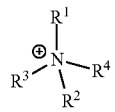

molar ratio of about 1:3.

In some embodiments, the compound comprises a

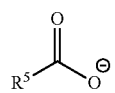

to

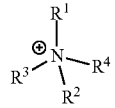

molar ratio of about 1:4.

In some embodiments, the compound comprises a

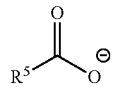

to

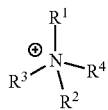

molar ratio of about 1:5.

In some embodiments, the compound comprises a

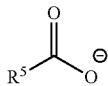

to

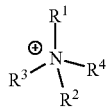

molar ratio of about 1:10.

In some embodiments, the compound comprises a

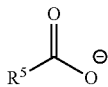

to

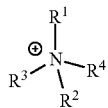

molar ratio of about 1:20.

In another aspect, provided herein is a method of increasing the solubility of a dual GIP/GLP-1 receptor agonist or functional variant thereof comprising preparing a composition comprising a compound according to Formula II:

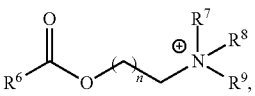

Formula II wherein:
- $R^6$ is a dual GIP/GLP-1 receptor agonist or functional variant thereof;
- $R^7$, $R^8$, and $R^9$ are independently unsubstituted or substituted $C_1$-$C_5$ alkyl; and
- n is 1, 2, 3, 4, or 5.

In another aspect, provided herein is a method of enhancing or improving the delivery efficiency a dual GIP/GLP-1 receptor agonist or functional variant thereof in a subject in need thereof comprising preparing a composition comprising compound according to Formula II:

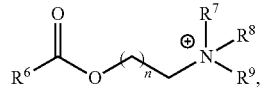

Formula II wherein:
- $R^6$ is a dual GIP/GLP-1 receptor agonist or functional variant thereof;
- $R^7$, $R^8$, and $R^9$ are independently unsubstituted or substituted $C_1$-$C_5$ alkyl; and
- n is 1, 2, 3, 4, or 5, and administering the composition to the subject.

In some embodiments, $R^7$, $R^8$, and $R^9$ are methyl.
In some embodiments, $R^7$, $R^8$, and $R^9$ are ethyl.
In some embodiments, $R^7$, $R^8$, and $R^9$ are propyl.
In some embodiments, $R^7$ and $R^8$ are methyl, and $R^9$ is ethyl.
In some embodiments, $R^7$ and $R^9$ are methyl, and $R^8$ is ethyl.
In some embodiments, $R^7$ and $R^8$ are ethyl, and $R^9$ is methyl.
In some embodiments, $R^7$ and $R^9$ are ethyl, and $R^8$ is methyl.
In some embodiments, $R^7$ and $R^8$ are propyl, and $R^9$ is methyl.
In some embodiments, $R^7$ and $R^9$ are propyl, and $R^8$ is methyl.
In some embodiments, n is 1.
In some embodiments, the compound is according to Formula IIa:

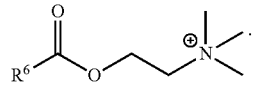

Formula IIa

In some embodiments, the compound is according to Formula IIb:

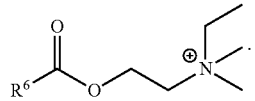

Formula IIb

In some embodiments, the compound is according to Formula IIc:

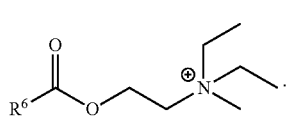

Formula IIc

In some embodiments, $R^6$ comprises a sequence with at least 75% sequence identity to the sequence of SEQ ID NO: 25.

In some embodiments, $R^6$ comprises the sequence of SEQ ID NO: 25.

In some embodiments, $R^6$ comprises C20 diacid-γ-Glu-(AEEA)2 attached to a residue of a sequence with at least 75% sequence identity to the sequence of SEQ ID NO: 25.

In some embodiments, $R^6$ comprises C20 diacid-γ-Glu-(AEEA)2 attached to a residue of the sequence of SEQ ID NO: 25.

In some embodiments, $R^6$ comprises C20 diacid-γ-Glu-(AEEA)2 attached to the Lys residue at the position 20 from the N-terminus of the sequence of SEQ ID NO: 25.

In some embodiments, the composition further comprises one or more ionic liquid.

In some embodiments, the one or more ionic liquid independently comprises a cation selected from the group consisting of aminoguanidine, choline or choline derivative, carnitine, acetylcholine, ammonium, tetramethyl ammonium, tetraethyl ammonium, tetrabutyl ammonium, and guanidine derivatives.

In some embodiments, the one or more ionic liquid independently comprises choline or choline derivative, carnitine, or acetylcholine.

In some embodiments, the one or more ionic liquid independently comprises an anion selected from the group consisting of (R)-α-Lipoic Acid, 12-Hydroxystearic Acid, 2-(4-Isobutylphenyl)propionic Acid, 2-(4,4-Dimethyl-2-pentanyl)-5,7,7-trimethyloctanoic Acid, 2-Aminoethanesulfonic Acid (Taurine Acid), 2-Hexyldecanoic Acid, 2-Hydroxyhippuric Acid, 3-(4-Hydroxyphenyl)propionic Acid, 3-Methylcrotonic Acid, 3,3-Diphenylpropionic Acid, 3,4-Dihydroxbenzoic Acid (Protocatechuic Acid), 3,7-Dimethyloctanoic Acid, 4-Hydroxybenzenesulfonic Acid, 4-Hydroxybenzoic Acid, 4-Methylhexanoic Acid, 4-Methyloctanoic Acid, 4-Methylvaleric Acid, 5-Norbornene-2-carboxylic Acid, 8-[(2-hydroxybenzoyl)amino] octanoic acid, Abietic Acid, Acetic Acid, Acetylcysteine, Aconitic Acid, Arachidonic Acid, Behenic Acid, Benzoic Acid, Caffeic Acid, Chenodeoxycholic Acid, Cis-Cinnamic acid, Citric Acid, Citronellic Acid, Crotonic Acid, D-(+)-Galactonic Acid, Decanoic Acid, Deoxycholic Acid, Dihydrocaffeic Acid, DL-2-Phenylpropionic (Hydratropic) Acid, DL-Tartaric Acid, DL-Tropic Acid, Eicosanedioic Acid, Eicosapentanoic Acid (EPA), Elaidic Acid, Ellagic Acid, Erucic Acid, Ethylenediaminetetraacetic Acid (EDTA), Formic Acid, Fumaric Acid, Geranic Acid, Glutaric Acid, Glycolic Acid, Heptanoic Acid, Hexanoic Acid, Hydrocinnamic Acid (3-Phenylpropionic Acid), Isobutyric Acid, Isovaleric Acid, L-(+)-Tartaric Acid, L-Ascorbic Acid, L-Aspartic Acid, L-Glutamic Acid, L-Glutathione reduced, Lactic Acid, Lauric Acid, Levulinic Acid, Linoleic Acid, Linolenic Acid, Lithocholic Acid, Maleic Acid, Malic Acid, Malonic Acid, Mandelic acid, Mesaconic Acid, Nicotinic Acid, Nonanoic Acid, Octanoic Acid, Oleic Acid, Oxalic Acid, p-Coumaric Acid, p-Toluenesulfonic Acid, Palmitic Acid, Perillic Acid, Phosphoric Acid, Pimelic Acid, Pivalic Acid, Propionic Acid, Pyroglutamic Acid, Pyruvic Acid, Ricinoleic Acid, Salicylic Acid (2-Hydroxybenzoic Acid), Sinapinic Acid (3,5-Dimethoxy-4-Hydroxycinnamic Acid), Sorbic Acid, Stearic acid, Succinic Acid, Syringic Acid, Tiglic Acid, Trans-2-Decenoic Acid, Trans-2-Hexenoic Acid, Trans-2-Octenoic Acid, Trans-3-Octenoic Acid, Trans-γ-Octenoic Acid, Trans-Cinnamic Acid, Trans-Ferulic Acid, Undecanoic Acid, Valeric Acid, Vanillic Acid, and α-Ketoglutaric Acid.

In some embodiments, the one or more ionic liquid independently comprises an anion selected from the group consisting of glycolic acid, tartaric acid, malic acid, hydrocinnamic acid, citric acid, cinnamic acid, mandelic acid, mesaconic acid, ricinoleic acid, linoleic acid, and tiglic acid.

In some embodiments, the one or more ionic liquid independently comprises an anion selected from the group consisting of cinnamic acid, mandelic acid, citric acid, ricinoleic acid, linoleic acid, and tiglic acid.

In some embodiments, the one or more ionic liquid independently comprises choline or choline derivative-cinnamic acid, choline or choline derivative-mandelic acid, choline or choline derivative-citric acid, choline or choline derivative-ricinoleic acid, choline or choline derivative-linoleic acid, or choline or choline derivative-tiglic acid.

In some embodiments, the one or more ionic liquid independently comprises carnitine-cinnamic acid, carnitine-mandelic acid, carnitine-citric acid, carnitine-ricinoleic acid, carnitine-linoleic acid, or carnitine-tiglic acid.

In some embodiments, the one or more ionic liquid independently comprises acetylcholine-cinnamic acid, acetylcholine-mandelic acid, acetylcholine-citric acid, acetylcholine-ricinoleic acid, acetylcholine-linoleic acid, or acetylcholine-tiglic acid.

In another aspect, provided herein is a method of increasing the solubility of a dual GIP/GLP-1 receptor agonist or functional variant thereof comprising preparing a composition comprising a dual GIP/GLP-1 receptor agonist or functional variant thereof and one or more ionic liquid.

In another aspect, provided herein is a method of enhancing or improving the delivery efficiency of a dual GIP/GLP-1 receptor agonist or functional variant thereof in a subject in need thereof comprising preparing a composition comprising a dual GIP/GLP-1 receptor agonist or functional variant thereof and one or more ionic liquid, and administering the composition to the subject.

In some embodiments, the one or more ionic liquid independently comprises a cation selected from the group consisting of aminoguanidine, choline or choline derivative, carnitine, acetylcholine, ammonium, tetramethyl ammonium, tetraethyl ammonium, tetrabutyl ammonium, and guanidine derivatives.

In some embodiments, the one or more ionic liquid independently comprises choline or choline derivative, carnitine, or acetylcholine.

In some embodiments, the one or more ionic liquid independently comprises an anion selected from the group consisting of (R)-α-Lipoic Acid, 12-Hydroxystearic Acid, 2-(4-Isobutylphenyl)propionic Acid, 2-(4,4-Dimethyl-2-pentanyl)-5,7,7-trimethyloctanoic Acid, 2-Aminoethanesulfonic Acid (Taurine Acid), 2-Hexyldecanoic Acid, 2-Hydroxyhippuric Acid, 3-(4-Hydroxyphenyl)propionic Acid, 3-Methylcrotonic Acid, 3,3-Diphenylpropionic Acid, 3,4-Dihydroxbenzoic Acid (Protocatechuic Acid), 3,7-Dimethyloctanoic Acid, 4-Hydroxybenzenesulfonic Acid, 4-Hydroxybenzoic Acid, 4-Methylhexanoic Acid, 4-Methyloctanoic Acid, 4-Methylvaleric Acid, 5-Norbornene-2-carboxylic Acid, 8-[(2-hydroxybenzoyl)amino] octanoic acid, Abietic Acid, Acetic Acid, Acetylcysteine, Aconitic Acid, Arachidonic Acid, Behenic Acid, Benzoic Acid, Caffeic Acid, Chenodeoxycholic Acid, Cis-Cinnamic acid, Citric Acid, Citronellic Acid, Crotonic Acid, D-(+)-Galactonic Acid, Decanoic Acid, Deoxycholic Acid, Dihydrocaffeic Acid, DL-2-Phenylpropionic (Hydratropic) Acid, DL-Tartaric Acid, DL-Tropic Acid, Eicosanedioic Acid, Eicosapentanoic Acid (EPA), Elaidic Acid, Ellagic Acid, Erucic Acid, Ethylenediaminetetraacetic Acid (EDTA), Formic Acid, Fumaric Acid, Geranic Acid, Glutaric Acid, Glycolic Acid, Heptanoic Acid, Hexanoic Acid, Hydrocinnamic Acid (3-Phenylpropionic Acid), Isobutyric Acid, Isovaleric Acid, L-(+)-Tartaric Acid, L-Ascorbic Acid, L-Aspartic Acid, L-Glutamic Acid, L-Glutathione reduced, Lactic Acid, Lauric Acid, Levulinic Acid, Linoleic Acid, Linolenic Acid, Lithocholic Acid, Maleic Acid, Malic Acid, Malonic Acid, Mandelic acid, Mesaconic Acid, Nicotinic Acid, Nonanoic Acid, Octanoic Acid, Oleic Acid, Oxalic Acid, p-Coumaric Acid, p-Toluenesulfonic Acid, Palmitic Acid, Perillic Acid, Phosphoric Acid, Pimelic Acid, Pivalic Acid, Propionic Acid, Pyroglutamic Acid, Pyruvic Acid, Ricinoleic Acid, Salicylic Acid (2-Hydroxybenzoic Acid), Sinapinic Acid (3,5-Dimethoxy-4-Hydroxycinnamic Acid), Sorbic Acid, Stearic acid, Succinic Acid, Syringic Acid, Tiglic Acid, Trans-2-Decenoic Acid, Trans-2-Hexenoic Acid, Trans-2-Octenoic Acid, Trans-3-Octenoic Acid, Trans-γ-Octenoic Acid, Trans-Cinnamic Acid, Trans-Ferulic Acid, Undecanoic Acid, Valeric Acid, Vanillic Acid, and α-Ketoglutaric Acid.

In some embodiments, the one or more ionic liquid independently comprises an anion selected from the group consisting of glycolic acid, tartaric acid, malic acid, hydrocinnamic acid, citric acid, cinnamic acid, mandelic acid, mesaconic acid, ricinoleic acid, linoleic acid, and tiglic acid.

In some embodiments, the one or more ionic liquid independently comprises an anion selected from the group consisting of cinnamic acid, mandelic acid, citric acid, ricinoleic acid, linoleic acid, and tiglic acid.

In some embodiments, the one or more ionic liquid independently comprises choline or choline derivative-cinnamic acid, choline or choline derivative-mandelic acid, choline or choline derivative-citric acid, choline or choline derivative-ricinoleic acid, choline or choline derivative-linoleic acid, or choline or choline derivative-tiglic acid.

In some embodiments, the one or more ionic liquid independently comprises carnitine-cinnamic acid, carnitine-mandelic acid, carnitine-citric acid, carnitine-ricinoleic acid, carnitine-linoleic acid, or carnitine-tiglic acid.

In some embodiments, the one or more ionic liquid independently comprises acetylcholine-cinnamic acid, acetylcholine-mandelic acid, acetylcholine-citric acid, acetylcholine-ricinoleic acid, acetylcholine-linoleic acid, or acetylcholine-tiglic acid.

In another aspect, provided herein is a method of enhancing the hydrophobicity of a therapeutic agent, comprising linking $R^{12}$ to a therapeutic agent, wherein $R^{12}$ is substituted or unsubstituted $C_5$-$C_{10}$; and wherein the therapeutic agent is a dual GIP/GLP-1 receptor agonist or functional variant thereof.

In some embodiments, $R^{12}$ is linked to

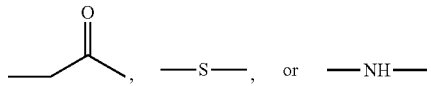

of the therapeutic agent.

In some embodiments, $R^{12}$ is linked to the therapeutic agent via a covalent bond or a linker.

In some embodiments, the linker is a non-cleavable linker.

In some embodiments, the linker comprises a maleimide alkane linker or a maleimide cyclohexane linker.

In some embodiments, the linker comprises or

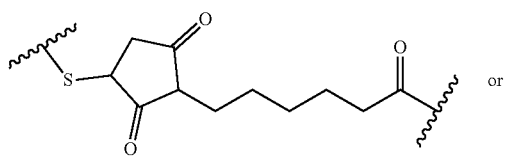

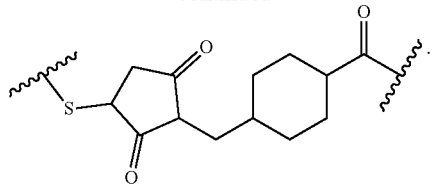

In some embodiments, the linker is a chemically cleavable linker.

In some embodiments, the linker comprises a hydrazone linker or a disulfide linker.

In some embodiments, the linker comprises or

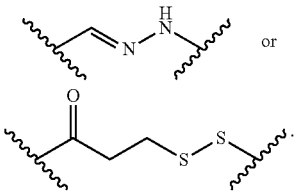

In some embodiments, $R^{12}$ is substituted or unsubstituted $C_{10}$.

In some embodiments, therapeutic agent comprises a sequence with at least 75% sequence identity to the sequence of SEQ ID NO: 25.

In some embodiments, the therapeutic agent comprises the sequence of SEQ ID NO: 25.

In some embodiments, the therapeutic agent comprises C20 diacid-γ-Glu-(AEEA)2 attached to a residue of a sequence with at least 75% sequence identity to the sequence of SEQ ID NO: 25.

In some embodiments, the therapeutic agent comprises C20 diacid-γ-Glu-(AEEA)2 attached to a residue of the sequence of SEQ ID NO: 25.

In some embodiments, the therapeutic agent comprises C20 diacid-γ-Glu-(AEEA)2 attached to the Lys residue at the position 20 from the N-terminus of the sequence of SEQ ID NO: 25.

In another aspect, provided herein is a method of enhancing or improving a delivery efficiency of a therapeutic agent in a subject in need thereof comprising adding at least one permeation enhancer to the compound as described herein, the composition as described herein, or the pharmaceutical composition as described herein, and administering the composition, the compound, or the pharmaceutical composition to the subject.

In some embodiments, the at least one permeation enhancer is selected from the group consisting of salcaprozate sodium (SNAC), sodium caprylate, sodium caprate, a bile salt, ethylenediaminetetraacetic acid (EDTA), ethylene glycol-bis-(2-aminoethylether)-N,N,N',N'-tetraacetic acid (EGTA), and 3-[N,N-Dimethyl(3-palmitoylaminopropyl)-ammonio]-propanesulfonate (PPS), and any combination thereof.

In some embodiments, the bile salt is selected from the group consisting of sodium deoxycholate, sodium chenodeoxycholate, sodium taurodeoxycholate, and a combination thereof.

Antibody or Antibody Fragment Thereof

As used herein, the term "antibody" refers to a protein or a polypeptide derived from an immunoglobulin molecule that specifically binds to an antigen. In some embodiments, an antibody is polyclonal or monoclonal. In some embodiments, an antibody comprises multiple chains or a single chain. In some embodiments, an antibody comprises an intact immunoglobulins. In some embodiments, an antibody is naturally driven. In some embodiments, an antibody is recombinantly driven. In some embodiments, an antibody is in the form of a single domain antibody, a maxibody, a minibody, a nanobody, an intrabody, a diabody, a triabody, a tetrabody, and a multispecific antibody.

As used herein, the term "antibody fragment" refers to at least a portion of an intact antibody or recombinant variants thereof. In some embodiments, the antibody fragment is an antigen binding domain that recognizes and specifically binds to an antigen. Exemplary antibody fragments include, but are not limited to, an Fab, an Fab', an F(ab')2, an Fv fragment, a scFv antibody fragments, a single domain antibodies (sdAb), a camelid VhH domain, and a single domain shark variable domain (BNAR).

In some embodiments, an antibody or an antibody fragment comprises an anti-tumor necrosis factor-alpha (TNF-α) antibody or an anti-TNF-α antibody fragment. In some embodiments, an antibody or an antibody fragment comprises a chimeric monoclonal anti-TNF-α antibody or an antibody fragment thereof. In some embodiments, an antibody or an antibody fragment comprises infliximab or an antibody fragment thereof.

As used herein, the term "infliximab" refers to a chimeric monoclonal antibody that binds to tumor necrosis factor-alpha (TNF-α).

In some embodiments, a chimeric monoclonal anti-TNF-α antibody or an antibody fragment thereof neutralizes TNF-α by preventing TNF-α from interacting with its receptors on the cell. In some embodiments, a chimeric monoclonal anti-TNF-α antibody or an antibody fragment thereof is used to treat autoimmune diseases, such as Crohn's disease, ulcerative colitis, rheumatoid arthritis, ankylosing spondylitis, psoriasis, psoriatic arthritis, and Behget's disease.

In some embodiments, a chimeric monoclonal anti-TNF-α antibody or an antibody fragment thereof comprises the heavy chain comprising the sequence of:

```
                                          (SEQ ID NO: 1)
EVKLEESGGGLVQPGGSMKLSCVASGFIFSNHWMNWVRQSPEKGLEWVA

EIRSKSINSATHYAESVKGRFTISRDDSKSAVYLQMTDLRTEDTGVYYC

SRNYYGSTYDYWGQGTTLTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK.
```

In some embodiments, a chimeric monoclonal anti-TNF-α antibody or an antibody fragment thereof comprises the heavy chain comprising the sequence of:

```
                                         (SEQ ID NO: 24)
EVKLEESGGGLVQPGGSMKLSCVASGFIFSNHWMNWVRQSPEKGLEWVA

EIRSKSINSATHYAESVKGRFTISRDDSKSAVYLQMTDLRTEDTGVYYC

SRNYYGSTYDYWGQGTTLTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKT.
```

In some embodiments, a chimeric monoclonal anti-TNF-α antibody or an antibody fragment thereof comprises the heavy chain comprising the sequence identified as PDB: 4G3Y_H by Pubmed.

In some embodiments, a chimeric monoclonal anti-TNF-α antibody or an antibody fragment thereof comprises the light chain comprising the sequence of:

```
                                          (SEQ ID NO: 2)
DILLTQSPAILSVSPGERVSFSCRASQFVGSSIHWYQQRINGSPRLLIK

YASESMSGIPSRFSGSGSGTDFTLSINTVESEDIADYYCQQSHSWPFTF

GSGTNLEVKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.
```

In some embodiment, Asn 300 (asparagine at the position 300) of the heavy chain of a chimeric monoclonal anti-TNF-α antibody or an antibody fragment thereof is a glycosylation site. In some embodiment, Asn 300 of the heavy chain of a chimeric monoclonal anti-TNF-α antibody or an antibody fragment thereof is glycosylated.

In some embodiments, a chimeric monoclonal anti-TNF-α antibody or an antibody fragment thereof comprises the light chain comprising the sequence identified as PDB: 4G3Y_L by Pubmed.

In some embodiments, an antibody or an antibody fragment comprises an anti-tumor necrosis factor-alpha (TNF-α) antibody or an anti-TNF-α antibody fragment. In some embodiments, an antibody or an antibody fragment comprises a monoclonal anti-TNF-α antibody or an antibody fragment thereof. In some embodiments, an antibody or an antibody fragment comprises adalimumab or an antibody fragment thereof.

As used herein, the term "adalimumab" refers to a monoclonal antibody that binds to TNF-α.

In some embodiments, a monoclonal anti-TNF-α antibody or an antibody fragment thereof works by inactivating TNF-α. In some embodiments, a monoclonal anti-TNF-α antibody or an antibody fragment thereof is used to treat rheumatoid arthritis, psoriatic arthritis, ankylosing spondylitis, Crohn's disease, ulcerative colitis, plaque psoriasis, hidradenitis suppurativa, uveitis, and juvenile idiopathic arthritis. In some embodiments, a monoclonal anti-TNF-α antibody or an antibody fragment thereof is a disease-modifying antirheumatic drug (DMARD).

In some embodiments, a monoclonal anti-TNF-α antibody or an antibody fragment thereof comprises the heavy chain comprising the sequence of:

(SEQ ID NO: 3)
EVQLVESGGGLVQPGRSLRLSCAASGFTFDDYAMHWVRQAPGKGLEWVS

AITWNSGHIDYADSVEGRFTISRDNAKNSLYLQMNSLRAEDTAVYYCAK

VSYLSTASSLDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSC.

In some embodiments, a monoclonal anti-TNF-α antibody or an antibody fragment thereof comprises the heavy chain comprising the sequence of:

(SEQ ID NO: 4)
EVQLVESGGGLVQPGRSLRLSCAASGFTFDDYAMHWVRQAPGKGLEWV

SAITWNSGHIDYADSVEGRFTISRDNAKNSLYLDMNSLRAEDTAVYYC

AKVSYLSTASSLDYWGQGTLVTVSSASTKGPSVFPLAPSSKSTSGGTA

ALGCLVKDYFPEPVTVSWNSGALTSGVHTFPAVLQSSGLYSLSSVVTV

PSSSLGTQTYICNVNHKPSNTKVDKKI.

In some embodiments, a monoclonal anti-TNF-α antibody or an antibody fragment thereof comprises the heavy chain comprising the sequence of:

(SEQ ID NO: 5)
EVQLVESGGGLVQPGRSLRLSCAASGFTFDDYAMHWVRQAPGKGLEWV

SAITWNSGHIDYADSVEGRFTISRDNAKNSLYLQMNSLRAEDTAVYYC

AKVSYLSTASSLDYWGQGTLVTVSSASTKGPSVFPLAPSSKSTSGGTA

ALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLG

GPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVM

HEALHNHYTQKSLSLSPGK.

In some embodiments, a monoclonal anti-TNF-α antibody or an antibody fragment thereof comprises the heavy chain comprising the sequence of: identified as PDB: 3WD5_H by Pubmed.

In some embodiments, a monoclonal anti-TNF-α antibody or an antibody fragment thereof comprises the light chain comprising the sequence of:

(SEQ ID NO: 6)
DIQMTQSPSSLSASVGDRVTITCRASQGIRNYLAWYQQKPGKAPKLLIY

AASTLQSGVPSRFSGSGSGTDFTLTISSLQPEDVATYYCQRYNRAPYTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

In some embodiments, a monoclonal anti-TNF-α antibody or an antibody fragment thereof comprises the light chain comprising the sequence of:

(SEQ ID NO: 7)
DIQMTQSPSSLSASVGDRVTITCRASQGIRNYLAWYQQKPGKAPKLLIY

AASTLQSGVPSRFSGSGSGTDFTLTISSLQPEDVATYYCQRYNRAPYTF

GQGTKVEIKRTVAAPTVKILQSSCDGGGHFPPTIQLLCLVSGYTPGTIQ

ITWLEDGQVMDVDLSTASTTQEGELASTQSELTLSQKHWLSDRTYTCQV

TYQGHTFEDSGKKCA.

In some embodiments, a monoclonal anti-TNF-α antibody or an antibody fragment thereof comprises the light chain comprising the sequence identified as PDB: 3WD5_L by Pubmed.

In some embodiments, an antibody or an antibody fragment comprises an anti-human interleukin 12 (IL-12) and interleukin 23 (IL-23) subunit antibody or an antibody fragment thereof. In some embodiments, an antibody or an antibody fragment comprises ustekinumab or an antibody fragment thereof.

As used herein, the term "ustekinumab" refers to a monoclonal antibody that targets a subunit of human interleukin 12 (IL-12) and interleukin 23 (IL-23), which regulate the immune system and immune-mediated inflammatory disorders.

In some embodiments, an anti-human IL-12 and IL-23 subunit antibody or an antibody fragment thereof is used to treat Crohn's disease, ulcerative colitis, plaque psoriasis and psoriatic arthritis.

In some embodiments, an anti-human IL-12 and IL-23 subunit antibody or an antibody fragment thereof comprises the heavy chain comprising the sequence of:

(SEQ ID NO: 8)
EVQLVQSGAEVKKPGESLKISCKGSGYSFTTYWLGWVRQMPGKGLDWIG

IMSPVDSDIRYSPSFQGQVTMSVDKSITTAYLQWNSLKASDTAMYYCAR

RRPGQGYFDFWGQGTLVTVSSSSTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKRVEPKSCDKTH.

In some embodiments, an anti-human IL-12 and IL-23 subunit antibody or an antibody fragment thereof comprises the heavy chain comprising the sequence identified as PDB: 3HMX_H by Pubmed.

In some embodiments, an anti-human IL-12 and IL-23 subunit antibody or an antibody fragment thereof comprises the light chain comprising the sequence of:

(SEQ ID NO: 9)
DIQMTQSPSSLSASVGDRVTITCRASQGISSWLAWYQQKPEKAPKSLIY

AASSLQSGVPSRFSGSGSGTDFTLTISSLQPEDFATYYCQQYNIYPYTF

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

In some embodiments, an anti-human IL-12 and IL-23 subunit antibody or an antibody fragment thereof comprises the light chain comprising the sequence identified as PDB: 3HMX_L by Pubmed.

In some embodiments, an antibody or an antibody fragment comprises a monoclonal anti-TNF-α antibody or an antibody fragment thereof. In some embodiments, an antibody or an antibody fragment comprises a human monoclonal anti-TNF-α antibody or an antibody fragment thereof. In some embodiments, an antibody or an antibody fragment comprises golimumab or an antibody fragment thereof.

As used herein, the term "golimumab" refers to a human monoclonal antibody that targets TNF-α.

In some embodiments, a human monoclonal anti-TNF-α antibody or an antibody fragment thereof works as a TNF-α inhibitor. In some embodiments, a human monoclonal anti-TNF-α antibody or an antibody fragment thereof functions as an effective modulator of inflammatory markers and bone metabolism. In some embodiments, a human monoclonal anti-TNF-α antibody or an antibody fragment thereof is used as an immunosuppressive medication.

In some embodiments, a human monoclonal anti-TNF-α antibody or an antibody fragment thereof comprises the heavy chain comprising the sequence of:

(SEQ ID NO: 10)
SKLQVQLVESGGGVVQPGRSLRLSCAASGFIFSSYAMHWVRQAPGNGLEW

VAFMSYDGSNKKYADSVKGRFTISRDNSKNTLYLQMNSLRAEDTAVYYCA

RDRGIAAGGNYYYGMDVWGQGTTVTVSS.

In some embodiments, a human monoclonal anti-TNF-α antibody or an antibody fragment thereof comprises the heavy chain comprising the sequence identified as PDB: 5YOY_R by Pubmed.

In some embodiments, a human monoclonal anti-TNF-α antibody or an antibody fragment thereof comprises the light chain comprising the sequence of:

(SEQ ID NO: 11)
AGSEIVLTQSPATLSLSPGERATLSCRASQSVYSYLAWYQQKPGQAPRLL

IYDASNRATGIPARFSGSGSGTDFTLTISSLEPEDFAVYYCQQRSNWPPF

TFGPGTKVDIKTSENLYFQ.

In some embodiments, a human monoclonal anti-TNF-α antibody or an antibody fragment thereof comprises the light chain comprising the sequence identified as PDB: 5YOY_O by Pubmed.

In some embodiments, an antibody or an antibody fragment comprises an anti-integrin α4β1 antibody or an antibody fragment thereof. In some embodiments, an antibody or an antibody fragment comprises a monoclonal anti-integrin α4β1 antibody or an antibody fragment thereof. In some embodiments, an antibody or an antibody fragment comprises natalizumab or an antibody fragment thereof.

As used herein, the term "natalizumab" refers to a monoclonal antibody that targets integrin α4β1.

In some embodiments, an anti-integrin α4β1 antibody or an antibody fragment thereof targets integrin α4β1 on white blood cells involved in inflammation. In some embodiments, an anti-integrin α4β1 antibody or an antibody fragment thereof stops white blood cells from entering the brain and spinal cord tissue by attaching to integrin, thereby reducing inflammation and the resulting nerve damage. In some embodiments, an anti-integrin α4β1 antibody or an antibody fragment thereof works by reducing the ability of inflammatory immune cells to attach to and pass through the cell layers lining the intestines and blood-brain barrier. In some embodiments, an anti-integrin α4β1 antibody or an antibody fragment thereof is used to treat the symptoms of both diseases, preventing relapse, vision loss, cognitive decline. In some embodiments, an anti-integrin α4β1 antibody or an antibody fragment thereof is used to treat multiple sclerosis and Crohn's disease. In some embodiments, an anti-integrin α4β1 antibody or an antibody fragment thereof increases rates of remission and prevents relapse in multiple sclerosis.

In some embodiments, an anti-integrin α4β1 antibody or an antibody fragment thereof comprises the heavy chain comprising the sequence of:

(SEQ ID NO: 12)
QVQLVQSGAEVKKPGASVKVSCKASGFNIKDTYIHWVRQAPGQRLEWMGR

IDPANGYTKYDPKFQGRVTITADTSASTAYMELSSLRSEDEAVYYCAREG

YYGNYGVYAMDYWGQGTLVTVSSASTKGPSVFPLAPCSRSTSESTAALGC

LVKDYFPEPVTVSWNSGALTSGVHTFPAVLQSSGLYSLSSVVTVPSSSLG

TKTYTCNVDHKPSNTKVDKRVE.

In some embodiments, an anti-integrin α4β1 antibody or an antibody fragment thereof comprises the heavy chain comprising the sequence of:

(SEQ ID NO: 13)
QVQLVQSGAEVKKPGASVKVSCKASGFNIKDTYIHWVRQAPGQRLEWMGR

IDPANGYTKYDPKFQGRVTITADTSASTAYMELSSLRSEDEAVYYCAREG

YYGNYGVYAMDYWGQGTLVTVSSASTKGPSVFPLAPCSRSTSESTAALGC

LVKDYFPEPVTVSWNSGALTSGVHTFPAVLQSSGLYSLSSVVTVPSSSLG

TKTYTCNVDHKPSNTKVDKRVESKYGPPENLYFQ.

In some embodiments, an anti-integrin α4β1 antibody or an antibody fragment thereof comprises the heavy chain comprising the sequence identified as PDB: 4IRZ_H by Pubmed.

In some embodiments, an anti-integrin α4β1 antibody or an antibody fragment thereof comprises the light chain comprising the sequence of:

(SEQ ID NO: 14)
DIQMTQSPSSLSASVGDRVTITCKTSQDINKYMAWYQQTPGKAPRLLIHY

TSALQPGIPSRFSGSGSGRDYTFTISSLQPEDIATYYCLQYDNLWTFGQG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNR.

In some embodiments, an anti-integrin α4β1 antibody or an antibody fragment thereof comprises the light chain comprising the sequence of:

(SEQ ID NO: 15)
DIQMTQSPSSLSASVGDRVTITCKTSQDINKYMAWYQQTPGKAPRLLIHY

TSALQPGIPSRFSGSGSGRDYTFTISSLQPEDIATYYCLQYDNLWTFGQG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRG.

In some embodiments, an anti-integrin α4β1 antibody or an antibody fragment thereof comprises the light chain comprising the sequence identified as PDB: 4IRZ_L by Pubmed.

In some embodiments, an antibody or an antibody fragment comprises an anti-integrin α4β7 antibody or an antibody fragment thereof. In some embodiments, an antibody or an antibody fragment comprises a monoclonal anti-integrin α4β7 antibody or an antibody fragment thereof. In some embodiments, an antibody or an antibody fragment comprises vedolizumab or an antibody fragment thereof.

As used herein, the term "vedolizumab" refers to a monoclonal antibody that targets integrin α4β7.

In some embodiments, an anti-integrin α4β7 antibody or an antibody fragment thereof blocks integrin α4β7, resulting in gut-selective anti-inflammatory activity. In some embodiments, an anti-integrin α4β7 antibody or an antibody fragment thereof is used to treat ulcerative colitis and Crohn's disease.

In some embodiments, an anti-integrin α4β7 antibody or an antibody fragment thereof comprises the heavy chain comprising the sequence of:

(SEQ ID NO: 16)
QVQLVQSGAEVKKPGASVKVSCKGSGYTFTSYWMHWVRQAPGQRLEWIGE

IDPSESNTNYNQKFKGRVTLTVDISASTAYMELSSLRSEDTAVYYCARGG

YDGWDYAIDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELAGAPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K.

In some embodiments, an anti-integrin α4β7 antibody or an antibody fragment thereof comprises the light chain comprising the sequence of:

(SEQ ID NO: 17)
DVVMTQSPLSLPVTPGEPASISCRSSQSLAKSYGNTYLSWYLQKPGQSPQ

LLIYGISNRFSGVPDRFSGSGSGTDFTLKISRVEAEDVGVYYCLQGTHQP

YTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

In some embodiments, an antibody or an antibody fragment comprises a fragment of an anti-TNF-α antibody. In some embodiments, an antibody or an antibody fragment comprises a fragment of a monoclonal anti-TNF-α antibody. In some embodiments, an antibody or an antibody fragment comprises certolizumab pegol.

As used herein, the term "certolizumab pegol" refers to a fragment of a monoclonal antibody specific to TNF-α.

In some embodiments, a fragment of an anti-TNF-α antibody is used to treat Crohn's disease, rheumatoid arthritis, psoriatic arthritis and ankylosing spondylitis.

In some embodiments, a fragment of an anti-TNF-α antibody comprises the heavy chain comprising the sequence of:

(SEQ ID NO: 18)
EVQLVESGGGLVQPGGSLRLSCAASGYVFTDYGMNWVRQAPGKGLEWMGW

INTYIGEPIYADSVKGRFTFSLDTSKSTAYLQMNSLRAEDTAVYYCARGY

RSYAMDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCAA.

In some embodiments, a fragment of an anti-TNF-α antibody comprises the light chain comprising the sequence of:

(SEQ ID NO: 19)
DIQMTQSPSSLSASVGDRVTITCKASQNVGTNVAWYQQKPGKAPKALIYS

ASFLYSGVPYRFSGSGSGTDFTLTISSLQPEDFATYYCQQYNIYPLTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some embodiments, the therapeutic agent or an antibody or an antibody fragment comprises: (i) a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 1 or SEQ ID NO: 24, a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 2, or a combination thereof, (ii) a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 3, SEQ ID NO: 4, or SEQ ID NO: 5, a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 6 or SEQ ID NO: 7, or any combination thereof; (iii) a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 8, a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 9, or a combination thereof; (iv) a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 10, a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 11, or a combination thereof; (v) a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 12 or SEQ ID NO: 13, a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 14 or SEQ ID NO: 15, or any combination thereof; (vi) a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 16, a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 17, or a combination thereof, or (vii) a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 18, a sequence with at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% sequence identity to the sequence of SEQ ID NO: 19, or a combination thereof.

In some embodiments, the therapeutic agent comprises: (i) the sequence of SEQ ID NO: 1 or SEQ ID NO: 24, the sequence of SEQ ID NO: 2, or a combination thereof; (ii) the sequence of SEQ ID NO: 3, SEQ ID NO: 4, or SEQ ID NO: 5, the sequence of SEQ ID NO: 6 or SEQ ID NO: 7, or any combination thereof; (iii) the sequence of SEQ ID NO: 8, the sequence of SEQ ID NO: 9, or a combination thereof; (iv) the sequence of SEQ ID NO: 10, the sequence of SEQ ID NO: 11, or a combination thereof; (v) the sequence of SEQ ID NO: 12 or SEQ ID NO: 13, the sequence of SEQ ID NO: 14 or SEQ ID NO: 15, or any combination thereof; (vi) the sequence of SEQ ID NO: 16, the sequence of SEQ ID NO: 17, or a combination thereof; or (vii) the sequence of SEQ ID NO: 18, the sequence of SEQ ID NO: 19, or a combination thereof.

In some embodiments, the therapeutic agent comprises: (i) the sequence of SEQ ID NO: 1 or SEQ ID NO: 24 and the sequence of SEQ ID NO: 2; (ii) the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7; (iii) the sequence of SEQ ID NO: 8 and the sequence of SEQ ID NO: 9; (iv) the sequence of SEQ ID NO: 10 and the sequence of SEQ ID NO: 11; (v) the sequence of SEQ ID NO: 12 and the sequence of SEQ ID NO: 14, or the sequence of SEQ ID NO: 13 and the sequence of SEQ ID NO: 15; (vi) the sequence of SEQ ID NO: 16 and the sequence of SEQ ID NO: 17; or (vii) the sequence of SEQ ID NO: 18 and the sequence of SEQ ID NO: 19.

As used herein, "TNF-α," also known as tumor necrosis factor alpha, TNF, DIF, TNF-alpha, TNFA, TNFSF2, Tumour necrosis factor, tumor necrosis factor, TNLG1F, refers to a member of the TNF superfamily, which consists of various transmembrane proteins with a homologous TNF domain. In some embodiments, TNF-α, as an adipokine, promotes insulin resistance, and is associated with obesity-induced type 2 diabetes. In some embodiments, TNF-α, as a cytokine, is used by the immune system for cell signaling. TNF-α, as used herein, includes any of the recombinant or naturally-occurring forms of TNF-α or variants or homologs thereof that have or maintain TNF-α activity (e.g., at least 40% 50%, 60%, 70%, 80%, 90%, 95%, 96%, 97%, 98%, 99% or 100% activity). In some aspects, the variants or homologs have at least 40%, 45%, 50%, 55%, 60%, 65%, 70%, 75%, 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring TNF-α. In some embodiments, TNF-α is substantially identical to the protein identified by the UniProt reference number P01375 or a variant or homolog having substantial identity thereto.

As used herein, "IL-12," also known as interleukin 12, refers to a heterodimeric cytokine encoded by two separate genes, IL-12A (p35) and IL-12B (p40). In some embodiments, IL-12 is naturally produced by dendritic cells, macrophages, neutrophils, and human B-lymphoblastoid cells in response to antigenic stimulation. IL-12 belongs to the IL-12 family, which comprises the heterodimeric cytokines including IL-12, IL-23, IL-27 and IL-35 "IL-12A," as used herein, includes any of the recombinant or naturally-occurring forms of IL-12A or variants or homologs thereof that have or maintain IL-12A activity (e.g., at least 40% 50%, 60%, 70%, 80%, 90%, 95%, 96%, 97%, 98%, 99% or 100% activity). In some aspects, the variants or homologs have at least 40%, 45%, 50%, 55%, 60%, 65%, 70%, 75%, 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring IL-12A. In some embodiments, IL-12A is substantially identical to the protein identified by the UniProt reference number P29459 or a variant or homolog having substantial identity thereto. "IL-12B," as used herein, includes any of the recombinant or naturally-occurring forms of IL-12B or variants or homologs thereof that have or maintain IL-12B activity (e.g., at least 40% 50%, 60%, 70%, 80%, 90%, 95%, 96%, 97%, 98%, 99% or 100% activity). In some aspects, the variants or homologs have at least 40%, 45%, 50%, 55%, 60%, 65%, 70%, 75%, 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring IL-12B. In some embodiments, IL-12B is substantially identical to the protein identified by the UniProt reference number P29460 or a variant or homolog having substantial identity thereto.

As used herein, "IL-23," also known as interleukin 23, refers to a heterodimeric cytokine composed of an IL-12B (IL-12p40) subunit and an IL-23A (IL-23p19) subunit. IL-23 belongs to the IL-12 family of cytokines. In some embodiments, IL-23 is an inflammatory cytokine that plays a key role for T helper type 17 cell (Th17 cell) maintenance and expansion. "IL-23A," as used herein, includes any of the recombinant or naturally-occurring forms of IL-23A or variants or homologs thereof that have or maintain IL-23A activity (e.g., at least 40% 50%, 60%, 70%, 80%, 90%, 95%, 96%, 97%, 98%, 99% or 100% activity). In some aspects, the variants or homologs have at least 40%, 45%, 50%, 55%, 60%, 65%, 70%, 75%, 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring IL-23A. In some embodiments, IL-23A is substantially identical to the protein identified by the UniProt reference number Q9NPF7 or a variant or homolog having substantial identity thereto.

As used herein, "integrin α4β1," also known as very late antigen-4 refers to an integrin dimer composed of CD49d (alpha 4) and CD29 (beta 1). "integrin α4 (integrin alpha-4)," as used herein, includes any of the recombinant or naturally-occurring forms of integrin α4 or variants or homologs thereof that have or maintain integrin α4 activity (e.g., at least 40% 50%, 60%, 70%, 80%, 90%, 95%, 96%, 97%, 98%, 99% or 100% activity). In some aspects, the variants or homologs have at least 40%, 45%, 50%, 55%, 60%, 65%, 70%, 75%, 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring integrin α4. In some embodiments, integrin α4 is substantially identical to the protein identified by the UniProt reference number P13612 or a variant or homolog having substantial identity thereto. "integrin β1 (integrin beta-1)," as used herein, includes any of the recombinant or naturally-occurring forms of integrin β1 or variants or homologs thereof that have or maintain integrin β1 activity (e.g., at least 40% 50%, 60%, 70%, 80%, 90%, 95%, 96%, 97%, 98%, 99% or 100% activity). In some aspects, the variants or homologs have at least 40%, 45%, 50%, 55%, 60%, 65%, 70%, 75%, 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring integrin β1. In some embodiments, integrin β1 is substantially identical to the protein identified by the UniProt reference number P05556 or a variant or homolog having substantial identity thereto.

As used herein, "integrin α4β7," also known as LPAM-1, lymphocyte Peyer's patch adhesion molecule 1, a dimer of Integrin alpha-4 and Integrin beta-7 refers to an integrin dimer composed of CD49d (alpha 4) and beta 7. "integrin β7 (integrin beta-7)," as used herein, includes any of the recombinant or naturally-occurring forms of integrin β1 or variants or homologs thereof that have or maintain integrin β7 activity (e.g., at least 40% 50%, 60%, 70%, 80%, 90%, 95%, 96%, 97%, 98%, 99% or 100% activity). In some aspects, the variants or homologs have at least 40%, 45%, 50%, 55%, 60%, 65%, 70%, 75%, 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring integrin β7. In some embodiments, integrin β7 is substantially identical to the protein identified by the UniProt reference number P26010 or a variant or homolog having substantial identity thereto.

In some embodiments, an antibody or an antibody fragment encompasses polypeptides having the sequences specified, or sequences substantially identical or similar thereto, for example, sequences at least 60%, 65%, 70%, 75%, 80%, 85%, 90%. 91%, 92%, 93%, 94%, 95%, 96%, 97%, 98%, 99%, 99.5%, 99.6%, 99.7%, 99.8%, or 99.9% identical or higher to the sequence specified.

The terms "homology" and "sequence identity" are used interchangeably herein and refer to the subunit sequence identity between two polypeptide molecules. The percent identity between the two sequences is a function of the number of identical positions shared by the sequences, taking into account the number of gaps, and the length of each gap. The comparison of sequences and determination of percent identity between two sequences can be accomplished using a mathematical algorithm. In some embodiments, the percent identity between two amino acid sequences is determined using the Needleman and Wunsch ((1970) J. Mol. Biol. 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In some embodiments, the percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4. In some embodiments, the percent identity can be determined using the on-line homology algorithm "BLAST" program, publicly available at http)://www.ncbi.nlm.nih-.gov/BLAST/.

A nucleic acid molecule, as described herein, can be a vector, an expression vector, an inhibitory nucleic acid, an aptamer, a template molecule or cassette (e.g., for gene editing), or a targeting molecule (e.g., for CRISPR-Cas technologies), or any other natural or synthetic nucleic acid molecule intended for delivery to an organism.

The term "unsubstituted," as used herein, means that the specified group bears no substituents. The term "substituted," as used herein, unless otherwise indicated, can refer to the replacement of one or more hydrogen radicals in a given structure individually and independently with the radical of a specified substituent.

In any of the embodiments, the drug may be designed with the intent of treating a local tissue, for example, the mucosal membrane of the intestine, a distant tissue, e.g., the liver, or systemic circulation.

In some embodiments, a composition as described herein, e.g., a composition comprising ionic liquids and a drug, can further comprise a pharmaceutically acceptable excipient. Suitable excipients include, for example, water, saline, glycerol, ethanol or the like and combinations thereof. In addition, if desired, the composition can contain minor amounts of additional excipients such as emulsifying agents, surfactants, pH buffering agents and the like which enhance the effectiveness of the drug.

In some embodiments, the composition comprising an ionic liquid may be further encapsulated in a dosage designed to facilitate delivery to an organism. Non-limiting examples of such doses include capsules, tablets, or syrups.

In some embodiments, formulation may require excipients sugars such as lactose; starches, such as corn starch; cellulose, cellulose derivatives, such as sodium carboxymethyl cellulose; gelatin; and other compatible substances considered commonly in pharmaceutical formulations.

The term "effective amount" as used herein refers to the amount of a composition needed to alleviate at least one or more symptom of the disease or disorder and relates to a sufficient amount of pharmacological composition to provide the desired effect.

In some embodiments, the composition comprises a

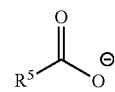

to

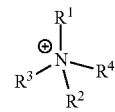

molar ratio of from about 1:1 to about 1:164. In some embodiments, the composition comprises a

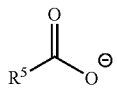

to

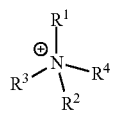

molar ratio of from about 1:1 to about 1:500, from about 1:1 to about 1:499, from about 1:1 to about 1:498, from about 1:1 to about 1:497, from about 1:1 to about 1:496, from about 1:1 to about 1:495, from about 1:1 to about 1:494, from about 1:1 to about 1:493, from about 1:1 to about 1:492, from about 1:1 to about 1:491, from about 1:1 to about 1:490, from about 1:1 to about 1:489, from about 1:1 to about 1:488, from about 1:1 to about 1:487, from about 1:1 to about 1:486, from about 1:1 to about 1:485, from about 1:1 to about 1:484, from about 1:1 to about 1:483, from about 1:1 to about 1:482, from about 1:1 to about 1:481, from about 1:1 to about 1:480, from about 1:1 to about 1:479, from about 1:1 to about 1:478, from about 1:1 to about 1:477, from about 1:1 to about 1:476, from about 1:1 to about 1:475, from about 1:1 to about 1:474, from about 1:1 to about 1:473, from about 1:1 to about 1:472, from about 1:1 to about 1:471, from about 1:1 to about 1:470, from about 1:1 to about 1:469, from about 1:1 to about 1:468, from about 1:1 to about 1:467, from about 1:1 to about 1:466, from about 1:1 to about 1:465, from about 1:1 to about 1:464, from about 1:1 to about 1:463, from about 1:1 to about 1:462, from about 1:1 to about 1:461, from about 1:1 to about 1:460, from about 1:1 to about 1:459, from about 1:1 to about 1:458, from about 1:1 to about 1:457, from about 1:1 to about 1:456, from about 1:1 to about 1:455, from about 1:1 to about 1:454, from about 1:1 to about 1:453, from about 1:1 to about 1:452, from about 1:1 to about 1:451, from about 1:1 to about 1:450, from about 1:1 to about 1:449, from about 1:1 to about 1:448, from about 1:1 to about 1:447, from about 1:1 to about 1:446, from about 1:1 to about 1:445, from about 1:1 to about 1:444, from about 1:1 to about 1:443, from about 1:1 to about 1:442, from about 1:1 to about 1:441, from about 1:1 to about 1:440, from about 1:1 to about 1:439, from about 1:1 to about 1:438, from about 1:1 to about 1:437, from about 1:1 to about 1:436, from about 1:1 to about 1:435, from about 1:1 to about 1:434, from about 1:1 to about 1:433, from about 1:1 to about 1:432, from about 1:1 to about 1:431, from about 1:1 to about 1:430, from about 1:1 to about 1:429, from about 1:1 to about 1:428, from about 1:1 to about 1:427, from about 1:1 to about 1:426, from about 1:1 to about 1:425, from about 1:1 to about 1:424, from about 1:1 to about 1:423, from about 1:1 to about 1:422, from about 1:1 to about 1:421, from about 1:1 to about 1:420, from about 1:1 to about 1:419, from about 1:1 to about 1:418, from about 1:1 to about 1:417, from about 1:1 to about 1:416, from about 1:1 to about 1:415, from about 1:1 to about 1:414, from about 1:1 to about 1:413, from about 1:1 to about 1:412, from about 1:1 to about 1:411, from about 1:1 to about 1:410, from about 1:1 to about 1:409, from about 1:1 to about 1:408, from about 1:1 to about 1:407, from about 1:1 to about 1:406, from about 1:1 to about 1:405, from about 1:1 to about 1:404, from about 1:1 to about 1:403, from about 1:1 to about 1:402, from about 1:1 to about 1:401, from about 1:1 to about 1:400, from about 1:1 to about 1:399, from about 1:1 to about 1:398, from about 1:1 to about 1:397, from about 1:1 to about 1:396, from about 1:1 to about 1:395, from about 1:1 to about 1:394, from about 1:1 to about 1:393, from about 1:1 to about 1:392, from about 1:1 to about 1:391, from about 1:1 to about 1:390, from about 1:1 to about 1:389, from about 1:1 to about 1:388, from about 1:1 to about 1:387, from about 1:1 to about 1:386, from about 1:1 to about 1:385, from about 1:1 to about 1:384, from about 1:1 to about 1:383, from about 1:1 to about 1:382, from about 1:1 to about 1:381, from about 1:1 to about 1:380, from about 1:1 to about 1:379, from about 1:1 to about 1:378, from about 1:1 to about 1:377, from about 1:1 to about 1:376, from about 1:1 to about 1:375, from about 1:1 to about 1:374, from about 1:1 to about 1:373, from about 1:1 to about 1:372, from about 1:1 to about 1:371, from about 1:1 to about 1:370, from about 1:1 to about 1:369, from about 1:1 to about 1:368, from about 1:1 to about 1:367, from about 1:1 to about 1:366, from about 1:1 to about 1:365, from about 1:1 to about 1:364, from about 1:1 to about 1:363, from about 1:1 to about 1:362, from about 1:1 to about 1:361, from about 1:1 to about 1:360, from about 1:1 to about 1:359, from about 1:1 to about 1:358, from about 1:1 to about 1:357, from about 1:1 to about 1:356, from about 1:1 to about 1:355, from about 1:1 to about 1:354, from about 1:1 to about 1:353, from about 1:1 to about 1:352, from about 1:1 to about 1:351, from about 1:1 to about 1:350, from about 1:1 to about 1:349, from about 1:1 to about 1:348, from about 1:1 to about 1:347, from about 1:1 to about 1:346, from about 1:1 to about 1:345, from about 1:1 to about 1:344, from about 1:1 to about 1:343, from about 1:1 to about 1:342, from about 1:1 to about 1:341, from about 1:1 to about 1:340, from about 1:1 to about 1:339, from about 1:1 to about 1:338, from about 1:1 to about 1:337, from about 1:1 to about 1:336, from about 1:1 to about 1:335, from about 1:1 to about 1:334, from about 1:1 to about 1:333, from about 1:1 to about 1:332, from about 1:1 to about 1:331, from about 1:1 to about 1:330, from about 1:1 to about 1:329, from about 1:1 to about 1:328, from about 1:1 to about 1:327, from about 1:1 to about 1:326, from about 1:1 to about 1:325, from about 1:1 to about 1:324, from about 1:1 to about 1:323, from about 1:1 to about 1:322, from about 1:1 to about 1:321, from about 1:1 to about 1:320, from about 1:1 to about 1:319, from about 1:1 to about 1:318, from about 1:1 to about 1:317, from about 1:1 to about 1:316, from about 1:1 to about 1:315, from about 1:1 to about 1:314, from about 1:1 to about 1:313, from about 1:1 to about 1:312, from about 1:1 to about 1:311, from about 1:1 to about 1:310, from about 1:1 to about 1:309, from about 1:1 to about 1:308, from about 1:1 to about 1:307, from about 1:1 to about 1:306, from about 1:1 to about 1:305, from about 1:1 to about 1:304, from about 1:1 to about 1:303, from about 1:1 to about 1:302, from about 1:1 to about 1:301, from about 1:1 to about 1:300, from about 1:1 to about 1:299, from about 1:1 to about 1:298, from about 1:1 to about 1:297, from about 1:1 to about 1:296, from about 1:1 to about 1:295, from about 1:1 to about 1:294, from about 1:1 to about 1:293, from about 1:1 to about 1:292, from about 1:1 to about 1:291, from about 1:1 to about 1:290, from about 1:1 to about 1:289, from about 1:1 to about 1:288, from about 1:1 to about 1:287, from about 1:1 to about 1:286, from about 1:1 to about 1:285, from about 1:1 to about 1:284, from about 1:1 to about 1:283, from about 1:1 to about 1:282, from about 1:1 to about 1:281, from about 1:1 to about 1:280, from about 1:1 to about 1:279, from about 1:1 to about 1:278, from about 1:1 to about 1:277, from about 1:1 to about 1:276, from about 1:1 to about 1:275, from about 1:1 to about 1:274, from about 1:1 to about 1:273, from about 1:1 to about 1:272, from about 1:1 to about 1:271, from about 1:1 to about 1:270, from about 1:1 to about 1:269, from about 1:1 to about 1:268, from about 1:1 to about 1:267, from about 1:1 to about 1:266, from about 1:1 to about 1:265, from about 1:1 to about 1:264, from about 1:1 to about 1:263, from about 1:1 to about 1:262, from about 1:1 to about 1:261, from about 1:1 to about 1:260, from about 1:1 to about 1:259, from about 1:1 to about 1:258, from about 1:1 to about 1:257, from about 1:1 to about 1:256, from about 1:1 to about 1:255, from about 1:1 to about 1:254, from about 1:1 to about 1:253, from about 1:1 to about 1:252, from about 1:1 to about 1:251, from about 1:1 to about 1:250, from about 1:1 to about 1:249, from about 1:1 to about 1:248, from about 1:1 to about 1:247, from about 1:1 to about 1:246, from about 1:1 to about 1:245, from about 1:1 to about 1:244, from about 1:1 to about 1:243, from about 1:1 to about 1:242, from about 1:1 to about 1:241, from about 1:1 to about 1:240, from about 1:1 to about 1:239, from about 1:1 to about 1:238, from about 1:1 to about 1:237, from about 1:1 to about 1:236, from about 1:1 to about 1:235, from about 1:1 to about 1:234, from about 1:1 to about 1:233, from about 1:1 to about 1:232, from about 1:1 to about 1:231, from about 1:1 to about 1:230, from about 1:1 to about 1:229, from about 1:1 to about 1:228, from about 1:1 to about 1:227, from about 1:1 to about 1:226, from about 1:1 to about 1:225, from about 1:1 to about 1:224, from about 1:1 to about 1:223, from about 1:1 to about 1:222, from about 1:1 to about 1:221, from about 1:1 to about 1:220, from about 1:1 to about 1:219, from about 1:1 to about 1:218, from about 1:1 to about 1:217, from about 1:1 to about 1:216, from about 1:1 to about 1:215, from about 1:1 to about 1:214, from about 1:1 to about 1:213, from about 1:1 to about 1:212, from about 1:1 to about 1:211, from about 1:1 to about 1:210, from about 1:1 to about 1:209, from about 1:1 to about 1:208, from about 1:1 to about 1:207, from about 1:1 to about 1:206, from about 1:1 to about 1:205, from about 1:1 to about 1:204, from about 1:1 to about 1:203, from about 1:1 to about 1:202, from about 1:1 to about 1:201, from about 1:1 to about 1:200, from about 1:1 to about 1:199, from about 1:1 to about 1:198, from about 1:1 to about 1:197, from about 1:1 to about 1:196, from about 1:1 to about 1:195, from about 1:1 to about 1:194, from about 1:1 to about 1:193, from about 1:1 to about 1:192, from about 1:1 to about 1:191, from about 1:1 to about 1:190, from about 1:1 to about 1:189, from about 1:1 to about 1:188, from about 1:1 to about 1:187, from about 1:1 to about 1:186, from about 1:1 to about 1:185, from about 1:1 to about 1:184, from about 1:1 to about 1:183, from about 1:1 to about 1:182, from about 1:1 to about 1:181, from about 1:1 to about 1:180, from about 1:1 to about 1:179, from about 1:1 to about 1:178, from about 1:1 to about 1:177, from about 1:1 to about 1:176, from about 1:1 to about 1:175, from about 1:1 to about 1:174, from about 1:1 to about 1:173, from about 1:1 to about 1:172, from about 1:1 to about 1:171, from about 1:1 to about 1:170, from about 1:1 to about 1:169, from about 1:1 to about 1:168, from about 1:1 to about 1:167, from about 1:1 to about 1:166, from about 1:1 to about 1:165, from about 1:1 to about 1:164, from about 1:1 to about 1:163, from about 1:1 to about 1:162, from about 1:1 to about 1:161, from about 1:1 to about 1:160, from about 1:1 to about 1:159, from about 1:1 to about 1:158, from about 1:1 to about 1:157, from about 1:1 to about 1:156, from about 1:1 to about 1:155, from about 1:1 to about 1:154, from about 1:1 to about 1:153, from about 1:1 to about 1:152, from about 1:1 to about 1:151, from about 1:1 to about 1:150, from about 1:1 to about 1:149, from about 1:1 to about 1:148, from about 1:1 to about 1:147, from about 1:1 to about 1:146, from about 1:1 to about 1:145, from about 1:1 to about 1:144, from about 1:1 to about 1:143, from about 1:1 to about 1:142, from about 1:1 to about 1:141, from about 1:1 to about 1:140, from about 1:1 to about 1:139, from about 1:1 to about 1:138, from about 1:1 to about 1:137, from about 1:1 to about 1:136, from about 1:1 to about 1:135, from about 1:1 to about 1:134, from about 1:1 to about 1:133, from about 1:1 to about 1:132, from about 1:1 to about 1:131, from about 1:1 to about 1:130, from about 1:1 to about 1:129, from about 1:1 to about 1:128, from about 1:1 to about 1:127, from about 1:1 to about 1:126, from about 1:1 to about 1:125, from about 1:1 to about 1:124, from about 1:1 to about 1:123, from about 1:1 to about 1:122, from about 1:1 to about 1:121, from about 1:1 to about 1:120, from about 1:1 to about 1:119, from about 1:1 to about 1:118, from about 1:1 to about 1:117, from about 1:1 to about 1:116, from about 1:1 to about 1:115, from about 1:1 to about 1:114, from about 1:1 to about 1:113, from about 1:1 to about 1:112, from about 1:1 to about 1:111, from about 1:1 to about 1:110, from about 1:1 to about 1:109, from about 1:1 to about 1:108, from about 1:1 to about 1:107, from about 1:1 to about 1:106, from about 1:1 to about 1:105, from about 1:1 to about 1:104, from about 1:1 to about 1:103, from about 1:1 to about 1:102, from about 1:1 to about 1:101, from about 1:1 to about 1:100, from about 1:1 to about 1:99, from about 1:1 to about 1:98, from about 1:1 to about 1:97, from about 1:1 to about 1:96, from about 1:1 to about 1:95, from about 1:1 to about 1:94, from about 1:1 to about 1:93, from about 1:1 to about 1:92, from about 1:1 to about 1:91, from about 1:1 to about 1:90, from about 1:1 to about 1:89, from about 1:1 to about 1:88, from about 1:1 to about 1:87, from about 1:1 to about 1:86, from about 1:1 to about 1:85, from about 1:1 to about 1:84, from about 1:1 to about 1:83, from about 1:1 to about 1:82, from about 1:1 to about 1:81, from about 1:1 to about 1:80, from about 1:1 to about 1:79, from about 1:1 to about 1:78, from about 1:1 to about 1:77, from about 1:1 to about 1:76, from about 1:1 to about 1:75, from about 1:1 to about 1:74, from about 1:1 to about 1:73, from about 1:1 to about 1:72, from about 1:1 to about 1:71, from about 1:1 to about 1:70, from about 1:1 to about 1:69, from about 1:1 to about 1:68, from about 1:1 to about 1:67, from about 1:1 to about 1:66, from about 1:1 to about 1:65, from about 1:1 to about 1:64, from about 1:1 to about 1:63, from about 1:1 to about 1:62, from about 1:1 to about 1:61, from about 1:1 to about 1:60, from about 1:1 to about 1:59, from about 1:1 to about 1:58, from about 1:1 to about 1:57, from about 1:1 to about 1:56, from about 1:1 to about 1:55, from about 1:1 to about 1:54, from about 1:1 to about 1:53, from about 1:1 to about 1:52, from about 1:1 to about 1:51, from about 1:1 to about 1:50, from about 1:1 to about 1:49, from about 1:1 to about 1:48, from about 1:1 to about 1:47, from about 1:1 to about 1:46, from about 1:1 to about 1:45, from about 1:1 to about 1:44, from about 1:1 to about 1:43, from about 1:1 to about 1:42, from about 1:1 to about 1:41, from about 1:1 to about 1:40, from about 1:1 to about 1:39, from about 1:1 to about 1:38, from about 1:1 to about 1:37, from about 1:1 to about 1:36, from about 1:1 to about 1:35, from about 1:1 to about 1:34, from about 1:1 to about 1:33, from about 1:1 to about 1:32, from about 1:1 to about 1:31, from about 1:1 to about 1:30, from about 1:1 to about 1:29, from about 1:1 to about 1:28, from about 1:1 to about 1:27, from about 1:1 to about 1:26, from about 1:1 to about 1:25, from about 1:1 to about 1:24, from about 1:1 to about 1:23, from about 1:1 to about 1:22, from about 1:1 to about 1:21, from about 1:1 to about 1:20, from about 1:1 to about 1:19, from about 1:1 to about 1:18, from about 1:1 to about 1:17, from about 1:1 to about 1:16, from about 1:1 to about 1:15, from about 1:1 to about 1:14, from about 1:1 to about 1:13, from about 1:1 to about 1:12, from about 1:1 to about 1:11, from about 1:1 to about 1:10, from about 1:1 to about 1:9, from about 1:1 to about 1:8, from about 1:1 to about 1:7, from about 1:1 to about 1:6, from about 1:1 to about 1:5, from about 1:1 to about 1:4, from about 1:1 to about 1:3, or from about 1:1 to about 1:2.

In some embodiments, the composition comprises a

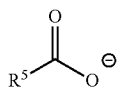

to

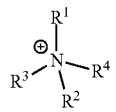

molar ratio of about 1:500, about 1:499, about 1:498, about 1:497, about 1:496, about 1:495, about 1:494, about 1:493, about 1:492, about 1:491, about 1:490, about 1:489, about 1:488, about 1:487, about 1:486, about 1:485, about 1:484, about 1:483, about 1:482, about 1:481, about 1:480, about 1:479, about 1:478, about 1:477, about 1:476, about 1:475, about 1:474, about 1:473, about 1:472, about 1:471, about 1:470, about 1:469, about 1:468, about 1:467, about 1:466, about 1:465, about 1:464, about 1:463, about 1:462, about 1:461, about 1:460, about 1:459, about 1:458, about 1:457, about 1:456, about 1:455, about 1:454, about 1:453, about 1:452, about 1:451, about 1:450, about 1:449, about 1:448, about 1:447, about 1:446, about 1:445, about 1:444, about 1:443, about 1:442, about 1:441, about 1:440, about 1:439, about 1:438, about 1:437, about 1:436, about 1:435, about 1:434, about 1:433, about 1:432, about 1:431, about 1:430, about 1:429, about 1:428, about 1:427, about 1:426, about 1:425, about 1:424, about 1:423, about 1:422, about 1:421, about 1:420, about 1:419, about 1:418, about 1:417, about 1:416, about 1:415, about 1:414, about 1:413, about 1:412, about 1:411, about 1:410, about 1:409, about 1:408, about 1:407, about 1:406, about 1:405, about 1:404, about 1:403, about 1:402, about 1:401, about 1:400, about 1:399, about 1:398, about 1:397, about 1:396, about 1:395, about 1:394, about 1:393, about 1:392, about 1:391, about 1:390, about 1:389, about 1:388, about 1:387, about 1:386, about 1:385, about 1:384, about 1:383, about 1:382, about 1:381, about 1:380, about 1:379, about 1:378, about 1:377, about 1:376, about 1:375, about 1:374, about 1:373, about 1:372, about 1:371, about 1:370, about 1:369, about 1:368, about 1:367, about 1:366, about 1:365, about 1:364, about 1:363, about 1:362, about 1:361, about 1:360, about 1:359, about 1:358, about 1:357, about 1:356, about 1:355, about 1:354, about 1:353, about 1:352, about 1:351, about 1:350, about 1:349, about 1:348, about 1:347, about 1:346, about 1:345, about 1:344, about 1:343, about 1:342, about 1:341, about 1:340, about 1:339, about 1:338, about 1:337, about 1:336, about 1:335, about 1:334, about 1:333, about 1:332, about 1:331, about 1:330, about 1:329, about 1:328, about 1:327, about 1:326, about 1:325, about 1:324, about 1:323, about 1:322, about 1:321, about 1:320, about 1:319, about 1:318, about 1:317, about 1:316, about 1:315, about 1:314, about 1:313, about 1:312, about 1:311, about 1:310, about 1:309, about 1:308, about 1:307, about 1:306, about 1:305, about 1:304, about 1:303, about 1:302, about 1:301, about 1:300, about 1:299, about 1:298, about 1:297, about 1:296, about 1:295, about 1:294, about 1:293, about 1:292, about 1:291, about 1:290, about 1:289, about 1:288, about 1:287, about 1:286, about 1:285, about 1:284, about 1:283, about 1:282, about 1:281, about 1:280, about 1:279, about 1:278, about 1:277, about 1:276, about 1:275, about 1:274, about 1:273, about 1:272, about 1:271, about 1:270, about 1:269, about 1:268, about 1:267, about 1:266, about 1:265, about 1:264, about 1:263, about 1:262, about 1:261, about 1:260, about 1:259, about 1:258, about 1:257, about 1:256, about 1:255, about 1:254, about 1:253, about 1:252, about 1:251, about 1:250, about 1:249, about 1:248, about 1:247, about 1:246, about 1:245, about 1:244, about 1:243, about 1:242, about 1:241, about 1:240, about 1:239, about 1:238, about 1:237, about 1:236, about 1:235, about 1:234, about 1:233, about 1:232, about 1:231, about 1:230, about 1:229, about 1:228, about 1:227, about 1:226, about 1:225, about 1:224, about 1:223, about 1:222, about 1:221, about 1:220, about 1:219, about 1:218, about 1:217, about 1:216, about 1:215, about 1:214, about 1:213, about 1:212, about 1:211, about 1:210, about 1:209, about 1:208, about 1:207, about 1:206, about 1:205, about 1:204, about 1:203, about 1:202, about 1:201, about 1:200, about 1:199, about 1:198, about 1:197, about 1:196, about 1:195, about 1:194, about 1:193, about 1:192, about 1:191, about 1:190, about 1:189, about 1:188, about 1:187, about 1:186, about 1:185, about 1:184, about 1:183, about 1:182, about 1:181, about 1:180, about 1:179, about 1:178, about 1:177, about 1:176, about 1:175, about 1:174, about 1:173, about 1:172, about 1:171, about 1:170, about 1:169, about 1:168, about 1:167, about 1:166, about 1:165, about 1:164, about 1:163, about 1:162, about 1:161, about 1:160, about 1:159, about 1:158, about 1:157, about 1:156, about 1:155, about 1:154, about 1:153, about 1:152, about 1:151, about 1:150, about 1:149, about 1:148, about 1:147, about 1:146, about 1:145, about 1:144, about 1:143, about 1:142, about 1:141, about 1:140, about 1:139, about 1:138, about 1:137, about 1:136, about 1:135, about 1:134, about 1:133, about 1:132, about 1:131, about 1:130, about 1:129, about 1:128, about 1:127, about 1:126, about 1:125, about 1:124, about 1:123, about 1:122, about 1:121, about 1:120, about 1:119, about 1:118, about 1:117, about 1:116, about 1:115, about 1:114, about 1:113, about 1:112, about 1:111, about 1:110, about 1:109, about 1:108, about 1:107, about 1:106, about 1:105, about 1:104, about 1:103, about 1:102, about 1:101, about 1:100, about 1:99, about 1:98, about 1:97, about 1:96, about 1:95, about 1:94, about 1:93, about 1:92, about 1:91, about 1:90, about 1:89, about 1:88, about 1:87, about 1:86, about 1:85, about 1:84, about 1:83, about 1:82, about 1:81, about 1:80, about 1:79, about 1:78, about 1:77, about 1:76, about 1:75, about 1:74, about 1:73, about 1:72, about 1:71, about 1:70, about 1:69, about 1:68, about 1:67, about 1:66, about 1:65, about 1:64, about 1:63, about 1:62, about 1:61, about 1:60, about 1:59, about 1:58, about 1:57, about 1:56, about 1:55, about 1:54, about 1:53, about 1:52, about 1:51, about 1:50, about 1:49, about 1:48, about 1:47, about 1:46, about 1:45, about 1:44, about 1:43, about 1:42, about 1:41, about 1:40, about 1:39, about 1:38, about 1:37, about 1:36, about 1:35, about 1:34, about 1:33, about 1:32, about 1:31, about 1:30, about 1:29, about 1:28, about 1:27, about 1:26, about 1:25, about 1:24, about 1:23, about 1:22, about 1:21, about 1:20, about 1:19, about 1:18, about 1:17, about 1:16, about 1:15, about 1:14, about 1:13, about 1:12, about 1:11, about 1:10, about 1:9, about 1:8, about 1:7, about 1:6, about 1:5, about 1:4, about 1:3, about 1:2 or about 1:1.

In some embodiments, the antibody or an antibody fragment thereof comprises one or more choline or choline derivative-peptide derivative formed on the C-terminus of a light chain. In some embodiments, the antibody or an antibody fragment thereof comprises one or more choline or choline derivative-peptide derivative formed on the C-terminus of a heavy chain. In some embodiments, the antibody or an antibody fragment thereof comprises one or more choline or choline derivative-peptide derivative formed on the C-terminus of a light chain and on the C-terminus of a heavy chain.

In some embodiments, the antibody or an antibody fragment thereof comprises one or more choline or choline derivative-peptide ester formed on the C-terminus of a light chain, the C-terminus of a heavy chain or a combination thereof. In some embodiments, the antibody or the antibody fragment thereof comprises one or more choline or choline derivative-peptide ester formed on the C-terminus of a light chain. In some embodiments, the antibody or the antibody fragment thereof comprises one or more choline or choline derivative-peptide ester formed on the C-terminus of a heavy chain. In some embodiments, the antibody or the antibody fragment thereof comprises one or more choline or choline derivative-peptide ester formed on the C-terminus of a light chain and the C-terminus of a heavy chain.

In some embodiments, the antibody or an antibody fragment thereof comprises one or more choline or choline derivative-peptide ester formed on a Cys residue. In some embodiments, the antibody or an antibody fragment thereof comprises one or more choline or choline derivative-peptide ester formed on a Lys residue. In some embodiments, the antibody or an antibody fragment thereof comprises one or more choline or choline derivative-peptide ester formed on a Cys residue and a Lys residue. In some embodiments, the one or more choline or choline derivative-peptide ester formed on the Cys residue comprises a linker-to-antibody ratio of 1-30, 2-30, 3-30, 4-30, 5-30, 6-30, 7-30, 8-30, 9-30, 10-30, 11-30, 12-30, 13-30, 14-30, 15-30, 16-30, 17-30, 18-30, 19-30, 20-30, 21-30, 22-30, 23-30, 24-30, 25-30, 26-30, 27-30, 28-30, or 29-30. In some embodiments, the one or more choline or choline derivative-peptide ester formed on the Cys residue comprises a linker-to-antibody ratio of 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, the one or more choline or choline derivative-peptide ester formed on the Cys residue comprises a linker-to-antibody ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In some embodiments, the one or more choline or choline derivative-peptide ester formed on the Cys residue comprises a linker-to-antibody ratio of 1-6, 2-8, 3-10, 4-12, 5-14, 6-16, 7-18, 8-20, 9-22, 10-24, 11-26, 12-28, or 14-30.

In some embodiments, the one or more choline or choline derivative-peptide ester formed on the Lys residue comprises a linker-to-antibody ratio of 1-30, 2-30, 3-30, 4-30, 5-30, 6-30, 7-30, 8-30, 9-30, 10-30, 11-30, 12-30, 13-30, 14-30, 15-30, 16-30, 17-30, 18-30, 19-30, 20-30, 21-30, 22-30, 23-30, 24-30, 25-30, 26-30, 27-30, 28-30, or 29-30. In some embodiments, the one or more choline or choline derivative-peptide ester formed on the Lys residue comprises a linker-to-antibody ratio of 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, the one or more choline or choline derivative-peptide ester formed on the Lys residue comprises a linker-to-antibody ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, or30. In some embodiments, the one or more choline or choline derivative-peptide ester formed on the Lys residue comprises a linker-to-antibody ratio of 1-2, 2-4, 3-6, 4-8, 5-10, 6-12, 7-14, 8-16, 9-18, 10-20, 11-22, 12-24, 13-26, 14-28, or 15-30.

In some embodiments, the antibody or the antibody fragment comprises a diacid consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 carbons in length.

In some embodiments, the antibody or an antibody fragment thereof comprising one or more fatty acid linked to the C-terminus of a light chain. In some embodiments, the antibody or an antibody fragment thereof comprising one or more fatty acid linked to the C-terminus of a heavy chain. In some embodiments, the antibody or an antibody fragment thereof comprising one or more fatty acid linked to the C-terminus of a light chain and the C-terminus of a heavy chain.

In some embodiments, the antibody or an antibody fragment thereof comprises one or more fatty acid linked to a Lys residue. In some embodiments, the antibody or an antibody fragment thereof comprises one or more fatty acid linked to a Cys residue. In some embodiments, the antibody or an antibody fragment thereof comprises one or more fatty acid linked to a Lys residue and a Cys residue. In some embodiments, the antibody or an antibody fragment thereof comprises one or more fatty acid linked to a Lys residue with a linker-to-antibody ratio of 1-30, 2-30, 3-30, 4-30, 5-30, 6-30, 7-30, 8-30, 9-30, 10-30, 11-30, 12-30, 13-30, 14-30, 15-30, 16-30, 17-30, 18-30, 19-30, 20-30, 21-30, 22-30, 23-30, 24-30, 25-30, 26-30, 27-30, 28-30, or 29-30. In some embodiments, the antibody or an antibody fragment thereof comprises one or more fatty acid linked to a Lys residue with a linker-to-antibody ratio of 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, the antibody or an antibody fragment thereof comprises one or more fatty acid linked to a Lys residue with a linker-to-antibody ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In some embodiments, the antibody or an antibody fragment thereof comprises one or more fatty acid linked to a Lys residue with a linker-to-antibody ratio of 1-2, 2-4, 3-6, 4-8, 5-10, 6-12, 7-14, 8-16, 9-18, 10-20, 11-22, 12-24, 13-26, 14-28, or 15-30.

In some embodiments, the antibody or an antibody fragment thereof comprises one or more fatty acid linked to a Cys residue with a linker-to-antibody ratio of 1-30, 2-30, 3-30, 4-30, 5-30, 6-30, 7-30, 8-30, 9-30, 10-30, 11-30, 12-30, 13-30, 14-30, 15-30, 16-30, 17-30, 18-30, 19-30, 20-30, 21-30, 22-30, 23-30, 24-30, 25-30, 26-30, 27-30, 28-30, or 29-30. In some embodiments, the antibody or an antibody fragment thereof comprises one or more fatty acid linked to a Cys residue with a linker-to-antibody ratio of 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, the antibody or an antibody fragment thereof comprises one or more fatty acid linked to a Cys residue with a linker-to-antibody ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In some embodiments, the antibody or an antibody fragment thereof comprises one or more fatty acid linked to a Cys residue with a linker-to-antibody ratio of 1-6, 2-8, 3-10, 4-12, 5-14, 6-16, 7-18, 8-20, 9-22, 10-24, 11-26, 12-28, or 14-30.

In some embodiments, an antibody or an antibody fragment thereof is linked to fatty acids via a dual conjugation. In some embodiments, the dual conjugation comprises a linker-to-antibody ratio of 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, the dual conjugation comprises a linker-to-antibody ratio of 1-30, 2-30, 3-30, 4-30, 5-30, 6-30, 7-30, 8-30, 9-30, 10-30, 11-30, 12-30, 13-30, 14-30, 15-30, 16-30, 17-30, 18-30, 19-30, 20-30, 21-30, 22-30, 23-30, 24-30, 25-30, 26-30, 27-30, 28-30, or 29-30. In some embodiments, the dual conjugation comprises a linker-to-antibody ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In some embodiments, the dual conjugation comprises a linker-to-antibody ratio of 1-2, 2-3, 3-4, 4-5, 5-6, 6-7, 7-8, 8-9, 9-10, 10-11, 11-12, 12-13, 13-14, 14-15, 15-16, 16-17, 17-18, 19-20, 20-21, 21-22, 22-23, 23-24, 25-26, 27-28, 28-29, or 29-30.

In some embodiments, the fatty acid is a substituted or unsubstituted C1, C2, C3, C4, C5, C6, C7, C8, C9, C10, C11, C12, C13, C14, C15, C16, C17, C18, C19, C20, C21, C22, C23, C24, C25, C26, C27, C28, C29, or C30 fatty acid. In some embodiments, the fatty acid is a substituted or unsubstituted C1-C30, C1-C29, C1-C28, C1-C27, C1-C26, C1-C25, C1-C24, C1-C23, C1-C22, C1-C21, C1-C20, C1-C19, C1-C18, C1-C17, C1-C16, C1-C15, C1-C14, C1-C13, C1-C12, C1-C11, C1-C10, C1-C9, C1-C8, C1-C7, C1-C6, C1-C5, C1-C4, C1-C3, or C1-C2 fatty acid. In some embodiments, the fatty acid is a substituted or unsubstituted C2-C30, C3-C30, C4-C30, C5-C30, C6-C30, C7-C30, C8-C30, C9-C30, C10-C30, C11-C30, C12-C30, C13-C30, C14-C30, C15-C30, C16-C30, C17-C30, C18-C30, C19-C30, C20-C30, C21-C30, C22-C30, C23-C30, C24-C30, C25-C30, C26-C30, C27-C30, C28-C30, or C29-C30 fatty acid. In some embodiments, the fatty acid is a substituted or unsubstituted C2-C25, C3-C20, C4-C15 or C5-C10 fatty acid.

In another aspect, provided herein is a pharmaceutical composition comprising the composition as provided herein or the compound as provided herein, and one or more ionic liquid.

In some embodiments, the one or more ionic liquid independently comprises a cation selected from the group consisting of aminoguanidine, choline or choline derivative, ammonium, tetramethyl ammonium, tetraethyl ammonium, tetrabutyl ammonium, and guanidine derivatives.

In some embodiments, the one or more ionic liquid independently comprises choline or choline derivative.

In some embodiments, the one or more ionic liquid independently comprises an anion selected from the group consisting of (R)-α-lipoic acid, 2-(4-isobutylphenyl)propionic acid, 2-(4,4-dimethyl-2-pentanyl)-5,7,7-trimethyloctanoic acid, 2-hexyldecanoic acid, 2-hydroxyhippuric acid, 3,7-dimethyloctanoic acid, 4-methylhexanoic acid, 4-methyloctanoic acid, 4-methylvaleric acid, 5-norbornene-2-carboxylic acid, abietic acid, acetic acid, acetylcysteine, arachidonic acid, caffeic acid, cinnamic acid, citric acid, citronellic acid, crotonic acid, D-(+)-galactonic acid, decanoic acid, deoxycholic acid, eicosapentanoic acid, fumaric acid, geranic acid, glutaric acid, glycolic acid, hexanoic acid, 3-phenylpropionic acid, isovaleric acid, L-(+)-tartaric acid, L-ascorbic acid, L-glutathione reduced, lactic acid, lauric acid, levulinic acid, linoleic acid, linolenic acid, maleic acid, malonic acid, mesaconic acid, mandelic acid, nonanoic acid, octanoic acid, oleic acid, p-toluenesulfonic acid, perillic acid, phosphoric acid, pimelic acid, propionic acid, pyroglutamic acid, pyruvic acid, ricinoleic acid, sorbic acid, syringic acid, trans-2-decenoic acid, trans-2-hexenoic acid, trans-2-octenoic acid, trans-3-octenoic acid, trans-γ-octenoic acid, transferulic acid, undecanoic acid, vanillic acid, and α-ketoglutaric acid.

In some embodiments, the one or more ionic liquid independently comprises an anion selected from the group consisting of glycolic acid, tartaric acid, malic acid, hydrocinnamic acid, citric acid, cinnamic acid, mandelic acid, and mesaconic acid.

In some embodiments, the one or more ionic liquid independently comprises choline or choline derivative-cinnamic acid, choline or choline derivative-mandelic acid, or choline or choline derivative-citric acid.

In some embodiments, the pharmaceutical composition comprises the composition as provided herein or the compound as provided herein, and the first, the second, the third, the fourth, the fifth, the sixth, the eighth, the ninth, the tenth, or more ionic liquids.

In some embodiments, the first, the second, the third, the fourth, the fifth, the sixth, the eighth, the ninth, the tenth, or more ionic liquids independently comprises a cation selected from the group consisting of aminoguanidine, choline or choline derivative, ammonium, tetramethyl ammonium, tetraethyl ammonium, tetrabutyl ammonium, and guanidine derivatives.

In some embodiments, the first, the second, the third, the fourth, the fifth, the sixth, the eighth, the ninth, the tenth, or more ionic liquids independently comprises choline or choline derivative.

In some embodiments, the first, the second, the third, the fourth, the fifth, the sixth, the eighth, the ninth, the tenth, or more ionic liquids independently comprises an anion selected from the group consisting of (R)-α-lipoic acid, 2-(4-isobutylphenyl)propionic acid, 2-(4,4-dimethyl-2-pentanyl)-5,7,7-trimethyloctanoic acid, 2-hexyldecanoic acid, 2-hydroxyhippuric acid, 3,7-dimethyloctanoic acid, 4-methylhexanoic acid, 4-methyloctanoic acid, 4-methylvaleric acid, 5-norbornene-2-carboxylic acid, abietic acid, acetic acid, acetylcysteine, arachidonic acid, caffeic acid, cinnamic acid, citric acid, citronellic acid, crotonic acid, D-(+)-galactonic acid, decanoic acid, deoxycholic acid, eicosapentanoic acid, fumaric acid, geranic acid, glutaric acid, glycolic acid, hexanoic acid, 3-phenylpropionic acid, isovaleric acid, L-(+)-tartaric acid, L-ascorbic acid, L-glutathione reduced, lactic acid, lauric acid, levulinic acid, linoleic acid, linolenic acid, maleic acid, malonic acid, mesaconic acid, mandelic acid, nonanoic acid, octanoic acid, oleic acid, p-toluenesulfonic acid, perillic acid, phosphoric acid, pimelic acid, propionic acid, pyroglutamic acid, pyruvic acid, ricinoleic acid, sorbic acid, syringic acid, trans-2-decenoic acid, trans-2-hexenoic acid, trans-2-octenoic acid, trans-3-octenoic acid, trans-γ-octenoic acid, transferulic acid, undecanoic acid, vanillic acid, and α-ketoglutaric acid.

In some embodiments, the first, the second, the third, the fourth, the fifth, the sixth, the eighth, the ninth, the tenth, or more ionic liquids independently comprises an anion selected from the group consisting of glycolic acid, tartaric acid, malic acid, hydrocinnamic acid, citric acid, cinnamic acid, mandelic acid, and mesaconic acid.

In some embodiments, the first, the second, the third, the fourth, the fifth, the sixth, the eighth, the ninth, the tenth, or more ionic liquids independently comprises choline or choline derivative-cinnamic acid, choline or choline derivative-mandelic acid, or choline or choline derivative-citric acid.

In some aspects, provided herein, inter alia, is a composition comprising a compound according to Formula I:

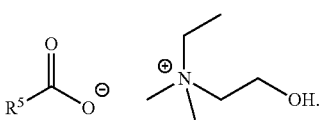

Formula I wherein:

$R^1$, $R^2$, and $R^3$ are independently $C_1$-$C_5$ alkyl;

$R^4$ is $C_2$-$C_5$ alkyl, wherein the $C_2$-$C_5$ alkyl is unsubstituted or substituted with 1 or more hydroxyl;

$R^5$ is a therapeutic agent.

In some embodiments, $R^1$, $R^2$, and $R^3$ are methyl.

In some embodiments, $R^1$, $R^2$, and $R^3$ are ethyl.

In some embodiments, $R^1$, $R^2$, and $R^3$ are propyl.

In some embodiments, $R^1$ and $R^2$ are methyl, and $R^3$ is ethyl.

In some embodiments, $R^1$ and $R^3$ are methyl, and $R^2$ is ethyl.

In some embodiments, $R^1$ and $R^2$ are ethyl, and $R^3$ is methyl.

In some embodiments, $R^1$ and $R^3$ are ethyl, and $R^2$ is methyl.

In some embodiments, $R^1$ and $R^2$ are propyl, and $R^3$ is methyl.

In some embodiments, $R^1$ and $R^3$ are propyl, and $R^2$ is methyl.

In some embodiments, $R^4$ is $C_2$-$C_5$ alkyl substituted with a hydroxyl.

In some embodiments, $R^4$ is

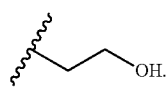 [SMILES: *CCO]

In some embodiments, the compound is according to Formula Ia:

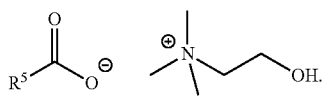

Formula Ia

In some embodiments, the compound is according to Formula Ib:

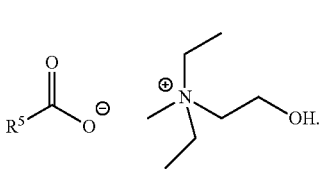

Formula Ib

In some embodiments, the compound is according to Formula Ic:

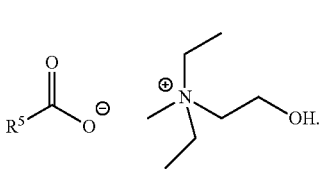

Formula Ic

In some embodiments, the therapeutic agent is an antibody or an antibody fragment thereof.

In some embodiments, the therapeutic agent is any one selected from the group consisting of a chimeric monoclonal anti-TNF-α antibody or an antibody fragment thereof, a monoclonal anti-TNF-α antibody or an antibody fragment thereof, an anti-human IL-12 and IL-23 subunit antibody or an antibody fragment thereof, a human monoclonal anti-TNF-α antibody or an antibody fragment thereof, an anti-integrin α4β1 antibody or an antibody fragment thereof, an anti-integrin α4β7 antibody or an antibody fragment thereof, and a fragment of an anti-TNF-α antibody.

In some embodiments, the therapeutic agent is any one selected from the group consisting of infliximab or an antibody fragment thereof, adalimumab or an antibody fragment thereof, ustekinumab or an antibody fragment thereof, golimumab or an antibody fragment thereof, natalizumab or an antibody fragment thereof, vedolizumab or an antibody fragment thereof, and certolizumab pegol or an antibody fragment thereof.

In some embodiments, the therapeutic agent comprises: (i) a sequence with at least 75% sequence identity to the sequence of SEQ ID NO: 1 or SEQ ID NO: 24, a sequence with at least 75% sequence identity to the sequence of SEQ ID NO: 2, or a combination thereof; (ii) a sequence with at least 75% sequence identity to the sequence of SEQ ID NO: 3, SEQ ID NO: 4, or SEQ ID NO: 5, a sequence with at least 75% sequence identity to the sequence of SEQ ID NO: 6 or SEQ ID NO: 7, or any combination thereof, (iii) a sequence with at least 75% sequence identity to the sequence of SEQ ID NO: 8, a sequence with at least 75% sequence identity to the sequence of SEQ ID NO: 9, or a combination thereof, (iv) a sequence with at least 75% sequence identity to the sequence of SEQ ID NO: 10, a sequence with at least 75% sequence identity to the sequence of SEQ ID NO: 11, or a combination thereof, (v) a sequence with at least 75% sequence identity to the sequence of SEQ ID NO: 12 or SEQ ID NO: 13, a sequence with at least 75% sequence identity to the sequence of SEQ ID NO: 14 or SEQ ID NO: 15, or any combination thereof; (vi) a sequence with at least 75% sequence identity to the sequence of SEQ ID NO: 16, a sequence with at least 75% sequence identity to the sequence of SEQ ID NO: 17, or a combination thereof, or (vii) a sequence with at least 75% sequence identity to the sequence of SEQ ID NO: 18, a sequence with at least 75% sequence identity to the sequence of SEQ ID NO: 19, or a combination thereof.

In some embodiments, the therapeutic agent comprises: (i) the sequence of SEQ ID NO: 1 or SEQ ID NO: 24, the sequence of SEQ ID NO: 2, or a combination thereof; (ii) the sequence of SEQ ID NO: 3, SEQ ID NO: 4, or SEQ ID NO: 5, the sequence of SEQ ID NO: 6 or SEQ ID NO: 7, or any combination thereof; (iii) the sequence of SEQ ID NO: 8, the sequence of SEQ ID NO: 9, or a combination thereof; (iv) the sequence of SEQ ID NO: 10, the sequence of SEQ ID NO: 11, or a combination thereof; (v) the sequence of SEQ ID NO: 12 or SEQ ID NO: 13, the sequence of SEQ ID NO: 14 or SEQ ID NO: 15, or any combination thereof; (vi) the sequence of SEQ ID NO: 16, the sequence of SEQ ID NO: 17, or a combination thereof; or (vii) the sequence of SEQ ID NO: 18, the sequence of SEQ ID NO: 19, or a combination thereof.

In some embodiments, the therapeutic agent comprises: (i) the sequence of SEQ ID NO: 1 or SEQ ID NO: 24, and the sequence of SEQ ID NO: 2; (ii) the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7; (iii) the sequence of SEQ ID NO: 8 and the sequence of SEQ ID NO: 9; (iv) the sequence of SEQ ID NO: 10 and the sequence of SEQ ID NO: 11; (v) the sequence of SEQ ID NO: 12 and the sequence of SEQ ID NO: 14, or the sequence of SEQ ID NO: 13 and the sequence of SEQ ID NO: 15; (vi) the sequence of SEQ ID NO: 16 and the sequence of SEQ ID NO: 17; or (vii) the sequence of SEQ ID NO: 18 and the sequence of SEQ ID NO: 19.

In some embodiments, the therapeutic agent is a chimeric monoclonal anti-TNF-α antibody or an antibody fragment thereof.

In some embodiments, the therapeutic agent comprises the sequence of SEQ ID NO: 1 or SEQ ID NO: 24, and the sequence of SEQ ID NO: 2.

In some embodiments, the composition comprises a

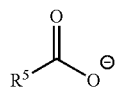

to

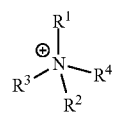

molar ratio of from about 1:1 to about 1:164.

In some embodiments, the composition comprises a

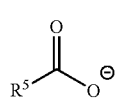

to

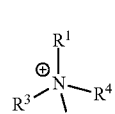

molar ratio of about 1:1.

In some embodiments, the composition comprises a

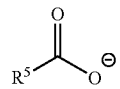

to

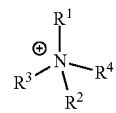

molar ratio of about 1:33.

In some embodiments, the composition comprises a

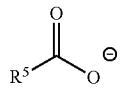

to

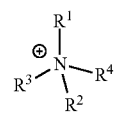

molar ratio of about 1:41.

In some embodiments, the composition comprises a

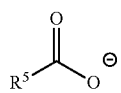

to

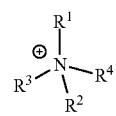

molar ratio of about 1:66.

In some embodiments, the composition comprises a

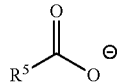

to

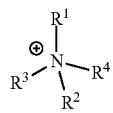

molar ratio of about 1:82.

In some embodiments, the composition comprises a

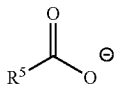

to

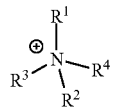

molar ratio of about 1:132.

In some embodiments, the composition comprises a

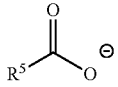

to

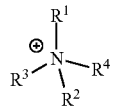

molar ratio of about 1:164.

In some embodiments, the therapeutic agent is a monoclonal anti-TNF-α antibody or an antibody fragment thereof.

In some embodiments, the therapeutic agent comprises the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7.

In some embodiments, the composition comprises a

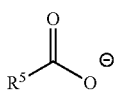

to

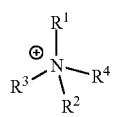

molar ratio of from about 1:1 to about 1:144.

In some embodiments, the therapeutic agent is an anti-human IL-12 and IL-23 subunit antibody or an antibody fragment thereof.

In some embodiments, the therapeutic agent comprises the sequence of SEQ ID NO: 8 and the sequence of SEQ ID NO: 9.

In some embodiments, the composition comprises a

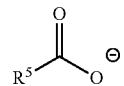

to

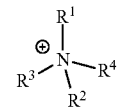

molar ratio of from about 1:1 to about 1:140.

In some embodiments, the therapeutic agent is a human monoclonal anti-TNF-α antibody or an antibody fragment thereof.

In some embodiments, the therapeutic agent comprises the sequence of SEQ ID NO: 10 and the sequence of SEQ ID NO: 11.

In some embodiments, the composition comprises a

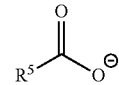

to

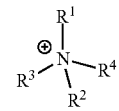

molar ratio of from about 1:1 to about 1:80.

In some embodiments, the therapeutic agent is an anti-integrin α4β1 antibody or an antibody fragment thereof.

In some embodiments, the therapeutic agent comprises the sequence of SEQ ID NO: 12 and the sequence of SEQ ID NO: 14, or the sequence of SEQ ID NO: 13 and the sequence of SEQ ID NO: 15.

In some embodiments, the composition comprises a

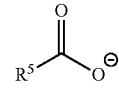

to

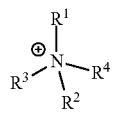

molar ratio of from about 1:1 to about 1:156.

In some embodiments, the therapeutic agent is an anti-integrin α4β7 antibody or an antibody fragment thereof.

In some embodiments, the therapeutic agent comprises the sequence of SEQ ID NO: 16 and the sequence of SEQ ID NO: 17.

In some embodiments, the composition comprises a

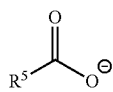

to

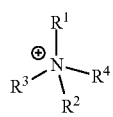

molar ratio of from about 1:1 to about 1:256.

In some embodiments, the therapeutic agent is a fragment of an anti-TNF-α antibody.

In some embodiments, the therapeutic agent comprises the sequence of SEQ ID NO: 18 and the sequence of SEQ ID NO: 19.

In some embodiments, the composition comprises a

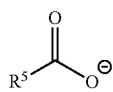

to

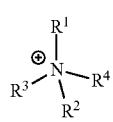

molar ratio of from about 1:1 to about 1:70.

In some embodiments, the composition comprises a

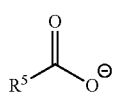

to

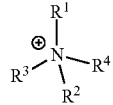

molar ratio of from about 1:1 to about 1:20. In some embodiments, the composition comprises a

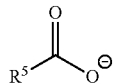

to

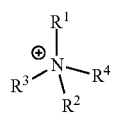

molar ratio of from about 1:1 to about 1:260, from about 1:1 to about 1:259, from about 1:1 to about 1:258, from about 1:1 to about 1:257, from about 1:1 to about 1:256, from about 1:1 to about 1:255, from about 1:1 to about 1:254, from about 1:1 to about 1:253, from about 1:1 to about 1:252, from about 1:1 to about 1:251, from about 1:1 to about 1:250, from about 1:1 to about 1:249, from about 1:1 to about 1:248, from about 1:1 to about 1:247, from about 1:1 to about 1:246, from about 1:1 to about 1:245, from about 1:1 to about 1:244, from about 1:1 to about 1:243, from about 1:1 to about 1:242, from about 1:1 to about 1:241, from about 1:1 to about 1:240, from about 1:1 to about 1:239, from about 1:1 to about 1:238, from about 1:1 to about 1:237, from about 1:1 to about 1:236, from about 1:1 to about 1:235, from about 1:1 to about 1:234, from about 1:1 to about 1:233, from about 1:1 to about 1:232, from about 1:1 to about 1:231, from about 1:1 to about 1:230, from about 1:1 to about 1:229, from about 1:1 to about 1:228, from about 1:1 to about 1:227, from about 1:1 to about 1:226, from about 1:1 to about 1:225, from about 1:1 to about 1:224, from about 1:1 to about 1:223, from about 1:1 to about 1:222, from about 1:1 to about 1:221, from about 1:1 to about 1:220, from about 1:1 to about 1:219, from about 1:1 to about 1:218, from about 1:1 to about 1:217, from about 1:1 to about 1:216, from about 1:1 to about 1:215, from about 1:1 to about 1:214, from about 1:1 to about 1:213, from about 1:1 to about 1:212, from about 1:1 to about 1:211, from about 1:1 to about 1:210, from about 1:1 to about 1:209, from about 1:1 to about 1:208, from about 1:1 to about 1:207, from about 1:1 to about 1:206, from about 1:1 to about 1:205, from about 1:1 to about 1:204, from about 1:1 to about 1:203, from about 1:1 to about 1:202, from about 1:1 to about 1:201, from about 1:1 to about 1:200, from about 1:1 to about 1:199, from about 1:1 to about 1:198, from about 1:1 to about 1:197, from about 1:1 to about 1:196, from about 1:1 to about 1:195, from about 1:1 to about 1:194, from about 1:1 to about 1:193, from about 1:1 to about 1:192, from about 1:1 to about 1:191, from about 1:1 to about 1:190, from about 1:1 to about 1:189, from about 1:1 to about 1:188, from about 1:1 to about 1:187, from about 1:1 to about 1:186, from about 1:1 to about 1:185, from about 1:1 to about 1:184, from about 1:1 to about 1:183, from about 1:1 to about 1:182, from about 1:1 to about 1:181, from about 1:1 to about 1:180, from about 1:1 to about 1:179, from about 1:1 to about 1:178, from about 1:1 to about 1:177, from about 1:1 to about 1:176, from about 1:1 to about 1:175, from about 1:1 to about 1:174, from about 1:1 to about 1:173, from about 1:1 to about 1:172, from about 1:1 to about 1:171, from about 1:1 to about 1:170, from about 1:1 to about 1:169, from about 1:1 to about 1:168, from about 1:1 to about 1:167, from about 1:1 to about 1:166, from about 1:1 to about 1:165, from about 1:1 to about 1:164, from about 1:1 to about 1:163, from about 1:1 to about 1:162, from about 1:1 to about 1:161, from about 1:1 to about 1:160, from about 1:1 to about 1:159, from about 1:1 to about 1:158, from about 1:1 to about 1:157, from about 1:1 to about 1:156, from about 1:1 to about 1:155, from about 1:1 to about 1:154, from about 1:1 to about 1:153, from about 1:1 to about 1:152, from about 1:1 to about 1:151, from about 1:1 to about 1:150, from about 1:1 to about 1:149, from about 1:1 to about 1:148, from about 1:1 to about 1:147, from about 1:1 to about 1:146, from about 1:1 to about 1:145, from about 1:1 to about 1:144, from about 1:1 to about 1:143, from about 1:1 to about 1:142, from about 1:1 to about 1:141, from about 1:1 to about 1:140, from about 1:1 to about 1:139, from about 1:1 to about 1:138, from about 1:1 to about 1:137, from about 1:1 to about 1:136, from about 1:1 to about 1:135, from about 1:1 to about 1:134, from about 1:1 to about 1:133, from about 1:1 to about 1:132, from about 1:1 to about 1:131, from about 1:1 to about 1:130, from about 1:1 to about 1:129, from about 1:1 to about 1:128, from about 1:1 to about 1:127, from about 1:1 to about 1:126, from about 1:1 to about 1:125, from about 1:1 to about 1:124, from about 1:1 to about 1:123, from about 1:1 to about 1:122, from about 1:1 to about 1:121, from about 1:1 to about 1:120, from about 1:1 to about 1:119, from about 1:1 to about 1:118, from about 1:1 to about 1:117, from about 1:1 to about 1:116, from about 1:1 to about 1:115, from about 1:1 to about 1:114, from about 1:1 to about 1:113, from about 1:1 to about 1:112, from about 1:1 to about 1:111, from about 1:1 to about 1:110, from about 1:1 to about 1:109, from about 1:1 to about 1:108, from about 1:1 to about 1:107, from about 1:1 to about 1:106, from about 1:1 to about 1:105, from about 1:1 to about 1:104, from about 1:1 to about 1:103, from about 1:1 to about 1:102, from about 1:1 to about 1:101, from about 1:1 to about 1:100, from about 1:1 to about 1:99, from about 1:1 to about 1:98, from about 1:1 to about 1:97, from about 1:1 to about 1:96, from about 1:1 to about 1:95, from about 1:1 to about 1:94, from about 1:1 to about 1:93, from about 1:1 to about 1:92, from about 1:1 to about 1:91, from about 1:1 to about 1:90, from about 1:1 to about 1:89, from about 1:1 to about 1:88, from about 1:1 to about 1:87, from about 1:1 to about 1:86, from about 1:1 to about 1:85, from about 1:1 to about 1:84, from about 1:1 to about 1:83, from about 1:1 to about 1:82, from about 1:1 to about 1:81, from about 1:1 to about 1:80, from about 1:1 to about 1:79, from about 1:1 to about 1:78, from about 1:1 to about 1:77, from about 1:1 to about 1:76, from about 1:1 to about 1:75, from about 1:1 to about 1:74, from about 1:1 to about 1:73, from about 1:1 to about 1:72, from about 1:1 to about 1:71, from about 1:1 to about 1:70, from about 1:1 to about 1:69, from about 1:1 to about 1:68, from about 1:1 to about 1:67, from about 1:1 to about 1:66, from about 1:1 to about 1:65, from about 1:1 to about 1:64, from about 1:1 to about 1:63, from about 1:1 to about 1:62, from about 1:1 to about 1:61, from about 1:1 to about 1:60, from about 1:1 to about 1:59, from about 1:1 to about 1:58, from about 1:1 to about 1:57, from about 1:1 to about 1:56, from about 1:1 to about 1:55, from about 1:1 to about 1:54, from about 1:1 to about 1:53, from about 1:1 to about 1:52, from about 1:1 to about 1:51, from about 1:1 to about 1:50, from about 1:1 to about 1:49, from about 1:1 to about 1:48, from about 1:1 to about 1:47, from about 1:1 to about 1:46, from about 1:1 to about 1:45, from about 1:1 to about 1:44, from about 1:1 to about 1:43, from about 1:1 to about 1:42, from about 1:1 to about 1:41, from about 1:1 to about 1:40, from about 1:1 to about 1:39, from about 1:1 to about 1:38, from about 1:1 to about 1:37, from about 1:1 to about 1:36, from about 1:1 to about 1:35, from about 1:1 to about 1:34, from about 1:1 to about 1:33, from about 1:1 to about 1:32, from about 1:1 to about 1:31, from about 1:1 to about 1:30, from about 1:1 to about 1:29, from about 1:1 to about 1:28, from about 1:1 to about 1:27, from about 1:1 to about 1:26, from about 1:1 to about 1:25, from about 1:1 to about 1:24, from about 1:1 to about 1:23, from about 1:1 to about 1:22, from about 1:1 to about 1:21, from about 1:1 to about 1:20, from about 1:1 to about 1:19, from about 1:1 to about 1:18, from about 1:1 to about 1:17, from about 1:1 to about 1:16, from about 1:1 to about 1:15, from about 1:1 to about 1:14, from about 1:1 to about 1:13, from about 1:1 to about 1:12, from about 1:1 to about 1:11, from about 1:1 to about 1:10, from about 1:1 to about 1:9, from about 1:1 to about 1:8, from about 1:1 to about 1:7, from about 1:1 to about 1:6, from about 1:1 to about 1:5, from about 1:1 to about 1:4, from about 1:1 to about 1:3, or from about 1:1 to about 1:2.

In some embodiments, the composition comprises a

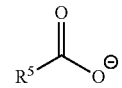

to

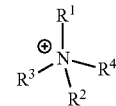

molar ratio of about 1:260, about 1:259, about 1:258, about 1:257, about 1:256, about 1:255, about 1:254, about 1:253, about 1:252, about 1:251, about 1:250, about 1:249, about 1:248, about 1:247, about 1:246, about 1:245, about 1:244, about 1:243, about 1:242, about 1:241, about 1:240, about 1:239, about 1:238, about 1:237, about 1:236, about 1:235, about 1:234, about 1:233, about 1:232, about 1:231, about 1:230, about 1:229, about 1:228, about 1:227, about 1:226, about 1:225, about 1:224, about 1:223, about 1:222, about 1:221, about 1:220, about 1:219, about 1:218, about 1:217, about 1:216, about 1:215, about 1:214, about 1:213, about 1:212, about 1:211, about 1:210, about 1:209, about 1:208, about 1:207, about 1:206, about 1:205, about 1:204, about 1:203, about 1:202, about 1:201, about 1:200, about 1:199, about 1:198, about 1:197, about 1:196, about 1:195, about 1:194, about 1:193, about 1:192, about 1:191, about 1:190, about 1:189, about 1:188, about 1:187, about 1:186, about 1:185, about 1:184, about 1:183, about 1:182, about 1:181, about 1:180, about 1:179, about 1:178, about 1:177, about 1:176, about 1:175, about 1:174, about 1:173, about 1:172, about 1:171, about 1:170, about 1:169, about 1:168, about 1:167, about 1:166, about 1:165, about 1:164, about 1:163, about 1:162, about 1:161, about 1:160, about 1:159, about 1:158, about 1:157, about 1:156, about 1:155, about 1:154, about 1:153, about 1:152, about 1:151, about 1:150, about 1:149, about 1:148, about 1:147, about 1:146, about 1:145, about 1:144, about 1:143, about 1:142, about 1:141, about 1:140, about 1:139, about 1:138, about 1:137, about 1:136, about 1:135, about 1:134, about 1:133, about 1:132, about 1:131, about 1:130, about 1:129, about 1:128, about 1:127, about 1:126, about 1:125, about 1:124, about 1:123, about 1:122, about 1:121, about 1:120, about 1:119, about 1:118, about 1:117, about 1:116, about 1:115, about 1:114, about 1:113, about 1:112, about 1:111, about 1:110, about 1:109, about 1:108, about 1:107, about 1:106, about 1:105, about 1:104, about 1:103, about 1:102, about 1:101, about 1:100, about 1:99, about 1:98, about 1:97, about 1:96, about 1:95, about 1:94, about 1:93, about 1:92, about 1:91, about 1:90, about 1:89, about 1:88, about 1:87, about 1:86, about 1:85, about 1:84, about 1:83, about 1:82, about 1:81, about 1:80, about 1:79, about 1:78, about 1:77, about 1:76, about 1:75, about 1:74, about 1:73, about 1:72, about 1:71, about 1:70, about 1:69, about 1:68, about 1:67, about 1:66, about 1:65, about 1:64, about 1:63, about 1:62, about 1:61, about 1:60, about 1:59, about 1:58, about 1:57, about 1:56, about 1:55, about 1:54, about 1:53, about 1:52, about 1:51, about 1:50, about 1:49, about 1:48, about 1:47, about 1:46, about 1:45, about 1:44, about 1:43, about 1:42, about 1:41, about 1:40, about 1:39, about 1:38, about 1:37, about 1:36, about 1:35, about 1:34, about 1:33, about 1:32, about 1:31, about 1:30, about 1:29, about 1:28, about 1:27, about 1:26, about 1:25, about 1:24, about 1:23, about 1:22, about 1:21, about 1:20, about 1:19, about 1:18, about 1:17, about 1:16, about 1:15, about 1:14, about 1:13, about 1:12, about 1:11, about 1:10, about 1:9, about 1:8, about 1:7, about 1:6, about 1:5, about 1:4, about 1:3, about 1:2 or about 1:1.

In some embodiments, the composition comprises an antibody or an antibody fragment thereof having a modified antibody structure.

In some embodiments, the composition comprises an antibody or an antibody fragment thereof having a choline or choline derivative-modified antibody structure.

In some embodiments, the composition comprises an antibody or an antibody fragment thereof having a cation moiety comprising choline or choline derivative.

In some embodiments, the composition comprises an antibody or an antibody fragment thereof having a cation moiety comprising a choline or choline derivative-like residue.

In some embodiments, the composition comprises an antibody or an antibody fragment thereof comprising one or more choline or choline derivative-peptide derivative formed on the C-terminus of a light chain, the C-terminus of a heavy chain or a combination thereof.

In some embodiments, the composition comprises an antibody or an antibody fragment thereof comprising one or more choline or choline derivative-peptide derivative formed on a Glu residue, a Asp residue, or a combination thereof.

In some embodiments, the composition comprises an antibody or an antibody fragment thereof comprising a linker comprising one or more gamma glutamate (γGlu) residues, one or more 8-amino-3,6-dioxaoctanoic acid (OEG) residues, or a combination thereof.

In some embodiments, the composition comprises an antibody or an antibody fragment thereof comprising a linker comprising one or more gamma glutamate (γGlu) residues.

In some embodiments, the composition comprises an antibody or an antibody fragment comprising a choline or choline derivative-peptide ester that is formed on the carboxylic acid of the one or more gamma glutamate residues of the linker In some embodiments, the composition comprises an antibody or an antibody fragment thereof comprising a choline or choline derivative-peptide derivative that is formed on the carboxylic acid of the one or more gamma glutamate residues of the linker.

In some embodiments, the composition comprises an antibody or an antibody fragment thereof comprising a diacid consisting of 18 or 20 carbons in length.

In some embodiments, the diacid comprises a C20 fatty diacid.

In some embodiments, the diacid comprises 1,20-icosane-dioic acid.

In another aspect, provided herein is a compound according to Formula II:

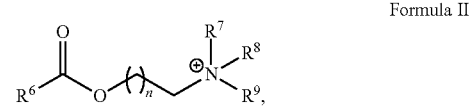

Formula II wherein:
$R^6$ is a therapeutic agent.
$R^7$, $R^8$, and $R^9$ are independently $C_1$-$C_5$ alkyl; and
n is 1, 2, 3, 4, or 5.
In some embodiments, $R^7$, $R^8$, and $R^9$ are methyl.
In some embodiments, $R^7$, $R^8$, and $R^9$ are ethyl.
In some embodiments, $R^7$, $R^8$, and $R^9$ are propyl.
In some embodiments, $R^7$ and $R^8$ are methyl, and $R^9$ is ethyl.
In some embodiments, $R^7$ and $R^9$ are methyl, and $R^8$ is ethyl.
In some embodiments, $R^7$ and $R^8$ are ethyl, and $R^9$ is methyl.
In some embodiments, $R^7$ and $R^9$ are ethyl, and $R^8$ is methyl.
In some embodiments, $R^7$ and $R^8$ are propyl, and $R^9$ is methyl.
In some embodiments, $R^7$ and $R^9$ are propyl, and $R^8$ is methyl.
In some embodiments, n is 1.
In some embodiments, the compound is according to Formula IIa:

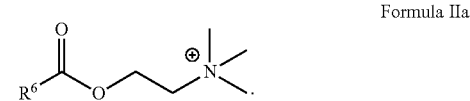

Formula IIa

In some embodiments, the compound is according to Formula IIb:

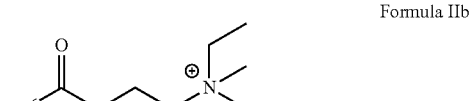

Formula IIb

In some embodiments, the compound is according to Formula IIc:

Formula IIc

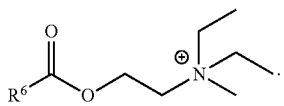

In some embodiments, the therapeutic agent is an antibody or an antibody fragment thereof.

In some embodiments, the therapeutic agent is any one selected from the group consisting of a chimeric monoclonal anti-TNF-α antibody or an antibody fragment thereof, a monoclonal anti-TNF-α antibody or an antibody fragment thereof, an anti-human IL-12 and IL-23 subunit antibody or an antibody fragment thereof, a human monoclonal anti-TNF-α antibody or an antibody fragment thereof, an anti-integrin α4β1 antibody or an antibody fragment thereof, an anti-integrin α4β7 antibody or an antibody fragment thereof, and a fragment of an anti-TNF-α antibody.

In some embodiments, the therapeutic agent is any one selected from the group consisting of infliximab or an antibody fragment thereof, adalimumab or an antibody fragment thereof, ustekinumab or an antibody fragment thereof, golimumab or an antibody fragment thereof, natalizumab or an antibody fragment thereof, vedolizumab or an antibody fragment thereof, and certolizumab pegol or an antibody fragment thereof.

In some embodiments, the therapeutic agent comprises: (i) a sequence with at least 75% sequence identity to the sequence of SEQ ID NO: 1 or SEQ ID NO: 24, a sequence with at least 75% sequence identity to the sequence of SEQ ID NO: 2, or a combination thereof; (ii) a sequence with at least 75% sequence identity to the sequence of SEQ ID NO: 3, SEQ ID NO: 4, or SEQ ID NO: 5, a sequence with at least 75% sequence identity to the sequence of SEQ ID NO: 6 or SEQ ID NO: 7, or any combination thereof; (iii) a sequence with at least 75% sequence identity to the sequence of SEQ ID NO: 8, a sequence with at least 75% sequence identity to the sequence of SEQ ID NO: 9, or a combination thereof, (iv) a sequence with at least 75% sequence identity to the sequence of SEQ ID NO: 10, a sequence with at least 75% sequence identity to the sequence of SEQ ID NO: 11, or a combination thereof, (v) a sequence with at least 75% sequence identity to the sequence of SEQ ID NO: 12 or SEQ ID NO: 13, a sequence with at least 75% sequence identity to the sequence of SEQ ID NO: 14 or SEQ ID NO: 15, or any combination thereof; (vi) a sequence with at least 75% sequence identity to the sequence of SEQ ID NO: 16, a sequence with at least 75% sequence identity to the sequence of SEQ ID NO: 17, or a combination thereof; or (vii) a sequence with at least 75% sequence identity to the sequence of SEQ ID NO: 18, a sequence with at least 75% sequence identity to the sequence of SEQ ID NO: 19, or a combination thereof.

In some embodiments, the therapeutic agent comprises: (i) the sequence of SEQ ID NO: 1 or SEQ ID NO: 24, the sequence of SEQ ID NO: 2, or a combination thereof; (ii) the sequence of SEQ ID NO: 3, SEQ ID NO: 4, or SEQ ID NO: 5, the sequence of SEQ ID NO: 6 or SEQ ID NO: 7, or any combination thereof; (iii) the sequence of SEQ ID NO: 8, the sequence of SEQ ID NO: 9, or a combination thereof; (iv) the sequence of SEQ ID NO: 10, the sequence of SEQ ID NO: 11, or a combination thereof; (v) the sequence of SEQ ID NO: 12 or SEQ ID NO: 13, the sequence of SEQ ID NO: 14 or SEQ ID NO: 15, or any combination thereof; (vi) the sequence of SEQ ID NO: 16, the sequence of SEQ ID NO: 17, or a combination thereof; or (vii) the sequence of SEQ ID NO: 18, the sequence of SEQ ID NO: 19, or a combination thereof.

In some embodiments, the therapeutic agent comprises: (i) the sequence of SEQ ID NO: 1 or SEQ ID NO: 24, and the sequence of SEQ ID NO: 2; (ii) the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7; (iii) the sequence of SEQ ID NO: 8 and the sequence of SEQ ID NO: 9; (iv) the sequence of SEQ ID NO: 10 and the sequence of SEQ ID NO: 11; (v) the sequence of SEQ ID NO: 12 and the sequence of SEQ ID NO: 14, or the sequence of SEQ ID NO: 13 and the sequence of SEQ ID NO: 15; (vi) the sequence of SEQ ID NO: 16 and the sequence of SEQ ID NO: 17; or (vii) the sequence of SEQ ID NO: 18 and the sequence of SEQ ID NO: 19.

In some embodiments, the therapeutic agent is a chimeric monoclonal anti-TNF-α antibody or an antibody fragment thereof.

In some embodiments, the therapeutic agent comprises the sequence of SEQ ID NO: 1 or SEQ ID NO: 24, and the sequence of SEQ ID NO: 2.

In some embodiments, the therapeutic agent is a monoclonal anti-TNF-α antibody or an antibody fragment thereof.

In some embodiments, the therapeutic agent comprises the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7.

In some embodiments, the therapeutic agent is an anti-human IL-12 and IL-23 subunit antibody or an antibody fragment thereof.

In some embodiments, the therapeutic agent comprises the sequence of SEQ ID NO: 8 and the sequence of SEQ ID NO: 9.

In some embodiments, the therapeutic agent is a human monoclonal anti-TNF-α antibody or an antibody fragment thereof.

In some embodiments, the therapeutic agent comprises the sequence of SEQ ID NO: 10 and the sequence of SEQ ID NO: 11.

In some embodiments, the therapeutic agent is an anti-integrin α4β1 antibody or an antibody fragment thereof.

In some embodiments, the therapeutic agent comprises the sequence of SEQ ID NO: 12 and the sequence of SEQ ID NO: 14, or the sequence of SEQ ID NO: 13 and the sequence of SEQ ID NO: 15.

In some embodiments, the therapeutic agent is an anti-integrin α4β7 antibody or an antibody fragment thereof.

In some embodiments, the therapeutic agent comprises the sequence of SEQ ID NO: 16 and the sequence of SEQ ID NO: 17.

In some embodiments, the therapeutic agent is a fragment of an anti-TNF-α antibody.

In some embodiments, the therapeutic agent comprises the sequence of SEQ ID NO: 18 and the sequence of SEQ ID NO: 19.

In some embodiments, the compound comprises an antibody or an antibody fragment thereof having a modified antibody structure.

In some embodiments, the compound comprises an antibody or an antibody fragment thereof having a choline or choline derivative-modified antibody structure.

In some embodiments, the compound comprises an antibody or an antibody fragment thereof having a cation moiety comprising choline or choline derivative.

In some embodiments, the compound comprises an antibody or an antibody fragment thereof having a choline or choline derivative-modified ester structure.

In some embodiments, the compound comprises an antibody or an antibody fragment thereof having a cation moiety comprising a choline or choline derivative-like residue.

In some embodiments, the compound comprises an antibody or an antibody fragment thereof comprising one or more choline or choline derivative-peptide ester formed on the C-terminus of a light chain, the C-terminus of a heavy chain or a combination thereof.

In some embodiments, the compound comprises an antibody or an antibody fragment thereof comprising one or more choline or choline derivative-peptide ester formed on a Cys residue, a Lys residue, or any combination thereof.

In some embodiments, the one or more choline or choline derivative-peptide ester formed on the Cys residue comprises a linker-to-antibody ratio of 2-8, the one or more choline or choline derivative-peptide ester formed on the Lys residue comprises a linker-to-antibody ratio of 2-4, or a combination thereof.

In some embodiments, the compound comprises an antibody or an antibody fragment comprising a linker comprising one or more gamma glutamate (γGlu) residues, one or more 8-amino-3,6-dioxaoctanoic acid (OEG) residues, or a combination thereof.

In some embodiments, the compound comprises an antibody or an antibody fragment comprising a linker comprising one or more gamma glutamate (γGlu) residues.

In some embodiments, the compound comprises an antibody or an antibody fragment comprising a choline or choline derivative-peptide derivative that is formed on the carboxylic acid of the one or more gamma glutamate residues of the linker.

In some embodiments, the compound comprises an antibody or an antibody fragment comprising a choline or choline derivative-peptide ester that is formed on the carboxylic acid of the one or more gamma glutamate residues of the linker.

In some embodiments, the compound comprises an antibody or an antibody fragment comprising a diacid consisting of 18 or 20 carbons in length.

In some embodiments, the diacid comprises a $C_{20}$ fatty diacid.

In some embodiments, the diacid comprises 1,20-icosanedioic acid.

In another aspect, provided herein is a compound according to Formula III:

Formula III

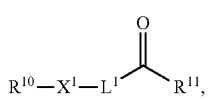

wherein:

$R^{10}$ is a therapeutic agent;

$R^{11}$ is substituted or unsubstituted $C_5$-$C_{10}$;

$X^1$ is

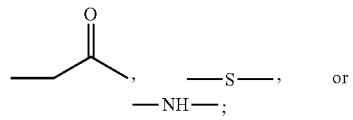

and $L^1$ is a covalent bond or a linker.

In some embodiments, $L^1$ is a non-cleavable linker.

In some embodiments, $L^1$ comprises a maleimide alkane linker or a maleimide cyclohexane linker.

In some embodiments, $L^1$ comprises

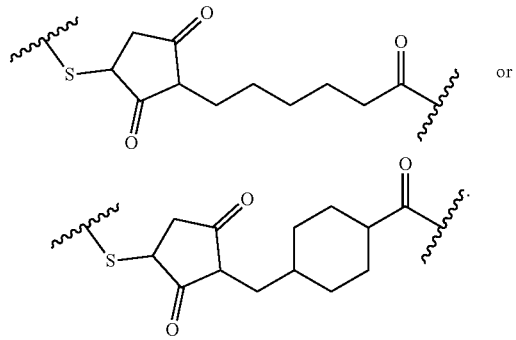

In some embodiments, $L^1$ is a chemically cleavable linker.

In some embodiments, $L^1$ comprises a hydrazone linker or a disulfide linker.

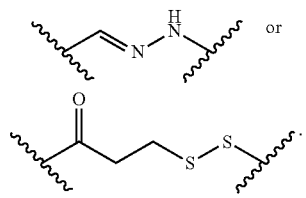

In some embodiments, $L^1$ comprises or

In some embodiments, $R^{11}$ is substituted or unsubstituted $C_{10}$.

In some embodiments, the therapeutic agent is an antibody or an antibody fragment thereof.

In some embodiments, the therapeutic agent is any one selected from the group consisting of a chimeric monoclonal anti-TNF-α antibody or an antibody fragment thereof, a monoclonal anti-TNF-α antibody or an antibody fragment thereof, an anti-human IL-12 and IL-23 subunit antibody or an antibody fragment thereof, a human monoclonal anti-TNF-α antibody or an antibody fragment thereof, an anti-integrin α4β1 antibody or an antibody fragment thereof, an anti-integrin α4β7 antibody or an antibody fragment thereof, and a fragment of an anti-TNF-α antibody.

In some embodiments, the therapeutic agent is any one selected from the group consisting of infliximab or an antibody fragment thereof, adalimumab or an antibody fragment thereof, ustekinumab or an antibody fragment thereof, golimumab or an antibody fragment thereof, natalizumab or an antibody fragment thereof, vedolizumab or an antibody fragment thereof, and certolizumab pegol or an antibody fragment thereof.

In some embodiments, the therapeutic agent comprises: (i) a sequence with at least 75% sequence identity to the sequence of SEQ ID NO: 1 or SEQ ID NO: 24, a sequence with at least 75% sequence identity to the sequence of SEQ ID NO: 2, or a combination thereof; (ii) a sequence with at least 75% sequence identity to the sequence of SEQ ID NO: 3, SEQ ID NO: 4, or SEQ ID NO: 5, a sequence with at least 75% sequence identity to the sequence of SEQ ID NO: 6 or SEQ ID NO: 7, or any combination thereof, (iii) a sequence with at least 75% sequence identity to the sequence of SEQ ID NO: 8, a sequence with at least 75% sequence identity to the sequence of SEQ ID NO: 9, or a combination thereof, (iv) a sequence with at least 75% sequence identity to the sequence of SEQ ID NO: 10, a sequence with at least 75% sequence identity to the sequence of SEQ ID NO: 11, or a combination thereof, (v) a sequence with at least 75% sequence identity to the sequence of SEQ ID NO: 12 or SEQ ID NO: 13, a sequence with at least 75% sequence identity to the sequence of SEQ ID NO: 14 or SEQ ID NO: 15, or any combination thereof; (vi) a sequence with at least 75% sequence identity to the sequence of SEQ ID NO: 16, a sequence with at least 75% sequence identity to the sequence of SEQ ID NO: 17, or a combination thereof, or (vii) a sequence with at least 75% sequence identity to the sequence of SEQ ID NO: 18, a sequence with at least 75% sequence identity to the sequence of SEQ ID NO: 19, or a combination thereof.

In some embodiments, the therapeutic agent comprises: (i) the sequence of SEQ ID NO: 1 or SEQ ID NO: 24, the sequence of SEQ ID NO: 2, or a combination thereof; (ii) the sequence of SEQ ID NO: 3, SEQ ID NO: 4, or SEQ ID NO: 5, the sequence of SEQ ID NO: 6 or SEQ ID NO: 7, or any combination thereof; (iii) the sequence of SEQ ID NO: 8, the sequence of SEQ ID NO: 9, or a combination thereof; (iv) the sequence of SEQ ID NO: 10, the sequence of SEQ ID NO: 11, or a combination thereof; (v) the sequence of SEQ ID NO: 12 or SEQ ID NO: 13, the sequence of SEQ ID NO: 14 or SEQ ID NO: 15, or any combination thereof; (vi) the sequence of SEQ ID NO: 16, the sequence of SEQ ID NO: 17, or a combination thereof; or (vii) the sequence of SEQ ID NO: 18, the sequence of SEQ ID NO: 19, or a combination thereof.

In some embodiments, the therapeutic agent comprises: (i) the sequence of SEQ ID NO: 1 or SEQ ID NO: 24, and the sequence of SEQ ID NO: 2; (ii) the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7; (iii) the sequence of SEQ ID NO: 8 and the sequence of SEQ ID NO: 9; (iv) the sequence of SEQ ID NO: 10 and the sequence of SEQ ID NO: 11; (v) the sequence of SEQ ID NO: 12 and the sequence of SEQ ID NO: 14, or the sequence of SEQ ID NO: 13 and the sequence of SEQ ID NO: 15; (vi) the sequence of SEQ ID NO: 16 and the sequence of SEQ ID NO: 17; or (vii) the sequence of SEQ ID NO: 18 and the sequence of SEQ ID NO: 19.

In some embodiments, the therapeutic agent is a chimeric monoclonal anti-TNF-α antibody or an antibody fragment thereof.

In some embodiments, the therapeutic agent comprises the sequence of SEQ ID NO: 1 or SEQ ID NO: 24, and the sequence of SEQ ID NO: 2.

In some embodiments, the therapeutic agent is a monoclonal anti-TNF-α antibody or an antibody fragment thereof.

In some embodiments, the therapeutic agent comprises the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7.

In some embodiments, the therapeutic agent is an anti-human IL-12 and IL-23 subunit antibody or an antibody fragment thereof.

In some embodiments, the therapeutic agent comprises the sequence of SEQ ID NO: 8 and the sequence of SEQ ID NO: 9.

In some embodiments, the therapeutic agent is a human monoclonal anti-TNF-α antibody or an antibody fragment thereof.

In some embodiments, the therapeutic agent comprises the sequence of SEQ ID NO: 10 and the sequence of SEQ ID NO: 11.

In some embodiments, the therapeutic agent is an anti-integrin α4β1 antibody or an antibody fragment thereof.

In some embodiments, the therapeutic agent comprises the sequence of SEQ ID NO: 12 and the sequence of SEQ ID NO: 14, or the sequence of SEQ ID NO: 13 and the sequence of SEQ ID NO: 15.

In some embodiments, the therapeutic agent is an anti-integrin α4β7 antibody or an antibody fragment thereof.

In some embodiments, the therapeutic agent comprises the sequence of SEQ ID NO: 16 and the sequence of SEQ ID NO: 17.

In some embodiments, the therapeutic agent is a fragment of an anti-TNF-α antibody.

In some embodiments, the therapeutic agent comprises the sequence of SEQ ID NO: 18 and the sequence of SEQ ID NO: 19.

In some embodiments, the compound comprises an antibody or an antibody fragment thereof having a modified antibody structure.

In some embodiments, the compound comprises an antibody or an antibody fragment thereof having a choline or choline derivative-modified antibody structure.

In some embodiments, the compound comprises an antibody or an antibody fragment thereof having a cation moiety comprising choline or choline derivative.

In some embodiments, the compound comprises an antibody or an antibody fragment thereof having a choline or choline derivative-modified ester structure.

In some embodiments, the compound comprises an antibody or an antibody fragment thereof having a cation moiety comprising a choline or choline derivative-like residue.

In some embodiments, the compound comprises an antibody or an antibody fragment thereof comprising one or more $R^{11}$ linked to the C-terminus of a light chain, the C-terminus of a heavy chain or a combination thereof.

In some embodiments, the compound comprises an antibody or an antibody fragment thereof comprising one or more $R^{11}$ linked to a Lys residue, a Cys residue, or any combination thereof.

In some embodiments, $R^{11}$ is linked to the Lys residue with a linker-to-antibody ratio of 2-4, $R^{11}$ is linked to the Cys residue with a linker-to-antibody ratio of 2-8 or with a linker-to-antibody ratio of 4, or a combination thereof.

In some embodiments, the compound comprises an antibody or an antibody fragment thereof comprising a dual conjugation.

In some embodiments, the dual conjugation comprises a linker-to-antibody ratio of 1-2.

In some embodiments, the compound comprises an antibody or an antibody fragment comprising a linker comprising one or more gamma glutamate (γGlu) residues, one or more 8-amino-3,6-dioxaoctanoic acid (OEG) residues, or a combination thereof.

In some embodiments, the compound comprises an antibody or an antibody fragment comprising a linker comprising one or more gamma glutamate (γGlu) residues.

In some embodiments, the compound comprises an antibody or an antibody fragment comprising a choline or choline derivative-peptide derivative that is formed on the carboxylic acid of the one or more gamma glutamate residues of the linker.

In some embodiments, the compound comprises an antibody or an antibody fragment comprising a choline or choline derivative-peptide ester that is formed on the carboxylic acid of the one or more gamma glutamate residues of the linker.

In some embodiments, the compound comprises an antibody or an antibody fragment comprising a diacid consisting of 18 or 20 carbons in length.

In some embodiments, the diacid comprises a $C_{20}$ fatty diacid.

In some embodiments, the diacid comprises 1,20-icosanedioic acid.

In another aspect, provided herein is a pharmaceutical composition comprising the composition as provided herein or the compound as provided herein, and one or more ionic liquid.

In some embodiments, the one or more ionic liquid independently comprises a cation selected from the group consisting of aminoguanidine, choline or choline derivative, ammonium, tetramethyl ammonium, tetraethyl ammonium, tetrabutyl ammonium, and guanidine derivatives.

In some embodiments, the one or more ionic liquid independently comprises choline or choline derivative.

In some embodiments, the one or more ionic liquid independently comprises an anion selected from the group consisting of (R)-α-lipoic acid, 2-(4-isobutylphenyl)propionic acid, 2-(4,4-dimethyl-2-pentanyl)-5,7,7-trimethyloctanoic acid, 2-hexyldecanoic acid, 2-hydroxyhippuric acid, 3,7-dimethyloctanoic acid, 4-methylhexanoic acid, 4-methyloctanoic acid, 4-methylvaleric acid, 5-norbornene-2-carboxylic acid, abietic acid, acetic acid, acetylcysteine, arachidonic acid, caffeic acid, cinnamic acid, citric acid, citronellic acid, crotonic acid, D-(+)-galactonic acid, decanoic acid, deoxycholic acid, eicosapentanoic acid, fumaric acid, geranic acid, glutaric acid, glycolic acid, hexanoic acid, 3-phenylpropionic acid, isovaleric acid, L-(+)-tartaric acid, L-ascorbic acid, L-glutathione reduced, lactic acid, lauric acid, levulinic acid, linoleic acid, linolenic acid, maleic acid, malonic acid, mesaconic acid, mandelic acid, nonanoic acid, octanoic acid, oleic acid, p-toluenesulfonic acid, perillic acid, phosphoric acid, pimelic acid, propionic acid, pyroglutamic acid, pyruvic acid, ricinoleic acid, sorbic acid, syringic acid, trans-2-decenoic acid, trans-2-hexenoic acid, trans-2-octenoic acid, trans-3-octenoic acid, trans-γ-octenoic acid, trans-ferulic acid, undecanoic acid, vanillic acid, and α-ketoglutaric acid.

In some embodiments, the one or more ionic liquid independently comprises an anion selected from the group consisting of glycolic acid, tartaric acid, malic acid, hydrocinnamic acid, citric acid, cinnamic acid, mandelic acid, and mesaconic acid.

In some embodiments, the one or more ionic liquid independently comprises choline or choline derivative-cinnamic acid, choline or choline derivative-mandelic acid, or choline or choline derivative-citric acid.

In some embodiments, the pharmaceutical composition further comprises at least one permeation enhancer.

In some embodiments, the at least one permeation enhancer is selected from the group consisting of salcaprozate sodium (SNAC), sodium caprylate, sodium caprate, a bile salt, ethylenediaminetetraacetic acid (EDTA), ethylene glycol-bis-(2-aminoethylether)-N,N,N',N'-tetraacetic acid (EGTA), and 3-[N,N-Dimethyl(3-palmitoylaminopropyl)-ammonio]-propanesulfonate (PPS), and any combination thereof.

In some embodiments, the bile salt is selected from the group consisting of sodium deoxycholate, sodium chenodeoxycholate, sodium taurodeoxycholate, and a combination thereof.

In some embodiments, the pharmaceutical composition further comprises at least one pharmaceutically acceptable excipient.

In another aspect, provided herein is a pharmaceutical composition comprising the composition as provided herein or the compound as provided herein, and at least one pharmaceutically acceptable excipient.

In another aspect, provided herein is a method of treating a disease or disorder in a subject in need thereof, comprising administering to the subject a therapeutically effective amount of the composition as provided herein, the compound as provided herein, or the pharmaceutical composition as provided herein.

In some embodiments, the disease or disorder is an autoimmune or immunological disease or disorder.

In some embodiments, the disease or disorder is Crohn's disease, ulcerative colitis, rheumatoid arthritis, ankylosing spondylitis, psoriasis, psoriatic arthritis, Behget's disease, plaque psoriasis, hidradenitis suppurativa, uveitis, and juvenile idiopathic arthritis, plaque psoriasis, multiple sclerosis, or eosinophilic esophagitis.

In some embodiments, the composition, the compound, or the pharmaceutical composition is administered via subcutaneous, intravenous, or oral administration.

In some embodiments, the composition, the compound, or the pharmaceutical composition is administered orally.

In some embodiments, the composition, the compound, or the pharmaceutical composition is administered as a liquid-filled capsule.

In some embodiments, the composition, the compound, or the pharmaceutical composition is administered in multiple doses.

In some embodiments, the composition, the compound, or the pharmaceutical composition is administered in a single dose.

In some embodiments, the composition, the compound, or the pharmaceutical composition is administered to a mucus membrane.

In some embodiments, the concentration of the compound as provided herein is at least 0.1% weight per volume.

In some embodiments, the concentration of the compound as provided herein is at least 0.05M.

In some embodiments, the composition further comprises one or more additional agents.

In some embodiments, the one or more additional agent is selected from the group consisting of a nucleic acid, a small molecule, and a polypeptide.

In some embodiments, the one or more additional agent is a nucleic acid.

In some embodiments, the one or more additional agent is a small molecule.

In some embodiments, the one or more additional agent is a polypeptide.

In another aspect, provided herein is a method of enhancing the hydrophobicity of a therapeutic agent, comprising linking $R^{12}$ to a therapeutic agent, wherein $R^{12}$ is substituted or unsubstituted $C_5$-$C_{10}$; and wherein the therapeutic agent is an antibody or an antibody fragment thereof.

In some embodiments, $R^{12}$ is linked to

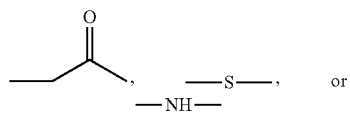

of the therapeutic agent.

In some embodiments, $R^{12}$ is linked to the therapeutic agent via a covalent bond or a linker.

In some embodiments, the linker is a non-cleavable linker.

In some embodiments, the linker comprises a maleimide alkane linker or a maleimide cyclohexane linker.

In some embodiments, the linker comprises

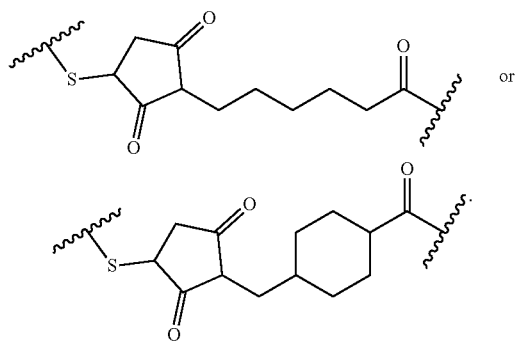

In some embodiments, the linker is a chemically cleavable linker.

In some embodiments, the linker comprises a hydrazone linker or a disulfide linker.

In some embodiments, the linker comprises

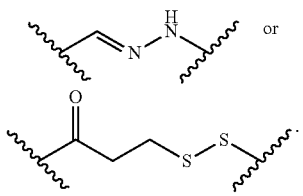

In some embodiments, $R^{12}$ is substituted or unsubstituted $C_{10}$.

In some embodiments, the therapeutic agent is any one selected from the group consisting of a chimeric monoclonal anti-TNF-α antibody or an antibody fragment thereof, a monoclonal anti-TNF-α antibody or an antibody fragment thereof, an anti-human IL-12 and IL-23 subunit antibody or an antibody fragment thereof, a human monoclonal anti-TNF-α antibody or an antibody fragment thereof, an anti-integrin α4β1 antibody or an antibody fragment thereof, an anti-integrin α4β7 antibody or an antibody fragment thereof, and a fragment of an anti-TNF-α antibody.

In some embodiments, the therapeutic agent is any one selected from the group consisting of infliximab or an antibody fragment thereof, adalimumab or an antibody fragment thereof, ustekinumab or an antibody fragment thereof, golimumab or an antibody fragment thereof, natalizumab or an antibody fragment thereof, vedolizumab or an antibody fragment thereof, and certolizumab pegol or an antibody fragment thereof.

In some embodiments, the therapeutic agent comprises: (i) a sequence with at least 75% sequence identity to the sequence of SEQ ID NO: 1 or SEQ ID NO: 24, a sequence with at least 75% sequence identity to the sequence of SEQ ID NO: 2, or a combination thereof; (ii) a sequence with at least 75% sequence identity to the sequence of SEQ ID NO: 3, SEQ ID NO: 4, or SEQ ID NO: 5, a sequence with at least 75% sequence identity to the sequence of SEQ ID NO: 6 or SEQ ID NO: 7, or any combination thereof, (iii) a sequence with at least 75% sequence identity to the sequence of SEQ ID NO: 8, a sequence with at least 75% sequence identity to the sequence of SEQ ID NO: 9, or a combination thereof; (iv) a sequence with at least 75% sequence identity to the sequence of SEQ ID NO: 10, a sequence with at least 75% sequence identity to the sequence of SEQ ID NO: 11, or a combination thereof, (v) a sequence with at least 75% sequence identity to the sequence of SEQ ID NO: 12 or SEQ ID NO: 13, a sequence with at least 75% sequence identity to the sequence of SEQ ID NO: 14 or SEQ ID NO: 15, or any combination thereof; (vi) a sequence with at least 75% sequence identity to the sequence of SEQ ID NO: 16, a sequence with at least 75% sequence identity to the sequence of SEQ ID NO: 17, or a combination thereof, or (vii) a sequence with at least 75% sequence identity to the sequence of SEQ ID NO: 18, a sequence with at least 75% sequence identity to the sequence of SEQ ID NO: 19, or a combination thereof.

In some embodiments, the therapeutic agent comprises: (i) the sequence of SEQ ID NO: 1 or SEQ ID NO: 24, the sequence of SEQ ID NO: 2, or a combination thereof; (ii) the sequence of SEQ ID NO: 3, SEQ ID NO: 4, or SEQ ID NO: 5, the sequence of SEQ ID NO: 6 or SEQ ID NO: 7, or any combination thereof; (iii) the sequence of SEQ ID NO: 8, the sequence of SEQ ID NO: 9, or a combination thereof; (iv) the sequence of SEQ ID NO: 10, the sequence of SEQ ID NO: 11, or a combination thereof; (v) the sequence of SEQ ID NO: 12 or SEQ ID NO: 13, the sequence of SEQ ID NO: 14 or SEQ ID NO: 15, or any combination thereof, (vi) the sequence of SEQ ID NO: 16, the sequence of SEQ ID NO: 17, or a combination thereof; or (vii) the sequence of SEQ ID NO: 18, the sequence of SEQ ID NO: 19, or a combination thereof.

In some embodiments, the therapeutic agent comprises: (i) the sequence of SEQ ID NO: 1 or SEQ ID NO: 24, and the sequence of SEQ ID NO: 2; (ii) the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7; (iii) the sequence of SEQ ID NO: 8 and the sequence of SEQ ID NO: 9; (iv) the sequence of SEQ ID NO: 10 and the sequence of SEQ ID NO: 11; (v) the sequence of SEQ ID NO: 12 and the sequence of SEQ ID NO: 14, or the sequence of SEQ ID NO: 13 and the sequence of SEQ ID NO: 15; (vi) the sequence of SEQ ID NO: 16 and the sequence of SEQ ID NO: 17; or (vii) the sequence of SEQ ID NO: 18 and the sequence of SEQ ID NO: 19.

In another aspect, provided herein is a method of enhancing or improving a delivery efficiency of a therapeutic agent in a subject in need thereof comprising adding at least one permeation enhancer to the composition as provided herein, the compound as provided herein, or the pharmaceutical composition as provided herein; and administering the composition, the compound, or the pharmaceutical composition to the subject.

In some embodiments, the at least one permeation enhancer is selected from the group consisting of salcaprozate sodium (SNAC), sodium caprylate, sodium caprate, a bile salt, ethylenediaminetetraacetic acid (EDTA), ethylene glycol-bis-(2-aminoethylether)-N,N,N',N'-tetraacetic acid (EGTA), and 3-[N,N-Dimethyl(3-palmitoylaminopropyl)-ammonio]-propanesulfonate (PPS), and any combination thereof.

In some embodiments, the bile salt is selected from the group consisting of sodium deoxycholate, sodium chenodeoxycholate, sodium taurodeoxycholate, and a combination thereof.

In some embodiments, to enhance the hydrophobicity of an antibody or antibody fragment thereof, an antibody or antibody fragment thereof is linked to one or more fatty acids or carboxylic acid-containing molecules. In some embodiments, one or more fatty acids or carboxylic acid-containing molecules are linked to an antibody or antibody fragment thereof via a dual conjugation (or dual covalent conjugation). In some embodiments, one or more fatty acids or carboxylic acid-containing molecules comprise cinnamic acid. In some embodiments, one or more fatty acids or carboxylic acid-containing molecules are cinnamic acid.

In some embodiments, one or more fatty acids or carboxylic acid-containing molecules are non-covalently associated with a free amine of an antibody or antibody fragment thereof. In some embodiments, one or more fatty acids or carboxylic acid-containing molecules are non-covalently associated with the N-terminal amine in the peptide backbone of an antibody or antibody fragment thereof. In some embodiments, one or more fatty acids or carboxylic acid-containing molecules are non-covalently associated with the amine group of a Gln residue, the amine group of an Asn residue, the amine group of an Arg residue, the amine group of a Lys residue, the amine group of a His residue, or a combination thereof of an antibody or antibody fragment thereof.

In some embodiments, one or more fatty acids or carboxylic acid-containing molecules are covalently conjugated to a free amine of an antibody or antibody fragment thereof. In some embodiments, one or more fatty acids or carboxylic acid-containing molecules are covalently conjugated to the N-terminal amine in the peptide backbone of an antibody or antibody fragment thereof. In some embodiments, one or more fatty acids or carboxylic acid-containing molecules are covalently conjugated to the amine group of a Gln residue, the amine group of an Asn residue, the amine group of an Arg residue, the amine group of a Lys residue, the amine group of a His residue, or a combination thereof of an antibody or antibody fragment thereof.

Amylin Analog or Functional Variant Thereof or Mimetic Thereof or Functional Homolog Thereof In one embodiment, described herein is a method of treatment of diabetes comprising orally administering an oral formulation of an amylin analog or functional variant thereof or mimetic thereof in combination with ionic liquid.

In some embodiments, an amylin analog or functional variant thereof or mimetic or functional analog thereof or functional homolog thereof is pramlintide or functional variant thereof or mimetic or functional homolog thereof. As used herein, "Pramlintide," also known as Symlin, refers to an injectable amylin analog drug for diabetes (both type 1 and 2).

In some embodiments, an amylin analog or functional variant thereof is an acetate derivative form. In some embodiments, an amylin analog or functional variant thereof, in synergy with endogenous amylin, aids in the regulation of blood glucose by slowing gastric emptying, promoting satiety via hypothalamic receptors, and inhibiting inappropriate secretion of glucagon, a catabolic hormone that opposes the effects of insulin and amylin. In some embodiments, an amylin analog or functional variant thereof has effects in raising the acute first-phase insulin response threshold following a meal.

In some embodiments, an amylin analog or functional variant thereof comprises the following sequence:

```
                                            (SEQ ID NO: 20)
   KCNTATCATQRLANFLVHSSNNFGPILPPTNVGSNTY-amide.
```

In some embodiments, Cys at the position 2 and Cys at the position 7 forms a disulfide bond.

Figure 1B:
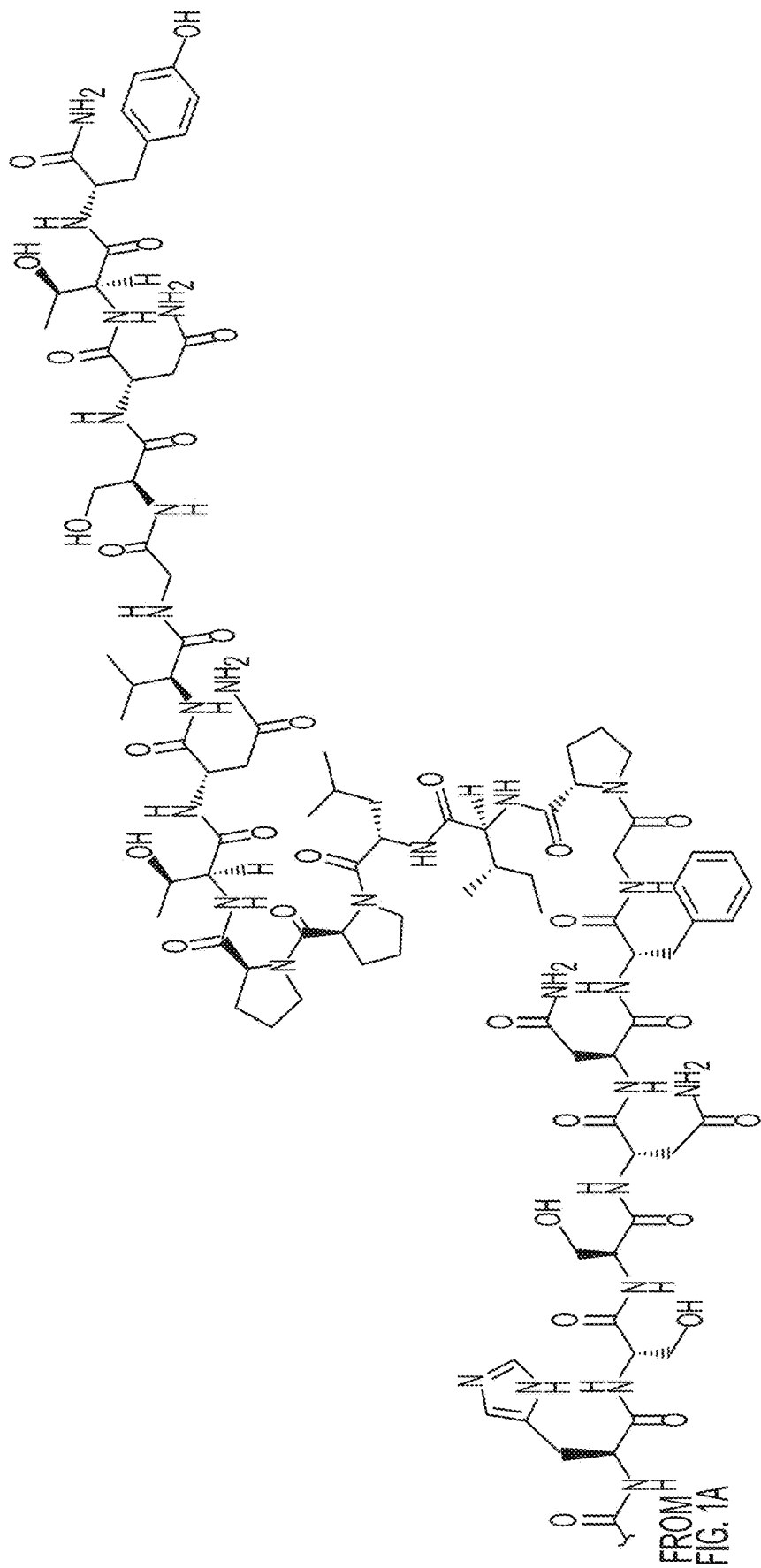

In some embodiments, an amylin analog or functional variant thereof comprises the structure as shown in FIG. 1A and FIG. 1B.

In some embodiments, an amylin analog or functional variant thereof or mimetic thereof comprises the following sequence:

```
                                            (SEQ ID NO: 21)
[diacid]-[linker]-KCNTATCATQ RLANFLVHSS NNFGPILPPT NVGSNTY-amide.
```

Figure 2A:
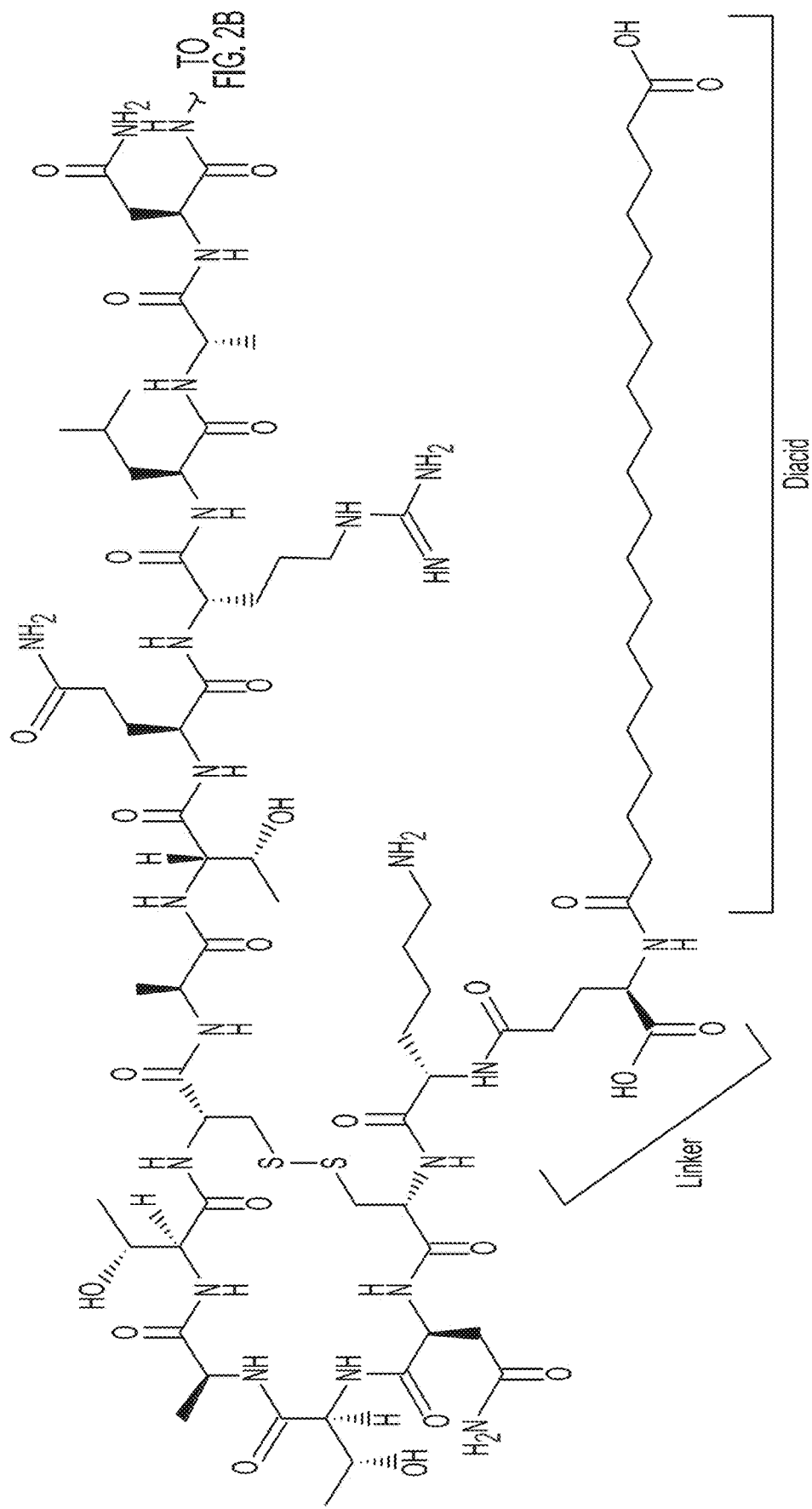
FIGS. 2A, 2B, and 2C depict exemplary embodiments of an amylin analog or functional variant thereof or mimetic thereof with modified amylin analog or functional variant thereof or mimetic thereof structures.
Figure 2B:
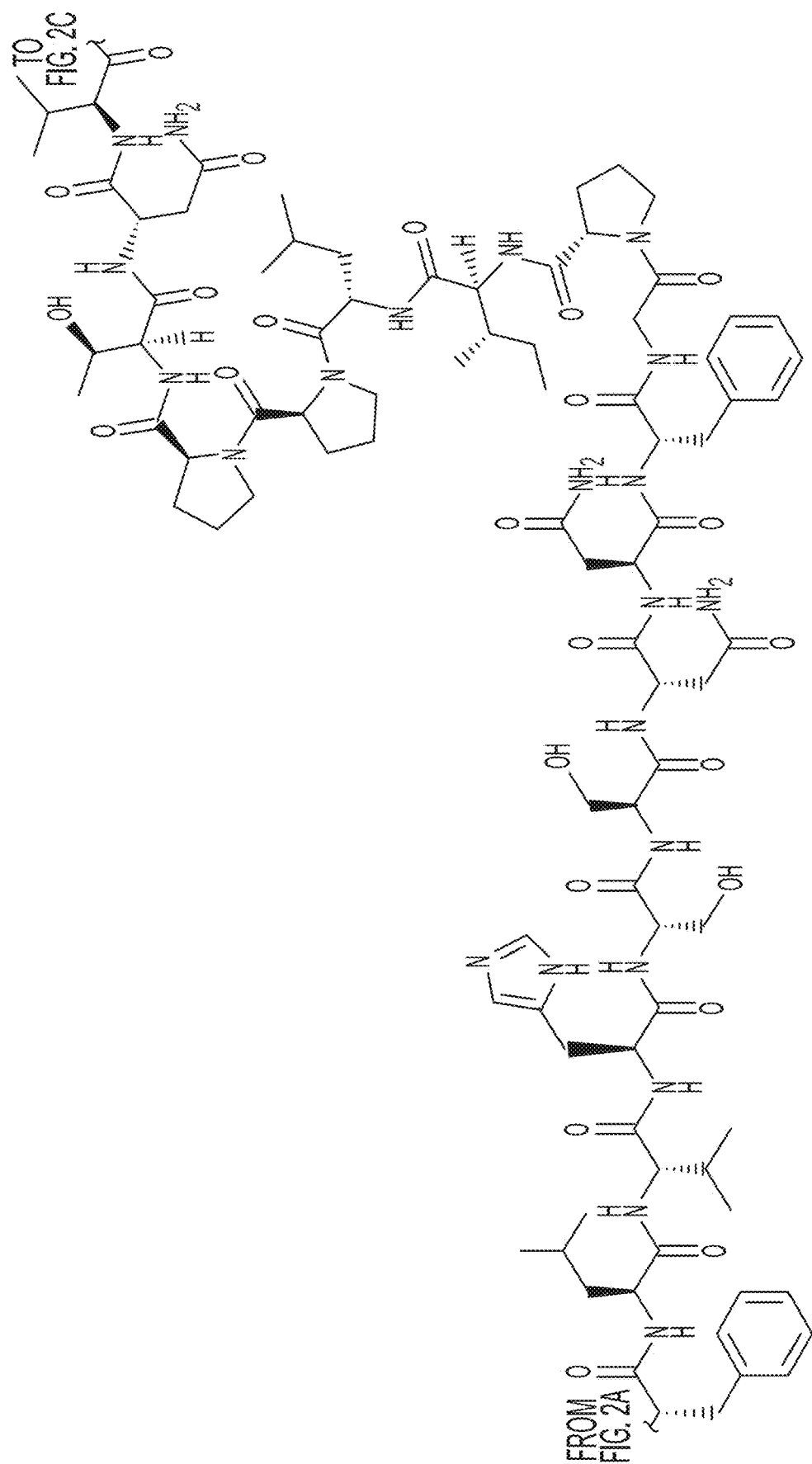
Figure 2C:
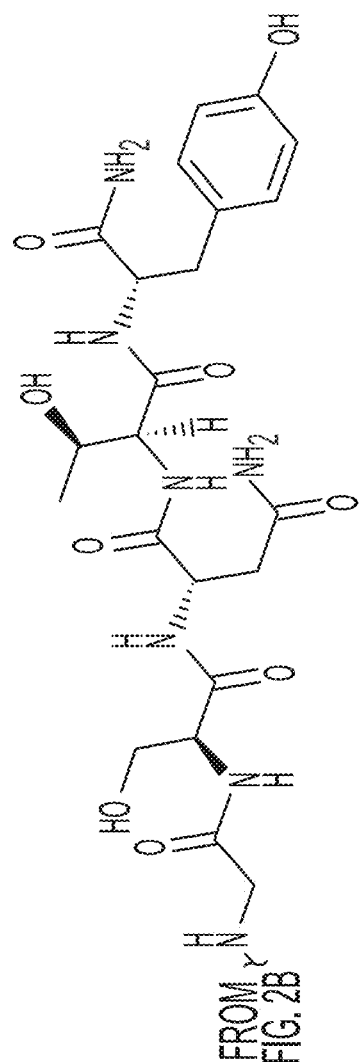

In some embodiments, an amylin analog or functional variant thereof or mimetic thereof comprises the structure as shown in FIGS. 2A, 2B, and 2C.

In some embodiments, an amylin analog or functional variant thereof or mimetic thereof comprises one or more of the following amino acid substitutions: N14E, V17R, Y37P, F15E, L16E, and V17E. In some embodiments, an amylin analog or functional variant thereof or mimetic thereof comprises an amino acid substitution of N14E. In some embodiments, an amylin analog or functional variant thereof or mimetic thereof comprises an amino acid substitution of V17R. In some embodiments, an amylin analog or functional variant thereof or mimetic thereof comprises an amino acid substitution of Y37P. In some embodiments, an amylin analog or functional variant thereof or mimetic thereof comprises an amino acid substitution of F15E. In some embodiments, an amylin analog or functional variant thereof or mimetic thereof comprises an amino acid substitution of L16E. In some embodiments, an amylin analog or functional variant thereof or mimetic thereof comprises an amino acid substitution of V17E. In some embodiments, an amylin analog or functional variant thereof or mimetic thereof comprises an amino acid substitution of N14E, V17R, Y37P, F15E, L16E, V17E, or any combination thereof.

In some embodiments, the linker comprises one or more gamma glutamate (γGlu) residues and/or one or more 8-amino-3,6-dioxaoctanoic acid (OEG) residues. In some embodiments, the linker comprises one or more gamma glutamate (γGlu) residues. In some embodiments, the linker comprises one or more 8-amino-3,6-dioxaoctanoic acid (OEG) residues. In some embodiments, the linker comprises gamma glutamate (γGlu).

In some embodiments, the diacid comprises diacids consisting of 18 or 20 carbons in length. In some embodiments, the diacid comprises a C20 fatty diacid. In some embodiments, the diacid comprises 1,20-icosanedioic acid.

Figure 3A:
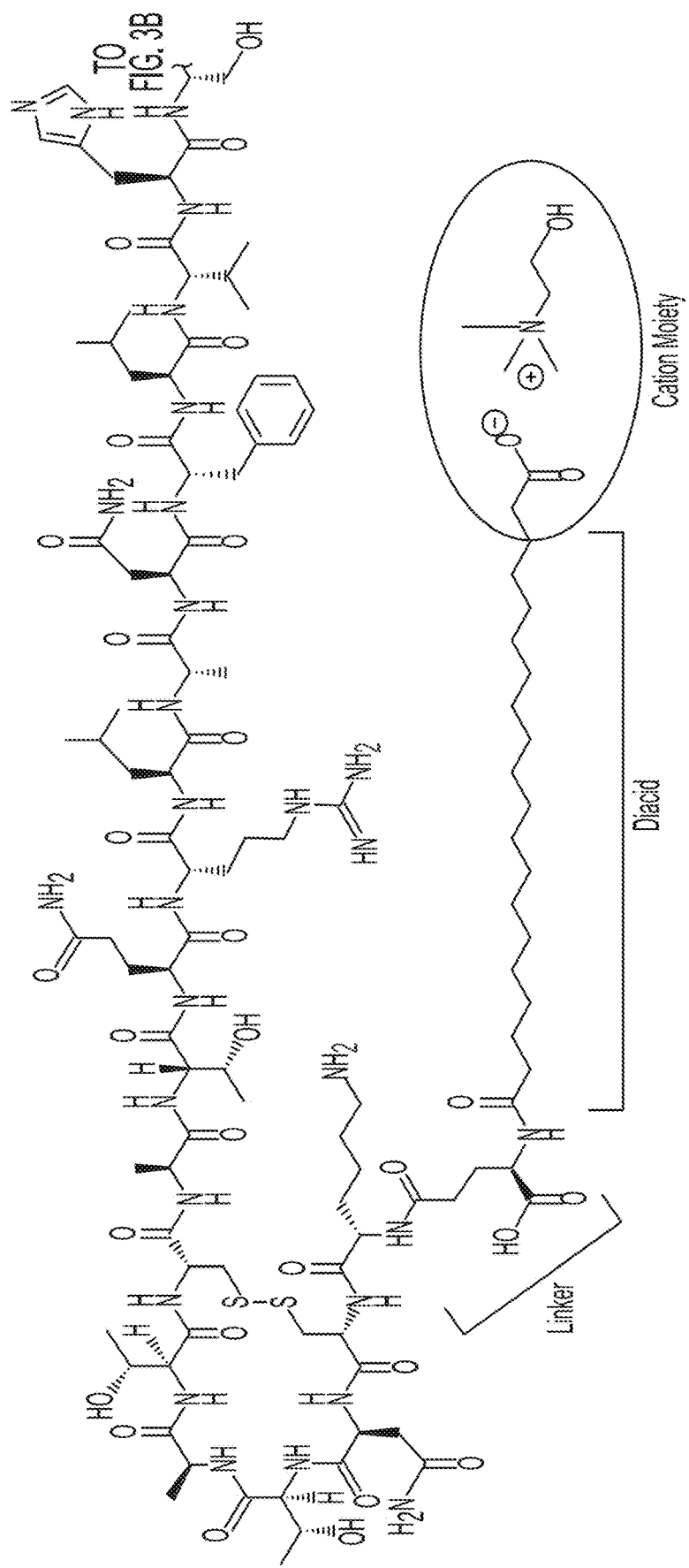
FIG. 3A and FIG. 3B depict exemplary embodiments of an amylin analog or functional variant thereof or mimetic thereof with choline-modified amylin analog or functional variant thereof or mimetic thereof derivative structures.
Figure 3B:
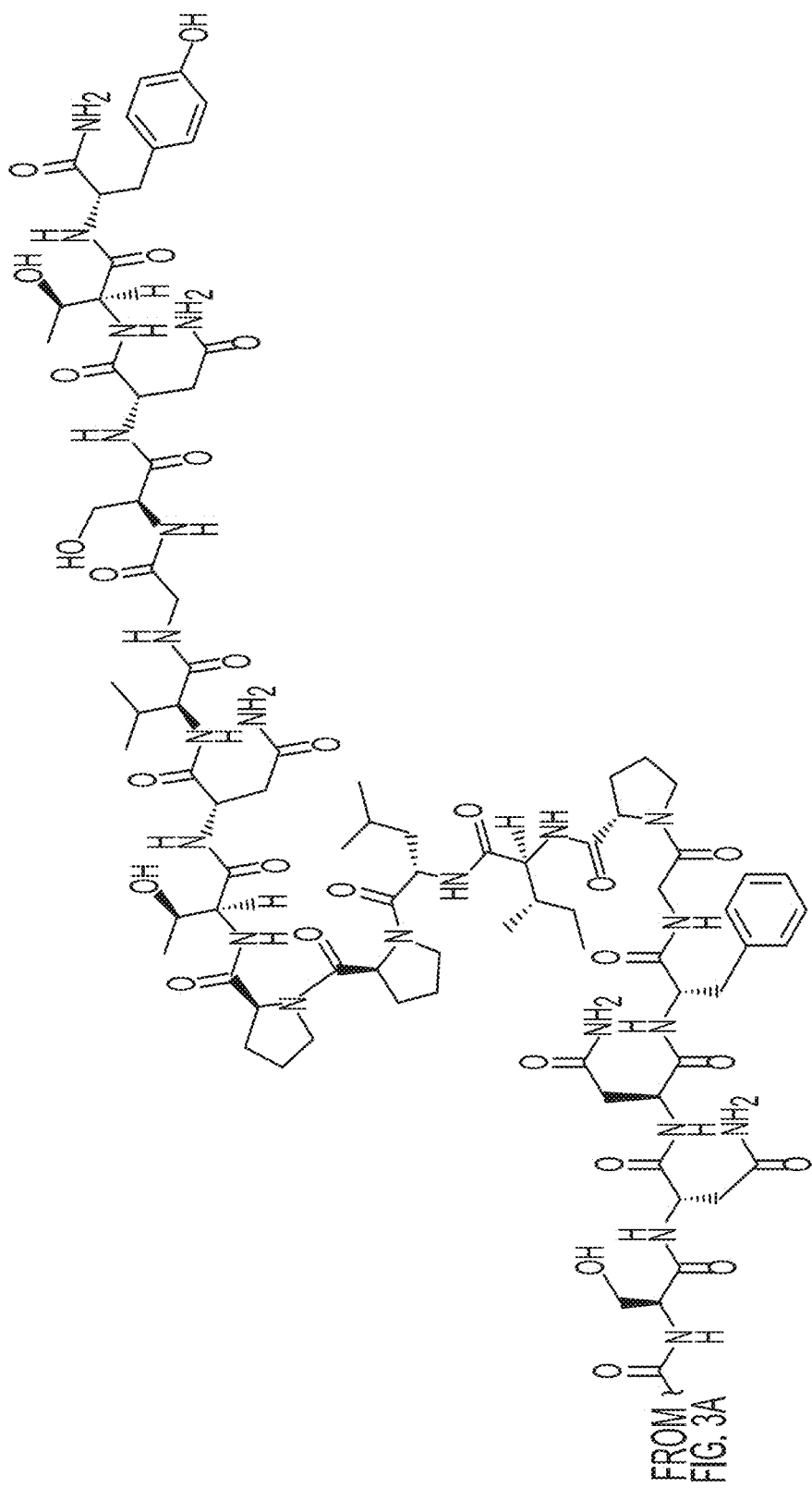

In some embodiments, an amylin analog or functional variant thereof or mimetic thereof comprises the structure as shown in FIGS. 3A and 3B.

In some embodiments, the cation moiety comprises choline or choline derivative.

In some embodiments, an amylin analog or functional variant thereof or mimetic thereof comprises one or more of the following amino acid substitutions: N14E, V17R, Y37P, F15E, L16E, and V17E. In some embodiments, an amylin analog or functional variant thereof or mimetic thereof comprises an amino acid substitution of N14E. In some embodiments, an amylin analog or functional variant thereof or mimetic thereof comprises an amino acid substitution of V17R. In some embodiments, an amylin analog or functional variant thereof or mimetic thereof comprises an amino acid substitution of Y37P. In some embodiments, an amylin analog or functional variant thereof or mimetic thereof comprises an amino acid substitution of F15E. In some embodiments, an amylin analog or functional variant thereof or mimetic thereof comprises an amino acid substitution of L16E. In some embodiments, an amylin analog or functional variant thereof or mimetic thereof comprises an amino acid substitution of V17E. In some embodiments, an amylin analog or functional variant thereof or mimetic thereof comprises an amino acid substitution of N14E, V17R, Y37P, F15E, L16E, V17E, or any combination thereof.

In some embodiments, the linker comprises one or more gamma glutamate (γGlu) residues and/or one or more 8-amino-3,6-dioxaoctanoic acid (OEG) residues. In some embodiments, the linker comprises one or more gamma glutamate (γGlu) residues. In some embodiments, the linker comprises one or more 8-amino-3,6-dioxaoctanoic acid (OEG) residues. In some embodiments, the linker comprises gamma glutamate (γGlu).

In some embodiments, the diacid comprises diacids consisting of 18 or 20 carbons in length. In some embodiments, the diacid comprises a C20 fatty diacid. In some embodiments, the diacid comprises 1,20-icosanedioic acid.

Figure 4A:
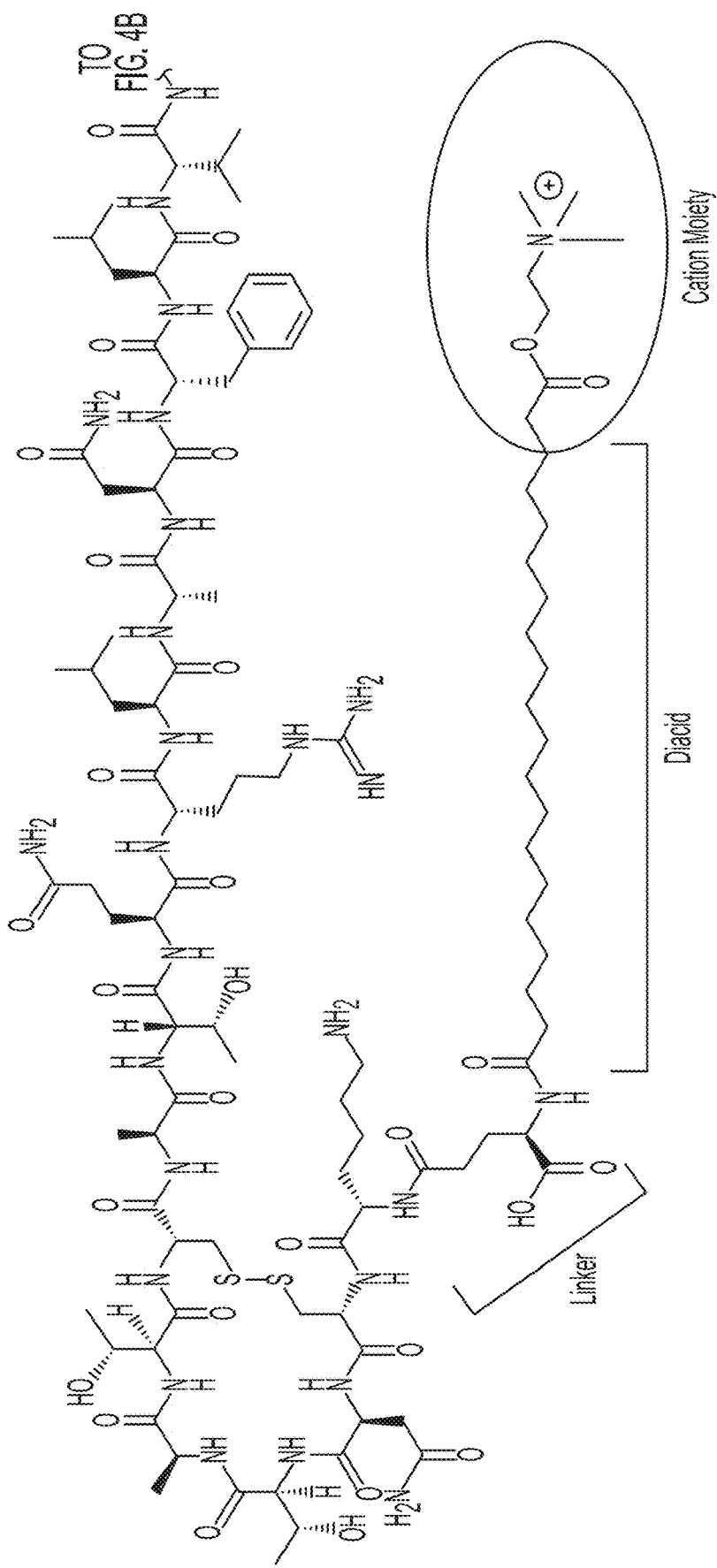
FIG. 4A and FIG. 4B depict exemplary embodiments of an amylin analog or functional variant thereof or mimetic thereof with choline-modified amylin analog or functional variant thereof or mimetic thereof ester structures.
Figure 4B:
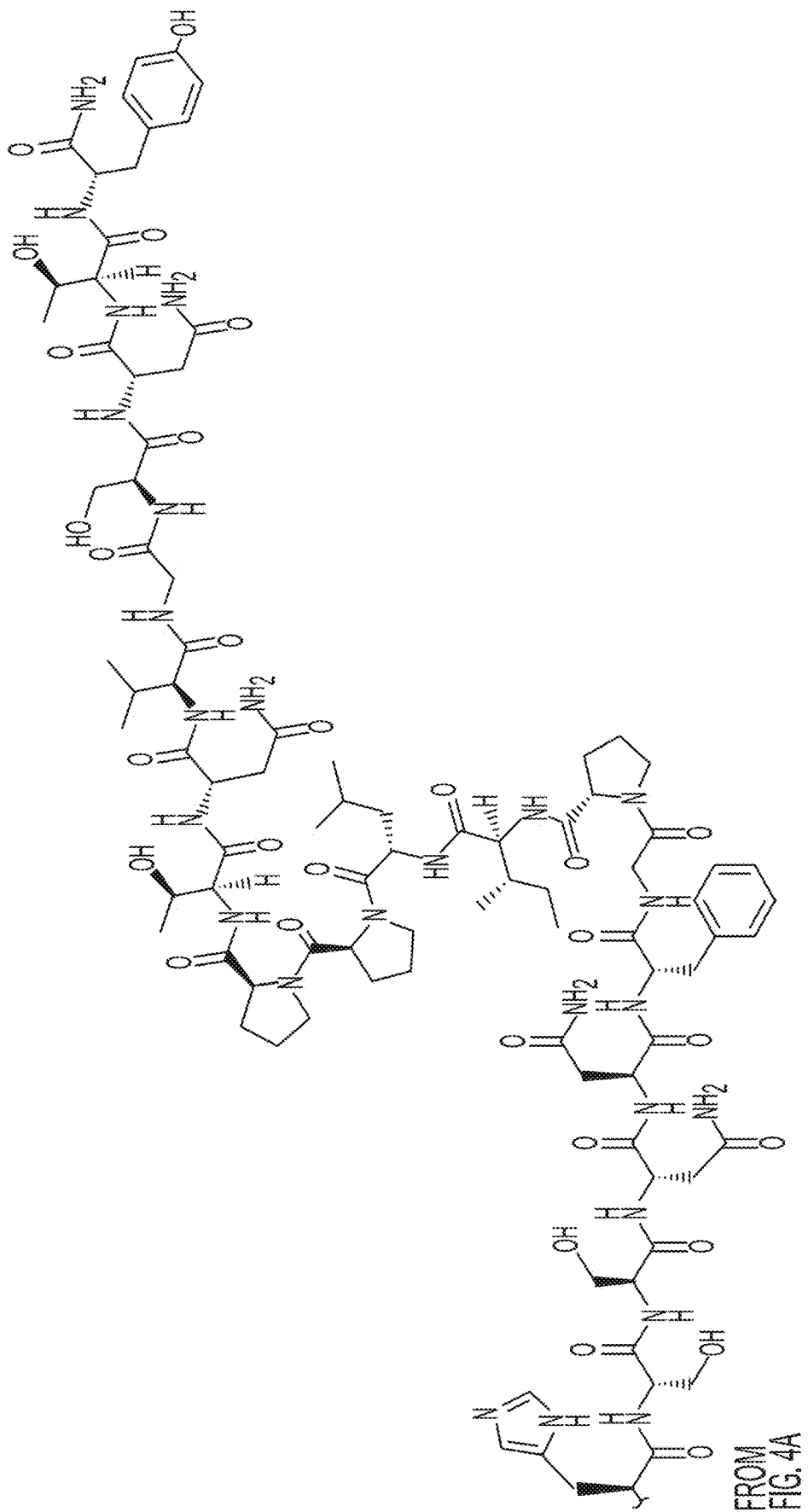

In some embodiments, an exemplary amylin analog or functional variant thereof or mimetic thereof comprises the structure as shown in FIG. 4A and FIG. 4B.

In some embodiments, the cation moiety comprises a choline or choline derivative-like residue.

In some embodiments, an amylin analog or functional variant thereof or mimetic thereof comprises one or more of the following amino acid substitutions: N14E, V17R, Y37P, F15E, L16E, and V17E. In some embodiments, an amylin analog or functional variant thereof or mimetic thereof comprises an amino acid substitution of N14E. In some embodiments, an amylin analog or functional variant thereof or mimetic thereof comprises an amino acid substitution of V17R. In some embodiments, an amylin analog or functional variant thereof or mimetic thereof comprises an amino acid substitution of Y37P. In some embodiments, an amylin analog or functional variant thereof or mimetic thereof comprises an amino acid substitution of F15E. In some embodiments, an amylin analog or functional variant thereof or mimetic thereof comprises an amino acid substitution of L16E. In some embodiments, an amylin analog or functional variant thereof or mimetic thereof comprises an amino acid substitution of V17E. In some embodiments, an amylin analog or functional variant thereof or mimetic thereof comprises an amino acid substitution of N14E, V17R, Y37P, F15E, L16E, V17E, or any combination thereof.

In some embodiments, the linker comprises one or more gamma glutamate (γGlu) residues and/or one or more 8-amino-3,6-dioxaoctanoic acid (OEG) residues. In some embodiments, the linker comprises one or more gamma glutamate (γGlu) residues. In some embodiments, the linker comprises one or more 8-amino-3,6-dioxaoctanoic acid (OEG) residues. In some embodiments, the linker comprises gamma glutamate (γGlu).

In some embodiments, the diacid comprises diacids consisting of 18 or 20 carbons in length. In some embodiments, the diacid comprises a C20 fatty diacid. In some embodiments, the diacid comprises 1,20-icosanedioic acid.

"Amylin," also known as islet amyloid polypeptide, IAPP, DAP, LAP, islet amyloid polypeptide, as used herein, refers to a 37-residue small peptide hormone that is released into the bloodstream by the β cells of the pancreas along with insulin after a meal. In some embodiments, amylin is co-secreted with insulin from the pancreatic β-cells in the ratio of approximately 100:1 (insulin:amylin). In some embodiments, amylin plays a role in glycemic regulation by slowing gastric emptying and promoting satiety, thereby preventing post-prandial spikes in blood glucose levels. In some embodiments, like insulin, amylin is completely absent in individuals with Type I diabetes. In some embodiments, amylin, as used herein, includes any of the recombinant or naturally-occurring forms of amylin or variants or homologs thereof that have or maintain amylin activity (e.g., at least 40% 50%, 60%, 70%, 80%, 90%, 95%, 96%, 97%, 98%, 99% or 100% activity). In some aspects, the variants or homologs have at least 40%, 45%, 50%, 55%, 60%, 65%, 70%, 75%, 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring amylin. In some embodiments, amylin is substantially identical to the protein identified by the UniProt reference number P10997 or a variant or homolog having substantial identity thereto. In some embodiments, UniProt reference number P10997 provides exemplary human amylin amino acid sequences. In some embodiments, amylin molecule is a naturally-existing amylin or a functional variant or fragment thereof.

In one aspect, provided herein, inter alia, is a composition comprising a compound according to Formula I:

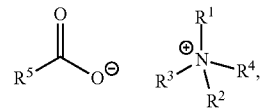

Formula I wherein:
R$^1$, R$^2$, and R$^3$ are independently C$_1$-C$_5$ alkyl;
R$^4$ is C$_2$-C$_5$ alkyl, wherein the C$_2$-C$_5$ alkyl is unsubstituted or substituted with 1 or more hydroxyl;
R$^5$ is amylin or mimetic or analog thereof, or an amylin analog or functional variant thereof or mimetic or analog thereof.

In some embodiments, R$^1$, R$^2$, and R$^3$ are methyl.
In some embodiments, R$^1$, R$^2$, and R$^3$ are ethyl.
In some embodiments, R$^1$, R$^2$, and R$^3$ are propyl.
In some embodiments, R$^1$ and R$^2$ are methyl, and R$^3$ is ethyl.

In some embodiments, R¹ and R³ are methyl, and R² is ethyl.

In some embodiments, R¹ and R² are ethyl, and R³ is methyl.

In some embodiments, R¹ and R³ are ethyl, and R² is methyl.

In some embodiments, R¹ and R² are propyl, and R³ is methyl.

In some embodiments, R¹ and R³ are propyl, and R² is methyl.

In some embodiments, R⁴ is C₂-C₅ alkyl substituted with a hydroxyl.

In some embodiments, the composition comprises a

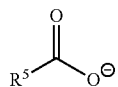

to

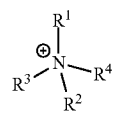

molar ratio of from about 1:1 to about 1:30.

In some embodiments, the composition comprises a

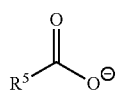

to

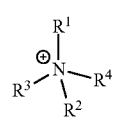

molar ratio of about 1:1.

In some embodiments, the composition comprises a

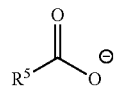

to

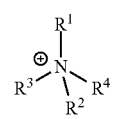

molar ratio of about 1:3.

In some embodiments, the composition comprises a

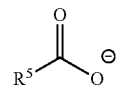

and

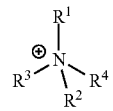

molar ratio of about 1:7.

In some embodiments, the composition comprises

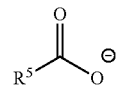

to

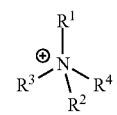

molar ratio of about 1:12.

In some embodiments, the composition comprises a

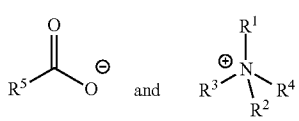

molar ratio of about 1:28.

In some embodiments, R⁴ is

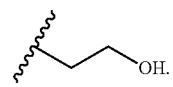

In some embodiments, the compound is according to Formula Ia:

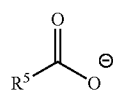 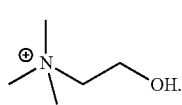

Formula Ia

In some embodiments, the compound is according to Formula Ib:

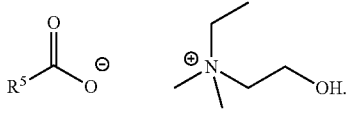

Formula Ib

In some embodiments, the compound is according to Formula Ic:

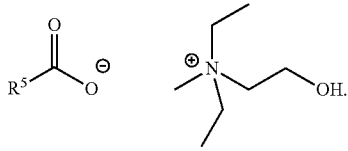

Formula Ic

In some embodiments, $R^5$ is amylin or mimetic thereof, or an amylin analog or functional variant thereof or mimetic thereof.

In some embodiments, $R^5$ is an amylin analog or functional variant thereof or mimetic thereof.

In some embodiments, $R^5$ is an amylin analog or functional variant thereof or mimetic thereof having the sequence of:

```
                                          (SEQ ID NO: 21)
[diacid]-[linker]-KCNTATCATQ RLANFLVHSS NNFGPILPPT NVGSNTY-amide.
```

In some embodiments, $R^5$ is an amylin analog or functional variant thereof or mimetic thereof having the structure as shown in FIGS. 2A, 2B, and 2C, FIG. 3A and FIG. 3B, or FIG. 4A and FIG. 4B.

In some embodiments, $R^5$ is an amylin analog or functional variant thereof or mimetic thereof having a modified amylin analog or functional variant thereof or mimetic thereof structure.

In some embodiments, $R^5$ is an amylin analog or functional variant thereof or mimetic thereof having a choline or choline derivative-modified amylin analog or functional variant thereof or mimetic thereof derivative structure.

In some embodiments, the amylin analog or functional variant thereof or mimetic thereof comprises a cation moiety comprising choline or choline derivative.

In some embodiments, $R^5$ is an amylin analog or functional variant thereof or mimetic thereof having a choline or choline derivative-modified amylin analog or functional variant thereof or mimetic thereof ester structure.

In some embodiments, the amylin analog or functional variant thereof or mimetic thereof comprises a cation moiety comprising a choline or choline derivative-like residue.

In some embodiments, the amylin analog or functional variant thereof or mimetic thereof comprises an amino acid substitution of N14E, V17R, Y37P, F15E, L16E, V17E, or any combination thereof.

In some embodiments, the amylin analog or functional variant thereof or mimetic thereof comprises a linker comprising one or more gamma glutamate (γGlu) residues, one or more 8-amino-3,6-dioxaoctanoic acid (OEG) residues, or a combination thereof.

In some embodiments, the amylin analog or functional variant thereof or mimetic thereof comprises a linker comprising one or more gamma glutamate (γGlu) residues.

In some embodiments, $R^5$ is an amylin analog or functional variant thereof or mimetic thereof having the choline or choline derivative-modified amylin analog or functional variant thereof or mimetic thereof derivative structure, and wherein the amylin analog or functional variant thereof or mimetic thereof comprises a choline or choline derivative-peptide derivative that is formed on the carboxylic acid of the one or more gamma glutamate residues of the linker.

In some embodiments, $R^5$ is an amylin analog or functional variant thereof or mimetic thereof having the choline or choline derivative-modified amylin analog or functional variant thereof or mimetic thereof ester structure, and wherein the amylin analog or functional variant thereof or mimetic thereof comprises a choline or choline derivative-peptide ester that is formed on the carboxylic acid of the one or more gamma glutamate residues of the linker.

In some embodiments, the amylin analog or functional variant thereof or mimetic thereof comprises the amino acid substitution of N14E.

In some embodiments, the amylin analog or functional variant thereof or mimetic thereof comprises a diacid consisting of 18 or 20 carbons in length.

In some embodiments, the diacid comprises a C20 fatty diacid.

In some embodiments, the diacid comprises 1,20-icosanedioic acid.

In another aspect, provided herein is a compound according to Formula II:

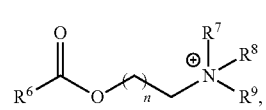

Formulla II wherein:
$R^6$ is amylin or mimetic thereof, or an amylin analog or functional variant thereof or mimetic thereof;
$R^7$, $R^8$, and $R^9$ are independently $C_1$-$C_5$ alkyl; and n is 1, 2, 3, 4, or 5.

In some embodiments, $R^7$, $R^8$, and $R^9$ are methyl.

In some embodiments, $R^7$, $R^8$, and $R^9$ are ethyl.

In some embodiments, $R^7$, $R^8$, and $R^9$ are propyl.

In some embodiments, $R^7$ and $R^8$ are methyl, and $R^9$ is ethyl.

In some embodiments, $R^7$ and $R^9$ are methyl, and $R^8$ is ethyl.

In some embodiments, $R^7$ and $R^8$ are ethyl, and $R^9$ is methyl.

In some embodiments, $R^7$ and $R^9$ are ethyl, and $R^8$ is methyl.

In some embodiments, $R^7$ and $R^8$ are propyl, and $R^9$ is methyl.

In some embodiments, $R^7$ and $R^9$ are propyl, and $R^8$ is methyl.

In some embodiments, n is 1.

In some embodiments, the compound is according to Formula IIa:

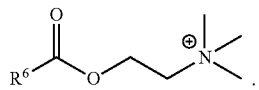

Formula IIa

In some embodiments, the compound is according to Formula IIb:

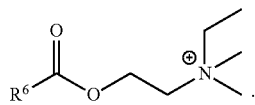

Formula IIb

In some embodiments, the compound is according to Formula IIc:

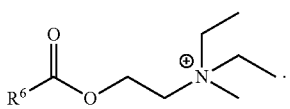

Formula IIc

In some embodiments, $R^6$ is amylin or mimetic thereof, or an amylin analog or functional variant thereof or mimetic thereof.

In some embodiments, $R^5$ is an amylin analog or functional variant thereof or mimetic thereof.

In some embodiments, $R^5$ is an amylin analog or functional variant thereof or mimetic thereof having the sequence of:

```
                                         (SEQ ID NO: 21)
[diacid]-[linker]-KCNTATCATQ RLANFLVHSS NNFGPILPPT NVGSNTY-amide.
```

In some embodiments, $R^5$ is an amylin analog or functional variant thereof or mimetic thereof having the structure as shown in FIGS. 2A, 2B, and 2C, FIG. 3A and FIG. 3B, or FIG. 4A and FIG. 4B.

In some embodiments, $R^5$ is an amylin analog or functional variant thereof or mimetic thereof having a modified amylin analog or functional variant thereof or mimetic thereof structure.

In some embodiments, $R^5$ is an amylin analog or functional variant thereof or mimetic thereof having a choline or choline derivative-modified amylin analog or functional variant thereof or mimetic thereof derivative structure.

In some embodiments, the amylin analog or functional variant thereof or mimetic thereof comprises a cation moiety comprising choline or choline derivative.

In some embodiments, $R^5$ is an amylin analog or functional variant thereof or mimetic thereof having a choline or choline derivative-modified amylin analog or functional variant thereof or mimetic thereof ester structure.

In some embodiments, the amylin analog or functional variant thereof or mimetic thereof comprises a cation moiety comprising a choline or choline derivative-like residue.

In some embodiments, the amylin analog or functional variant thereof or mimetic thereof comprises an amino acid substitution of N14E, V17R, Y37P, F15E, L16E, V17E, or any combination thereof.

In some embodiments, the amylin analog or functional variant thereof or mimetic thereof comprises a linker comprising one or more gamma glutamate (γGlu) residues, one or more 8-amino-3,6-dioxaoctanoic acid (OEG) residues, or a combination thereof.

In some embodiments, the amylin analog or functional variant thereof or mimetic thereof comprises a linker comprising one or more gamma glutamate (γGlu) residues.

In some embodiments, $R^5$ is the amylin analog or functional variant thereof or mimetic thereof having the choline or choline derivative-modified amylin analog or functional variant thereof or mimetic thereof derivative structure, and wherein the amylin analog or functional variant thereof or mimetic thereof comprises a choline or choline derivative-peptide derivative that is formed on the carboxylic acid of the one or more gamma glutamate residues of the linker.

In some embodiments, $R^5$ is an amylin analog or functional variant thereof or mimetic thereof having the choline or choline derivative-modified amylin analog or functional variant thereof or mimetic thereof ester structure, and wherein the amylin analog or functional variant thereof or mimetic thereof comprises a choline or choline derivative-peptide ester that is formed on the carboxylic acid of the one or more gamma glutamate residues of the linker.

In some embodiments, the amylin analog or functional variant thereof or mimetic thereof comprises the amino acid substitution of N14E.

In some embodiments, the amylin analog or functional variant thereof or mimetic thereof comprises a diacid consisting of 18 or 20 carbons in length.

In some embodiments, the diacid comprises a C20 fatty diacid.

In some embodiments, the diacid comprises 1,20-icosanedioic acid.

In another aspect, provided herein is a pharmaceutical composition comprising the composition as described herein or the compound as described herein, and at least one pharmaceutically acceptable excipient.

In another aspect, provided herein is a method of treating a disease or disorder in a subject in need thereof, comprising administering to the subject a therapeutically effective amount of the composition as described herein, the compound as described herein, or the pharmaceutical composition as described herein.

In some embodiments, the disease or disorder is diabetes.

In some embodiments, the disease or disorder is Type 1 diabetes.

In some embodiments, the disease or disorder is Type 2 diabetes.

In some embodiments, the disease or disorder is non-alcoholic steatohepatitis (NASH).

In another aspect, provided herein is a method of treating obesity, preventing weight gain, or reducing weight in a subject in need thereof, comprising administering to the subject a therapeutically effective amount of the composition as described herein, the compound as described herein, or the pharmaceutical composition as described herein.

In some embodiments, the composition, the compound, or the pharmaceutical composition is administered via subcutaneous, intravenous, or oral administration.

In some embodiments, the composition, the compound, or the pharmaceutical composition is administered orally.

In some embodiments, the composition, the compound, or the pharmaceutical composition is administered as a liquid-filled capsule.

In some embodiments, the composition, the compound, or the pharmaceutical composition is administered in multiple doses.

In some embodiments, the composition, the compound, or the pharmaceutical composition is administered in a single dose.

In some embodiments, the composition, the compound, or the pharmaceutical composition is administered to a mucus membrane.

In some embodiments, the concentration of the compound as described herein is at least 0.1% weight per volume.

In some embodiments, the concentration of the compound as described herein is at least 0.05M.

In some embodiments, the composition further comprises one or more additional agents.

In some embodiments, the one or more additional agent is selected from the group consisting of a nucleic acid, a small molecule, and a polypeptide.

In some embodiments, the one or more additional agent is a nucleic acid.

In some embodiments, the one or more additional agent is a small molecule.

In some embodiments, the one or more additional agent is a polypeptide.

As used herein, "diabetes" refers to diabetes mellitus, a metabolic disease characterized by a deficiency or absence of insulin secretion by the pancreas. As used throughout, "diabetes" includes all types including Type 1 and Type 2 diabetes mellitus unless otherwise specified herein. The two most common forms of diabetes are due to either a diminished production of insulin (in Type 1), or diminished response by the body to insulin (in Type 2). In Type 1 diabetes, the function of the pancreas is progressively lost, thus eventually making the patient entirely dependent on the exogenously delivered insulin for the management of diabetes. In Type 2, the patient maintains some functioning of the pancreas, but the sensitivity of the body to insulin is reduced, thus reducing the extent of glycemia maintained by the patient. Type 2 patients are treated by a variety of drugs including oral medications that increase glucose sensitivity, pramlintide, pramlintide mimetics/analogs, GLP-1, GLP-1 mimetics/analogs, or insulin.

Both types of diabetes lead to hyperglycemia, which causes the acute signs of diabetes: excessive urine production, increased thirst and increased fluid intake, blurred vision, unexplained weight loss, lethargy, and changes in energy metabolism. Diabetes can cause many complications including neuropathy, retinopathy, poor microvascular function, renal failure, and poor wound healing.

In some embodiments, a subject can be pre-diabetic, which can be characterized, for example, as having elevated fasting blood sugar or elevated post-prandial blood sugar such that the glucose levels do not fit the current medical definitions of diabetes.

In some embodiments, a subject can be newly diagnosed which means Type 1 diabetic patients that are within 1-3 years of their diagnosis. This patient population can be physiologically or emotionally different from the general Type 1 diabetic population.

In another aspect, provided herein is a composition comprising the amylin analog or functional variant thereof or mimetic thereof and an ionic liquid of a cholinium cation and an anion selected from cinnamic acid, hydrocinnamic acid, malonic acid, citronellic acid, glutaric acid, mandelic acid, oleic acid, linoleic acid, and ricinoleic acid.

In some embodiments, the therapeutic agent is an amylin analog or functional variant thereof or mimetic thereof.

In some embodiments, to enhance the hydrophobicity of an amylin analog or functional variant thereof or mimetic thereof, the amylin analog or functional variant thereof or mimetic thereof is linked to one or more fatty acids or carboxylic acid-containing molecules. In some embodiments, one or more fatty acids or carboxylic acid-containing molecules are linked to the amylin analog or functional variant thereof or mimetic thereof via a dual conjugation (or dual covalent conjugation). In some embodiments, one or more fatty acids or carboxylic acid-containing molecules comprise cinnamic acid. In some embodiments, one or more fatty acids or carboxylic acid-containing molecules are cinnamic acid.

In some embodiments, one or more fatty acids or carboxylic acid-containing molecules are non-covalently associated with a free amine of an amylin analog or functional variant thereof or mimetic thereof. In some embodiments, one or more fatty acids or carboxylic acid-containing molecules are non-covalently associated with the N-terminal amine in the peptide backbone of an amylin analog or functional variant thereof or mimetic thereof. In some embodiments, one or more fatty acids or carboxylic acid-containing molecules are non-covalently associated with the amine group of a Gln residue, the amine group of an Asn residue, the amine group of an Arg residue, the amine group of a Lys residue, the amine group of a His residue, or a combination thereof of an amylin analog or functional variant thereof or mimetic thereof.

In some embodiments, one or more fatty acids or carboxylic acid-containing molecules are covalently conjugated to a free amine of an amylin analog or functional variant thereof or mimetic thereof. In some embodiments, one or more fatty acids or carboxylic acid-containing molecules are covalently conjugated to the N-terminal amine in the peptide backbone of an amylin analog or functional variant thereof or mimetic thereof. In some embodiments, one or more fatty acids or carboxylic acid-containing molecules are covalently conjugated to the amine group of a Gln residue, the amine group of an Asn residue, the amine group of an Arg residue, the amine group of a Lys residue, the amine group of a His residue, or a combination thereof of an amylin analog or functional variant thereof or mimetic thereof.

GLP-1 or Mimetic or Functional Variant, Functional Analog, or Functional Homolog Thereof In one embodiment, described herein is a method of treatment of diabetes comprising orally administering an oral formulation of a GLP-1 polypeptide or mimetic or analog thereof in combination with ionic liquid.

Glucagon-Like Peptide-1 (GLP-1), is known to reduce food intake and hunger feelings in humans and is an incretin derived from the transcription product of the proglucagon gene that contributes to glucose homeostasis. Natural GLP-1 has an extremely short half-life which makes its use as a therapeutic challenging. Modified versions of GLP-1 exist to overcome the stability challenge. Such modifications can be done either in the sequence of the peptide or by conjugating another entity to the peptide. A common modification includes attachment of a lipid tail. GLP-1 mimetics are currently being used in the treatment of Type 2 diabetes. Recent clinical trials have shown that these treatments improve glucose homeostasis. They also help in achieving weight loss.

An exemplary GLP-1 Sequence is as follows: His-Ala-Glu-Gly-Thr-Phe-Thr-Ser-Asp-Val-Ser-Ser-Tyr-Leu-Glu-Gly-Glu-Ala-Ala-Lys-Glu-Phe-Ile-Ala-Trp-Leu-Val-Lys-Gly-Arg-Gly-OH (SEQ ID NO: 22).

Various GLP-1 mimetics are known in the art and used in the treatment of diabetes. GLP-1 mimetics (or analogs) can include exenatide.

An exemplary GLP-1 analog or functional variant thereof or mimetic thereof sequence is as follows: His-Gly-Glu-Gly-Thr-Phe-Thr-Ser-Asp-Leu-Ser-Lys-Gln-Met-Glu-Glu-Ala-Val-Arg-Leu-Phe-Ile-Glu-Trp-Lys-Asn-Gly-Gly-Pro-Ser-Ser-Gly-Ala-Pro-Pro-Ser-$NH_2$ (SEQ ID NO: 23).

Figure 15A:
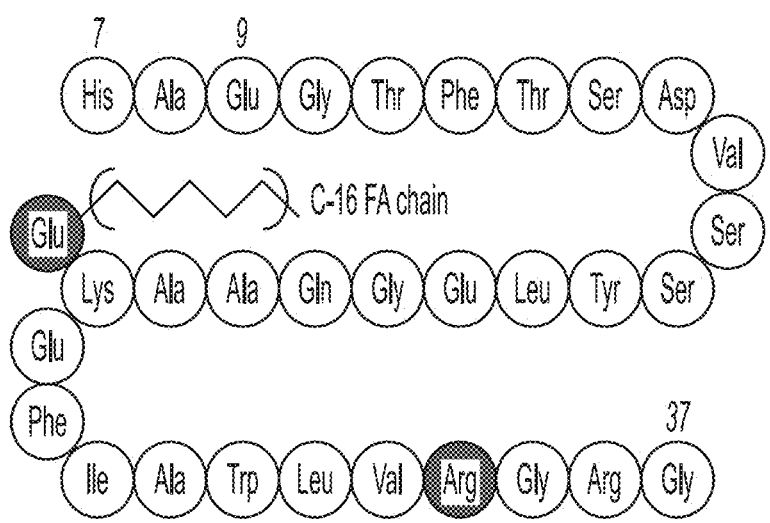
FIG. 15A depicts the sequence of an exemplary GLP-1 analog or functional variant thereof or mimetic thereof.
Figure 15B:
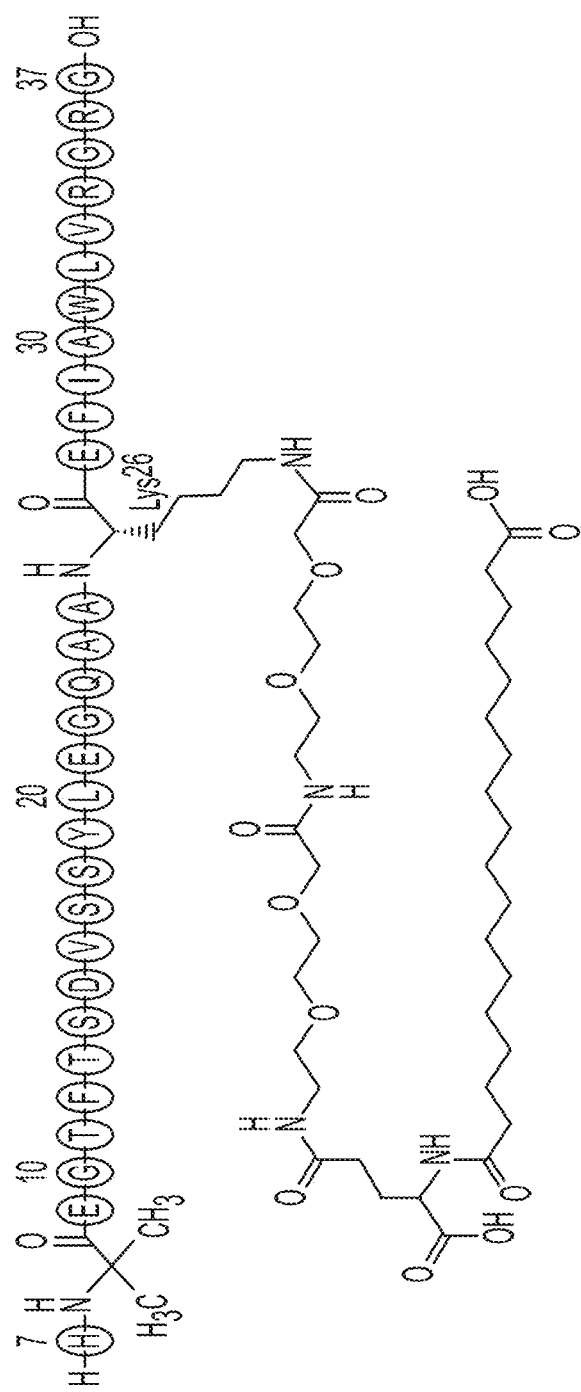
FIG. 15B depicts the sequence of another exemplary GLP-1 analog or functional variant thereof or mimetic thereof.

In some embodiments, other examples of GLP-1 analog or functional variant thereof or mimetic thereof include derivatives for reducing enzymatic degradation, e.g., lixisenatide, dulaglutide, semaglutide, albiglutide, liraglutide, and taspoglutide. For example, an exemplary GLP-1 analog or functional variant thereof or mimetic thereof is shown in FIG. 15A and another exemplary GLP-1 analog or functional variant thereof or mimetic thereof is shown in FIG. 15B.

The term "obesity" refers to excess fat in the body. Obesity can be determined by any measure accepted and utilized by those of skill in the art. Currently, an accepted measure of obesity is body mass index (BMI). Consequences of obesity include cardiovascular disease, high blood pressure (i.e., hypertension), osteoarthritis, cancer, and diabetes.

In one embodiment, modification of the peptide can take on the following formula comprising non-covalent attachment.

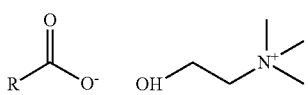

Figure 16:
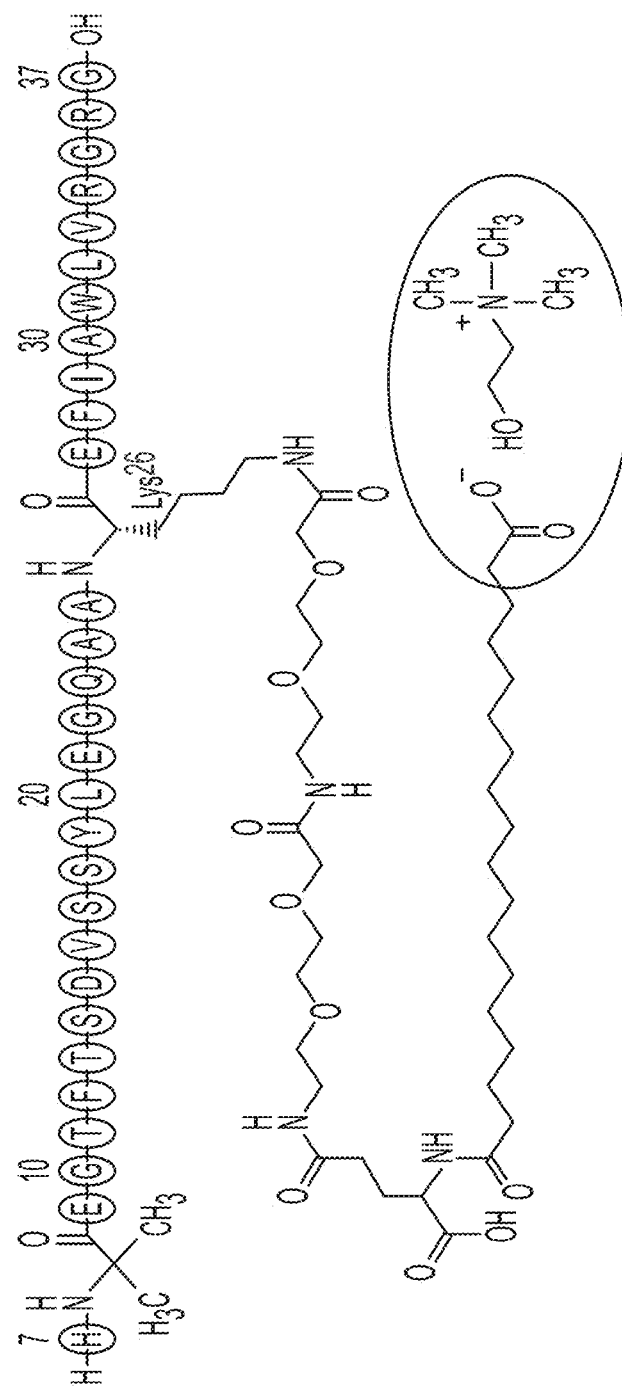
FIG. 16 depicts an exemplary embodiment of the compound according to Formula I.

R is a peptide including but not limited to an GLP-1 analog or functional variant thereof or mimetic thereof, Liraglutide, Exenatide, Peptide YY, Glucagon, GIP, Amylin. A representative example comprising the compound according to Formula I is shown in FIG. 16.

Figure 17A:
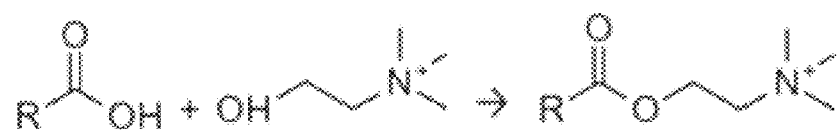
FIG. 17A depicts an exemplary form of covalent attachment.

In another embodiment, the modification can take an exemplary form of covalent attachment as shown in FIG. 17A.

In some embodiments, the subject is administered a composition comprising an ionic liquid to treat a metabolic disorder or metabolic syndrome. Metabolic disorders include but are not limited to obesity, diabetes, fatty liver disease, or non-alcoholic fatty liver disease.

In one aspect, provided herein is a composition comprising a compound according to Formula I:

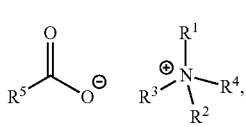

Formula I wherein:
$R^1$, $R^2$, and $R^3$ are independently $C_1$-$C_5$ alkyl;
$R^4$ is $C_2$-$C_5$ alkyl, wherein the $C_2$-$C_5$ alkyl is unsubstituted or substituted with 1 or more hydroxyl;

$R^5$ is an GLP-1 analog or functional variant thereof or mimetic thereof, Liraglutide, Exenatide, Peptide tyrosine tyrosine (YY), glucagon, gastric inhibitory polypeptide (GIP), or amylin.

In some embodiments, $R^1$, $R^2$, and $R^3$ are methyl.
In some embodiments, $R^1$, $R^2$, and $R^3$ are ethyl.
In some embodiments, $R^1$, $R^2$, and $R^3$ are propyl.
In some embodiments, $R^1$ and $R^2$ are methyl, and $R^3$ is ethyl.
In some embodiments, $R^1$ and $R^3$ are methyl, and $R^2$ is ethyl.
In some embodiments, $R^1$ and $R^2$ are ethyl, and $R^3$ is methyl.
In some embodiments, $R^1$ and $R^3$ are ethyl, and $R^2$ is methyl.
In some embodiments, $R^1$ and $R^2$ are propyl, and $R^3$ is methyl.
In some embodiments, $R^1$ and $R^3$ are propyl, and $R^2$ is methyl.
In some embodiments, $R^4$ is $C_2$-$C_5$ alkyl substituted with a hydroxyl.

In some embodiments, the composition comprises a

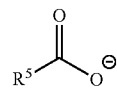

to

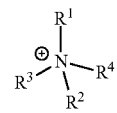

molar ratio of from about 1:1 to about 1:60.
In some embodiments, the composition comprises a

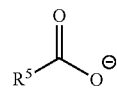

to

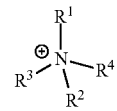

molar ratio of from about 1:1 to about 1:30.
In some embodiments, the composition comprises a

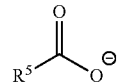

to

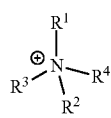

molar ratio of about 1:1.

In some embodiments, the composition comprises a

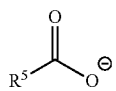

to

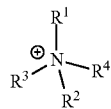

molar ratio of about 1:3.

In some embodiments, the composition comprises a

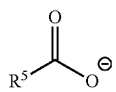

to

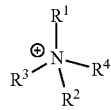

molar ratio of about 1:4.

In some embodiments, the composition comprises a

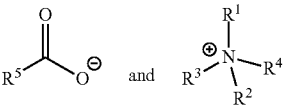

molar ratio of about 1:7.

In some embodiments, the composition comprises a

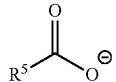

to

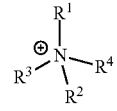

molar ratio of about 1:12.

In some embodiments, the composition comprises a

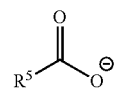

to

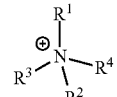

molar ratio of about 1:14.

In some embodiments, the composition comprises a

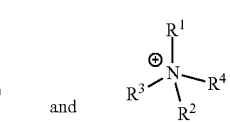

molar ratio of about 1:28.

In some embodiments, the composition comprises a

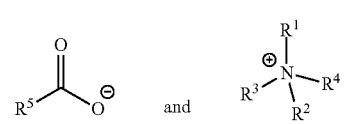

molar ratio of about 1:56.

In some embodiments, the composition comprises a

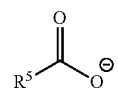

to

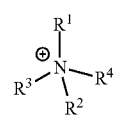

molar ratio of from about 1:1 to about 1:200, from about 1:1 to about 1:199, from about 1:1 to about 1:198, from about 1:1 to about 1:197, from about 1:1 to about 1:196, from about 1:1 to about 1:195, from about 1:1 to about 1:194, from about 1:1 to about 1:193, from about 1:1 to about 1:192, from about 1:1 to about 1:191, from about 1:1 to about 1:190, from about 1:1 to about 1:189, from about 1:1 to about 1:188, from about 1:1 to about 1:187, from about 1:1 to about 1:186, from about 1:1 to about 1:185, from about 1:1 to about 1:184, from about 1:1 to about 1:183, from about 1:1 to about 1:182, from about 1:1 to about 1:181, from about 1:1 to about 1:180, from about 1:1 to about 1:179, from about 1:1 to about 1:178, from about 1:1 to about 1:177, from about 1:1 to about 1:176, from about 1:1 to about 1:175, from about 1:1 to about 1:174, from about 1:1 to about 1:173, from about 1:1 to about 1:172, from about 1:1 to about 1:171, from about 1:1 to about 1:170, from about 1:1 to about 1:169, from about 1:1 to about 1:168, from about 1:1 to about 1:167, from about 1:1 to about 1:166, from about 1:1 to about 1:165, from about 1:1 to about 1:164, from about 1:1 to about 1:163, from about 1:1 to about 1:162, from about 1:1 to about 1:161, from about 1:1 to about 1:160, from about 1:1 to about 1:159, from about 1:1 to about 1:158, from about 1:1 to about 1:157, from about 1:1 to about 1:156, from about 1:1 to about 1:155, from about 1:1 to about 1:154, from about 1:1 to about 1:153, from about 1:1 to about 1:152, from about 1:1 to about 1:151, from about 1:1 to about 1:150, from about 1:1 to about 1:149, from about 1:1 to about 1:148, from about 1:1 to about 1:147, from about 1:1 to about 1:146, from about 1:1 to about 1:145, from about 1:1 to about 1:144, from about 1:1 to about 1:143, from about 1:1 to about 1:142, from about 1:1 to about 1:141, from about 1:1 to about 1:140, from about 1:1 to about 1:139, from about 1:1 to about 1:138, from about 1:1 to about 1:137, from about 1:1 to about 1:136, from about 1:1 to about 1:135, from about 1:1 to about 1:134, from about 1:1 to about 1:133, from about 1:1 to about 1:132, from about 1:1 to about 1:131, from about 1:1 to about 1:130, from about 1:1 to about 1:129, from about 1:1 to about 1:128, from about 1:1 to about 1:127, from about 1:1 to about 1:126, from about 1:1 to about 1:125, from about 1:1 to about 1:124, from about 1:1 to about 1:123, from about 1:1 to about 1:122, from about 1:1 to about 1:121, from about 1:1 to about 1:120, from about 1:1 to about 1:119, from about 1:1 to about 1:118, from about 1:1 to about 1:117, from about 1:1 to about 1:116, from about 1:1 to about 1:115, from about 1:1 to about 1:114, from about 1:1 to about 1:113, from about 1:1 to about 1:112, from about 1:1 to about 1:111, from about 1:1 to about 1:110, from about 1:1 to about 1:109, from about 1:1 to about 1:108, from about 1:1 to about 1:107, from about 1:1 to about 1:106, from about 1:1 to about 1:105, from about 1:1 to about 1:104, from about 1:1 to about 1:103, from about 1:1 to about 1:102, from about 1:1 to about 1:101, from about 1:1 to about 1:100, from about 1:1 to about 1:99, from about 1:1 to about 1:98, from about 1:1 to about 1:97, from about 1:1 to about 1:96, from about 1:1 to about 1:95, from about 1:1 to about 1:94, from about 1:1 to about 1:93, from about 1:1 to about 1:92, from about 1:1 to about 1:91, from about 1:1 to about 1:90, from about 1:1 to about 1:89, from about 1:1 to about 1:88, from about 1:1 to about 1:87, from about 1:1 to about 1:86, from about 1:1 to about 1:85, from about 1:1 to about 1:84, from about 1:1 to about 1:83, from about 1:1 to about 1:82, from about 1:1 to about 1:81, from about 1:1 to about 1:80, from about 1:1 to about 1:79, from about 1:1 to about 1:78, from about 1:1 to about 1:77, from about 1:1 to about 1:76, from about 1:1 to about 1:75, from about 1:1 to about 1:74, from about 1:1 to about 1:73, from about 1:1 to about 1:72, from about 1:1 to about 1:71, from about 1:1 to about 1:70, from about 1:1 to about 1:69, from about 1:1 to about 1:68, from about 1:1 to about 1:67, from about 1:1 to about 1:66, from about 1:1 to about 1:65, from about 1:1 to about 1:64, from about 1:1 to about 1:63, from about 1:1 to about 1:62, from about 1:1 to about 1:61, from about 1:1 to about 1:60, from about 1:1 to about 1:59, from about 1:1 to about 1:58, from about 1:1 to about 1:57, from about 1:1 to about 1:56, from about 1:1 to about 1:55, from about 1:1 to about 1:54, from about 1:1 to about 1:53, from about 1:1 to about 1:52, from about 1:1 to about 1:51, from about 1:1 to about 1:50, from about 1:1 to about 1:49, from about 1:1 to about 1:48, from about 1:1 to about 1:47, from about 1:1 to about 1:46, from about 1:1 to about 1:45, from about 1:1 to about 1:44, from about 1:1 to about 1:43, from about 1:1 to about 1:42, from about 1:1 to about 1:41, from about 1:1 to about 1:40, from about 1:1 to about 1:39, from about 1:1 to about 1:38, from about 1:1 to about 1:37, from about 1:1 to about 1:36, from about 1:1 to about 1:35, from about 1:1 to about 1:34, from about 1:1 to about 1:33, from about 1:1 to about 1:32, from about 1:1 to about 1:31, from about 1:1 to about 1:30, from about 1:1 to about 1:29, from about 1:1 to about 1:28, from about 1:1 to about 1:27, from about 1:1 to about 1:26, from about 1:1 to about 1:25, from about 1:1 to about 1:24, from about 1:1 to about 1:23, from about 1:1 to about 1:22, from about 1:1 to about 1:21, from about 1:1 to about 1:20, from about 1:1 to about 1:19, from about 1:1 to about 1:18, from about 1:1 to about 1:17, from about 1:1 to about 1:16, from about 1:1 to about 1:15, from about 1:1 to about 1:14, from about 1:1 to about 1:13, from about 1:1 to about 1:12, from about 1:1 to about 1:11, from about 1:1 to about 1:10, from about 1:1 to about 1:9, from about 1:1 to about 1:8, from about 1:1 to about 1:7, from about 1:1 to about 1:6, from about 1:1 to about 1:5, from about 1:1 to about 1:4, from about 1:1 to about 1:3, or from about 1:1 to about 1:2.

In some embodiments, the composition comprises a

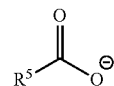

to

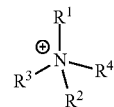

molar ratio of about 1:200, about 1:199, about 1:198, about 1:197, about 1:196, about 1:195, about 1:194, about 1:193, about 1:192, about 1:191, about 1:190, about 1:189, about 1:188, about 1:187, about 1:186, about 1:185, about 1:184, about 1:183, about 1:182, about 1:181, about 1:180, about 1:179, about 1:178, about 1:177, about 1:176, about 1:175, about 1:174, about 1:173, about 1:172, about 1:171, about 1:170, about 1:169, about 1:168, about 1:167, about 1:166, about 1:165, about 1:164, about 1:163, about 1:162, about 1:161, about 1:160, about 1:159, about 1:158, about 1:157, about 1:156, about 1:155, about 1:154, about 1:153, about 1:152, about 1:151, about 1:150, about 1:149, about 1:148, about 1:147, about 1:146, about 1:145, about 1:144, about 1:143, about 1:142, about 1:141, about 1:140, about 1:139, about 1:138, about 1:137, about 1:136, about 1:135, about 1:134, about 1:133, about 1:132, about 1:131, about 1:130, about 1:129, about 1:128, about 1:127, about 1:126, about 1:125, about 1:124, about 1:123, about 1:122, about 1:121, about 1:120, about 1:119, about 1:118, about 1:117, about 1:116, about 1:115, about 1:114, about 1:113, about 1:112, about 1:111, about 1:110, about 1:109, about 1:108, about 1:107, about 1:106, about 1:105, about 1:104, about 1:103, about 1:102, about 1:101, about 1:100, about 1:99, about 1:98, about 1:97, about 1:96, about 1:95, about 1:94, about 1:93, about 1:92, about 1:91, about 1:90, about 1:89, about 1:88, about 1:87, about 1:86, about 1:85, about 1:84, about 1:83, about 1:82, about 1:81, about 1:80, about 1:79, about 1:78, about 1:77, about 1:76, about 1:75, about 1:74, about 1:73, about 1:72, about 1:71, about 1:70, about 1:69, about 1:68, about 1:67, about 1:66, about 1:65, about 1:64, about 1:63, about 1:62, about 1:61, about 1:60, about 1:59, about 1:58, about 1:57, about 1:56, about 1:55, about 1:54, about 1:53, about 1:52, about 1:51, about 1:50, about 1:49, about 1:48, about 1:47, about 1:46, about 1:45, about 1:44, about 1:43, about 1:42, about 1:41, about 1:40, about 1:39, about 1:38, about 1:37, about 1:36, about 1:35, about 1:34, about 1:33, about 1:32, about 1:31, about 1:30, about 1:29, about 1:28, about 1:27, about 1:26, about 1:25, about 1:24, about 1:23, about 1:22, about 1:21, about 1:20, about 1:19, about 1:18, about 1:17, about 1:16, about 1:15, about 1:14, about 1:13, about 1:12, about 1:11, about 1:10, about 1:9, about 1:8, about 1:7, about 1:6, about 1:5, about 1:4, about 1:3, about 1:2 or about 1:1.

In some embodiments, $R^4$ is

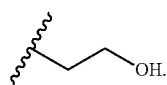

In some embodiments, the compound is according to Formula Ia:

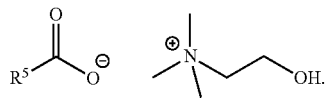

Formula Ia

In some embodiments, the compound is according to Formula Ib:

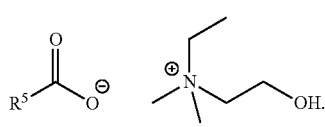

Formula Ib

In some embodiments, the compound is according to Formula Ic:

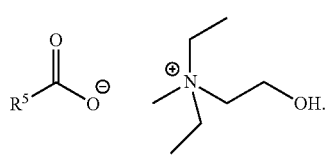

Formula Ic

In some embodiments, $R^5$ is an GLP-1 analog or functional variant thereof or mimetic thereof, Liraglutide, Exenatide, Peptide tyrosine tyrosine (YY), glucagon, gastric inhibitory polypeptide (GIP), or amylin.

In some embodiments, $R^5$ is an GLP-1 analog or functional variant thereof or mimetic thereof.

In some embodiments, the compound is the compound as shown in FIG. 16.

In another aspects, provided herein is a compound according to Formula II:

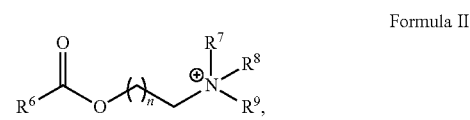

Formula II wherein:

$R^6$ is an GLP-1 analog or functional variant thereof or mimetic thereof, Liraglutide, Exenatide, Peptide tyrosine tyrosine (YY), glucagon, gastric inhibitory polypeptide (GIP), or amylin $R^7$, $R^8$, and $R^9$ are independently $C_1$-$C_5$ alkyl; and n is 1, 2, 3, 4, or 5.

In some embodiments, $R^7$, $R^8$, and $R^9$ are methyl.

In some embodiments, $R^7$, $R^8$, and $R^9$ are ethyl.

In some embodiments, $R^7$, $R^8$, and $R^9$ are propyl.

In some embodiments, $R^7$ and $R^8$ are methyl, and $R^9$ is ethyl.

In some embodiments, $R^7$ and $R^9$ are methyl, and $R^8$ is ethyl.

In some embodiments, $R^7$ and $R^8$ are ethyl, and $R^9$ is methyl.

In some embodiments, $R^7$ and $R^9$ are ethyl, and $R^8$ is methyl.

In some embodiments, $R^7$ and $R^8$ are propyl, and $R^9$ is methyl.

In some embodiments, $R^7$ and $R^9$ are propyl, and $R^8$ is methyl.

In some embodiments, n is 1.

In some embodiments, the compound is according to Formula IIa:

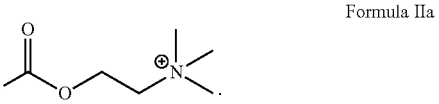

Formula IIa

In some embodiments, the compound is according to Formula IIb:

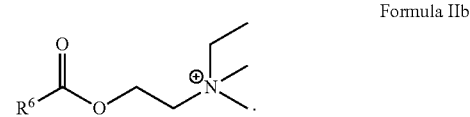

Formula IIb

In some embodiments, the compound is according to Formula IIc:

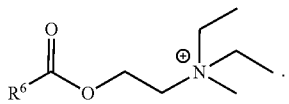

Formula IIc

In some embodiments, $R^6$ is an GLP-1 analog or functional variant thereof or mimetic thereof, Liraglutide, Exenatide, Peptide tyrosine tyrosine (YY), glucagon, gastric inhibitory polypeptide (GIP), or amylin.

In some embodiments, $R^5$ is an GLP-1 analog or functional variant thereof or mimetic thereof.

Figure 17B:
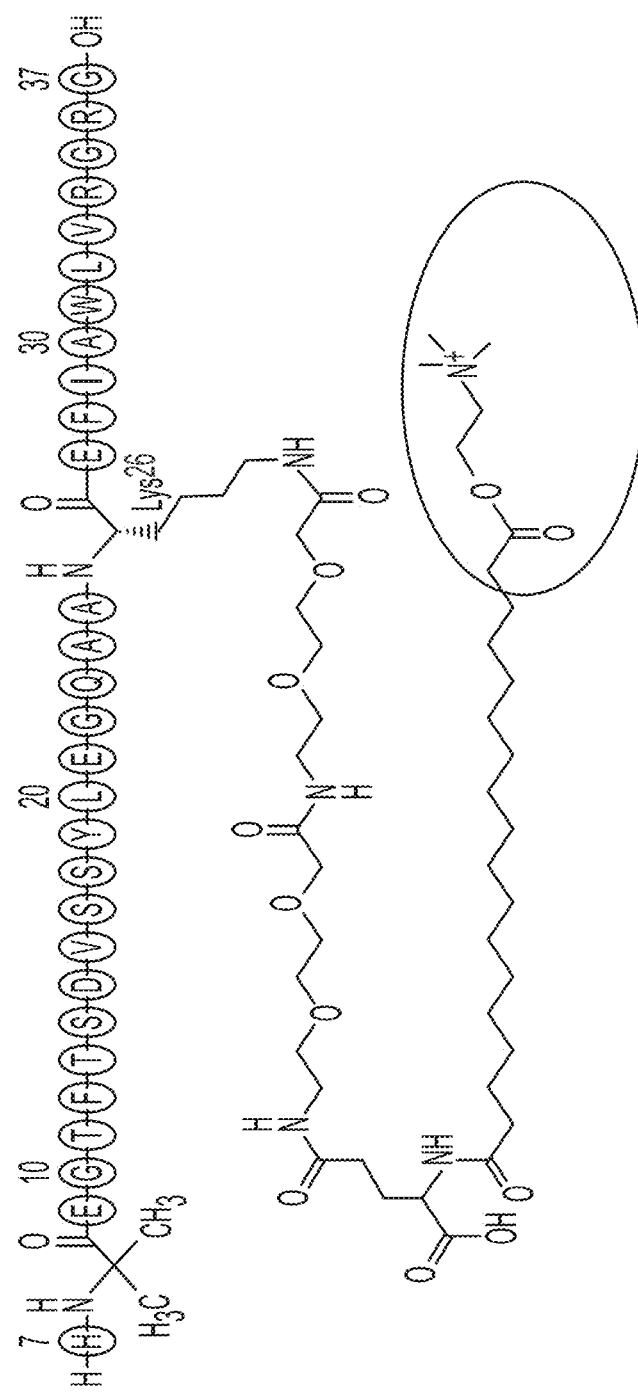
FIG. 17B depicts an exemplary embodiment of the compound according to Formula II.

In some embodiments, the compound is the compound as shown in FIG. 17B.

In another aspect, provided herein is a pharmaceutical composition comprising the composition as described herein, and at least one pharmaceutically acceptable excipient, carrier, or diluent.

In another aspect, provided herein is a method of treating a disease or disorder in a subject in need thereof, comprising administering to the subject a therapeutically effective amount of the composition as described herein, or the pharmaceutical composition as described herein.

In some embodiments, the disease or disorder is diabetes.

In some embodiments, the disease or disorder is Type 1 diabetes.

In some embodiments, the disease or disorder is Type 2 diabetes.

In some embodiments, the disease or disorder is non-alcoholic steatohepatitis (NASH).

In another aspect, provided herein is a method of treating obesity, preventing weight gain, or reducing weight in a subject in need thereof, comprising administering to the subject a therapeutically effective amount of the composition provided herein or the pharmaceutical composition as provided herein.

In another aspect, provided herein is a method of treating obesity, preventing weight gain, or reducing weight in a subject in need thereof, comprising administering to the subject a therapeutically effective amount of the compound as provided herein or the pharmaceutical composition as provided herein.

In some embodiments, the composition, the compound, or the pharmaceutical composition is administered via subcutaneous, intravenous, or oral administration.

In some embodiments, the composition, the compound, or the pharmaceutical composition is administered orally.

In some embodiments, the composition, the compound, or the pharmaceutical composition is administered as a liquid-filled capsule.

In some embodiments, the composition, the compound, or the pharmaceutical composition is administered in multiple doses.

In some embodiments, the composition, the compound, or the pharmaceutical composition is administered in a single dose.

In some embodiments, the composition, the compound, or the pharmaceutical composition is administered to a mucus membrane.

In some embodiments, the concentration of the compound is at least 0.1% weight per volume.

In some embodiments, the concentration of the compound is at least 0.05M.

In some embodiments, the composition further comprises one or more additional agents.

In some embodiments, the one or more additional agent is selected from a nucleic acid, a small molecule, and a polypeptide.

In some embodiments, the one or more additional agent is a nucleic acid.

In some embodiments, the one or more additional agent is a small molecule.

In some embodiments, the one or more additional agent is a polypeptide.

In some embodiments, the therapeutic agent is a GLP-1 polypeptide or mimetic or analog thereof.

In some embodiments, to enhance the hydrophobicity of a GLP-1 polypeptide or mimetic or analog thereof, the GLP-1 polypeptide or mimetic or analog thereof is linked to one or more fatty acids or carboxylic acid-containing molecules. In some embodiments, one or more fatty acids or carboxylic acid-containing molecules are linked to the GLP-1 polypeptide or mimetic or analog thereof via a dual conjugation (or dual covalent conjugation). In some embodiments, one or more fatty acids or carboxylic acid-containing molecules comprise cinnamic acid. In some embodiments, one or more fatty acids or carboxylic acid-containing molecules are cinnamic acid.

In some embodiments, one or more fatty acids or carboxylic acid-containing molecules are non-covalently associated with a free amine of a GLP-1 polypeptide or mimetic or analog thereof. In some embodiments, one or more fatty acids or carboxylic acid-containing molecules are non-covalently associated with the N-terminal amine in the peptide backbone of a GLP-1 polypeptide or mimetic or analog thereof. In some embodiments, one or more fatty acids or carboxylic acid-containing molecules are non-covalently associated with the amine group of a Gln residue, the amine group of an Asn residue, the amine group of an Arg residue, the amine group of a Lys residue, the amine group of a His residue, or a combination thereof of a GLP-1 polypeptide or mimetic or analog thereof.

In some embodiments, one or more fatty acids or carboxylic acid-containing molecules are covalently conjugated to a free amine of a GLP-1 polypeptide or mimetic or analog thereof. In some embodiments, one or more fatty acids or carboxylic acid-containing molecules are covalently conjugated to the N-terminal amine in the peptide backbone of a GLP-1 polypeptide or mimetic or analog thereof. In some embodiments, one or more fatty acids or carboxylic acid-containing molecules are covalently conjugated to the amine group of a Gln residue, the amine group of an Asn residue, the amine group of an Arg residue, the amine group of a Lys residue, the amine group of a His residue, or a combination thereof of a GLP-1 polypeptide or mimetic or analog thereof.

In some embodiments, to enhance the hydrophobicity of an GLP-1 analog or functional variant thereof or mimetic thereof, an GLP-1 analog or functional variant thereof or mimetic thereof is linked to one or more fatty acids or carboxylic acid-containing molecules. In some embodiments, one or more fatty acids or carboxylic acid-containing molecules are linked to an GLP-1 analog or functional variant thereof or mimetic thereof via a dual conjugation (or dual covalent conjugation). In some embodiments, one or more fatty acids or carboxylic acid-containing molecules comprise cinnamic acid. In some embodiments, one or more fatty acids or carboxylic acid-containing molecules are cinnamic acid.

In some embodiments, one or more fatty acids or carboxylic acid-containing molecules are non-covalently associated with a free amine of an GLP-1 analog or functional variant thereof or mimetic thereof. In some embodiments, one or more fatty acids or carboxylic acid-containing molecules are non-covalently associated with the N-terminal amine in the peptide backbone of an GLP-1 analog or functional variant thereof or mimetic thereof. In some embodiments, one or more fatty acids or carboxylic acid-containing molecules are non-covalently associated with the amine group of a Gln residue, the amine group of an Asn residue, the amine group of an Arg residue, the amine group of a Lys residue, the amine group of a His residue, or a combination thereof of an GLP-1 analog or functional variant thereof or mimetic thereof.

In some embodiments, cinnamic acid is non-covalently associated with a free amine of an GLP-1 analog or functional variant thereof or mimetic thereof. In some embodiments, cinnamic acid is non-covalently associated with the N-terminal amine in the peptide backbone of an GLP-1 analog or functional variant thereof or mimetic thereof. In some embodiments, cinnamic acid is non-covalently associated with the amine group of a Gln residue, the amine group of an Asn residue, the amine group of an Arg residue, the amine group of a Lys residue, the amine group of a His residue, or a combination thereof of an GLP-1 analog or functional variant thereof or mimetic thereof.

In some embodiments, one or more fatty acids or carboxylic acid-containing molecules are covalently conjugated to a free amine of an GLP-1 analog or functional variant thereof or mimetic thereof. In some embodiments, one or more fatty acids or carboxylic acid-containing molecules are covalently conjugated to the N-terminal amine in the peptide backbone of an GLP-1 analog or functional variant thereof or mimetic thereof. In some embodiments, one or more fatty acids or carboxylic acid-containing molecules are covalently conjugated to the amine group of a Gln residue, the amine group of an Asn residue, the amine group of an Arg residue, the amine group of a Lys residue, the amine group of a His residue, or a combination thereof of an GLP-1 analog or functional variant thereof or mimetic thereof.

In some embodiments, cinnamic acid is covalently conjugated to a free amine of an GLP-1 analog or functional variant thereof or mimetic thereof. In some embodiments, cinnamic acid is covalently conjugated to the N-terminal amine in the peptide backbone of an GLP-1 analog or functional variant thereof or mimetic thereof. In some embodiments, cinnamic acid is covalently conjugated to the amine group of a Gln residue, the amine group of an Asn residue, the amine group of an Arg residue, the amine group of a Lys residue, the amine group of a His residue, or a combination thereof of an GLP-1 analog or functional variant thereof or mimetic thereof.

Ionic Liquids

Figure 18:
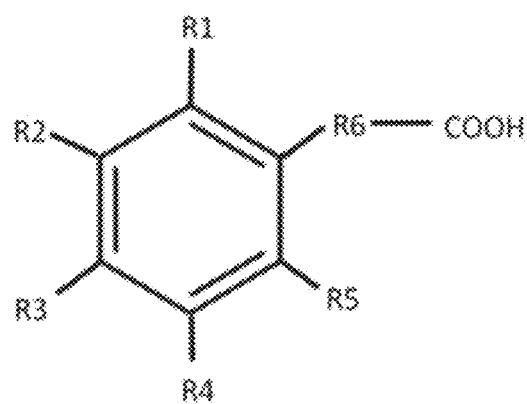
FIG. 18 depicts the chemical structure of an exemplary form of the cinnamic acid derivative.

In one embodiment, the anion in the ionic liquid may be chosen from cinnamic acid, hydrocinnamic acid, hydroxycinnamic (3-phenylpropanoic or benzylacetic) acid, methoxycinnamic acid, ferulic acid, isoferulic acid, 2-phenylpropionic (hydratropic acid), coumaric acid, 3,3-diphenylpropionic acid, 3,5-dimethoxy-4-hydroxy-cinnamic acid (sinapinic acid). Other structural analogs of cinnamic acid could be used. The chemical structure of the cinnamic acid derivative is of the form shown below (FIG. 18):

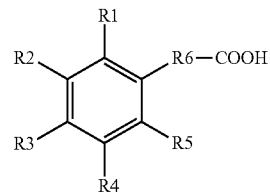

For cinnamic acid, R1=R2=R3=R4=R5 is H and R6 is CH=CH. For hydrocinnamic acid, R1=R2=R3=R4=R5 is H and R6 is $CH_2$—$CH_2$.

In one embodiment, the anion is a diacid of the formula,

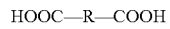

where, R can be $CH_2$ (malonic acid) or $CH_2$—$CH_2$—$CH_2$ (glutaric acid).

The examples listed here use choline or choline derivative (or cholinium) as the cation. However, it is clear to the person skilled in the art that the cation can be chosen from a variety of molecules including choline or choline derivatives, for example, choline or choline derivative chloride, derivates of choline, or any other biocompatible cation that is otherwise able to form an ionic liquid to with the anions described herein. In some embodiments, choline derivatives, as used herein, refers to a substance that is derived from choline.

Figure 19:
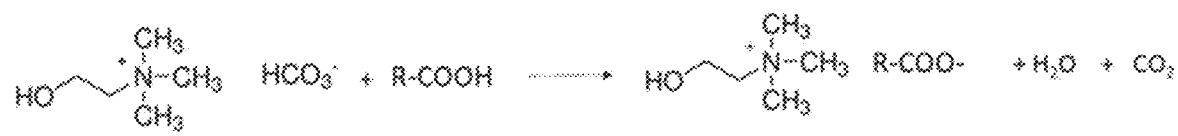
FIG. 19 depicts an exemplary process by which the ionic liquid is prepared by mixing an acid with choline or choline derivative bicarbonate.

In one embodiment, the ionic liquid is prepared by mixing an acid with choline or choline derivative bicarbonate by the process shown in FIG. 19. Choline or choline derivative bicarbonate reacts with carboxylic acid with a byproduct of water and carbon dioxide. Carbon dioxide is removed from the reaction mixture and water can be subsequently removed to leave behind an ionic liquid.

The resultant ionic liquid is represented by the following formula;

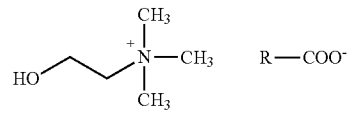

Depending on the ratio of anion and cation in the reaction mixture, the resultant mixture may also contain either excess acid or excess choline or choline derivative bicarbonate. The term ionic liquid used herein includes all stoichiometries including equimolar acid and choline or choline derivative carbonate, excess acid or excess choline or choline derivative bicarbonate.

The ionic liquid structures drawn with the with or without the proton are equivalent and interchangeable depending on the concentration and composition.

In some embodiments, the composition as used herein or the pharmaceutical the composition as used herein comprises one or more ionic liquids as listed in Table 1.

TABLE 1

Exemplary ionic liquids

| Anion | Cation |
|---|---|
| (R)-α-Lipoic Acid | Choline |
| 12-Hydroxystearic Acid | Choline |
| 2-(4-Isobutylphenyl)propionic Acid | Choline |
| 2-(4,4-Dimethyl-2-pentanyl)-5,7,7-trimethyloctanoic Acid | Choline |

TABLE 1-continued

Exemplary ionic liquids

| Anion | Cation |
|---|---|
| 2-Aminoethanesulfonic Acid (Taurine Acid) | Choline |
| 2-Hexyldecanoic Acid | Choline |
| 2-Hydroxyhippuric Acid | Choline |
| 3-(4-Hydroxyphenyl)propionic Acid | Choline |
| 3-Methylcrotonic Acid | Choline |
| 3,3-Diphenylpropionic Acid | Choline |
| 3,4-Dihydroxbenzoic Acid (Protocatechuic Acid) | Choline |
| 3,7-Dimethyloctanoic Acid | Choline |
| 4-Hydroxybenzenesulfonic Acid | Choline |
| 4-Hydroxybenzoic Acid | Choline |
| 4-Methylhexanoic Acid | Choline |
| 4-Methyloctanoic Acid | Choline |
| 4-Methylvaleric Acid | Choline |
| 5-Norbornene-2-carboxylic Acid | Choline |
| 8-[(2-hydroxybenzoyl)amino]octanoic acid | Choline |
| Abietic Acid | Choline |
| Acetic Acid | Choline |
| Acetylcysteine | Choline |
| Aconitic Acid | Choline |
| Arachidonic Acid | Choline |
| Behenic Acid | Choline |
| Benzoic Acid | Choline |
| Caffeic Acid | Choline |
| Chenodeoxycholic Acid | Choline |
| Cis-Cinnamic acid | Choline |
| Citric Acid | Choline |
| Citronellic Acid | Choline |
| Crotonic Acid | Choline |
| D-(+)-Galactonic Acid | Choline |
| Decanoic Acid | Choline |
| Deoxycholic Acid | Choline |
| Dihydrocaffeic Acid | Choline |
| DL-2-Phenylpropionic (Hydratropic) Acid | Choline |
| DL-Tartaric Acid | Choline |
| DL-Tropic Acid | Choline |
| Eicosanedioic Acid | Choline |
| Eicosapentanoic Acid (EPA) | Choline |
| Elaidic Acid | Choline |
| Ellagic Acid | Choline |
| Erucic Acid | Choline |
| Ethylenediaminetetraacetic Acid (EDTA) | Choline |
| Formic Acid | Choline |
| Fumaric Acid | Choline |
| Geranic Acid | Choline |
| Glutaric Acid | Choline |
| Glycolic Acid | Choline |
| Heptanoic Acid | Choline |
| Hexanoic Acid | Choline |
| Hydrocinnamic Acid (3-Phenylpropionic Acid) | Choline |
| Isobutyric Acid | Choline |
| Isovaleric Acid | Choline |
| L-(+)-Tartaric Acid | Choline |
| L-Ascorbic Acid | Choline |
| L-Aspartic Acid | Choline |
| L-Glutamic Acid | Choline |
| L-Glutathione reduced | Choline |
| Lactic Acid | Choline |
| Lauric Acid | Choline |
| Levulinic Acid | Choline |
| Linoleic Acid | Choline |
| Linolenic Acid | Choline |
| Lithocholic Acid | Choline |
| Maleic Acid | Choline |
| Malic Acid | Choline |
| Malonic Acid | Choline |
| Mandelic acid | Choline |
| Mesaconic Acid | Choline |
| Nicotinic Acid | Choline |
| Nonanoic Acid | Choline |
| Octanoic Acid | Choline |
| Oleic Acid | Choline |
| Oxalic Acid | Choline |
| p-Coumaric Acid | Choline |
| p-Toluenesulfonic Acid | Choline |
| Palmitic Acid | Choline |
| Perillic Acid | Choline |
| Phosphoric Acid | Choline |
| Pimelic Acid | Choline |
| Pivalic Acid | Choline |
| Propionic Acid | Choline |
| Pyroglutamic Acid | Choline |
| Pyruvic Acid | Choline |
| Ricinoleic Acid | Choline |
| Salicylic Acid (2-Hydroxybenzoic Acid) | Choline |
| Sinapinic Acid (3,5-Dimethoxy-4-Hydroxycinnamic Acid) | Choline |
| Sorbic Acid | Choline |
| Stearic acid | Choline |
| Succinic Acid | Choline |
| Syringic Acid | Choline |
| Tiglic Acid | Choline |
| Trans-2-Decenoic Acid | Choline |
| Trans-2-Hexenoic Acid | Choline |
| Trans-2-Octenoic Acid | Choline |
| Trans-3-Octenoic Acid | Choline |
| Trans-7-Octenoic Acid | Choline |
| Trans-Cinnamic Acid | Choline |
| Trans-Ferulic Acid | Choline |
| Undecanoic Acid | Choline |
| Valeric Acid | Choline |
| Vanillic Acid | Choline |
| α-Ketoglutaric Acid | Choline |

In some embodiments, the following cations are used in the products of an exemplary GLP-1 analog or functional variant thereof or mimetic thereof. In some embodiments, the following cations are used in the products of an exemplary GLP-1 analog or functional variant thereof or mimetic thereof as covalent attachment. In some embodiments, the following cations are used in the products of an exemplary GLP-1 analog or functional variant thereof or mimetic thereof as non-covalent attachment. In some embodiments, the cations in Table 2 are used in the therapeutic products. In some embodiments, the cations in Table 2 are used in an antibody or an antibody fragment thereof. In some embodiments, the cations in Table 2 are used in the products of an exemplary GLP-1 analog or functional variant thereof or mimetic thereof. In some embodiments, the cations in Table 2 are used in the products of an exemplary GLP-1 analog or functional variant thereof or mimetic thereof as covalent attachment. In some embodiments, the cations in Table 2 are used in the products of an GLP-1 analog or functional variant thereof or mimetic thereof as non-covalent attachment.

TABLE 2

Exemplary cations used in therapeutic agents.

| Cation |
|---|
| Acetylcholine |
| Aminoguanidine |
| Ammonium |
| Carnitine |
| Choline |
| Guanidine derivatives |
| Tetrabutyl ammonium |
| Tetraethyl ammonium |
| Tetramethyl ammonium |

In one aspect, provided herein is a method of treating a subject by oral administration of a composition comprising; a. a polypeptide with at least one associated ionic species, and b. at least one ionic liquid such that the said ionic species is substantially similar to the ion comprising the ionic liquid.

In some embodiments, the association between the said polypeptide and the ionic species is non-covalent.

In some embodiments, the association between the said polypeptide and the ionic species is covalent.

In some embodiments, the oral administration is intended for treating diabetes. In another aspect, provided herein is a composition comprising an ionic liquid wherein the anion has the chemical form of

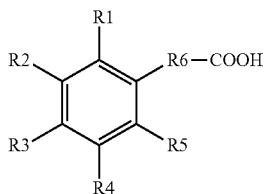

In some embodiments, R1, R2, R3, R4 and R5 are hydrogens and R6 is either CH=CH or $CH_2$—$CH_2$.

In another aspect, provided herein is a composition comprising an ionic liquid described by the formula

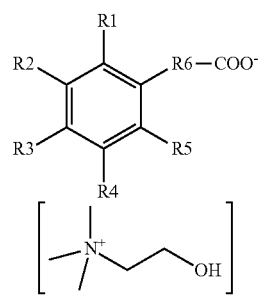

In some embodiments, R1, R2, R3, R4 and R5 are hydrogens and R6 is either CH=CH or $CH_2$—$CH_2$.

In another aspect, provided herein is a composition comprising an ionic liquid of a cholinium cation and an anion selected from the group consisting of cinnamic acid, hydrocinnamic acid, malonic acid, citronellic acid, glutaric acid, mandelic acid, oleic acid, linoleic acid, and ricinoleic acid.

In another aspect, provided herein is a capsule comprising a composition of embodiment 1, 3, or 6 with an additional pharmaceutically acceptable excipient.

In some embodiments, the drug is an GLP-1 analog or functional variant thereof or mimetic thereof.

In some embodiments, the drug is a GLP-1 mimetic drug selected from liraglutide, exenatide, or semaglutide.

In some embodiments, the drug is liraglutide, exenatide or semaglutide.

In another aspect, provided herein is a method of delivery of at least one drug, the method comprising administering the drug in combination with an ionic liquid to a mucus membrane.

In some embodiments, ionic liquid is at a concentration of at least 0.1% w/v.

In some embodiments, the ionic liquid comprises a ratio of cation:anion ratio from 2:1 to about 1:2.

In some embodiments, the active compound in combination with the ionic liquid is administered once.

In some embodiments, the active compound in combination with ionic liquid is administered in multiple doses.

In some embodiments, the active compound comprises a nucleic acid molecule.

In some embodiments, the active compound comprises a small molecule.

In some embodiments, the active compound comprises a polypeptide.

In another aspect, provided herein is a method of treating obesity, preventing weight gain, or reducing a subject's weight, the method comprising orally administering to the subject a composition comprising; a. a polypeptide with at least one associated ionic species; b. and at least one ionic liquid such that the said ionic species is also an ion in the ionic liquid.

In another aspect, provided herein is a method of treating diabetes by administering a composition comprising an ionic liquid wherein the administration induces at least some reduction of blood glucose levels.

In another aspect, provided herein is a composition comprising;

a. a chemical with the formula,

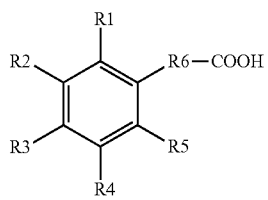

and b. a glucagon-like peptide-1 analog or functional variant thereof or mimetic thereof such that the said glucagon-like peptide-1 analog or functional variant thereof or mimetic thereof is associated with at least one ionic species.

In another aspect, provided herein is a composition comprising;

a. a chemical with the formula,

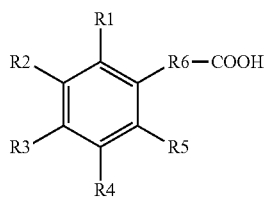

and b. a glucagon-like peptide selected from liraglutide, exenatide or semaglutide such that the said glucagon-like peptide is associated with at least one ionic species.

In some embodiments, R1, R2, R3, R4 and R5 are hydrogens and R6 is either CH=CH or $CH_2$—$CH_2$.

The inventors have found that certain modifications to proteins surprisingly improve their use with ionic liquid compositions for formulation and delivery. These formulations can be delivered orally to a patient for the purpose of treating the patient.

In one embodiment, described herein is a composition wherein a protein or a peptide is non-covalently attached to one more ions wherein such ions are also present in the said ionic liquid is present in the formulation.

In one embodiment, described herein is a composition wherein a protein or a peptide is covalently attached to one more ions wherein such ions are also present in the said ionic liquid is present in the formulation.

In one embodiment, the ion used for covalent or non-covalent modification of peptide is choline or choline derivative.

In some embodiments, the ionic liquid is a composition comprising a cation of choline or choline derivative and is cinnamic acid.

In some embodiment, the ionic liquid is at a concentration of at least 0.1% w/v. In some embodiment, the ionic liquid comprises a ratio of cation:anion from about 2:1 to about 1:2.

In some embodiments, the peptide formulation is administered once. In some embodiments, the formulation is administered in multiple doses.

In one embodiment, the ionic liquid is delivered as a liquid-filled capsule.

In some embodiments, the peptide delivered with the ionic liquid is a glucagon-like peptide (GLP-1) or glucagon-like peptide derivative.

In some embodiments, the protein delivered with the ionic liquid is an antibody or antibody fragment.

In one aspect of any of the embodiments, provided herein is a method of treating Type 1 diabetes, Type 2 diabetes, NASH, prediabetes, obesity, or other metabolic disorders.

In some embodiments, the ionic liquid is mixed with a pharmaceutically acceptable diluent such that the ionic liquid is present at a concentration of at least 0.05M.

In some embodiments, the ionic liquid dissolves after administration.

In some embodiments, the ionic liquid is a pure or anhydrous liquid. In some embodiments, the ionic liquid is an aqueous solution.

In some embodiments, the ionic liquid serves to solubilize and stabilize the peptide to be delivered.

In another aspect, provided herein is a composition comprising a therapeutic agent and one or more ionic liquid.

In some embodiments, the one or more ionic liquid independently comprises a cation selected from the group consisting of aminoguanidine, choline or choline derivative, carnitine, acetylcholine, ammonium, tetramethyl ammonium, tetraethyl ammonium, tetrabutyl ammonium, and guanidine derivatives.

In some embodiments, the one or more ionic liquid independently comprises choline or choline derivative, carnitine, or acetylcholine.

In some embodiments, the one or more ionic liquid independently comprises an anion selected from the group consisting of (R)-α-Lipoic Acid, 12-Hydroxystearic Acid, 2-(4-Isobutylphenyl)propionic Acid, 2-(4,4-Dimethyl-2-pentanyl)-5,7,7-trimethyloctanoic Acid, 2-Aminoethanesulfonic Acid (Taurine Acid), 2-Hexyldecanoic Acid, 2-Hydroxyhippuric Acid, 3-(4-Hydroxyphenyl)propionic Acid, 3-Methylcrotonic Acid, 3,3-Diphenylpropionic Acid, 3,4-Dihydroxbenzoic Acid (Protocatechuic Acid), 3,7-Dimethyloctanoic Acid, 4-Hydroxybenzenesulfonic Acid, 4-Hydroxybenzoic Acid, 4-Methylhexanoic Acid, 4-Methyloctanoic Acid, 4-Methylvaleric Acid, 5-Norbornene-2-carboxylic Acid, 8-[(2-hydroxybenzoyl)amino]octanoic acid, Abietic Acid, Acetic Acid, Acetylcysteine, Aconitic Acid, Arachidonic Acid, Behenic Acid, Benzoic Acid, Caffeic Acid, Chenodeoxycholic Acid, Cis-Cinnamic acid, Citric Acid, Citronellic Acid, Crotonic Acid, D-(+)-Galactonic Acid, Decanoic Acid, Deoxycholic Acid, Dihydrocaffeic Acid, DL-2-Phenylpropionic (Hydratropic) Acid, DL-Tartaric Acid, DL-Tropic Acid, Eicosanedioic Acid, Eicosapentanoic Acid (EPA), Elaidic Acid, Ellagic Acid, Erucic Acid, Ethylenediaminetetraacetic Acid (EDTA), Formic Acid, Fumaric Acid, Geranic Acid, Glutaric Acid, Glycolic Acid, Heptanoic Acid, Hexanoic Acid, Hydrocinnamic Acid (3-Phenylpropionic Acid), Isobutyric Acid, Isovaleric Acid, L-(+)-Tartaric Acid, L-Ascorbic Acid, L-Aspartic Acid, L-Glutamic Acid, L-Glutathione reduced, Lactic Acid, Lauric Acid, Levulinic Acid, Linoleic Acid, Linolenic Acid, Lithocholic Acid, Maleic Acid, Malic Acid, Malonic Acid, Mandelic acid, Mesaconic Acid, Nicotinic Acid, Nonanoic Acid, Octanoic Acid, Oleic Acid, Oxalic Acid, p-Coumaric Acid, p-Toluenesulfonic Acid, Palmitic Acid, Perillic Acid, Phosphoric Acid, Pimelic Acid, Pivalic Acid, Propionic Acid, Pyroglutamic Acid, Pyruvic Acid, Ricinoleic Acid, Salicylic Acid (2-Hydroxybenzoic Acid), Sinapinic Acid (3,5-Dimethoxy-4-Hydroxycinnamic Acid), Sorbic Acid, Stearic acid, Succinic Acid, Syringic Acid, Tiglic Acid, Trans-2-Decenoic Acid, Trans-2-Hexenoic Acid, Trans-2-Octenoic Acid, Trans-3-Octenoic Acid, Trans-γ-Octenoic Acid, Trans-Cinnamic Acid, Trans-Ferulic Acid, Undecanoic Acid, Valeric Acid, Vanillic Acid, and α-Ketoglutaric Acid.

In some embodiments, the one or more ionic liquid independently comprises an anion selected from the group consisting of glycolic acid, tartaric acid, malic acid, hydrocinnamic acid, citric acid, cinnamic acid, mandelic acid, mesaconic acid, ricinoleic acid, linoleic acid, and tiglic acid.

In some embodiments, the one or more ionic liquid independently comprises an anion selected from the group consisting of cinnamic acid, mandelic acid, citric acid, ricinoleic acid, linoleic acid, and tiglic acid.

In some embodiments, the one or more ionic liquid independently comprises choline or choline derivative-cinnamic acid, choline or choline derivative-mandelic acid, choline or choline derivative-citric acid, choline or choline derivative-ricinoleic acid, choline or choline derivative-linoleic acid, or choline or choline derivative-tiglic acid.

In some embodiments, the one or more ionic liquid independently comprises carnitine-cinnamic acid, carnitine-mandelic acid, carnitine-citric acid, carnitine-ricinoleic acid, carnitine-linoleic acid, or carnitine-tiglic acid.

In some embodiments, the one or more ionic liquid independently comprises acetylcholine-cinnamic acid, acetylcholine-mandelic acid, acetylcholine-citric acid, acetylcholine-ricinoleic acid, acetylcholine-linoleic acid, or acetylcholine-tiglic acid.

In some embodiments, the composition as described herein further comprises at least one permeation enhancer.

In some embodiments, the at least one permeation enhancer is selected from the group consisting of salcaprozate sodium (SNAC), sodium caprylate, sodium caprate, a bile salt, ethylenediaminetetraacetic acid (EDTA), ethylene glycol-bis-(2-aminoethylether)-N,N,N',N'-tetraacetic acid (EGTA), and 3-[N,N-Dimethyl(3-palmitoylaminopropyl)-ammonio]-propanesulfonate (PPS), and any combination thereof.

In some embodiments, the bile salt is selected from the group consisting of sodium deoxycholate, sodium chenodeoxycholate, sodium taurodeoxycholate, and a combination thereof.

In another aspect, provided herein is a method of increasing the solubility of a therapeutic agent comprising preparing a composition comprising the therapeutic agent and one or more ionic liquid.

In another aspect, provided herein is a method of enhancing or improving the delivery efficiency of a therapeutic agent in a subject in need thereof comprising preparing a composition comprising the therapeutic agent and one or more ionic liquid, and administering the composition to the subject.

In some embodiments, the one or more ionic liquid independently comprises a cation selected from the group consisting of aminoguanidine, choline or choline derivative, carnitine, acetylcholine, ammonium, tetramethyl ammonium, tetraethyl ammonium, tetrabutyl ammonium, and guanidine derivatives.

In some embodiments, the one or more ionic liquid independently comprises choline or choline derivative, carnitine, or acetylcholine.

In some embodiments, the one or more ionic liquid independently comprises an anion selected from the group consisting of (R)-α-Lipoic Acid, 12-Hydroxystearic Acid, 2-(4-Isobutylphenyl)propionic Acid, 2-(4,4-Dimethyl-2-pentanyl)-5,7,7-trimethyloctanoic Acid, 2-Aminoethanesulfonic Acid (Taurine Acid), 2-Hexyldecanoic Acid, 2-Hydroxyhippuric Acid, 3-(4-Hydroxyphenyl)propionic Acid, 3-Methylcrotonic Acid, 3,3-Diphenylpropionic Acid, 3,4-Dihydroxbenzoic Acid (Protocatechuic Acid), 3,7-Dimethyloctanoic Acid, 4-Hydroxybenzenesulfonic Acid, 4-Hydroxybenzoic Acid, 4-Methylhexanoic Acid, 4-Methyloctanoic Acid, 4-Methylvaleric Acid, 5-Norbornene-2-carboxylic Acid, 8-[(2-hydroxybenzoyl)amino]octanoic acid, Abietic Acid, Acetic Acid, Acetylcysteine, Aconitic Acid, Arachidonic Acid, Behenic Acid, Benzoic Acid, Caffeic Acid, Chenodeoxycholic Acid, Cis-Cinnamic acid, Citric Acid, Citronellic Acid, Crotonic Acid, D-(+)-Galactonic Acid, Decanoic Acid, Deoxycholic Acid, Dihydrocaffeic Acid, DL-2-Phenylpropionic (Hydratropic) Acid, DL-Tartaric Acid, DL-Tropic Acid, Eicosanedioic Acid, Eicosapentanoic Acid (EPA), Elaidic Acid, Ellagic Acid, Erucic Acid, Ethylenediaminetetraacetic Acid (EDTA), Formic Acid, Fumaric Acid, Geranic Acid, Glutaric Acid, Glycolic Acid, Heptanoic Acid, Hexanoic Acid, Hydrocinnamic Acid (3-Phenylpropionic Acid), Isobutyric Acid, Isovaleric Acid, L-(+)-Tartaric Acid, L-Ascorbic Acid, L-Aspartic Acid, L-Glutamic Acid, L-Glutathione reduced, Lactic Acid, Lauric Acid, Levulinic Acid, Linoleic Acid, Linolenic Acid, Lithocholic Acid, Maleic Acid, Malic Acid, Malonic Acid, Mandelic acid, Mesaconic Acid, Nicotinic Acid, Nonanoic Acid, Octanoic Acid, Oleic Acid, Oxalic Acid, p-Coumaric Acid, p-Toluenesulfonic Acid, Palmitic Acid, Perillic Acid, Phosphoric Acid, Pimelic Acid, Pivalic Acid, Propionic Acid, Pyroglutamic Acid, Pyruvic Acid, Ricinoleic Acid, Salicylic Acid (2-Hydroxybenzoic Acid), Sinapinic Acid (3,5-Dimethoxy-4-Hydroxycinnamic Acid), Sorbic Acid, Stearic acid, Succinic Acid, Syringic Acid, Tiglic Acid, Trans-2-Decenoic Acid, Trans-2-Hexenoic Acid, Trans-2-Octenoic Acid, Trans-3-Octenoic Acid, Trans-γ-Octenoic Acid, Trans-Cinnamic Acid, Trans-Ferulic Acid, Undecanoic Acid, Valeric Acid, Vanillic Acid, and α-Ketoglutaric Acid.

In some embodiments, the one or more ionic liquid independently comprises an anion selected from the group consisting of glycolic acid, tartaric acid, malic acid, hydrocinnamic acid, citric acid, cinnamic acid, mandelic acid, mesaconic acid, ricinoleic acid, linoleic acid, and tiglic acid.

In some embodiments, the one or more ionic liquid independently comprises an anion selected from the group consisting of cinnamic acid, mandelic acid, citric acid, ricinoleic acid, linoleic acid, and tiglic acid.

In some embodiments, the one or more ionic liquid independently comprises choline or choline derivative-cinnamic acid, choline or choline derivative-mandelic acid, choline or choline derivative-citric acid, choline or choline derivative-ricinoleic acid, choline or choline derivative-linoleic acid, or choline or choline derivative-tiglic acid.

In some embodiments, the one or more ionic liquid independently comprises carnitine-cinnamic acid, carnitine-mandelic acid, carnitine-citric acid, carnitine-ricinoleic acid, carnitine-linoleic acid, or carnitine-tiglic acid.

In some embodiments, the one or more ionic liquid independently comprises acetylcholine-cinnamic acid, acetylcholine-mandelic acid, acetylcholine-citric acid, acetylcholine-ricinoleic acid, acetylcholine-linoleic acid, or acetylcholine-tiglic acid.

In some embodiments, the one or more ionic liquid independently comprises a cation selected from the group of the cations listed in Table 2. In some embodiments, the one or more ionic liquid independently comprises an anion selected from the group of the anions listed in Table 1. In some embodiments, the one or more ionic liquid independently comprises an ionic liquid selected from the group of the ionic liquids listed in Table 2.

In some embodiments, the composition or the pharmaceutical composition as provided herein comprises the composition as provided herein or the compound as provided herein, and the first, the second, the third, the fourth, the fifth, the sixth, the eighth, the ninth, the tenth, or more ionic liquids.

In some embodiments, the first, the second, the third, the fourth, the fifth, the sixth, the eighth, the ninth, the tenth, or more ionic liquids independently comprises a cation selected from the group consisting of aminoguanidine, choline or choline derivative, carnitine, acetylcholine, ammonium, tetramethyl ammonium, tetraethyl ammonium, tetrabutyl ammonium, and guanidine derivatives. In some embodiments, the first, the second, the third, the fourth, the fifth, the sixth, the eighth, the ninth, the tenth, or more ionic liquids independently comprises choline or choline derivative, carnitine, or acetylcholine.

In some embodiments, the first, the second, the third, the fourth, the fifth, the sixth, the eighth, the ninth, the tenth, or more ionic liquids independently comprises an anion selected from the group consisting of (R)-α-Lipoic Acid, 12-Hydroxystearic Acid, 2-(4-Isobutylphenyl)propionic Acid, 2-(4,4-Dimethyl-2-pentanyl)-5,7,7-trimethyloctanoic Acid, 2-Aminoethanesulfonic Acid (Taurine Acid), 2-Hexyldecanoic Acid, 2-Hydroxyhippuric Acid, 3-(4-Hydroxyphenyl)propionic Acid, 3-Methylcrotonic Acid, 3,3-Diphenylpropionic Acid, 3,4-Dihydroxbenzoic Acid (Protocatechuic Acid), 3,7-Dimethyloctanoic Acid, 4-Hydroxybenzenesulfonic Acid, 4-Hydroxybenzoic Acid, 4-Methylhexanoic Acid, 4-Methyloctanoic Acid, 4-Methylvaleric Acid, 5-Norbornene-2-carboxylic Acid, 8-[(2-hydroxybenzoyl)amino]octanoic acid, Abietic Acid, Acetic Acid, Acetylcysteine, Aconitic Acid, Arachidonic Acid, Behenic Acid, Benzoic Acid, Caffeic Acid, Chenodeoxycholic Acid, Cis-Cinnamic acid, Citric Acid, Citronellic Acid, Crotonic Acid, D-(+)-Galactonic Acid, Decanoic Acid, Deoxycholic Acid, Dihydrocaffeic Acid, DL-2-Phenylpropionic (Hydratropic) Acid, DL-Tartaric Acid, DL-Tropic Acid, Eicosanedioic Acid, Eicosapentanoic Acid (EPA), Elaidic Acid, Ellagic Acid, Erucic Acid, Ethylenediaminetetraacetic Acid (EDTA), Formic Acid, Fumaric Acid, Geranic Acid, Glutaric Acid, Glycolic Acid, Heptanoic Acid, Hexanoic Acid, Hydrocinnamic Acid (3-Phenylpropionic Acid), Isobutyric Acid, Isovaleric Acid, L-(+)-Tartaric Acid, L-Ascorbic Acid, L-Aspartic Acid, L-Glutamic Acid, L-Glutathione reduced, Lactic Acid, Lauric Acid, Levulinic Acid, Linoleic Acid, Linolenic Acid, Lithocholic Acid, Maleic Acid, Malic Acid, Malonic Acid, Mandelic acid, Mesaconic Acid, Nicotinic Acid, Nonanoic Acid, Octanoic Acid, Oleic Acid, Oxalic Acid, p-Coumaric Acid, p-Toluenesulfonic Acid, Palmitic Acid, Perillic Acid, Phosphoric Acid, Pimelic Acid, Pivalic Acid, Propionic Acid, Pyroglutamic Acid, Pyruvic Acid, Ricinoleic Acid, Salicylic Acid (2-Hydroxybenzoic Acid), Sinapinic Acid (3,5-Dimethoxy-4-Hydroxycinnamic Acid), Sorbic Acid, Stearic acid, Succinic Acid, Syringic Acid, Tiglic Acid, Trans-2-Decenoic Acid, Trans-2-Hexenoic Acid, Trans-2-Octenoic Acid, Trans-3-Octenoic Acid, Trans-γ-Octenoic Acid, Trans-Cinnamic Acid, Trans-Ferulic Acid, Undecanoic Acid, Valeric Acid, Vanillic Acid, and α-Ketoglutaric Acid.

In some embodiments, the first, the second, the third, the fourth, the fifth, the sixth, the eighth, the ninth, the tenth, or more ionic liquids independently comprises an anion selected from the group consisting of (R)-α-lipoic acid, 2-(4-isobutylphenyl)propionic acid, 2-(4,4-dimethyl-2-pentanyl)-5,7,7-trimethyloctanoic acid, 2-hexyldecanoic acid, 2-hydroxyhippuric acid, 3,7-dimethyloctanoic acid, 4-methylhexanoic acid, 4-methyloctanoic acid, 4-methylvaleric acid, 5-norbornene-2-carboxylic acid, abietic acid, acetic acid, acetylcysteine, arachidonic acid, caffeic acid, cinnamic acid, citric acid, citronellic acid, crotonic acid, D-(+)-galactonic acid, decanoic acid, deoxycholic acid, eicosapentanoic acid, fumaric acid, geranic acid, glutaric acid, glycolic acid, hexanoic acid, 3-phenylpropionic acid, isovaleric acid, L-(+)-tartaric acid, L-ascorbic acid, L-glutathione reduced, lactic acid, lauric acid, levulinic acid, linoleic acid, linolenic acid, maleic acid, malonic acid, mesaconic acid, mandelic acid, nonanoic acid, octanoic acid, oleic acid, p-toluenesulfonic acid, perillic acid, phosphoric acid, pimelic acid, propionic acid, pyroglutamic acid, pyruvic acid, ricinoleic acid, sorbic acid, syringic acid, trans-2-decenoic acid, trans-2-hexenoic acid, trans-2-octenoic acid, trans-3-octenoic acid, trans-γ-octenoic acid, trans-ferulic acid, undecanoic acid, vanillic acid, α-ketoglutaric acid, 3,3-diphenylpropionic acid, 3,4-dihydroxbenzoic acid (protocatechuic acid), 3-(4-hydroxyphenyl)propionic acid, 3-methylcrotonic acid, 4-hydroxybenzenesulfonic acid, 4-hydroxybenzoic acid, aconitic acid, benzoic acid, chenodeoxycholic acid, dihydrocaffeic acid, DL-2-phenylpropionic (hydratropic) acid, DL-tropic acid, eicosanedioic acid, ellagic acid, formic acid, heptanoic acid, isobutyric acid, DL-tartaric acid, lithocholic acid, malic acid, nicotinic acid, p-coumaric acid, palmitic acid, pivalic acid, salicylic acid (2-hydroxybenzoic acid), sinapinic acid (3,5-dimethoxy-4-hydroxycinnamic acid), succinic acid, tiglic acid, valeric acid, stearic acid, and 8-[(2-hydroxybenzoyl)amino]octanoic acid. In some embodiments, the first, the second, the third, the fourth, the fifth, the sixth, the eighth, the ninth, the tenth, or more ionic liquids independently comprises an anion selected from the group consisting of glycolic acid, tartaric acid, malic acid, hydrocinnamic acid, citric acid, cinnamic acid, mandelic acid, mesaconic acid, ricinoleic acid, linoleic acid, and tiglic acid. In some embodiments, the first, the second, the third, the fourth, the fifth, the sixth, the eighth, the ninth, the tenth, or more ionic liquids independently comprises an anion selected from the group consisting of cinnamic acid, mandelic acid, citric acid, ricinoleic acid, linoleic acid, and tiglic acid.

In some embodiments, the first, the second, the third, the fourth, the fifth, the sixth, the eighth, the ninth, the tenth, or more ionic liquids independently comprises choline or choline derivative-cinnamic acid, choline or choline derivative-mandelic acid, choline or choline derivative-citric acid, choline or choline derivative-ricinoleic acid, choline or choline derivative-linoleic acid, or choline or choline derivative-tiglic acid.

In some embodiments, the one or more ionic liquid independently comprises carnitine-cinnamic acid, carnitine-mandelic acid, carnitine-citric acid, carnitine-ricinoleic acid, carnitine-linoleic acid, or carnitine-tiglic acid.

In some embodiments, the one or more ionic liquid independently comprises acetylcholine-cinnamic acid, acetylcholine-mandelic acid, acetylcholine-citric acid, acetylcholine-ricinoleic acid, acetylcholine-linoleic acid, or acetylcholine-tiglic acid.

In some embodiments, the first, the second, the third, the fourth, the fifth, the sixth, the eighth, the ninth, the tenth, or more ionic liquids independently comprises a cation selected from the group of the cations listed in Table 2. In some embodiments, the first, the second, the third, the fourth, the fifth, the sixth, the eighth, the ninth, the tenth, or more ionic liquids independently comprises an anion selected from the group of the anions listed in Table 1. In some embodiments, some embodiments, the first, the second, the third, the fourth, the fifth, the sixth, the eighth, the ninth, the tenth, or more ionic liquids independently comprises an ionic liquid selected from the group of the ionic liquids listed in Table 2.

Therapeutic Agents

In some aspects, provided herein, inter alia, is a compound according to Formula I:

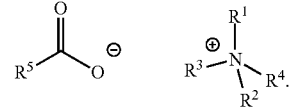

Formula I

In some embodiments, $R^1$, $R^2$, and $R^3$ are independently $C_1$-$C_5$ alkyl. In some embodiments, $R^1$ is $C_1$-$C_5$ alkyl. In some embodiments, $R^2$ is $C_1$-$C_5$ alkyl. In some embodiments, $R^3$ is $C_1$-$C_5$ alkyl.

In some embodiments, $R^1$, $R^2$, and $R^3$ are independently $C_1$-$C_{20}$ alkyl. In some embodiments, $R^1$ is $C_1$-$C_{20}$ alkyl. In some embodiments, $R^1$ is $C_1$-$C_{19}$ alkyl. In some embodiments, $R^1$ is $C_1$-$C_{18}$ alkyl. In some embodiments, $R^1$ is $C_1$-$C_{17}$ alkyl. In some embodiments, $R^1$ is $C_1$-$C_{16}$ alkyl. In some embodiments, $R^1$ is $C_1$-$C_{15}$ alkyl. In some embodiments, $R^1$ is $C_1$-$C_{14}$ alkyl. In some embodiments, $R^1$ is $C_1$-$C_{13}$ alkyl. In some embodiments, $R^1$ is $C_1$-$C_{12}$ alkyl. In some embodiments, $R^1$ is $C_1$-$C_{11}$ alkyl. In some embodiments, $R^1$ is $C_1$-$C_{10}$ alkyl. In some embodiments, $R^1$ is $C_1$-$C_9$ alkyl. In some embodiments, $R^1$ is $C_1$-$C_8$ alkyl. In some embodiments, $R^1$ is $C_1$-$C_7$ alkyl. In some embodiments, $R^1$ is $C_1$-$C_6$ alkyl. In some embodiments, $R^1$ is $C_1$-$C_5$ alkyl. In some embodiments, $R^1$ is $C_1$-$C_4$ alkyl. In some embodiments, $R^1$ is $C_1$-$C_3$ alkyl. In some embodiments, $R^1$ is $C_1$-$C_2$ alkyl. In some embodiments, $R^2$ is $C_1$-$C_{20}$ alkyl. In some embodiments, $R^2$ is $C_1$-$C_{19}$ alkyl. In some embodiments, $R^2$ is $C_1$-$C_{18}$ alkyl. In some embodiments, $R^2$ is $C_1$-$C_{17}$ alkyl. In some embodiments, $R^2$ is $C_1$-$C_{16}$ alkyl. In some embodiments, $R^2$ is $C_1$-$C_{15}$ alkyl. In some embodiments, $R^2$ is $C_1$-$C_{14}$ alkyl. In some embodiments, $R^2$ is $C_1$-$C_{13}$ alkyl. In some embodiments, $R^2$ is $C_1$-$C_{12}$ alkyl. In some embodiments, $R^2$ is $C_1$-$C_{11}$ alkyl. In some embodiments, $R^2$ is $C_1$-$C_{10}$ alkyl. In some embodiments, $R^2$ is $C_1$-$C_9$ alkyl. In some embodiments, $R^2$ is $C_1$-$C_5$ alkyl. In some embodiments, $R^2$ is $C_1$-$C_7$ alkyl. In some embodiments, $R^2$ is $C_1$-$C_6$ alkyl. In some embodiments, $R^2$ is $C_1$-$C_5$ alkyl. In some embodiments, $R^2$ is $C_1$-$C_4$ alkyl. In some embodiments, $R^2$ is $C_1$-$C_3$ alkyl. In some embodiments, $R^2$ is $C_1$-$C_2$ alkyl. In some embodiments, $R^3$ is $C_1$-$C_{20}$ alkyl. In some embodiments, $R^3$ is $C_1$-$C_{19}$ alkyl. In some embodiments, $R^3$ is $C_1$-$C_{18}$ alkyl. In some embodiments, $R^3$ is $C_1$-$C_{17}$ alkyl. In some embodiments, $R^3$ is $C_1$-$C_{16}$ alkyl. In some embodiments, $R^3$ is $C_1$-$C_{15}$ alkyl. In some embodiments, $R^3$ is $C_1$-$C_{14}$ alkyl. In some embodiments, $R^3$ is $C_1$-$C_{13}$ alkyl. In some embodiments, $R^3$ is $C_1$-$C_{12}$ alkyl. In some embodiments, $R^3$ is $C_1$-$C_{11}$ alkyl. In some embodiments, $R^3$ is $C_1$-$C_{10}$ alkyl. In some embodiments, $R^3$ is $C_1$-$C_9$ alkyl. In some embodiments, $R^3$ is $C_1$-$C_8$ alkyl. In some embodiments, $R^3$ is $C_1$-$C_7$ alkyl. In some embodiments, $R^3$ is $C_1$-$C_6$ alkyl. In some embodiments, $R^3$ is $C_1$-$C_5$ alkyl. In some embodiments, $R^3$ is $C_1$-$C_4$ alkyl. In some embodiments, $R^3$ is $C_1$-$C_3$ alkyl. In some embodiments, $R^3$ is $C_1$-$C_2$ alkyl.

In some embodiments, $R^1$ is $C_1$ alkyl. In some embodiments, $R^1$ is $C_2$ alkyl. In some embodiments, $R^1$ is $C_3$ alkyl. In some embodiments, $R^1$ is $C_4$ alkyl. In some embodiments, $R^1$ is $C_5$ alkyl. In some embodiments, $R^1$ is $C_6$ alkyl. In some embodiments, $R^1$ is $C_7$ alkyl. In some embodiments, $R^1$ is $C_8$ alkyl. In some embodiments, $R^1$ is $C_9$ alkyl. In some embodiments, $R^1$ is $C_{10}$ alkyl. In some embodiments, $R^1$ is $C_{11}$ alkyl. In some embodiments, $R^1$ is $C_{12}$ alkyl. In some embodiments, $R^1$ is $C_{13}$ alkyl. In some embodiments, $R^1$ is $C_{14}$ alkyl. In some embodiments, $R^1$ is $C_{15}$ alkyl. In some embodiments, $R^1$ is $C_{16}$ alkyl. In some embodiments, $R^1$ is $C_{17}$ alkyl. In some embodiments, $R^1$ is $C_{18}$ alkyl. In some embodiments, $R^1$ is $C_{19}$ alkyl. In some embodiments, $R^1$ is $C_{20}$ alkyl. In some embodiments, $R^2$ is $C_1$ alkyl. In some embodiments, $R^2$ is $C_2$ alkyl. In some embodiments, $R^2$ is $C_3$ alkyl. In some embodiments, $R^2$ is $C_4$ alkyl. In some embodiments, $R^2$ is $C_5$ alkyl. In some embodiments, $R^2$ is $C_6$ alkyl. In some embodiments, $R^2$ is $C_7$ alkyl. In some embodiments, $R^2$ is $C_8$ alkyl. In some embodiments, $R^2$ is $C_9$ alkyl. In some embodiments, $R^2$ is $C_{10}$ alkyl. In some embodiments, $R^2$ is $C_{11}$ alkyl. In some embodiments, $R^2$ is $C_{12}$ alkyl. In some embodiments, $R^2$ is $C_{13}$ alkyl. In some embodiments, $R^2$ is $C_{14}$ alkyl. In some embodiments, $R^2$ is $C_{15}$ alkyl. In some embodiments, $R^2$ is $C_{16}$ alkyl. In some embodiments, $R^2$ is $C_{17}$ alkyl. In some embodiments, $R^2$ is $C_{18}$ alkyl. In some embodiments, $R^2$ is $C_{19}$ alkyl. In some embodiments, $R^2$ is $C_{20}$ alkyl. In some embodiments, $R^3$ is $C_1$ alkyl. In some embodiments, $R^3$ is $C_2$ alkyl. In some embodiments, $R^3$ is $C_3$ alkyl. In some embodiments, $R^3$ is $C_4$ alkyl. In some embodiments, $R^3$ is $C_5$ alkyl. In some embodiments, $R^3$ is $C_6$ alkyl. In some embodiments, $R^3$ is $C_7$ alkyl. In some embodiments, $R^3$ is $C_8$ alkyl. In some embodiments, $R^3$ is $C_9$ alkyl. In some embodiments, $R^3$ is $C_{10}$ alkyl. In some embodiments, $R^3$ is $C_{11}$ alkyl. In some embodiments, $R^3$ is $C_{12}$ alkyl. In some embodiments, $R^3$ is $C_{13}$ alkyl. In some embodiments, $R^3$ is $C_{14}$ alkyl. In some embodiments, $R^3$ is $C_{15}$ alkyl. In some embodiments, $R^3$ is $C_{16}$ alkyl. In some embodiments, $R^3$ is $C_{17}$ alkyl. In some embodiments, $R^3$ is $C_{18}$ alkyl. In some embodiments, $R^3$ is $C_{19}$ alkyl. In some embodiments, $R^3$ is $C_{20}$ alkyl.

In some embodiments, $R^4$ is $C_2$-$C_5$ alkyl, wherein the $C_2$-$C_5$ alkyl is unsubstituted or substituted with 1 or more hydroxyl. In some embodiments, $R^4$ is $C_2$-$C_{20}$ alkyl, wherein the $C_2$-$C_5$ alkyl is unsubstituted or substituted with 1 or more hydroxyl. In some embodiments, $R^4$ is $C_2$-$C_{19}$ alkyl, wherein the $C_2$-$C_5$ alkyl is unsubstituted or substituted with 1 or more hydroxyl. In some embodiments, $R^4$ is $C_2$-$C_{18}$ alkyl, wherein the $C_2$-$C_5$ alkyl is unsubstituted or substituted with 1 or more hydroxyl. In some embodiments, $R^4$ is $C_2$-$C_{17}$ alkyl, wherein the $C_2$-$C_5$ alkyl is unsubstituted or substituted with 1 or more hydroxyl. In some embodiments, $R^4$ is $C_2$-$C_{16}$ alkyl, wherein the $C_2$-$C_5$ alkyl is unsubstituted or substituted with 1 or more hydroxyl. In some embodiments, $R^4$ is $C_2$-$C_{15}$ alkyl, wherein the $C_2$-$C_5$ alkyl is unsubstituted or substituted with 1 or more hydroxyl. In some embodiments, $R^4$ is $C_2$-$C_{14}$ alkyl, wherein the $C_2$-$C_5$ alkyl is unsubstituted or substituted with 1 or more hydroxyl. In some embodiments, $R^4$ is $C_2$-$C_{13}$ alkyl, wherein the $C_2$-$C_5$ alkyl is unsubstituted or substituted with 1 or more hydroxyl. In some embodiments, $R^4$ is $C_2$-$C_{12}$ alkyl, wherein the $C_2$-$C_5$ alkyl is unsubstituted or substituted with 1 or more hydroxyl. In some embodiments, $R^4$ is $C_2$-$C_{11}$ alkyl, wherein the $C_2$-$C_5$ alkyl is unsubstituted or substituted with 1 or more hydroxyl. In some embodiments, $R^4$ is $C_2$-$C_{10}$ alkyl, wherein the $C_2$-$C_5$ alkyl is unsubstituted or substituted with 1 or more hydroxyl. In some embodiments, $R^4$ is $C_2$-$C_9$ alkyl, wherein the $C_2$-$C_5$ alkyl is unsubstituted or substituted with 1 or more hydroxyl. In some embodiments, $R^4$ is $C_2$-$C_5$ alkyl, wherein the $C_2$-$C_5$ alkyl is unsubstituted or substituted with 1 or more hydroxyl. In some embodiments, $R^4$ is $C_2$-$C_7$ alkyl, wherein the $C_2$-$C_5$ alkyl is unsubstituted or substituted with 1 or more hydroxyl. In some embodiments, $R^4$ is $C_2$-$C_6$ alkyl, wherein the $C_2$-$C_5$ alkyl is unsubstituted or substituted with 1 or more hydroxyl. In some embodiments, $R^4$ is $C_2$-$C_5$ alkyl, wherein the $C_2$-$C_5$ alkyl is unsubstituted or substituted with 1 or more hydroxyl. In some embodiments, $R^4$ is $C_2$-$C_4$ alkyl, wherein the $C_2$-$C_5$ alkyl is unsubstituted or substituted with 1 or more hydroxyl. In some embodiments, $R^4$ is $C_2$-$C_3$ alkyl, wherein the $C_2$-$C_5$ alkyl is unsubstituted or substituted with 1 or more hydroxyl. In some embodiments, $R^4$ is $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl, wherein the $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl is unsubstituted or substituted with 1 or more hydroxyl.

In some embodiments, $R^5$ is a therapeutic agent.

In some embodiments, the compound comprises a therapeutic agent comprising a diacid consisting of 18 or 20 carbons in length. In some embodiments, the compound comprises a therapeutic agent comprising a diacid consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 carbons in length. In some embodiments, the diacid comprises a $C_{20}$ fatty diacid. In some embodiments, the diacid comprises a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ fatty diacid.

In some aspects, provided herein is a compound according to Formula II:

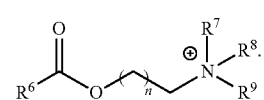

Formula II

In some embodiments, $R^7$, $R^8$, and $R^9$ are independently unsubstituted or substituted $C_1$-$C_5$ alkyl. In some embodiments, $R^7$ is unsubstituted or substituted $C_1$-$C_5$ alkyl. In some embodiments, $R^8$ is unsubstituted or substituted $C_1$-$C_5$ alkyl. In some embodiments, $R^9$ is unsubstituted or substituted $C_1$-$C_5$ alkyl.

In some embodiments, $R^7$, $R^8$, and $R^9$ are independently unsubstituted or substituted $C_1$-$C_{20}$ alkyl. In some embodiments, $R^7$ is unsubstituted or substituted $C_1$-$C_{20}$ alkyl. In some embodiments, $R^7$ is unsubstituted or substituted $C_1$-$C_{19}$ alkyl. In some embodiments, $R^7$ is unsubstituted or substituted $C_1$-$C_{18}$ alkyl. In some embodiments, $R^7$ is unsubstituted or substituted $C_1$-$C_{17}$ alkyl. In some embodiments, $R^7$ is unsubstituted or substituted $C_1$-$C_{16}$ alkyl. In some embodiments, $R^7$ is unsubstituted or substituted $C_1$-$C_{15}$ alkyl. In some embodiments, $R^7$ is unsubstituted or substituted $C_1$-$C_{14}$ alkyl. In some embodiments, $R^7$ is unsubstituted or substituted $C_1$-$C_{13}$ alkyl. In some embodiments, $R^7$ is unsubstituted or substituted $C_1$-$C_{12}$ alkyl. In some embodiments, $R^7$ is unsubstituted or substituted $C_1$-$C_{11}$ alkyl. In some embodiments, $R^7$ is unsubstituted or substituted $C_1$-$C_{10}$ alkyl. In some embodiments, $R^7$ is unsubstituted or substituted $C_1$-$C_9$ alkyl. In some embodiments, $R^7$ is unsubstituted or substituted $C_1$-$C_8$ alkyl. In some embodiments, $R^7$ is unsubstituted or substituted $C_1$-$C_7$ alkyl. In some embodiments, $R^7$ is unsubstituted or substituted $C_1$-$C_6$ alkyl. In some embodiments, $R^7$ is unsubstituted or substituted $C_1$-$C_5$ alkyl. In some embodiments, $R^7$ is unsubstituted or substituted $C_1$-$C_4$ alkyl. In some embodiments, $R^7$ is unsubstituted or substituted $C_1$-$C_3$ alkyl. In some embodiments, $R^7$ is unsubstituted or substituted $C_1$-$C_2$ alkyl. In some embodiments, $R^7$ is unsubstituted or substituted $C_1$-$C_{20}$ alkyl. In some embodiments, $R^8$ is unsubstituted or substituted $C_1$-$C_{19}$ alkyl. In some embodiments, $R^8$ is unsubstituted or substituted $C_1$-$C_{18}$ alkyl. In some embodiments, $R^8$ is unsubstituted or substituted $C_1$-$C_{17}$ alkyl. In some embodiments, $R^8$ is unsubstituted or substituted $C_1$-$C_{16}$ alkyl. In some embodiments, $R^8$ is unsubstituted or substituted $C_1$-$C_{15}$ alkyl. In some embodiments, $R^8$ is unsubstituted or substituted $C_1$-$C_{14}$ alkyl. In some embodiments, $R^8$ is unsubstituted or substituted $C_1$-$C_{13}$ alkyl. In some embodiments, $R^8$ is unsubstituted or substituted $C_1$-$C_{12}$ alkyl. In some embodiments, $R^8$ is unsubstituted or substituted $C_1$-$C_{11}$ alkyl. In some embodiments, $R^8$ is unsubstituted or substituted $C_1$-$C_{10}$ alkyl. In some embodiments, $R^8$ is unsubstituted or substituted $C_1$-$C_9$ alkyl. In some embodiments, $R^8$ is unsubstituted or substituted $C_1$-$C_8$ alkyl. In some embodiments, $R^8$ is unsubstituted or substituted $C_1$-$C_7$ alkyl. In some embodiments, $R^8$ is unsubstituted or substituted $C_1$-$C_6$ alkyl. In some embodiments, $R^8$ is unsubstituted or substituted $C_1$-$C_5$ alkyl. In some embodiments, $R^8$ is unsubstituted or substituted $C_1$-$C_4$ alkyl. In some embodiments, $R^8$ is unsubstituted or substituted $C_1$-$C_3$ alkyl. In some embodiments, $R^8$ is unsubstituted or substituted $C_1$-$C_2$ alkyl. In some embodiments, $R^9$ is unsubstituted or substituted $C_1$-$C_{20}$ alkyl. In some embodiments, $R^9$ is unsubstituted or substituted $C_1$-$C_{19}$ alkyl. In some embodiments, $R^9$ is unsubstituted or substituted $C_1$-$C_{18}$ alkyl. In some embodiments, $R^9$ is unsubstituted or substituted $C_1$-$C_{17}$ alkyl. In some embodiments, $R^9$ is unsubstituted or substituted $C_1$-$C_{16}$ alkyl. In some embodiments, $R^9$ is unsubstituted or substituted $C_1$-$C_{15}$ alkyl. In some embodiments, $R^9$ is unsubstituted or substituted $C_1$-$C_{14}$ alkyl. In some embodiments, $R^9$ is unsubstituted or substituted $C_1$-$C_{13}$ alkyl. In some embodiments, $R^9$ is unsubstituted or substituted $C_1$-$C_{12}$ alkyl. In some embodiments, $R^9$ is unsubstituted or substituted $C_1$-$C_{11}$ alkyl. In some embodiments, $R^9$ is unsubstituted or substituted $C_1$-$C_{10}$ alkyl. In some embodiments, $R^9$ is unsubstituted or substituted $C_1$-$C_9$ alkyl. In some embodiments, $R^9$ is unsubstituted or substituted $C_1$-$C_8$ alkyl. In some embodiments, $R^9$ is unsubstituted or substituted $C_1$-$C_7$ alkyl. In some embodiments, $R^9$ is unsubstituted or substituted $C_1$-$C_6$ alkyl. In some embodiments, $R^9$ is unsubstituted or substituted $C_1$-$C_5$ alkyl. In some embodiments, $R^9$ is unsubstituted or substituted $C_1$-$C_4$ alkyl. In some embodiments, $R^9$ is unsubstituted or substituted $C_1$-$C_3$ alkyl. In some embodiments, $R^9$ is unsubstituted or substituted $C_1$-$C_2$ alkyl.

In some embodiments, $R^7$ is unsubstituted or substituted $C_1$ alkyl. In some embodiments, $R^7$ is unsubstituted or substituted $C_2$ alkyl. In some embodiments, $R^7$ is unsubstituted or substituted $C_3$ alkyl. In some embodiments, $R^7$ is unsubstituted or substituted $C_4$ alkyl. In some embodiments, $R^7$ is unsubstituted or substituted $C_5$ alkyl. In some embodiments, $R^7$ is unsubstituted or substituted $C_6$ alkyl. In some embodiments, $R^7$ is unsubstituted or substituted $C_7$ alkyl. In some embodiments, $R^7$ is unsubstituted or substituted $C_8$ alkyl. In some embodiments, $R^7$ is unsubstituted or substituted $C_9$ alkyl. In some embodiments, $R^7$ is unsubstituted or substituted $C_{10}$ alkyl. In some embodiments, $R^7$ is unsubstituted or substituted $C_{11}$ alkyl. In some embodiments, $R^7$ is unsubstituted or substituted $C_{12}$ alkyl. In some embodiments, $R^7$ is unsubstituted or substituted $C_{13}$ alkyl. In some embodiments, $R^7$ is unsubstituted or substituted $C_{14}$ alkyl. In some embodiments, $R^7$ is unsubstituted or substituted $C_{15}$ alkyl. In some embodiments, $R^7$ is unsubstituted or substituted $C_{16}$ alkyl. In some embodiments, $R^7$ is unsubstituted or substituted $C_{17}$ alkyl. In some embodiments, $R^7$ is unsubstituted or substituted $C_{18}$ alkyl. In some embodiments, $R^7$ is unsubstituted or substituted $C_{19}$ alkyl. In some embodiments, $R^7$ is unsubstituted or substituted $C_{20}$ alkyl. In some embodiments, $R^8$ is unsubstituted or substituted $C_1$ alkyl. In some embodiments, $R^8$ is unsubstituted or substituted $C_2$ alkyl. In some embodiments, $R^8$ is unsubstituted or substituted $C_3$ alkyl. In some embodiments, $R^8$ is unsubstituted or substituted $C_4$ alkyl. In some embodiments, $R^8$ is unsubstituted or substituted $C_5$ alkyl. In some embodiments, $R^8$ is unsubstituted or substituted $C_6$ alkyl. In some embodiments, $R^8$ is unsubstituted or substituted $C_7$ alkyl. In some embodiments, $R^8$ is unsubstituted or substituted $C_8$ alkyl. In some embodiments, $R^8$ is unsubstituted or substituted $C_9$ alkyl. In some embodiments, $R^8$ is unsubstituted or substituted $C_{10}$ alkyl. In some embodiments, $R^8$ is unsubstituted or substituted $C_{11}$ alkyl. In some embodiments, $R^8$ is unsubstituted or substituted $C_{12}$ alkyl. In some embodiments, $R^8$ is unsubstituted or substituted $C_{13}$ alkyl. In some embodiments, $R^8$ is unsubstituted or substituted $C_{14}$ alkyl. In some embodiments, $R^8$ is unsubstituted or substituted $C_{15}$ alkyl. In some embodiments, $R^8$ is unsubstituted or substituted $C_{16}$ alkyl. In some embodiments, $R^8$ is unsubstituted or substituted $C_{17}$ alkyl. In some embodiments, $R^8$ is unsubstituted or substituted $C_{18}$ alkyl. In some embodiments, $R^8$ is unsubstituted or substituted $C_{19}$ alkyl. In some embodiments, $R^8$ is unsubstituted or substituted $C_{20}$ alkyl. In some embodiments, $R^9$ is unsubstituted or substituted $C_1$ alkyl. In some embodiments, $R^9$ is unsubstituted or substituted $C_2$ alkyl. In some embodiments, $R^9$ is unsubstituted or substituted $C_3$ alkyl. In some embodiments, $R^9$ is unsubstituted or substituted $C_4$ alkyl. In some embodiments, $R^9$ is unsubstituted or substituted $C_5$ alkyl. In some embodiments, $R^9$ is unsubstituted or substituted $C_6$ alkyl. In some embodiments, $R^9$ is unsubstituted or substituted $C_7$ alkyl. In some embodiments, $R^9$ is unsubstituted or substituted $C_8$ alkyl. In some embodiments, $R^9$ is unsubstituted or substituted $C_9$ alkyl. In some embodiments, $R^9$ is unsubstituted or substituted $C_{10}$ alkyl. In some embodiments, $R^9$ is unsubstituted or substituted $C_{11}$ alkyl. In some embodiments, $R^9$ is unsubstituted or substituted $C_{12}$ alkyl. In some embodiments, $R^9$ is unsubstituted or substituted $C_{13}$ alkyl. In some embodiments, $R^9$ is unsubstituted or substituted $C_{14}$ alkyl. In some embodiments, $R^9$ is unsubstituted or substituted $C_{15}$ alkyl. In some embodiments, $R^9$ is unsubstituted or substituted $C_{16}$ alkyl. In some embodiments, $R^9$ is unsubstituted or substituted $C_{17}$ alkyl. In some embodiments, $R^9$ is unsubstituted or substituted $C_{18}$ alkyl. In some embodiments, $R^9$ is unsubstituted or substituted $C_{19}$ alkyl. In some embodiments, $R^9$ is unsubstituted or substituted $C_{20}$ alkyl.

In some embodiments, n is 1, 2, 3, 4, or 5. In some embodiments, n is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In some embodiments, $R^6$ is a therapeutic agent.

In some embodiments, the compound comprises a therapeutic agent having a cation moiety comprising a choline or choline derivative-like residue.

In some embodiments, the compound comprises a therapeutic agent comprising one or more choline or choline derivative-peptide ester formed on a Cys residue, a Lys residue, or any combination thereof.

In some embodiments, the one or more choline or choline derivative-peptide ester formed on the Cys residue comprises a linker-to-a therapeutic agent ratio of 2-8, the one or more choline or choline derivative-peptide ester formed on the Lys residue comprises a linker-to-a therapeutic agent thereof ratio of 2-4, or a combination thereof.

In some embodiments, the one or more choline or choline derivative-peptide ester formed on the Cys residue comprises a linker-to-a therapeutic agent ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, the one or more choline or choline derivative-peptide ester formed on the Cys residue comprises a linker-to-a therapeutic agent ratio of 1-50, 1-49, 1-48, 1-47, 1-46, 1-45, 1-44, 1-43, 1-42, 1-41, 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, the one or more choline or choline derivative-peptide ester formed on the Cys residue comprises a linker-to-a therapeutic agent ratio of 2-50, 3-50, 4-50, 5-50, 6-50, 7-50, 8-50, 9-50, 10-50, 11-50, 12-50, 13-50, 14-50, 15-50, 16-50, 17-50, 18-50, 19-50, 20-50, 21-50, 22-50, 23-50, 24-50, 25-50, 26-50, 27-50, 28-50, 29-50, 30-50, 31-50, 32-50, 33-50, 34-50, 35-50, 36-50, 37-50, 38-50, 39-50, 40-50, 41-50, 42-50, 43-50, 44-50, 45-50, 46-50, 47-50, 48-50, or 49-50. In some embodiments, the one or more choline or choline derivative-peptide ester formed on the Cys residue comprises a linker-to-a therapeutic agent ratio of 1-7, 2-8, 3-9, 4-10, 5-11, 6-12, 7-13, 8-14, 9-15, 10-16, 11-17, 12-18, 13-19, 14-20, 15-21, 16-22, 17-23, 18-24, 19-25, 20-26, 21-27, 22-28, 23-29, 24-30, 25-31, 26-32, 27-33, 28-34, 29-35, 30-36, 31-37, 32-38, 33-39, 34-40, 35-41, 36-42, 37-43, 38-44, 39-45, 40-46, 41-47, 42-48, 43-49, or 44-50.

In some embodiments, the one or more choline or choline derivative-peptide ester formed on the Lys residue comprises a linker-to-a therapeutic agent ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, the one or more choline or choline derivative-peptide ester formed on the Lys residue comprises a linker-to-a therapeutic agent ratio of 1-50, 1-49, 1-48, 1-47, 1-46, 1-45, 1-44, 1-43, 1-42, 1-41, 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, the one or more choline or choline derivative-peptide ester formed on the Lys residue comprises a linker-to-a therapeutic agent ratio of 2-50, 3-50, 4-50, 5-50, 6-50, 7-50, 8-50, 9-50, 10-50, 11-50, 12-50, 13-50, 14-50, 15-50, 16-50, 17-50, 18-50, 19-50, 20-50, 21-50, 22-50, 23-50, 24-50, 25-50, 26-50, 27-50, 28-50, 29-50, 30-50, 31-50, 32-50, 33-50, 34-50, 35-50, 36-50, 37-50, 38-50, 39-50, 40-50, 41-50, 42-50, 43-50, 44-50, 45-50, 46-50, 47-50, 48-50, or 49-50. In some embodiments, the one or more choline or choline derivative-peptide ester formed on the Lys residue comprises a linker-to-a therapeutic agent ratio of 1-3, 2-4, 3-5, 4-6, 5-7, 6-8, 7-9, 8-10, 9-11, 10-12, 11-13, 12-14, 13-15, 14-16, 15-17, 16-18, 17-19, 18-20, 19-21, 20-22, 21-23, 22-24, 23-25, 24-26, 25-27, 26-28, 27-29, 28-30, 29-31, 30-32, 31-33, 32-34, 33-35, 34-36, 35-37, 36-38, 37-39, 38-40, 39-41, 40-42, 41-43, 42-44, 43-45, 44-46, 45-47, 46-48, 47-49, or 48-50.

In some embodiments, the compound comprises a therapeutic agent comprising a diacid consisting of 18 or 20 carbons in length. In some embodiments, the compound comprises a therapeutic agent comprising a diacid consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 carbons in length.

In some embodiments, the diacid comprises a $C_{20}$ fatty diacid. In some embodiments, the diacid comprises a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ fatty diacid.

In some aspects, provided herein is a compound according to Formula III:

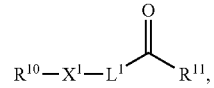

Formula III wherein:
$R^{10}$ is a therapeutic agent;
$R^{11}$ is substituted or unsubstituted $C_5$-$C_{10}$;
$X^1$ is

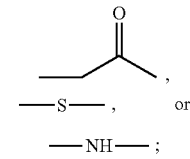

and
$L^1$ is a covalent bond or a linker.

In some embodiments, the compound comprises a therapeutic agent comprising one or more $R^{11}$ linked to a Lys residue, a Cys residue, or any combination thereof.

In some embodiments, $R^{11}$ is linked to the Lys residue with a linker-to-a therapeutic agent ratio of 2-4, $R^{11}$ is linked to the Cys residue with a linker-to-a therapeutic agent ratio of 2-8 or with a linker-to-a therapeutic agent ratio of 4, or a combination thereof.

In some embodiments, $R^{11}$ is linked to the Lys residue with a linker-to-a therapeutic agent ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, $R^{11}$ is linked to the Lys residue with a linker-to-a therapeutic agent ratio of 1-50, 1-49, 1-48, 1-47, 1-46, 1-45, 1-44, 1-43, 1-42, 1-41, 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, $R^{11}$ is linked to the Lys residue with a linker-to-a therapeutic agent ratio of 2-50, 3-50, 4-50, 5-50, 6-50, 7-50, 8-50, 9-50, 10-50, 11-50, 12-50, 13-50, 14-50, 15-50, 16-50, 17-50, 18-50, 19-50, 20-50, 21-50, 22-50, 23-50, 24-50, 25-50, 26-50, 27-50, 28-50, 29-50, 30-50, 31-50, 32-50, 33-50, 34-50, 35-50, 36-50, 37-50, 38-50, 39-50, 40-50, 41-50, 42-50, 43-50, 44-50, 45-50, 46-50, 47-50, 48-50, or 49-50. In some embodiments, $R^{11}$ is linked to the Lys residue with a linker-to-a therapeutic agent ratio of 1-3, 2-4, 3-5, 4-6, 5-7, 6-8, 7-9, 8-10, 9-11, 10-12, 11-13, 12-14, 13-15, 14-16, 15-17, 16-18, 17-19, 18-20, 19-21, 20-22, 21-23, 22-24, 23-25, 24-26, 25-27, 26-28, 27-29, 28-30, 29-31, 30-32, 31-33, 32-34, 33-35, 34-36, 35-37, 36-38, 37-39, 38-40, 39-41, 40-42, 41-43, 42-44, 43-45, 44-46, 45-47, 46-48, 47-49, or 48-50.

In some embodiments, $R^{11}$ is linked to the Cys residue with a linker-to-a therapeutic agent ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, $R^{11}$ is linked to the Cys residue with a linker-to-a therapeutic agent ratio of 1-50, 1-49, 1-48, 1-47, 1-46, 1-45, 1-44, 1-43, 1-42, 1-41, 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, $R^{11}$ is linked to the Cys residue with a linker-to-a therapeutic agent ratio of 2-50, 3-50, 4-50, 5-50, 6-50, 7-50, 8-50, 9-50, 10-50, 11-50, 12-50, 13-50, 14-50, 15-50, 16-50, 17-50, 18-50, 19-50, 20-50, 21-50, 22-50, 23-50, 24-50, 25-50, 26-50, 27-50, 28-50, 29-50, 30-50, 31-50, 32-50, 33-50, 34-50, 35-50, 36-50, 37-50, 38-50, 39-50, 40-50, 41-50, 42-50, 43-50, 44-50, 45-50, 46-50, 47-50, 48-50, or 49-50. In some embodiments, $R^{11}$ is linked to the Cys residue with a linker-to-a therapeutic agent ratio of 1-7, 2-8, 3-9, 4-10, 5-11, 6-12, 7-13, 8-14, 9-15, 10-16, 11-17, 12-18, 13-19, 14-20, 15-21, 16-22, 17-23, 18-24, 19-25, 20-26, 21-27, 22-28, 23-29, 24-30, 25-31, 26-32, 27-33, 28-34, 29-35, 30-36, 31-37, 32-38, 33-39, 34-40, 35-41, 36-42, 37-43, 38-44, 39-45, 40-46, 41-47, 42-48, 43-49, or 44-50.

In some embodiments, $R^{11}$ is linked to a therapeutic agent with a linker-to-a therapeutic agent ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In some embodiments, the compound comprises a therapeutic agent comprising a dual conjugation. In some embodiments, the dual conjugation comprises a linker-to-a therapeutic agent ratio of 1-2.

In some embodiments, the dual conjugation comprises a linker-to-a therapeutic agent ratio of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, the dual conjugation comprises a linker-to-a therapeutic agent ratio of 1-50, 1-49, 1-48, 1-47, 1-46, 1-45, 1-44, 1-43, 1-42, 1-41, 1-40, 1-39, 1-38, 1-37, 1-36, 1-35, 1-34, 1-33, 1-32, 1-31, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2. In some embodiments, the dual conjugation comprises a linker-to-a therapeutic agent ratio of 2-50, 3-50, 4-50, 5-50, 6-50, 7-50, 8-50, 9-50, 10-50, 11-50, 12-50, 13-50, 14-50, 15-50, 16-50, 17-50, 18-50, 19-50, 20-50, 21-50, 22-50, 23-50, 24-50, 25-50, 26-50, 27-50, 28-50, 29-50, 30-50, 31-50, 32-50, 33-50, 34-50, 35-50, 36-50, 37-50, 38-50, 39-50, 40-50, 41-50, 42-50, 43-50, 44-50, 45-50, 46-50, 47-50, 48-50, or 49-50. In some embodiments, the dual conjugation comprises a linker-to-a therapeutic agent ratio of 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, or 49-50.

In some embodiments, the concentration of the compound as described herein is at least 0.1% weight per volume.

In some embodiments, the concentration of the compound as described herein is at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or 99% weight per volume.

In some embodiments, the concentration of the compound as described herein is at least 0.05M. In some embodiments, the concentration of the compound as described herein is at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or 100 M.

In some embodiments, to enhance the hydrophobicity of a therapeutic agent, a therapeutic agent is linked to one or more fatty acids or carboxylic acid-containing molecules. In some embodiments, one or more fatty acids or carboxylic acid-containing molecules are linked to a therapeutic agent via a dual conjugation (or dual covalent conjugation). In some embodiments, one or more fatty acids or carboxylic acid-containing molecules comprise cinnamic acid. In some embodiments, one or more fatty acids or carboxylic acid-containing molecules are cinnamic acid.

In some embodiments, one or more fatty acids or carboxylic acid-containing molecules are non-covalently associated with a free amine of a therapeutic agent. In some embodiments, one or more fatty acids or carboxylic acid-containing molecules are non-covalently associated with the N-terminal amine in the peptide backbone of a therapeutic agent. In some embodiments, one or more fatty acids or carboxylic acid-containing molecules are non-covalently associated with the amine group of a Gln residue, the amine group of an Asn residue, the amine group of an Arg residue, the amine group of a Lys residue, the amine group of a His residue, or a combination thereof of a therapeutic agent.

In some embodiments, one or more fatty acids or carboxylic acid-containing molecules are covalently conjugated to a free amine of a therapeutic agent. In some embodiments, one or more fatty acids or carboxylic acid-containing molecules are covalently conjugated to the N-terminal amine in the peptide backbone of a therapeutic agent. In some embodiments, one or more fatty acids or carboxylic acid-containing molecules are covalently conjugated to the amine group of a Gln residue, the amine group of an Asn residue, the amine group of an Arg residue, the amine group of a Lys residue, the amine group of a His residue, or a combination thereof of a therapeutic agent.

EXAMPLES

Figure 5:
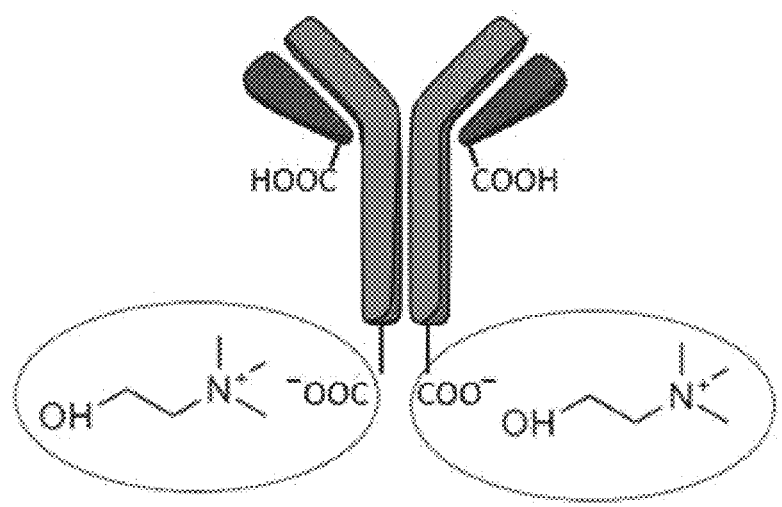
FIG. 5 depicts an exemplary embodiment of an antibody or an antibody fragment thereof comprising a choline-peptide derivative that is formed on the C-terminal carboxylic acid of the heavy chain.

Example 1: Choline-an Exemplary Chimeric Monoclonal Anti-TNF-α Antibody or an Antibody Fragment Thereof A non-covalent choline derivative of an exemplary chimeric monoclonal anti-TNF-α antibody or an antibody fragment thereof (e.g., FIG. 5) was prepared at ratios form 1:1 (choline: an exemplary chimeric monoclonal anti-TNF-α antibody or an antibody fragment thereof) to 164:1 (choline: an exemplary chimeric monoclonal anti-TNF-α antibody or an antibody fragment thereof). To prepare choline-an exemplary chimeric monoclonal anti-TNF-α antibody or an antibody fragment thereof, 164, 132, 82, 66, 41, 33, or 1 equivalents of choline bicarbonate (80 wt % solution) were added to 10 mg an exemplary chimeric monoclonal anti-TNF-α antibody or an antibody fragment thereof in 100 uL of phosphate buffered saline in a 5 mL Protein LoBind® Eppendorf Tube. Water was removed by lyophilization. The physical appearance of choline derivative of an exemplary chimeric monoclonal anti-TNF-α antibody or an antibody fragment thereof is a solid white crystal.

In some embodiments, the residues of an exemplary chimeric monoclonal anti-TNF-α antibody or an antibody fragment thereof able to react include: 44 E (Glutamic acid), 34 D (Aspartic acid) residues, 4 C-terminus regions (1 on each heavy and light chain), totaling 82 residues according to the sequences of SEQ ID NO: 24 and SEQ ID NO: 2. In some embodiments, the residues of the heavy chain of an exemplary chimeric monoclonal anti-TNF-α antibody or an antibody fragment thereof able to react include 10 E residues and 8 D on one heavy chain according to the sequence of SEQ ID NO: 24. In some embodiments, the residues of the light chain of an exemplary chimeric monoclonal anti-TNF-α antibody or an antibody fragment thereof able to react include 12 E and 9 D residues on each light chain according to the sequence of SEQ ID NO: 2. In some embodiments, the residues of an exemplary chimeric monoclonal anti-TNF-α antibody or an antibody fragment thereof able to react include 44 E residues and 34 D residues. In some embodiments, 4 C-terminus regions are ionizable. In some embodiments, an exemplary chimeric monoclonal anti-TNF-α antibody or an antibody fragment thereof totally comprises 82 ionizable residues.

Figure 6A:
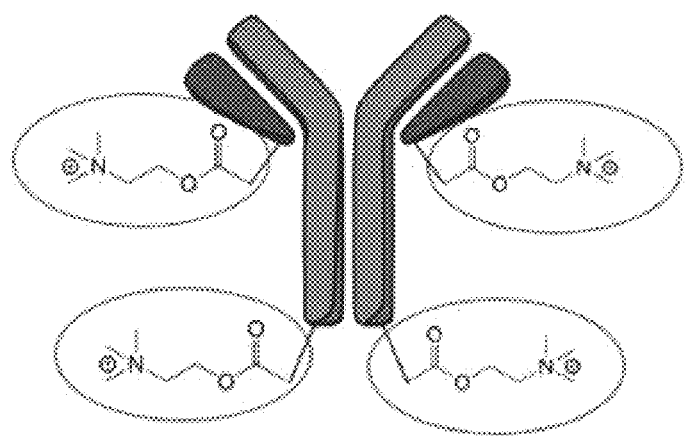
FIG. 6A depicts an exemplary embodiment of an antibody or an antibody fragment thereof comprising a choline-peptide ester that is formed on the C-terminal carboxylic acid of the heavy chain.
Figure 6B:
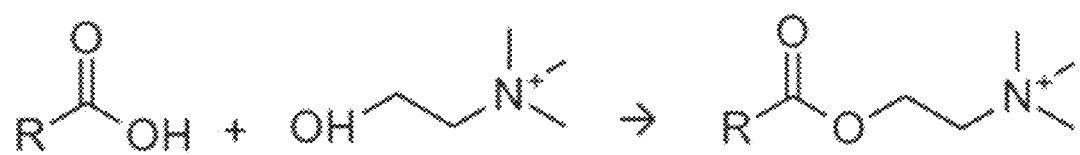
FIG. 6B depicts an exemplary chemical reaction to prepare a covalent choline derivative of an antibody or an antibody fragment thereof (e.g., choline-antibody covalent ester conjugation).
Figure 7:
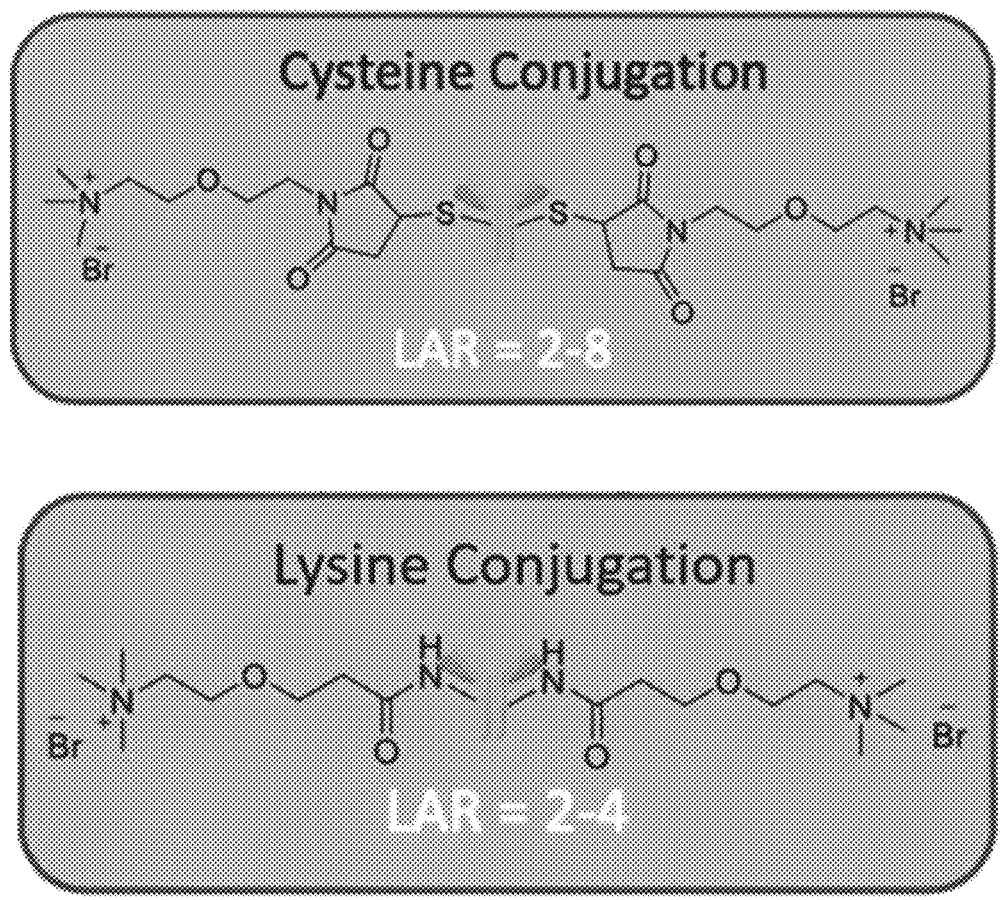
FIG. 7 depicts an exemplary embodiment of an antibody or an antibody fragment thereof comprising a choline-peptide ester that is formed on a Cys residue or a Lys residue of the heavy chain of the antibody or an antibody fragment thereof. In some embodiments, the Linker to Antibody Ratio (LAR) for Cysteine conjugation is 2-8. In some embodiments, the Linker to Antibody Ratio (LAR) is 2-4 for Lysine conjugation.

A covalent choline derivative of an exemplary chimeric monoclonal anti-TNF-α antibody or an antibody fragment thereof (e.g., FIG. 6A) is prepared by an exemplary chemical reaction, as shown by FIG. 6B, to link choline to an exemplary chimeric monoclonal anti-TNF-α antibody or an antibody fragment thereof. In some embodiments, one or more choline is further linked to lysine residues, cystine residues or a combination thereof of an exemplary chimeric monoclonal anti-TNF-α antibody or an antibody fragment thereof (e.g., FIG. 7)

Figure 8A:
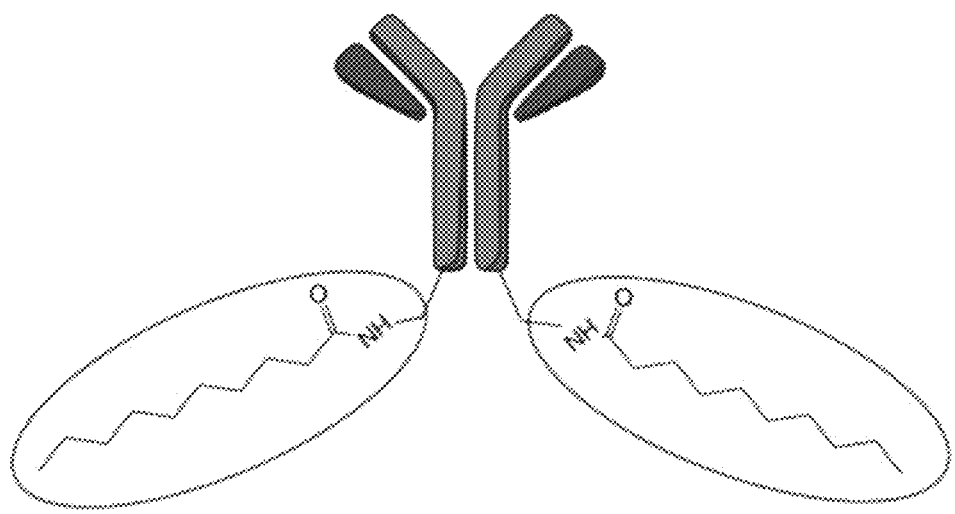
FIG. 8A depicts an exemplary embodiment of an antibody or an antibody fragment thereof linked to fatty acids on the C-terminal carboxylic acid of the heavy chain. Fatty acid may include other lengths between C5 (hexanoic acid) to C10 (decanoic acid).
Figure 8B:
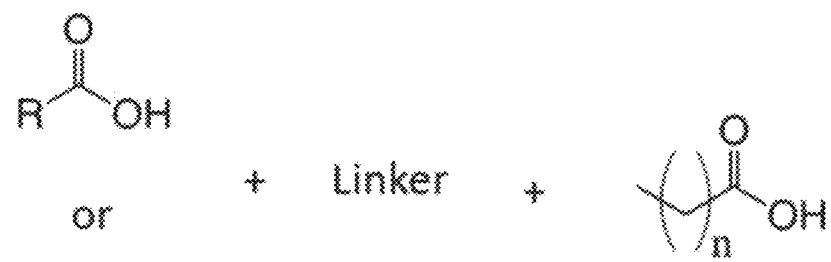
FIG. 8B depicts an exemplary chemical reaction to prepare an antibody or an antibody fragment thereof linked to fatty acids.
Figure 8C:
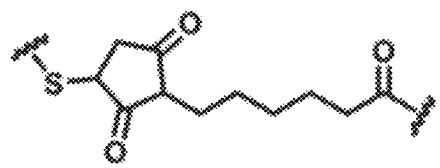
FIG. 8C depicts exemplary linkers that may be used to link an antibody or an antibody fragment thereof linked to fatty acids.
Figure 8C:
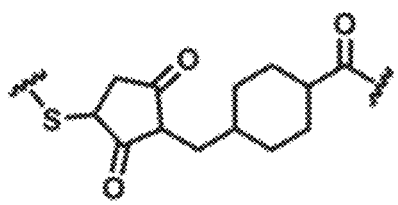
Figure 8C:
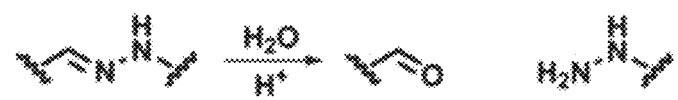
Figure 8C:
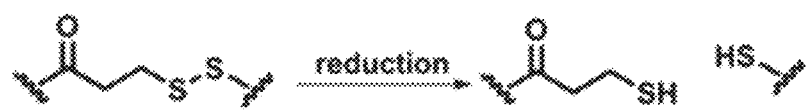
Figure 8D:
FIG. 8D depicts an exemplary fatty acid that may be linked to an antibody or an antibody fragment thereof.
Figure 9A:
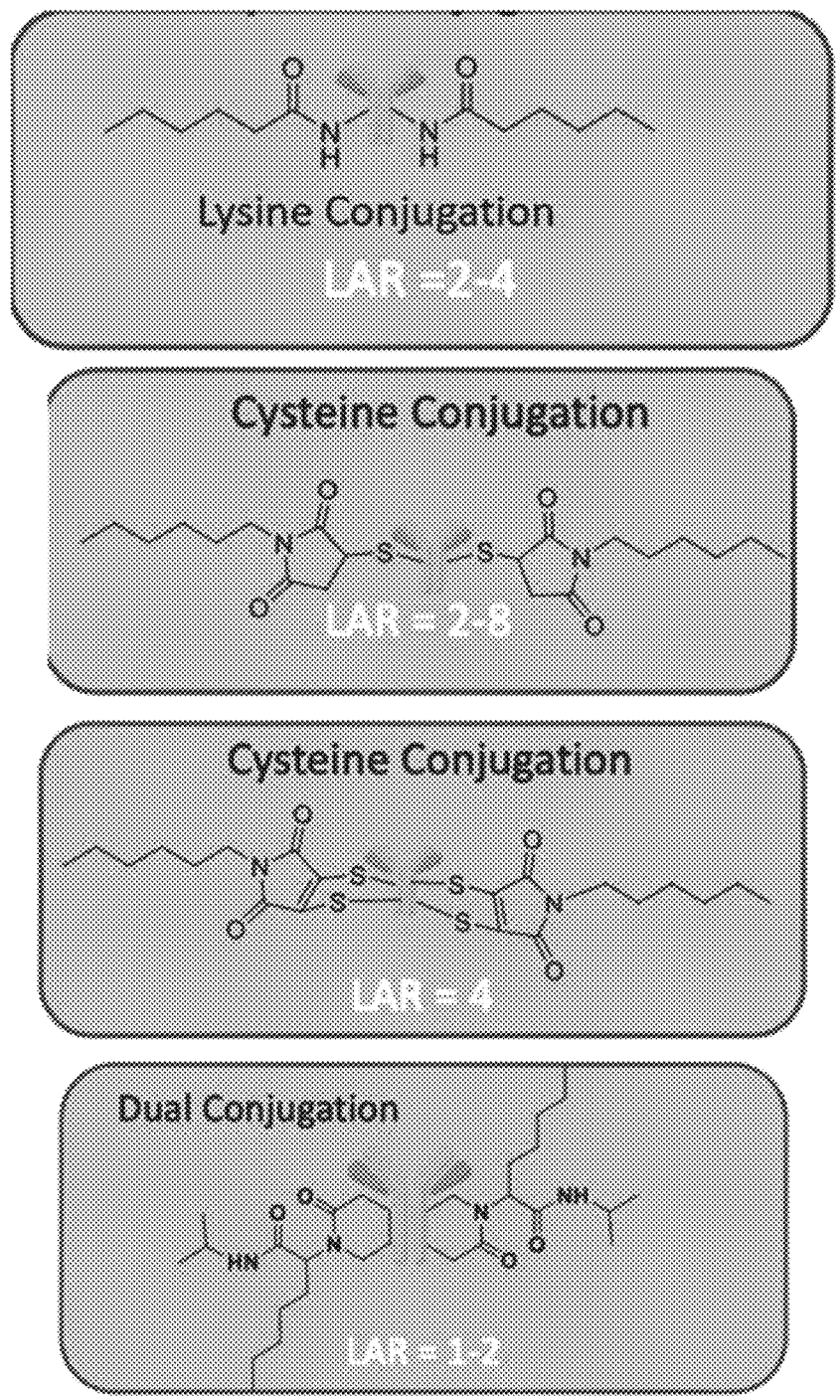
FIG. 9A depicts an exemplary embodiment of an antibody or an antibody fragment thereof linked to fatty acids on a Lys residue or a Cys residue or of the heavy chain of the antibody or an antibody fragment thereof, or an antibody or an antibody fragment thereof linked to fatty acids via a dual conjugation. In some embodiments, the Linker to Antibody Ratio (LAR) is 2-4 for Lysine conjugation is 2-4. In some embodiments, the Linker to Antibody Ratio (LAR) for Cysteine conjugation is 2-8. In some embodiments, the Linker to Antibody Ratio (LAR) for Cysteine conjugation is 4. In some embodiments, the Linker to Antibody Ratio (LAR) for an antibody or an antibody fragment thereof linked to fatty acids via a dual conjugation is 1-2.
Figure 9B:
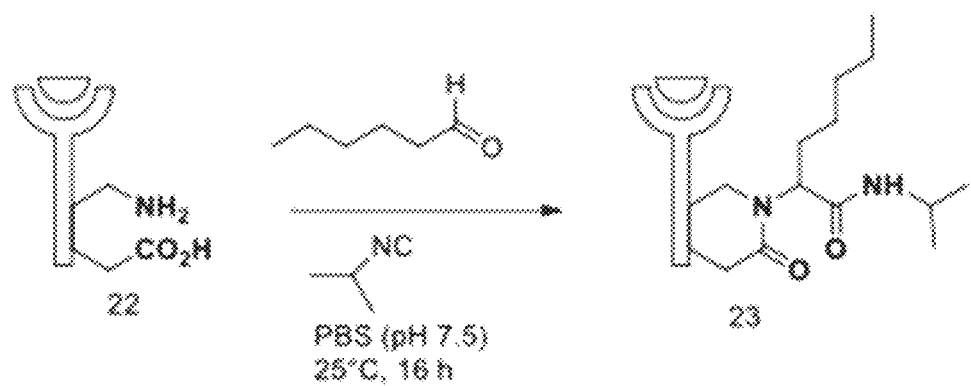
FIG. 9B depicts an exemplary chemical reaction to prepare an antibody or an antibody fragment thereof linked to fatty acids via a dual conjugation.
Figure 10:
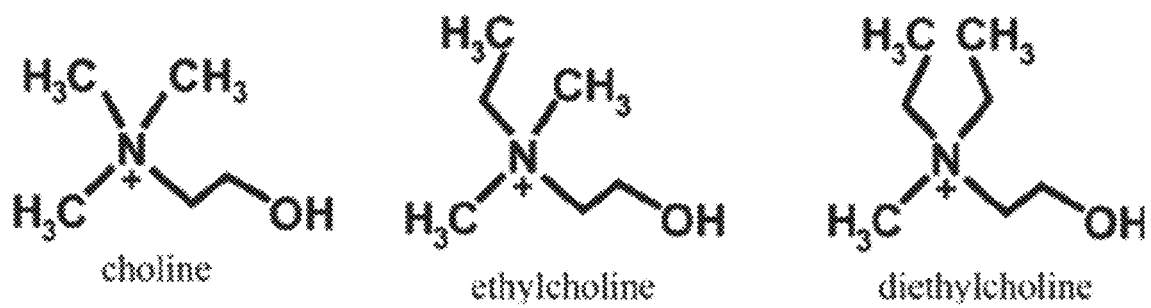
FIG. 10 depicts exemplary choline and choline derivatives.
Figure 11A:
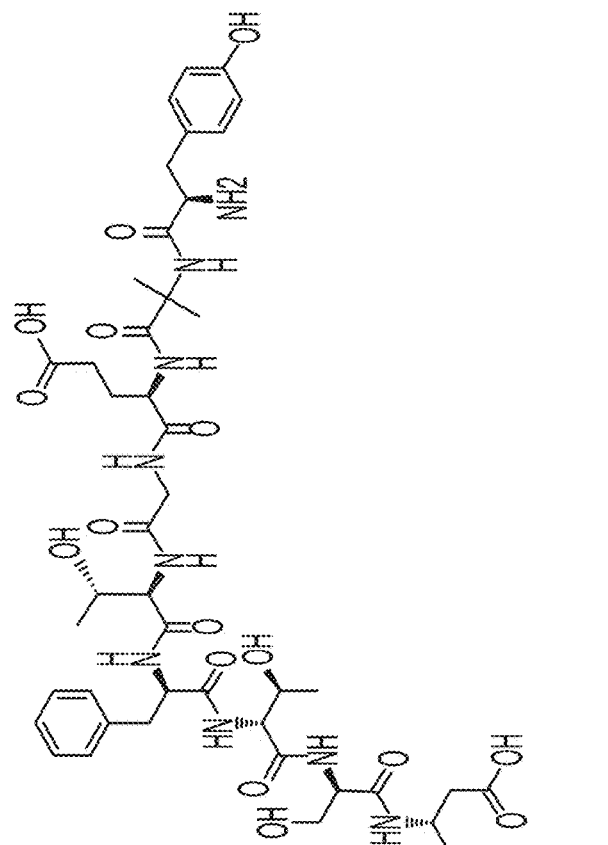
FIGS. 11A, 11B, and 11C depict the structure of an exemplary dual GIP/GLP-1 receptor agonist.
Figure 11A:
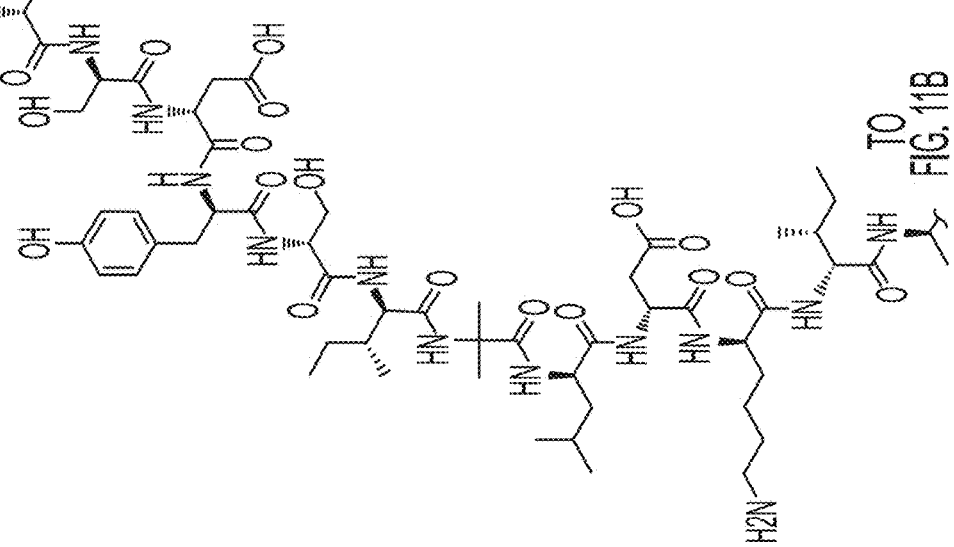
Figure 11B:
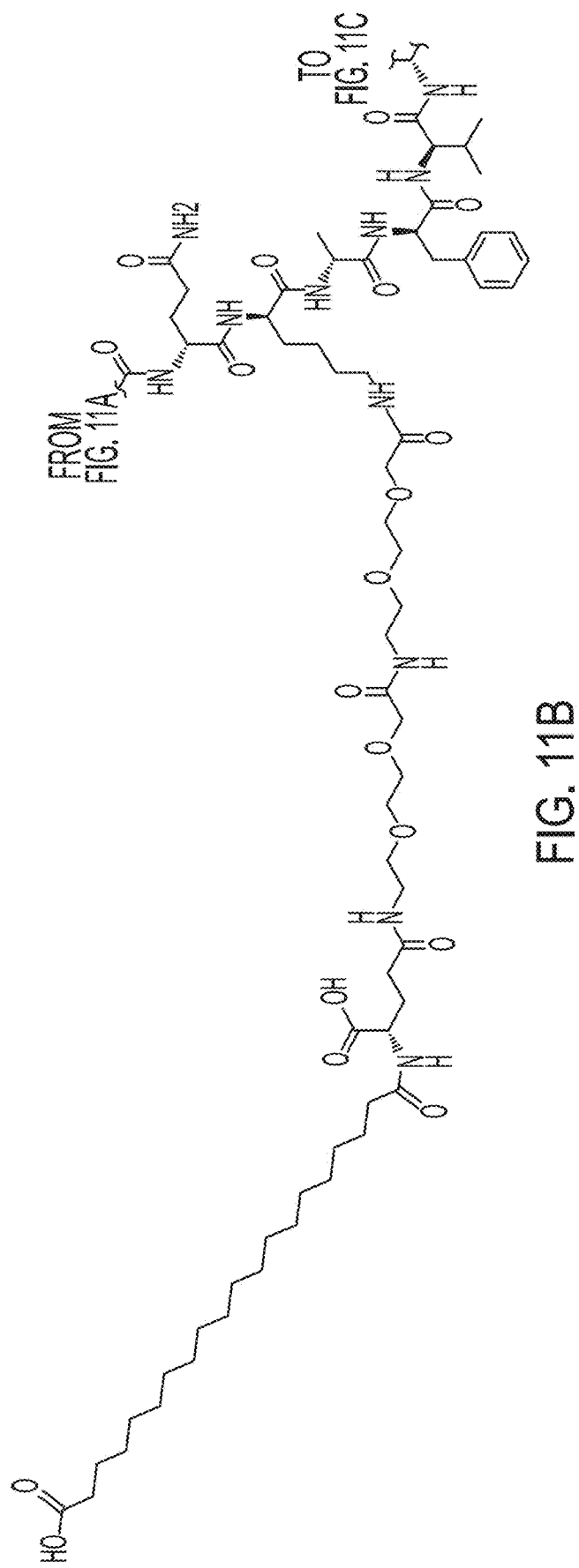
Figure 11C:
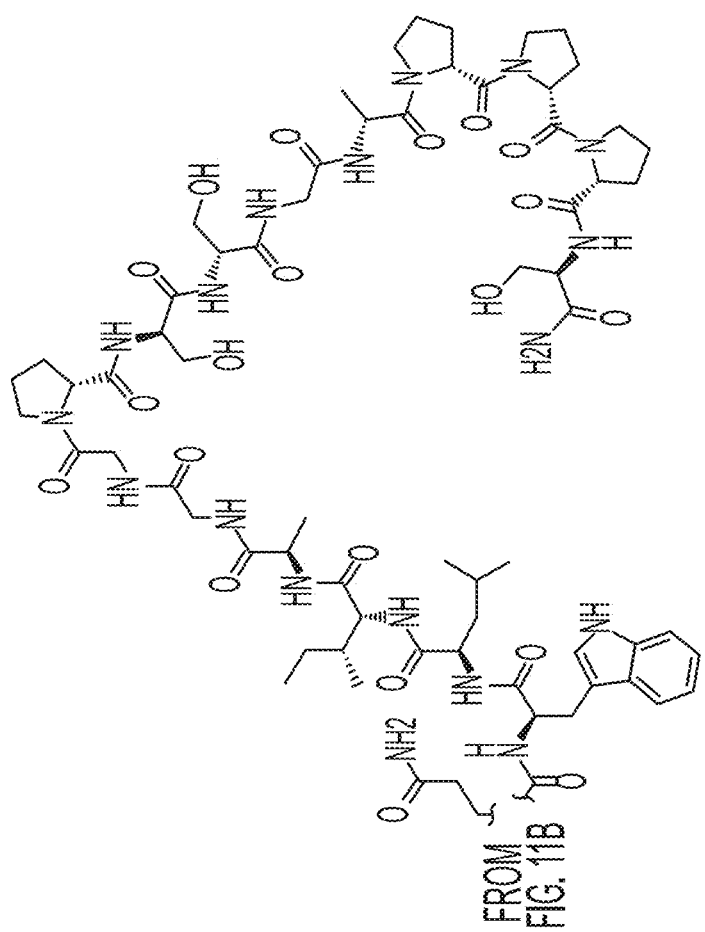
Figure 12:
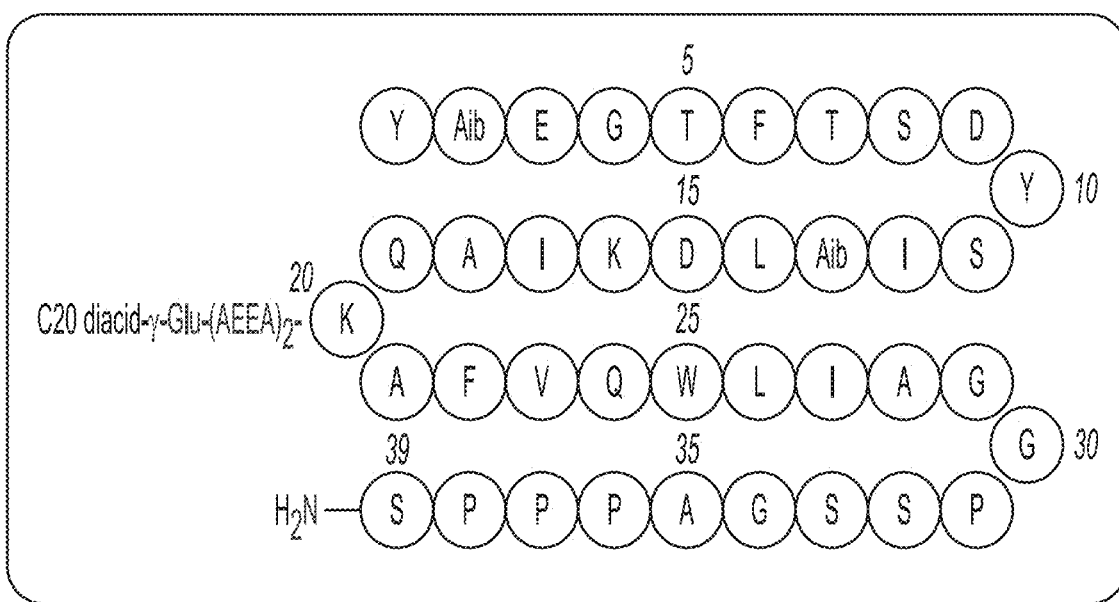
FIG. 12 depicts the structure schematic of an exemplary dual GIP/GLP-1 receptor agonist.

Example 2: An Exemplary Chimeric Monoclonal Anti-TNF-α Antibody or an Antibody Fragment Thereof Lipidation To enhance the hydrophobicity of an exemplary chimeric monoclonal anti-TNF-α antibody or an antibody fragment thereof, an exemplary chimeric monoclonal anti-TNF-α antibody or an antibody fragment thereof linked to fatty acids (e.g., FIG. 8A) is prepared by an exemplary chemical reaction as shown by FIG. 8B. In some embodiments, fatty acids or carboxylic acid-containing molecules are linked to an exemplary chimeric monoclonal anti-TNF-α antibody or an antibody fragment thereof via a dual conjugation (or dual covalent conjugation) (e.g., FIG. 9A) according to the reaction procedure (e.g., FIG. 9B) of which reaction conditions are generally described in, for example, Chaubet et al., Investigating Ugi/Passerini Multicomponent Reactions for the Site-Selective Conjugation of Native Trastuzumab, Chem. Eur. J. 2020, 26, 13797-13805.

Example 3: Choline-Other Antibodies

Using the similar procedure described in Example 1 and 2, choline derivatives forms of other antibodies and antibodies linked to fatty acids or carboxylic acid-containing molecules are prepared. In some embodiments, the exemplary antibodies include, but are not limited to, a monoclonal anti-TNF-α antibody or an antibody fragment thereof, an anti-human IL-12 and IL-23 subunit antibody or an antibody fragment thereof, a human monoclonal anti-TNF-α antibody, an anti-integrin α4β1 antibody, an anti-integrin α4β7 antibody, and a fragment of an anti-TNF-α antibody. In some embodiments, The exemplary antibodies include, but are not limited to, adalimumab, ustekinumab, golimumab, natalizumab, vedolizumab, and certolizumab pegol.

Example 4: Choline-an Exemplary GLP-1 Analog or Functional Variant Thereof or Mimetic Thereof A non-covalent derivative of choline was prepared at ratios from 1:1 (choline:an exemplary GLP-1 analog or functional variant thereof or mimetic thereof) to 28:1 (choline:an exemplary GLP-1 analog or functional variant thereof or mimetic thereof). It is clear to the one skilled in the art that similar procedure can be used to prepare choline derivatives forms of Peptide YY, Amylin, Glucagon, GIP, liraglutide, exenatide. To prepare choline-an exemplary GLP-1 analog or functional variant thereof or mimetic thereof, 28, 7, or 1 equivalents of choline bicarbonate (80 wt % solution) were added to 50 mg of an exemplary GLP-1 analog or functional variant thereof or mimetic thereof in 200 uL of purified water in a 250-mL round bottom flask. Water was removed by rotary evaporation at 40° C. for 1 hour at 15 mbar. The physical appearance of choline derivative of an exemplary GLP-1 analog or functional variant thereof or mimetic thereof is a solid white crystal.

Example 5: Covalent Choline-an Exemplary GLP-1 Analog or Functional Variant Thereof or Mimetic Thereof A covalent choline derivative of an exemplary GLP-1 analog or functional variant thereof or mimetic thereof (e.g., FIG. 17B) is prepared at ratios form 1:1 (choline:an exemplary GLP-1 analog or functional variant thereof or mimetic thereof) to 28:1 (choline:an exemplary GLP-1 analog or functional variant thereof or mimetic thereof).

In some embodiments, there are 7 potential sites of esterification on an exemplary GLP-1 analog or functional variant thereof or mimetic thereof with a cation (e.g., FIG. 17B). In some embodiments, choline-an exemplary GLP-1 analog or functional variant thereof or mimetic thereof ester derivatives can be formed by conjugating a cation (e.g., choline) to at least 1 or up to 7 sites on the exemplary GLP-1 analog or functional variant thereof or mimetic thereof structure.

Figure 20A:
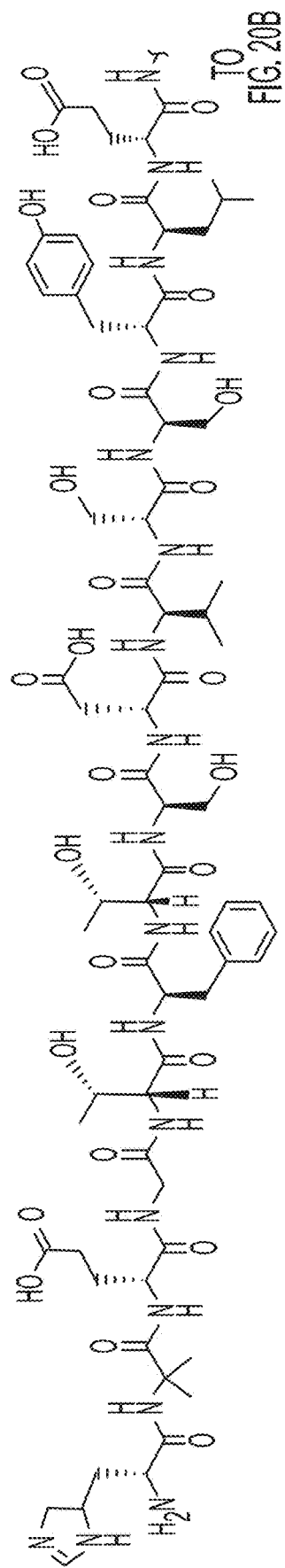
FIGS. 20A-20H depict exemplary chemical structural variations of choline-an exemplary GLP-1 analog or functional variant thereof or mimetic thereof.
Figure 20B:
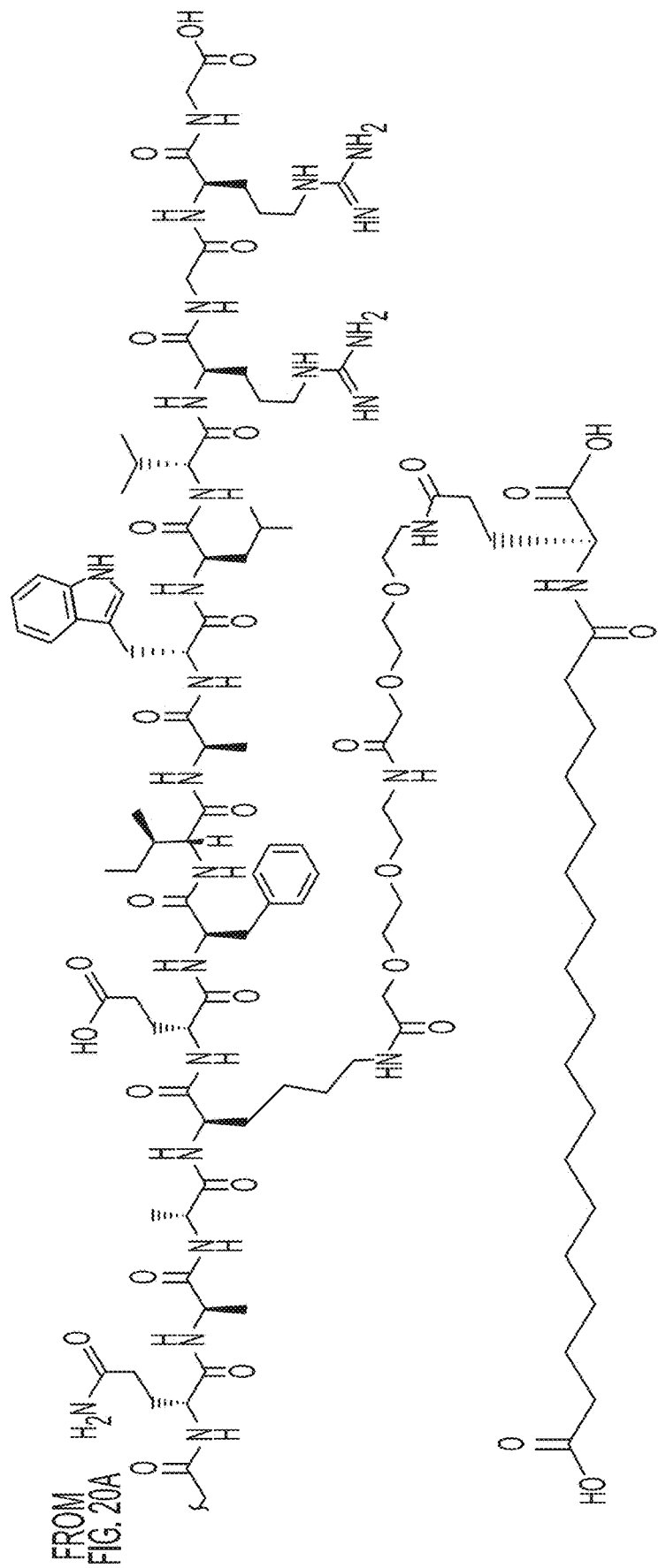
Figure 20C:
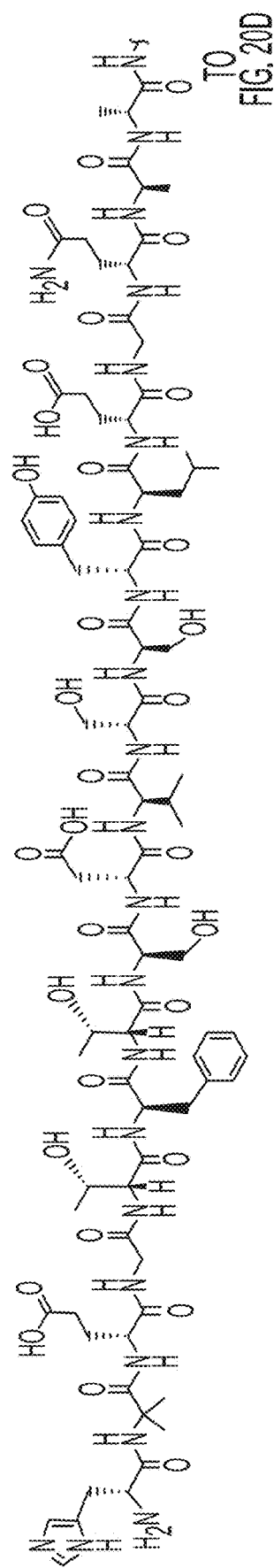
Figure 20D:
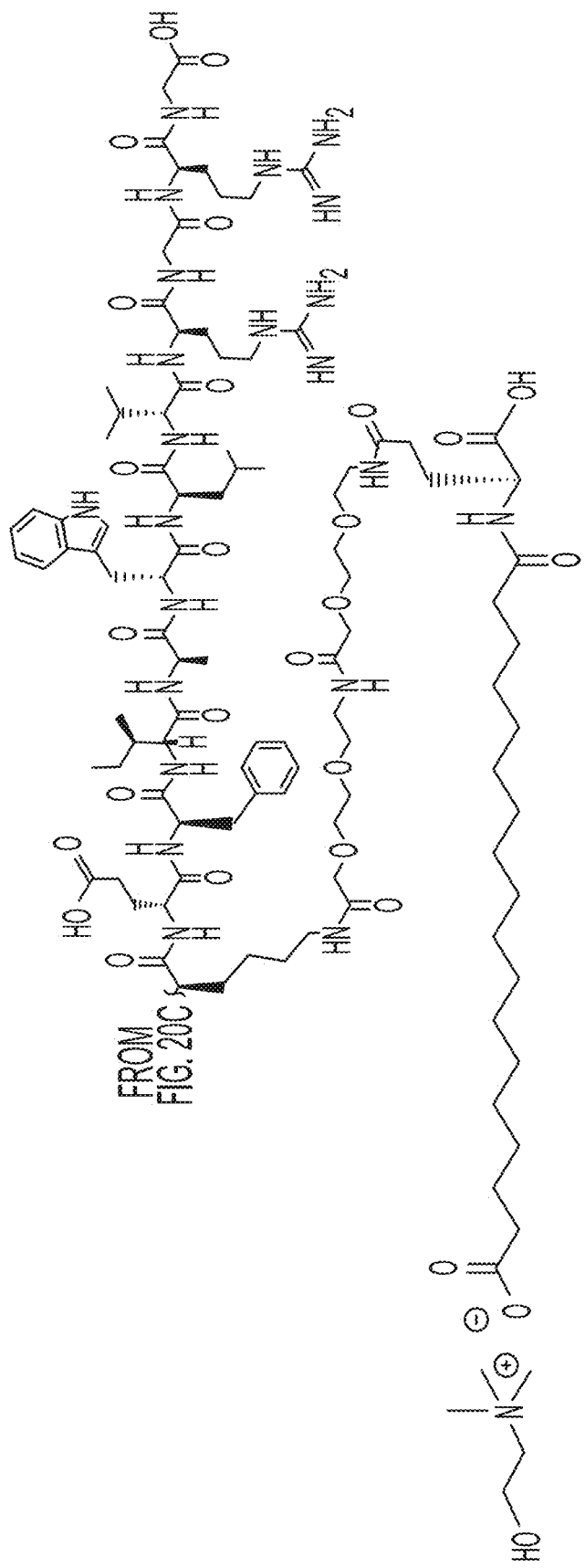
Figure 20E:
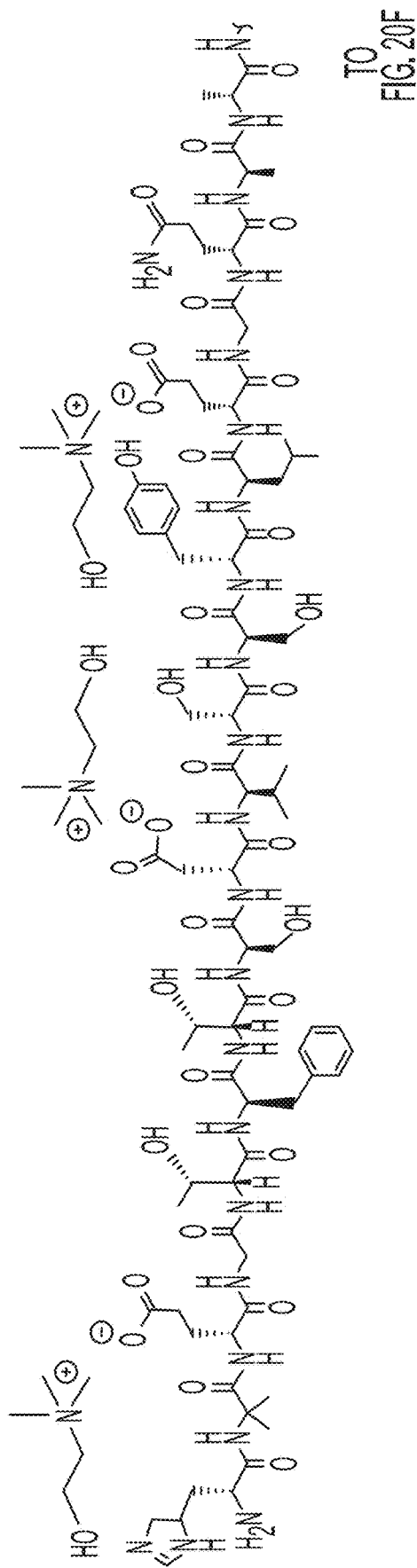
Figure 20F:
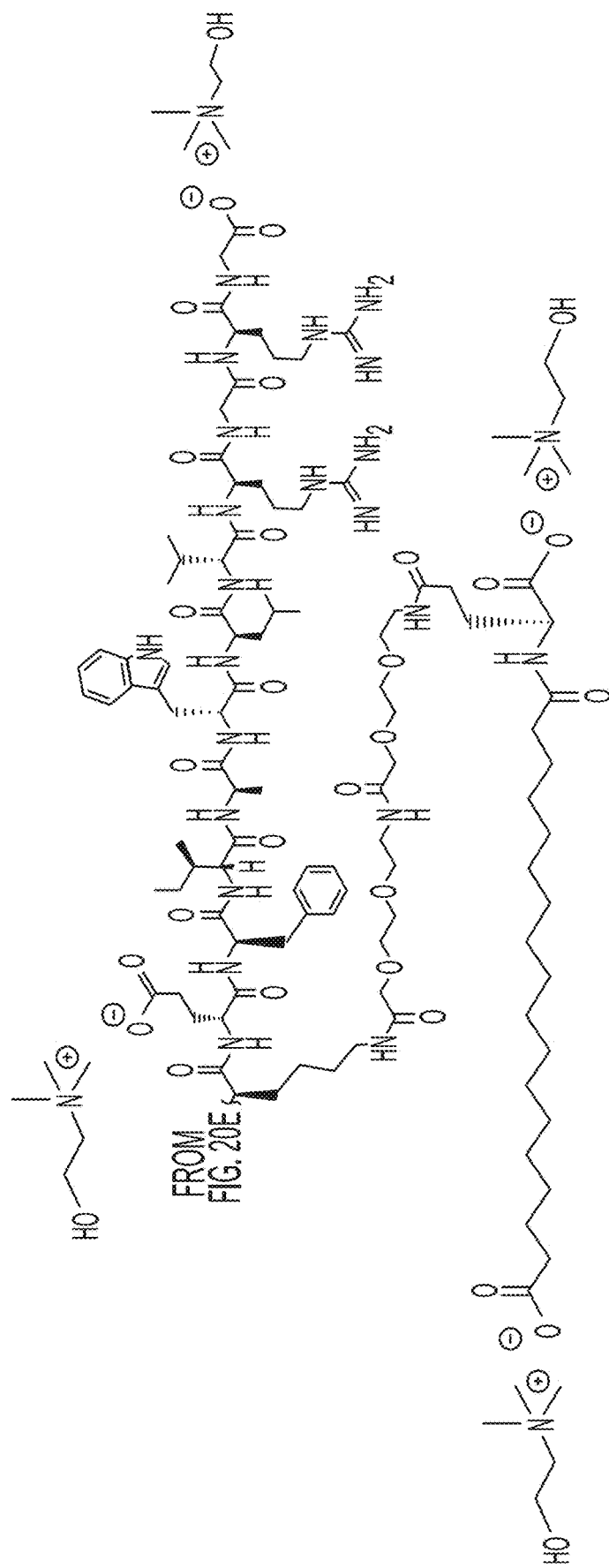
Figure 20G:
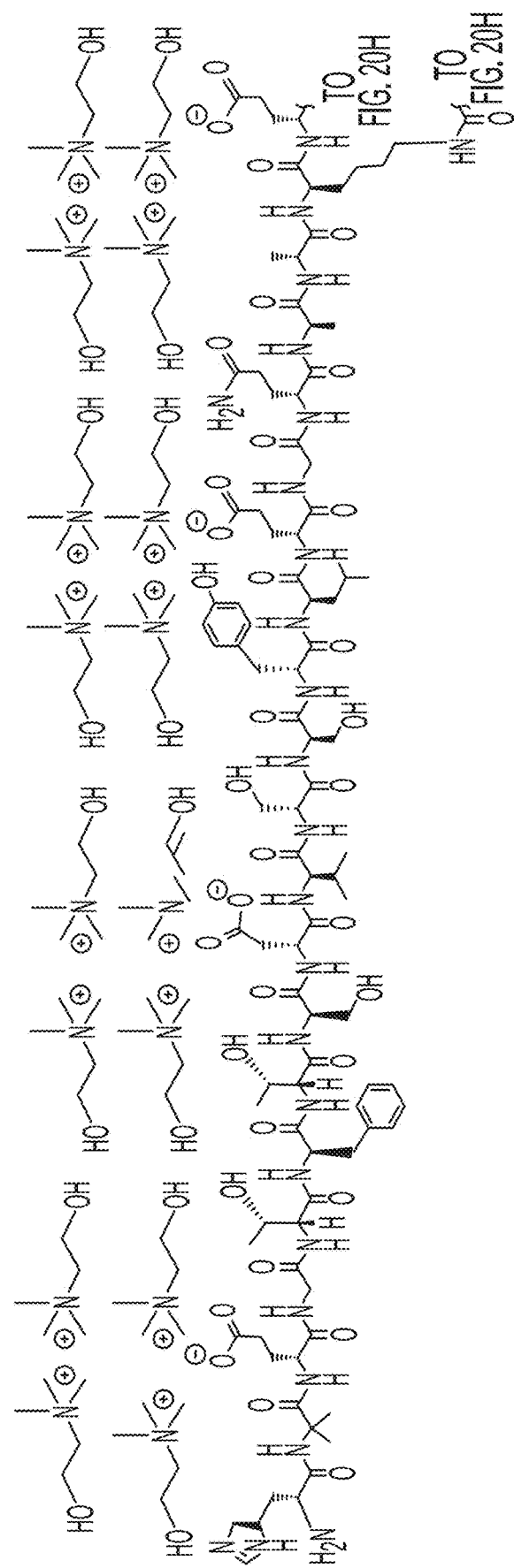
Figure 20H:
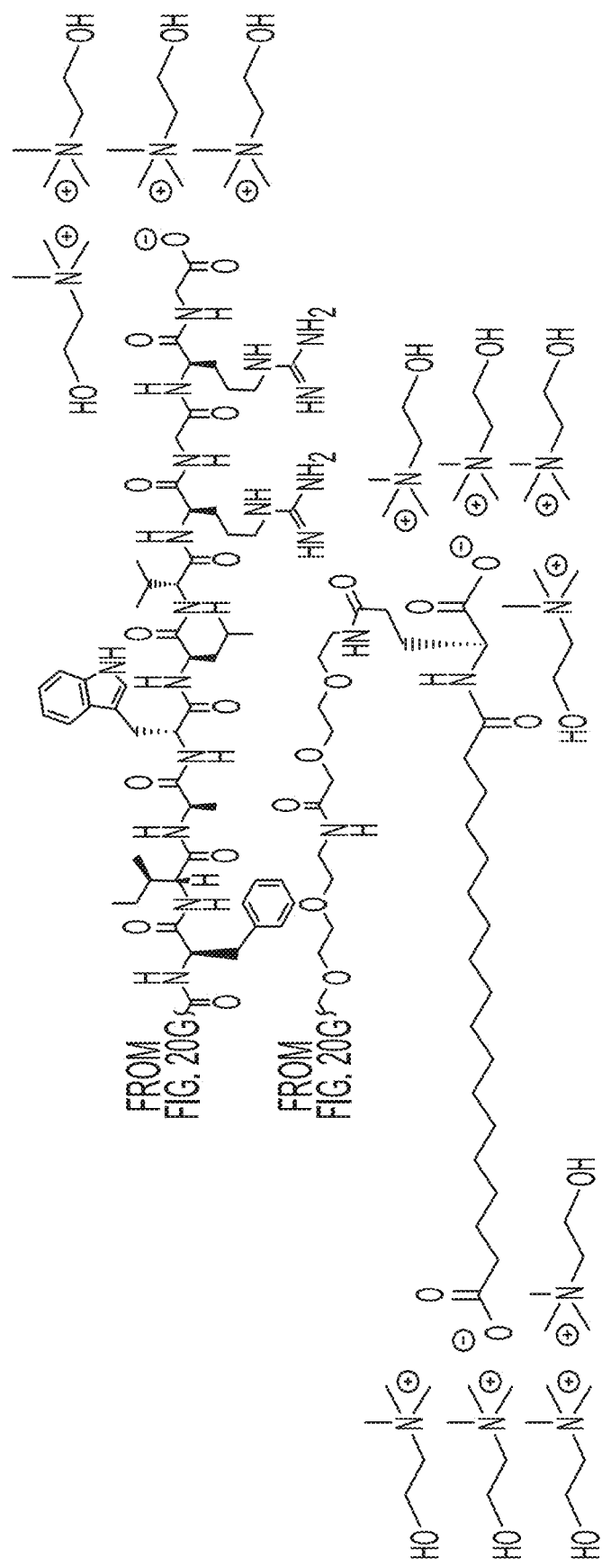

An exemplary chemical structure of an exemplary GLP-1 analog or functional variant thereof or mimetic thereof is shown in FIG. 20A and FIG. 20B, and exemplary structures of choline-an exemplary GLP-1 analog or functional variant thereof or mimetic thereof are shown in at the various ratios are shown in FIG. 20C and FIG. 20D (1:1 ratio), FIG. 20E and FIG. 20F (7:1 ratio), and FIG. 20G and FIG. 20H (28:1 ratio). In some embodiments, choline ionization could occur at any of the —COOH sites. In some embodiments, excess bicarbonate is also present in the 28:1 ratio.

Figure 22:
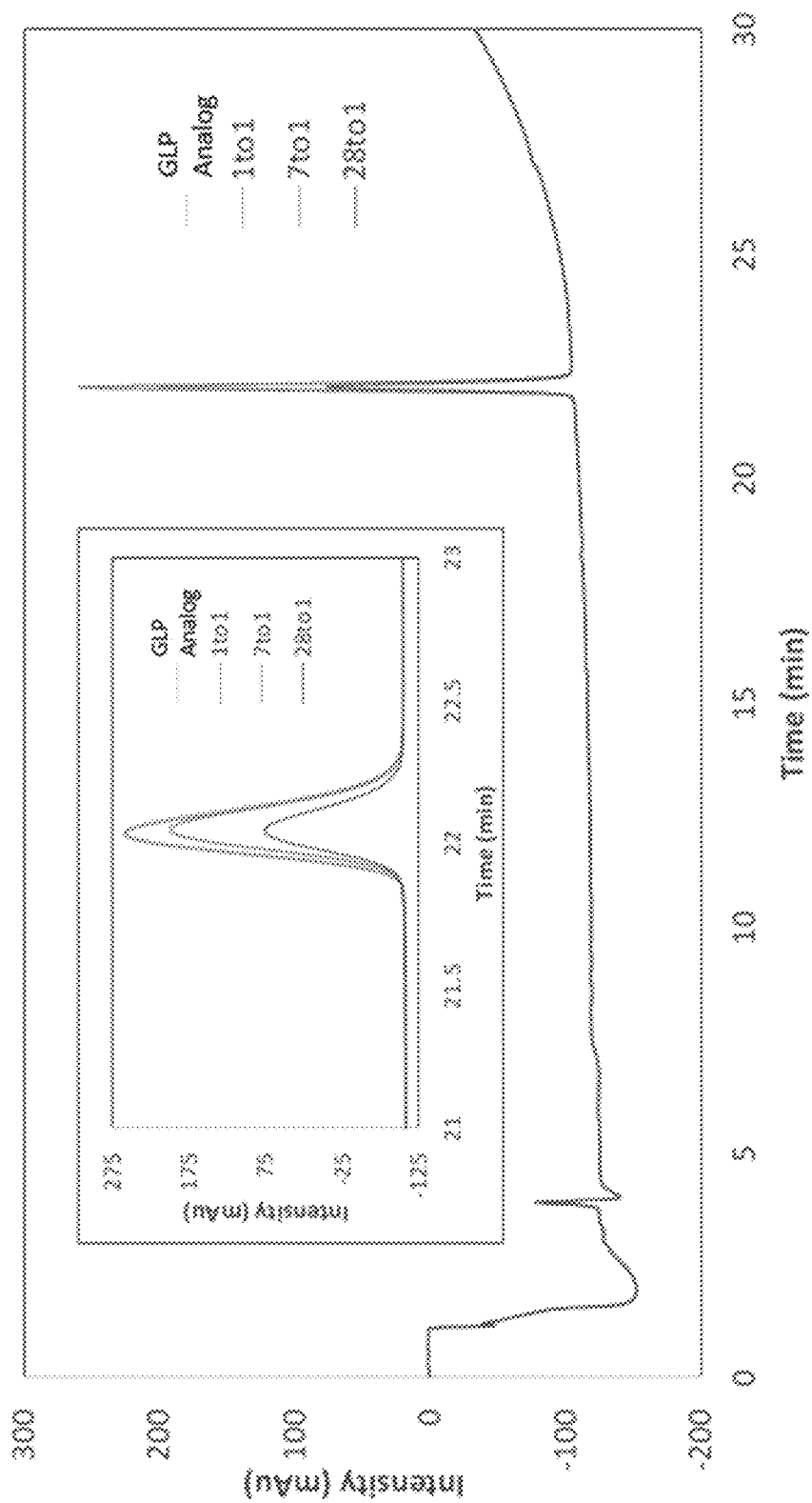
FIG. 22 shows exemplary analytical characterization of an exemplary GLP-1 analog or functional variant thereof or mimetic thereof ("GLP-1 analog") based on high-performance liquid chromatography (HPLC).

Example 6: Exemplary Analytical Characterization of Exemplary Embodiments of Choline-an Exemplary GLP-4 Analog or Functional Variant Thereof or Mimetic Thereof Based on HPLC Exemplary analytical characterization of exemplary embodiments of Choline-an exemplary GLP-1 analog or functional variant thereof or mimetic thereof based on high-performance liquid chromatography (HPLC) is shown in FIG. 22.

Retention Times was 22.039 min for an exemplary GLP-1 analog or functional variant thereof or mimetic thereof; 22.031 min for Choline-an exemplary GLP-1 analog or functional variant thereof or mimetic thereof at the ratio of 1:1; 22.047 min for Choline-an exemplary GLP-1 analog or functional variant thereof or mimetic thereof at the ratio of 7:1; and 22.043 min for Choline-an exemplary GLP-1 analog or functional variant thereof or mimetic thereof at the ratio of 28:1.

While the target concentration is 8.00 mg/mL, the concentration for Choline-an exemplary GLP-1 analog or functional variant thereof or mimetic thereof at the ratio of 1:1 was 7.848 mg/mL; the concentration for Choline-an exemplary GLP-1 analog or functional variant thereof or mimetic thereof at the ratio of 7:1 was 6.573 mg/mL; and the concentration for Choline-an exemplary GLP-1 analog or functional variant thereof or mimetic thereof at the ratio of 28:1 was 3.868 mg/mL.

The Calculated/Determined % Mass of an exemplary GLP-1 analog or functional variant thereof or mimetic thereof was 98%/98% for Choline-an exemplary GLP-1 analog or functional variant thereof or mimetic thereof at the ratio of 1:1; 85%/82% for Choline-an exemplary GLP-1 analog or functional variant thereof or mimetic thereof at the ratio of 7:1; and 50%/48% for Choline-an exemplary GLP-1 analog or functional variant thereof or mimetic thereof at the ratio of 28:1.

Conclusions

The same mass of choline-an exemplary GLP-1 analog or functional variant thereof or mimetic thereof was weighed out for each ion ratio.

Differences in peak area correspond to the % an exemplary GLP-1 analog or functional variant thereof or mimetic thereof present in each of the solid forms.

An exemplary GLP-1 analog or functional variant thereof or mimetic thereof peak is not shifted or altered when ionized with choline bicarbonate.

No new peaks appear, indicating the peptide remains intact during ionization reaction.

Figure 23A:
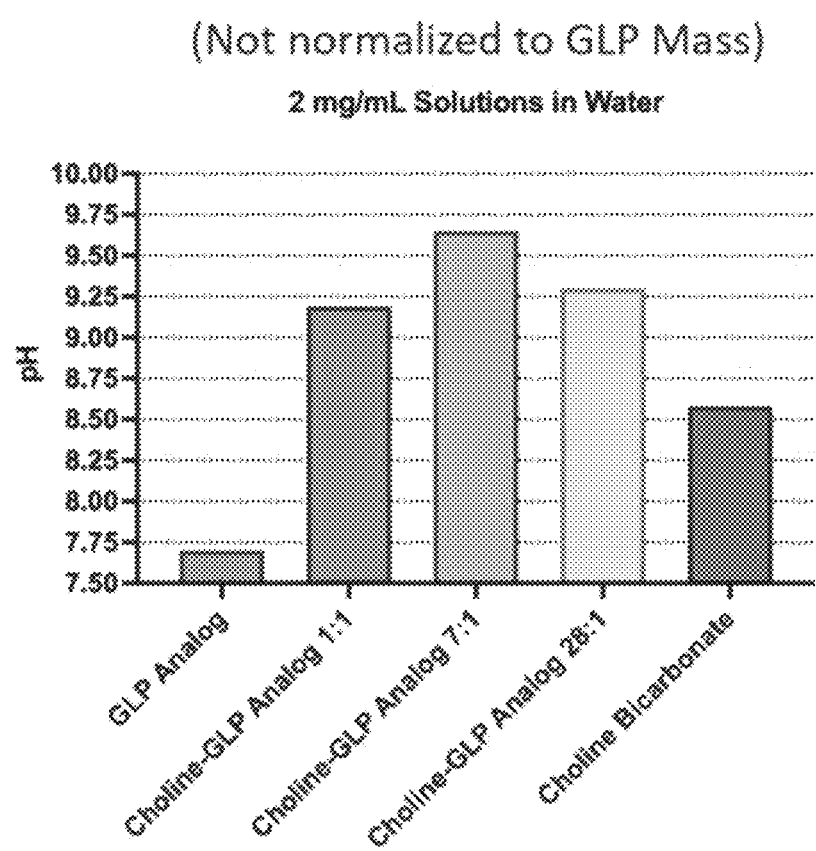
FIGS. 23A-23D show exemplary analytical characterization of an exemplary GLP-1 analog or functional variant thereof or mimetic thereof ("GLP-1 analog") based on pH.
Figure 23B:
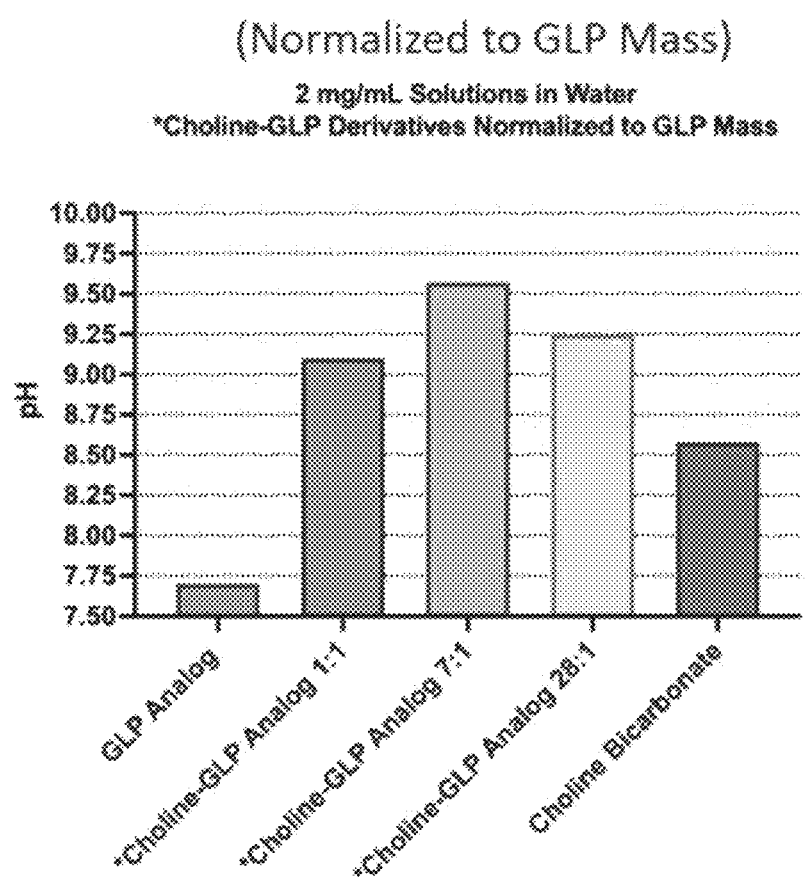

Example 7: Exemplary Analytical Characterization of Exemplary Embodiments of Choline-an Exemplary GLP-1 Analog or Functional Variant Thereof or Mimetic Thereof Based on pH Exemplary analytical characterization of exemplary embodiments of choline-an exemplary GLP-1 analog or functional variant thereof or mimetic thereof based on pH is shown in FIGS. 23A-23D. FIG. 23A depicts exemplary analytical characterization results of an exemplary GLP-1 analog or functional variant thereof or mimetic thereof ("GLP-1 analog") based on pH using 2 mg/mL solutions in water. The results are not normalized to an exemplary GLP-1 analog or functional variant thereof or mimetic thereof Mass. FIG. 23B depicts exemplary analytical characterization results of an exemplary GLP-1 analog or functional variant thereof or mimetic thereof ("GLP-1 analog") based on pH using 2 mg/mL solutions in water. The results of the choline-the exemplary GLP-1 analog or functional variant thereof or mimetic thereof are normalized to the exemplary GLP-1 analog or functional variant thereof or mimetic thereof Mass.

Reference Data—pKa of choline was approximately 14, and pKa of bicarbonate was approximately 6.

Conclusions

Very minor differences were observed when accounting for normalization of the exemplary GLP-1 analog or functional variant thereof or mimetic thereof mass present in each of the ion ratios.

Choline-the exemplary GLP-1 analog or functional variant thereof or mimetic thereof 7:1 has the most basic pH in water, compared with Choline-the exemplary GLP-1 analog or functional variant thereof or mimetic thereof 1:1 and Choline-the exemplary GLP-1 analog or functional variant thereof or mimetic thereof 28:1, which are slightly more acidic.

Choline-the exemplary GLP-1 analog or functional variant thereof or mimetic thereof 7:1 would have the least amount of bicarbonate present, as nearly 100% of bicarbonate would be consumed during the reaction, causing the solution to tend towards the choline pKa.

Because of the non-linear rising and falling in pH when more choline bicarbonate was added, this appears to indicate that the exemplary GLP-1 analog or functional variant thereof or mimetic thereof was ionized.

Figure 23C:
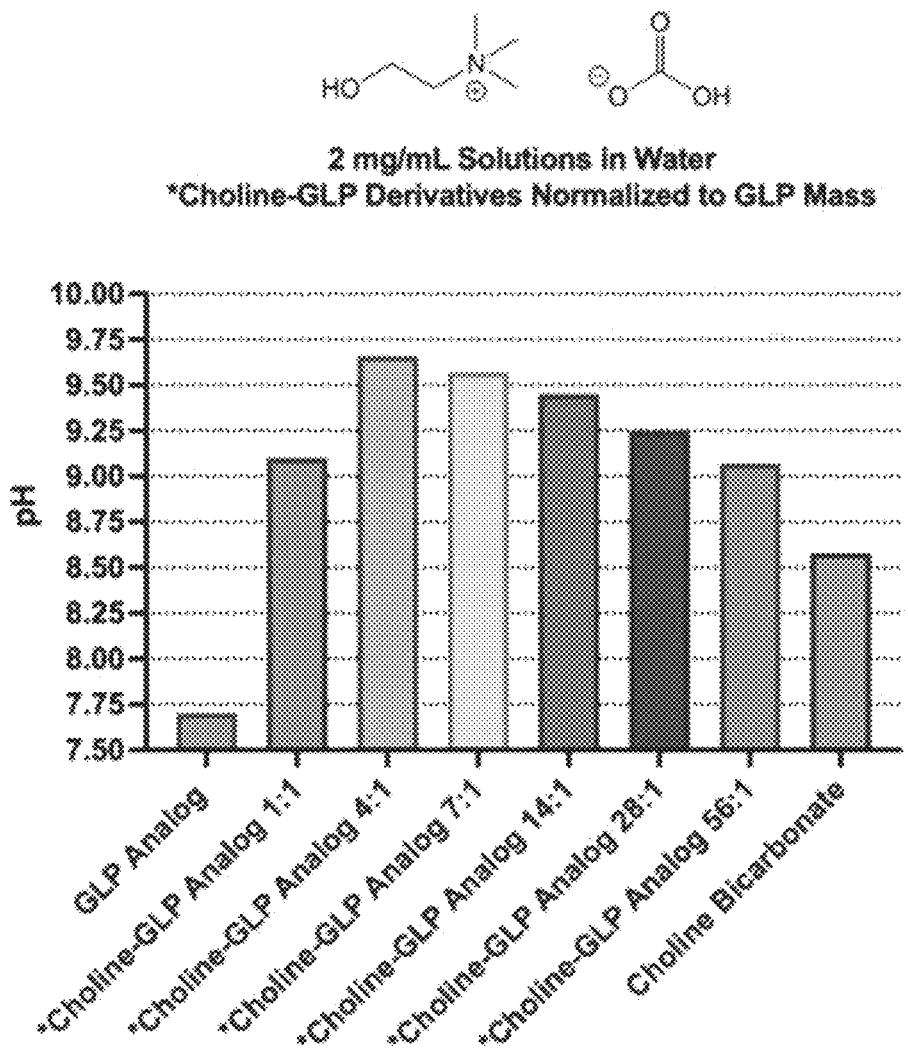
Figure 23D:
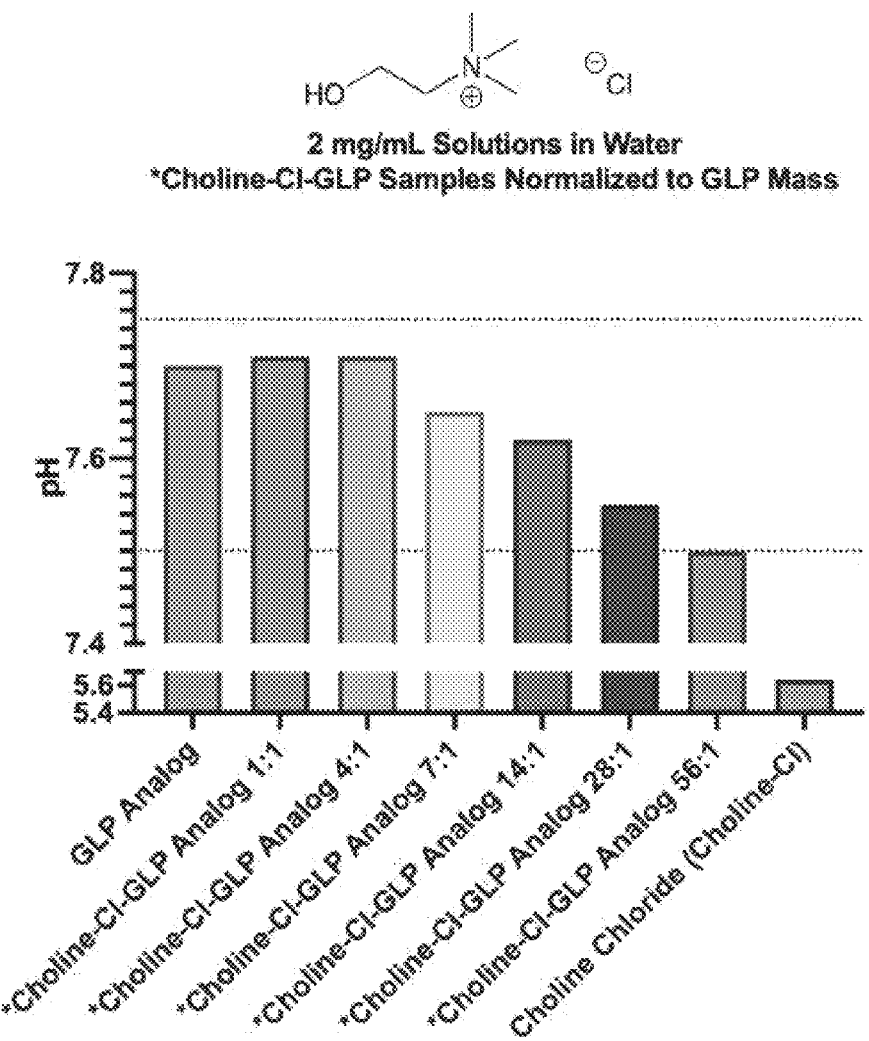

FIG. 23C depicts exemplary analytical characterization results of an exemplary GLP-1 analog or functional variant thereof or mimetic thereof ("GLP-1 analog") based on pH using 2 mg/mL solutions in water, wherein the exemplary reaction using choline bicarbonate as shown above the graph was used. The results of the choline-the exemplary GLP-1 analog or functional variant thereof or mimetic thereof are normalized to the exemplary GLP-1 analog or functional variant thereof or mimetic thereof Mass. FIG. 23D depicts exemplary analytical characterization results of the negative control of an exemplary GLP-1 analog or functional variant thereof or mimetic thereof ("GLP-1 analog") based on pH using 2 mg/mL solutions in water, wherein the exemplary reaction using choline chloride as shown above the graph was used. The results of the choline-Cl-the exemplary GLP-1 analog or functional variant thereof or mimetic thereof are normalized to the exemplary GLP-1 analog or functional variant thereof or mimetic thereof Mass.

Reference Data—pKa of choline was approximately 14, and pKa of bicarbonate was approximately 6.

Choline-the exemplary GLP-1 analog or functional variant thereof or mimetic thereof 4:1 has the most basic pH in water when formed using choline bicarbonate, whereas Choline-the exemplary GLP-1 analog or functional variant thereof or mimetic thereof 1:1, Choline-the exemplary GLP-1 analog or functional variant thereof or mimetic thereof 7:1, Choline-the exemplary GLP-1 analog or functional variant thereof or mimetic thereof 14:1, Choline-the exemplary GLP-1 analog or functional variant thereof or mimetic thereof 28:1, and Choline-the exemplary GLP-1 analog or functional variant thereof or mimetic thereof 56:1 show lower pH compared with Choline-the exemplary GLP-1 analog or functional variant thereof or mimetic thereof 4:1.

When choline chloride, instead of choline bicarbonate, was used for the reaction, the pH remained close to unconjugated exemplary GLP-1 analog or functional variant thereof or mimetic thereof at the ratios of 1:1 and 4:1, and became more acidic with increasing amounts of choline chloride.

Because of the non-linear rising and falling in pH when more choline bicarbonate was added, this appears to indicate that the GLP-1 analog or functional variant thereof or mimetic thereof was ionized, especially as this notion was not observed in the presence of the negative control, choline chloride.

In some embodiments, choline bicarbonate can react with free carboxylic groups on the GLP-1 analog or functional variant thereof or mimetic thereof to create the novel Choline-GLP-1 analog or functional variant thereof or mimetic thereof. In some embodiments, choline chloride can be used as a negative control, as it will not react with the free carboxylic acid groups. Non-reacted GLP-1 analog or functional variant thereof or mimetic thereof were listed as Choline-Cl-GLP Analog in the figures. The included pH data as described above further support that the GLP-1 analog or functional variant thereof or mimetic thereof is indeed ionized when choline bicarbonate is used.

Figure 24A:
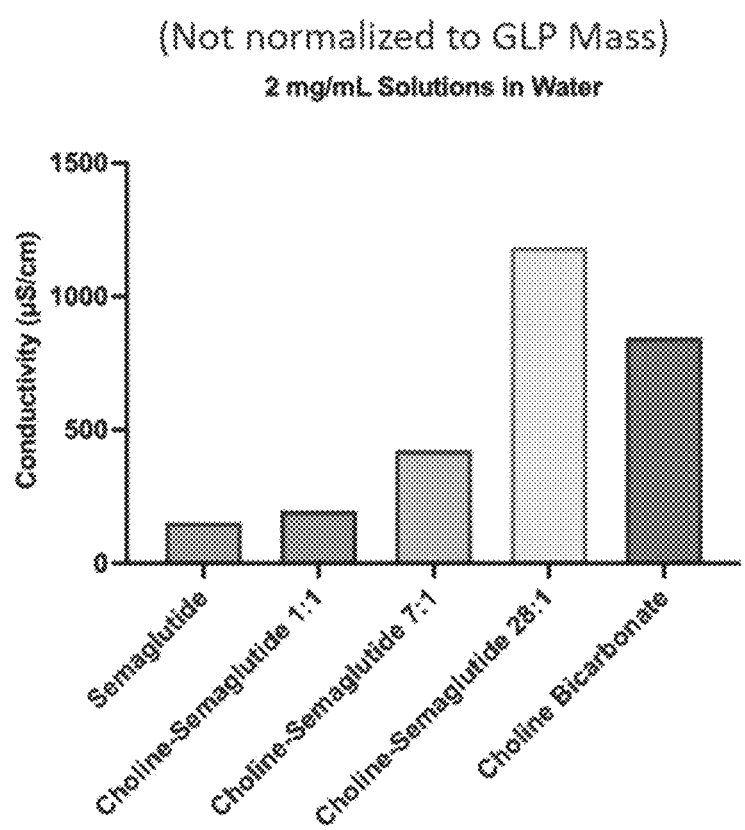
FIGS. 24A-24D show exemplary analytical characterization of an exemplary GLP-1 analog or functional variant thereof or mimetic thereof ("GLP-1 analog") based on conductivity.
Figure 24B:
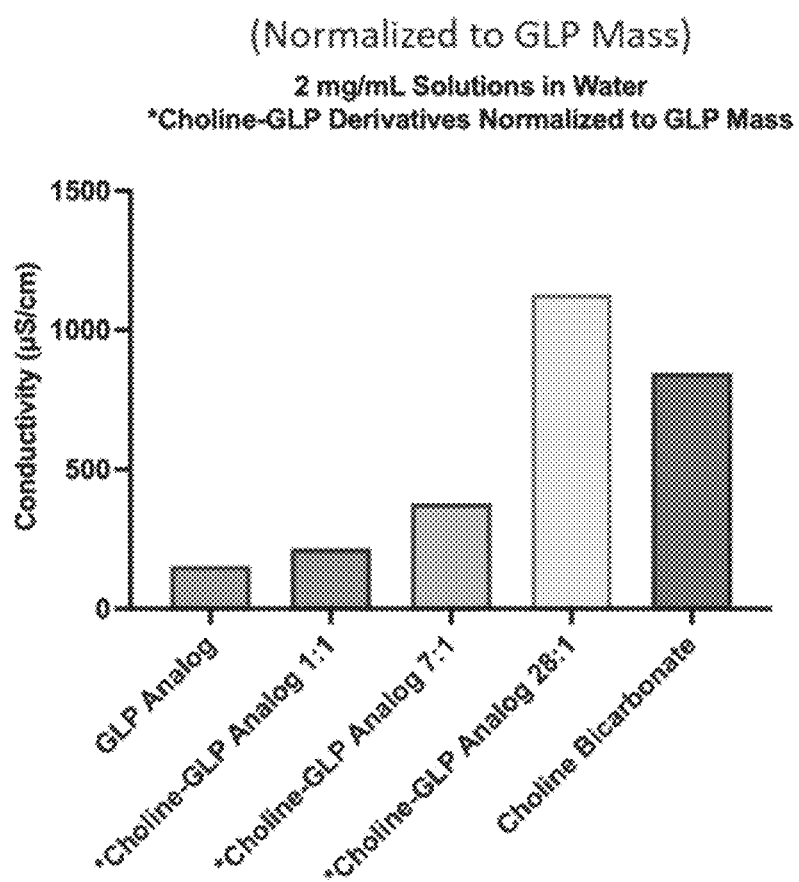

Example 8: Exemplary Analytical Characterization of Exemplary Embodiments of Choline-an Exemplary GLP-1 Analog or Functional Variant Thereof or Mimetic Thereof Based on Conductivity Exemplary analytical characterization of exemplary embodiments of Choline-an exemplary GLP-1 analog or functional variant thereof or mimetic thereof based on conductivity is shown in FIGS. 24A-24D. FIG. 24A depicts exemplary analytical characterization results of an exemplary GLP-1 analog or functional variant thereof or mimetic thereof ("GLP-1 analog") based on conductivity using 2 mg/mL solutions in water. The results are not normalized to an exemplary GLP-1 analog or functional variant thereof or mimetic thereof Mass. FIG. 24B depicts exemplary analytical characterization results of an exemplary GLP-1 analog or functional variant thereof or mimetic thereof ("GLP-1 analog") based on conductivity using 2 mg/mL solutions in water. The results of the choline-the exemplary GLP-1 analog or functional variant thereof or mimetic thereof are normalized to the exemplary GLP-1 analog or functional variant thereof or mimetic thereof Mass.

Conclusion

Conductivity of each of the choline-an exemplary GLP-1 analog or functional variant thereof or mimetic thereof at various ratios in solution increases with increasing choline amount, even after normalizing to the exemplary GLP-1 analog or functional variant thereof or mimetic thereof mass.

Figure 24C:
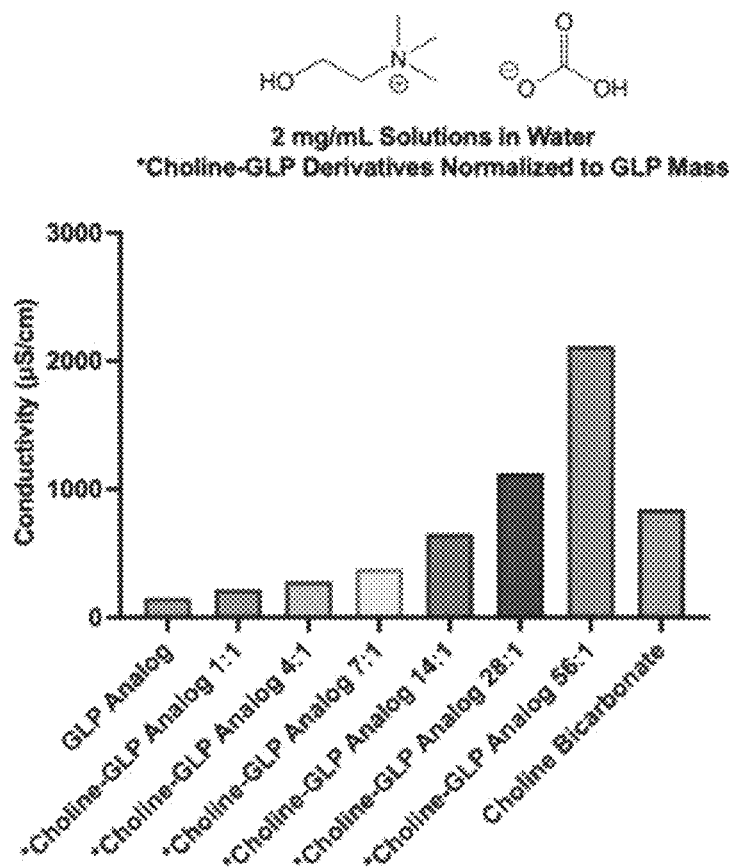
Figure 24D:
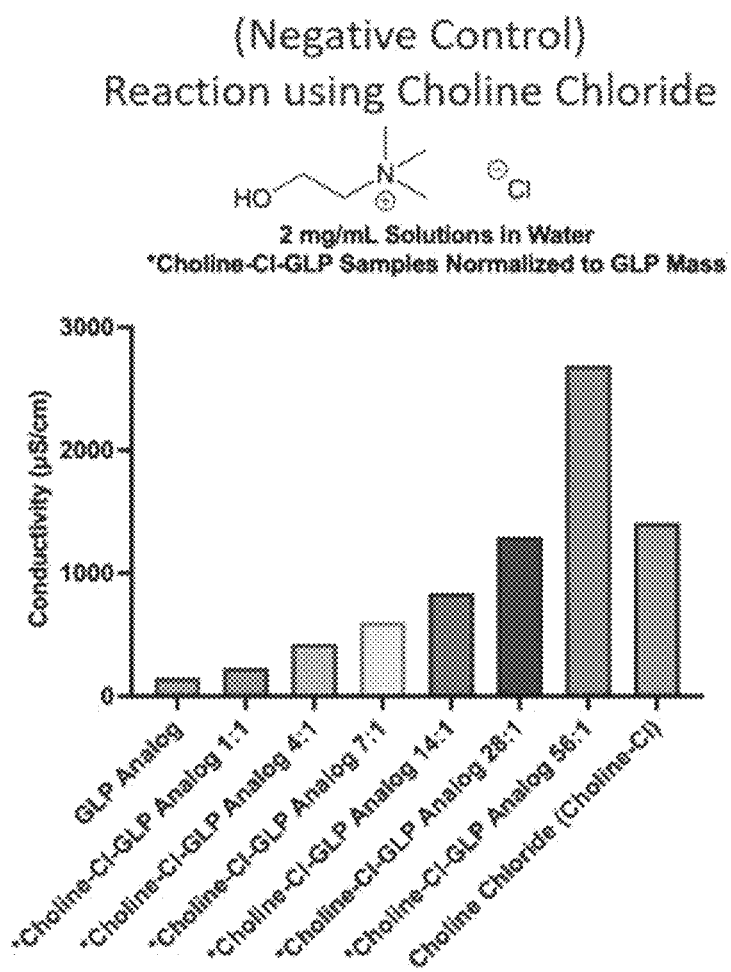

FIG. 24C depicts exemplary analytical characterization results of an exemplary GLP-1 analog or functional variant thereof or mimetic thereof ("GLP-1 analog") based on conductivity using 2 mg/mL solutions in water, wherein the exemplary reaction using choline bicarbonate as shown above the graph was used. The results of the choline-the exemplary GLP-1 analog or functional variant thereof or mimetic thereof are normalized to the exemplary GLP-1 analog or functional variant thereof or mimetic thereof Mass. FIG. 24D depicts exemplary analytical characterization results of the negative control of an exemplary GLP-1 analog or functional variant thereof or mimetic thereof ("GLP-1 analog") based on conductivity using 2 mg/mL solutions in water, wherein the exemplary reaction using choline chloride as shown above the graph was used. The results of the choline-Cl-the exemplary GLP-1 analog or functional variant thereof or mimetic thereof are normalized to the exemplary GLP-1 analog or functional variant thereof or mimetic thereof Mass.

Conclusion

Conductivity of each of the choline-an exemplary GLP-1 analog or functional variant thereof or mimetic thereof at various ratios in solution increases with increasing choline amount, even after normalizing to the exemplary GLP-1 analog or functional variant thereof or mimetic thereof mass.

Conductivity increased more gradually between ratios of 1:1 to 7:1 when choline bicarbonate was used in the reaction as compared to choline chloride (negative control), which suggests that the intended ionization of the GLP-1 analog or functional variant thereof or mimetic thereof occurred when using choline bicarbonate.

In some embodiments, choline bicarbonate can react with free carboxylic groups on the GLP-1 analog or functional variant thereof or mimetic thereof to create the novel Choline-GLP-1 analog or functional variant thereof or mimetic thereof. In some embodiments, choline chloride can be used as a negative control, as it will not react with the free carboxylic acid groups. Non-reacted GLP-1 analog or functional variant thereof or mimetic thereof were listed as Choline-Cl-GLP Analog in the figures. The conductivity data as described above further support that the GLP-1 analog or functional variant thereof or mimetic thereof is indeed ionized when choline bicarbonate is used.

Figure 25A:
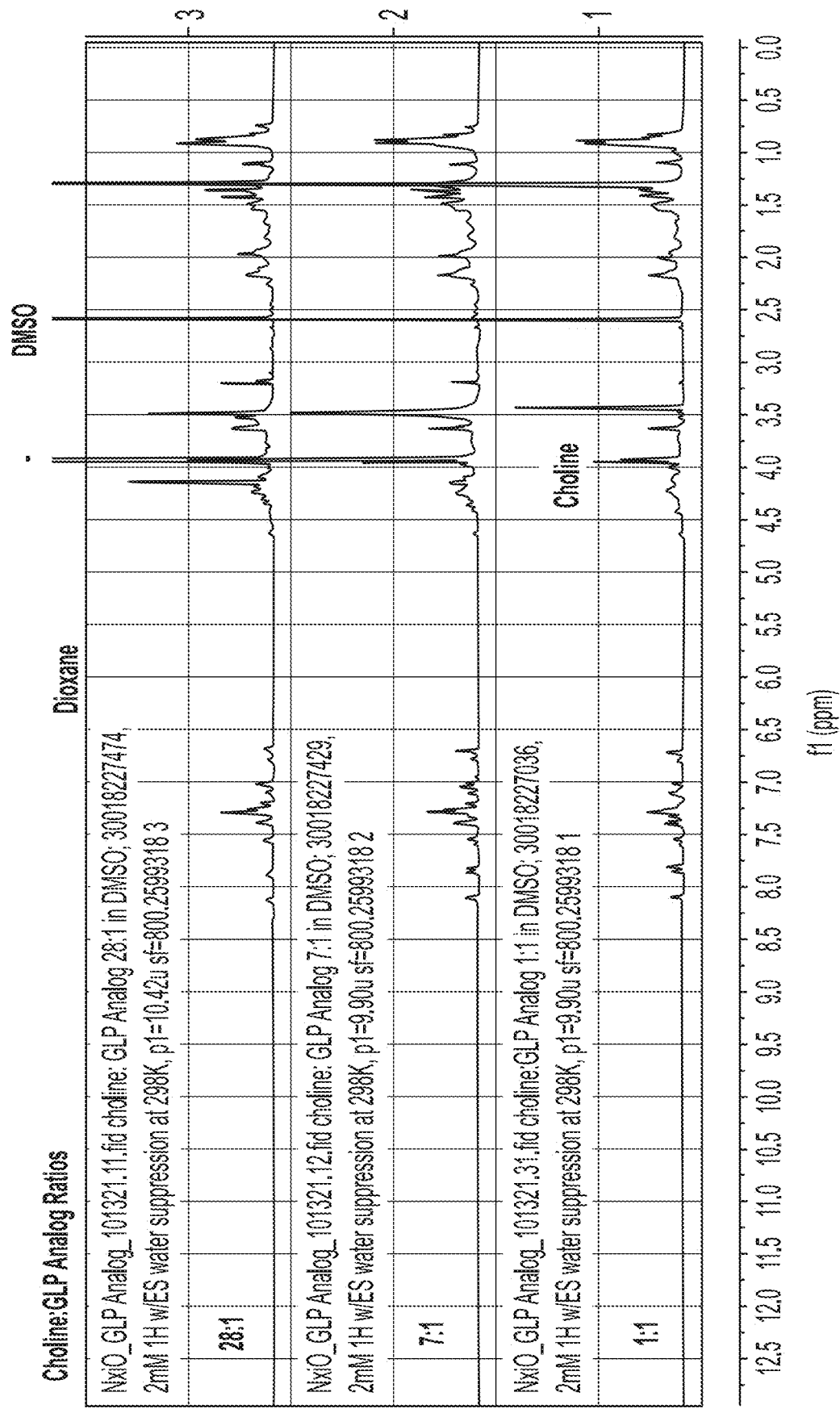
FIGS. 25A and 25B show exemplary analytical characterization based on NMR of choline-an exemplary GLP-1 analog or functional variant thereof or mimetic thereof ("GLP-1 analog") ratios.
Figure 25B:
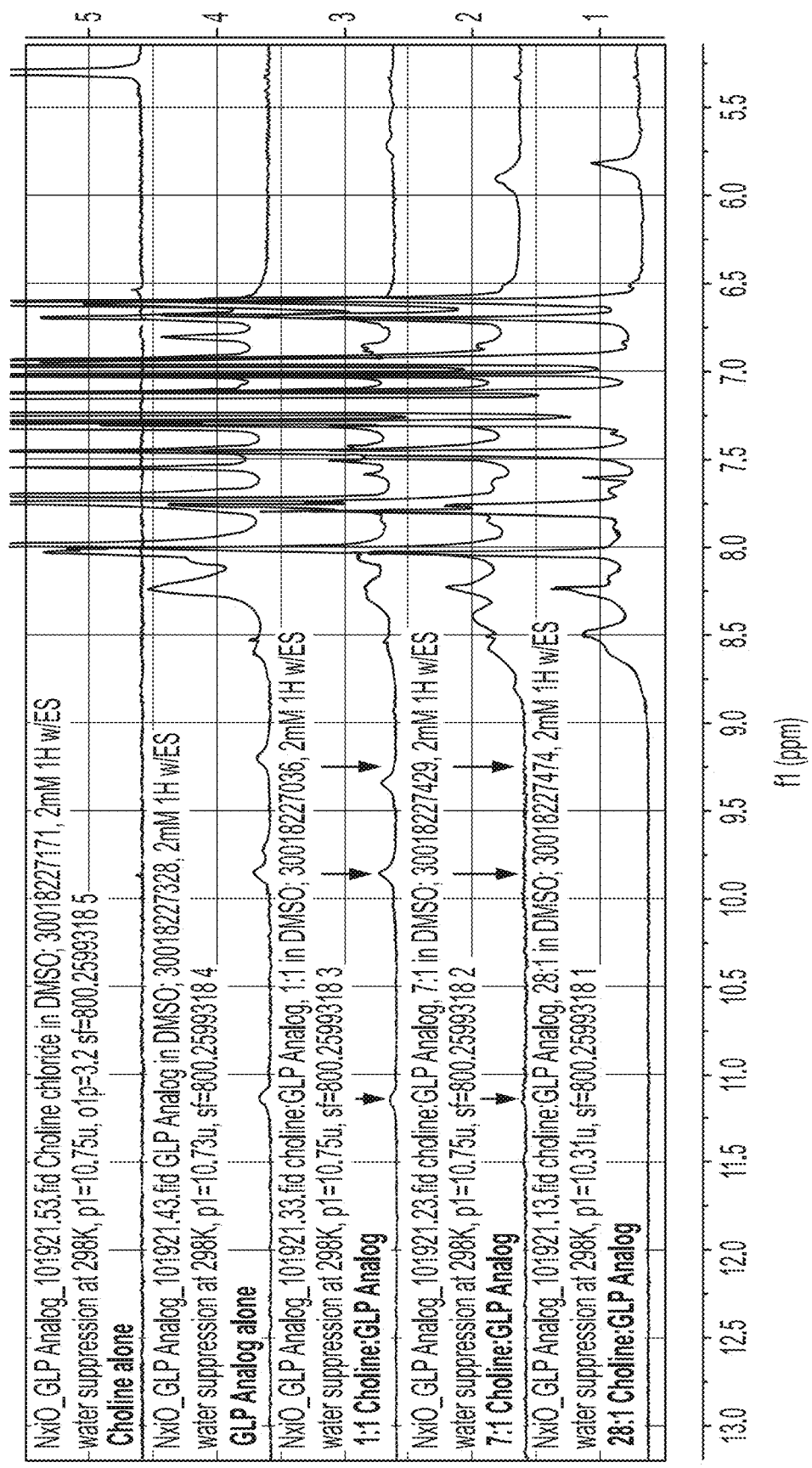

Example 9: Exemplary Analytical Characterization of Exemplary Embodiments of Choline-an Exemplary GLP-1 Analog or Functional Variant Thereof or Mimetic Thereof Based on NMR Exemplary analytical characterization of exemplary embodiments of Choline-an exemplary GLP-1 analog or functional variant thereof or mimetic thereof based on NMR is shown in FIGS. 25A and 25B. FIG. 25A depicts exemplary analytical characterization results based on NMR of choline-an exemplary GLP-1 analog or functional variant thereof or mimetic thereof ratios. FIG. 25B depicts exemplary analytical characterization results based on NMR of choline-an exemplary GLP-1 analog or functional variant thereof or mimetic thereof ratios in a larger view.

Conclusion

Carboxylic acid proton peaks (highlighted with arrows) disappear with increasing choline amount, indicating ionization of the peptide.

Example 10: Exemplary Analytical Characterization of Exemplary Embodiments of Choline-an Exemplary GLP-1 Analog or Functional Variant Thereof or Mimetic Thereof Based on Fourier-Transform Infrared Spectroscopy (FTIR)

Figure 26:
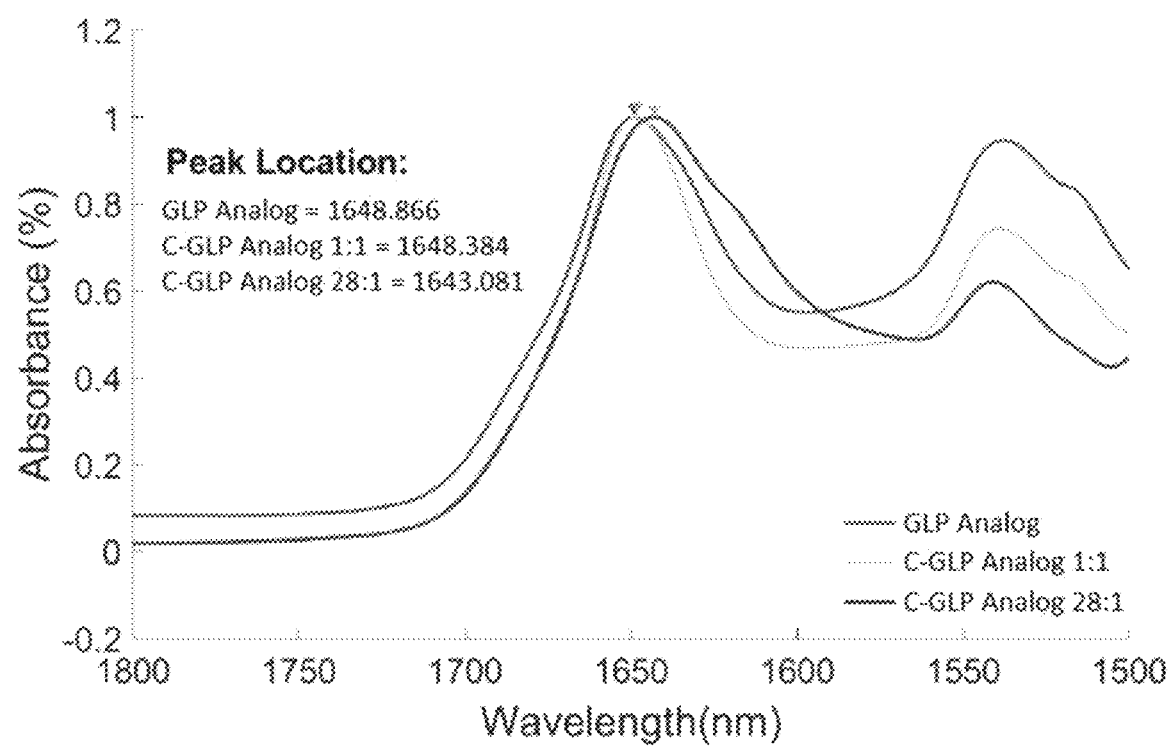
FIG. 26 shows exemplary analytical characterization based on Fourier-transform infrared spectroscopy (FTIR).

Exemplary analytical characterization of exemplary embodiments of Choline-an exemplary GLP-1 analog or functional variant thereof or mimetic thereof based on Fourier-transform infrared spectroscopy (FTIR) is shown in FIG. 26.

Conclusion

Carboxylic acid group-associated peak at around 1648 nm (highlighted with arrows) shifts with increasing choline amount, indicating a change in the bond energies.

Example 11: Cinnamic Acid-an Exemplary GLP-1 Analog or Functional Variant Thereof or Mimetic Thereof A covalent cinnamic acid derivative of an exemplary GLP-1 analog or functional variant thereof or mimetic thereof (e.g., FIG. 27A and FIG. 27B) is prepared at ratios form 1:1 (cinnamic acid:an exemplary GLP-1 analog or functional variant thereof or mimetic thereof) to 28:1 (cinnamic acid:an exemplary GLP-1 analog or functional variant thereof or mimetic thereof).

Figure 27A:
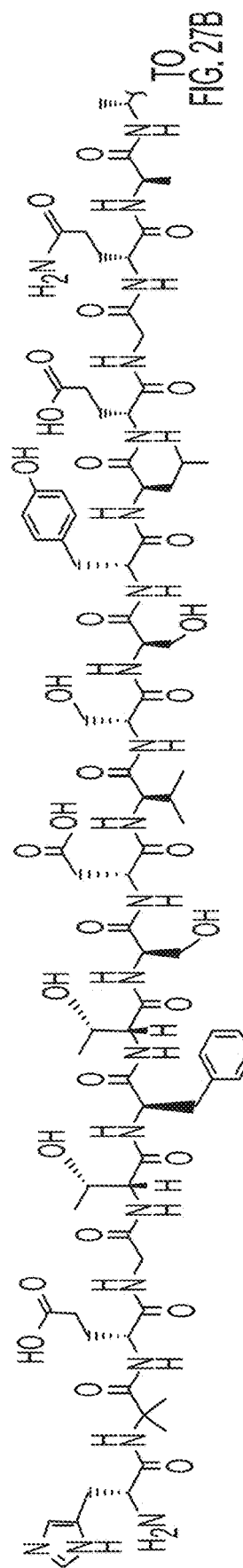
FIG. 27A and FIG. 27B depict an exemplary embodiment of a cinnamic acid-glucagon-like peptide (GLP-1) analog or functional variant thereof or mimetic thereof.
Figure 27B:
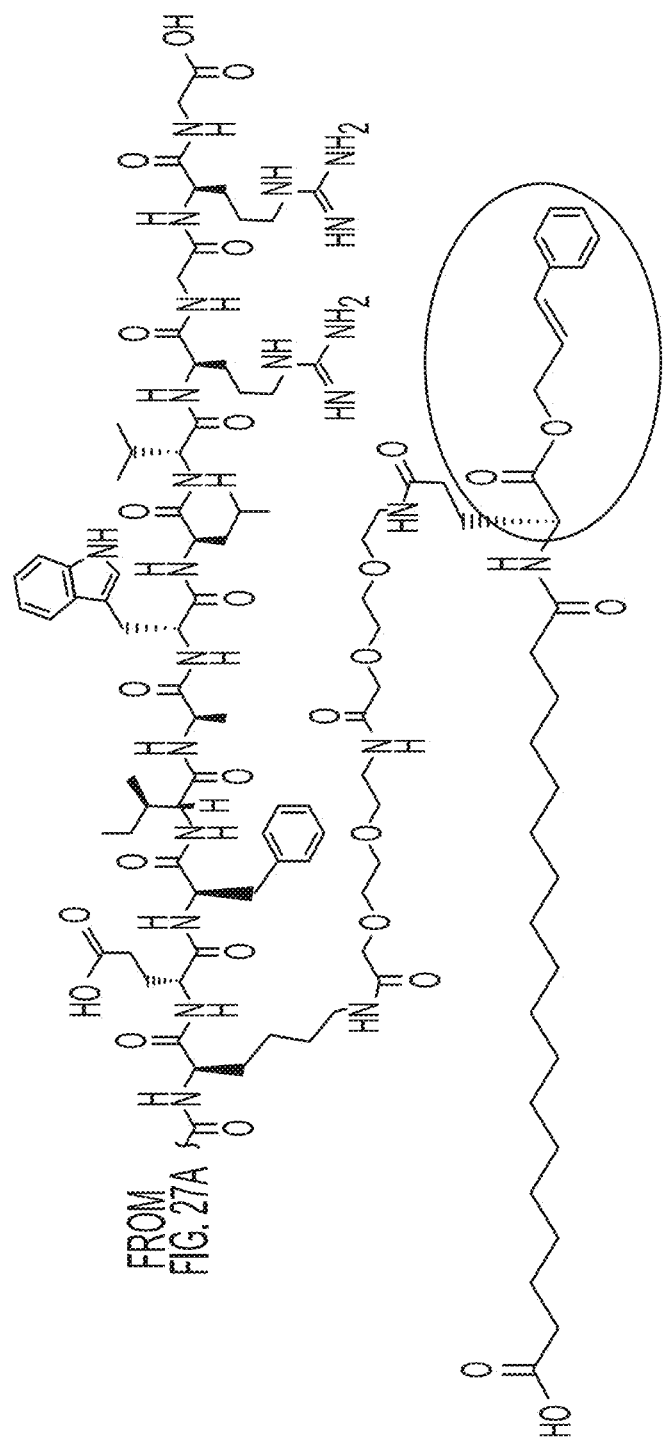

In some embodiments, there are 7 potential sites of esterification on an exemplary GLP-1 analog or functional variant thereof or mimetic thereof with an anion (e.g., FIG. 27A and FIG. 27B). In some embodiments, cinnamic acid-an exemplary GLP-1 analog or functional variant thereof or mimetic thereof ester derivatives can be formed by conjugating an anion (e.g., cinnamic acid) to at least 1 or up to 7 sites on the exemplary GLP-1 analog or functional variant thereof or mimetic thereof structure.

Example 12: An Exemplary Choline-Modified Dual GIP/GLP-1 Receptor Agonist or Functional Variant Thereof Ionic Derivative Structure Using an Exemplary Dual GIP/GLP-1 Receptor Agonist or Functional Variant Thereof Backbone A non-covalent choline derivative of an exemplary dual GIP/GLP-1 receptor agonist or functional variant thereof or functional variant thereof (e.g., FIGS. 13A, 13B, and 13C) is prepared at ratios form 1:1 (choline:an exemplary dual GIP/GLP-1 receptor agonist or functional variant thereof) to 20:1 (choline:an exemplary dual GIP/GLP-1 receptor agonist or functional variant thereof). To prepare choline-an exemplary chimeric monoclonal anti-TNF-α antibody or an antibody fragment thereof, 1, 2, 3, 4, 5, 10, or 20 equivalents of choline bicarbonate (80 wt % solution) are added to an exemplary dual GIP/GLP-1 receptor agonist or functional variant thereof in phosphate buffered saline in a 5 mL Protein LoBind® Eppendorf Tube. Water is removed by lyophilization.

In some embodiments, there are 5 ionizable groups present on an exemplary dual GIP/GLP-1 receptor agonist or functional variant thereof with a cation (e.g., FIGS. 13A, 13B, and 13C). In some embodiments, the choline:an exemplary dual GIP/GLP-1 receptor agonist or functional variant thereof ratio of the choline-an exemplary dual GIP/GLP-1 receptor agonist or functional variant thereof ionic derivatives is 1:1, 2:1, 3:1, 4:1, 5:1, 10:1, or 20:1.

Example 13: An Exemplary Choline-Modified Dual GIP/GLP-1 Receptor Agonist or Functional Variant Thereof Ester Structure Using an Exemplary Dual GIP/GLP-1 Receptor Agonist or Functional Variant Thereof Backbone A covalent choline derivative of an exemplary dual GIP/GLP-1 receptor agonist or functional variant thereof (e.g., FIGS. 14A, 14B, and 14C) is prepared at ratios form 1:1 (choline: an exemplary dual GlP/GLP-1 receptor agonist or functional variant thereof) to 20:1 (choline: an exemplary dual GIP/GLP-1 receptor agonist or functional variant thereof).

In some embodiments, there are 5 potential sites of esterification on an exemplary dual GIP/GLP-1 receptor agonist or functional variant thereof with a cation (e.g., FIGS. 14A, 14B, and 14C). In some embodiments, choline-an exemplary dual GIP/GLP-1 receptor agonist or functional variant thereof ester derivatives can be formed by conjugating a cation (e.g., choline) to at least 1 or up to 5 sites on the exemplary dual GIP/GLP-1 receptor agonist or functional variant thereof structure.

It will also be appreciated from reviewing the present disclosure, that it is contemplated that the one or more aspects or features presented in one of or a group of related clauses may also be included in other clauses or in combination with the one or more aspects or features in other clauses.

Exemplary Embodiments

In an aspect, provided herein, inter alia, is a compound according to Formula I:

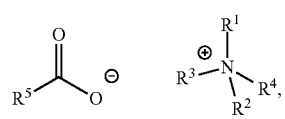

Formula I wherein:
$R^1$, $R^2$, and $R^3$ are independently $C_1$-$C_5$ alkyl;
$R^4$ is $C_2$-$C_5$ alkyl, wherein the $C_2$-$C_5$ alkyl is unsubstituted or substituted with 1 or more hydroxyl;
$R^5$ is a therapeutic agent.
In some embodiments, $R^1$, $R^2$, and $R^3$ are methyl.
In some embodiments, $R^1$, $R^2$, and $R^3$ are ethyl.
In some embodiments, $R^1$, $R^2$, and $R^3$ are propyl.
In some embodiments, $R^1$ and $R^2$ are methyl, and $R^3$ is ethyl.
In some embodiments, $R^1$ and $R^3$ are methyl, and $R^2$ is ethyl.
In some embodiments, $R^1$ and $R^2$ are ethyl, and $R^3$ is methyl.
In some embodiments, $R^1$ and $R^3$ are ethyl, and $R^2$ is methyl.
In some embodiments, $R^1$ and $R^2$ are propyl, and $R^3$ is methyl.

In some embodiments, $R^1$ and $R^3$ are propyl, and $R^2$ is methyl.

In some embodiments, $R^4$ is $C_2$-$C_5$ alkyl substituted with a hydroxyl.

In some embodiments, $R^4$ is

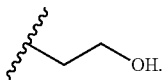 [SMILES: *CCO]

In some embodiments, the compound is according to Formula Ia:

Formula Ia

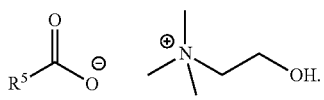

In some embodiments, the compound is according to Formula Ib:

Formula Ib

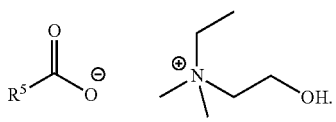

In some embodiments, the compound is according to Formula Ic:

Formula Ic

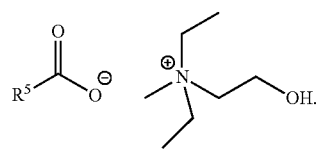

In some embodiments, the therapeutic agent is an GLP-1 analog or functional variant thereof or mimetic thereof, Liraglutide, Exenatide, Peptide tyrosine tyrosine (YY), glucagon, gastric inhibitory polypeptide (GIP), or amylin.

In some embodiments, the therapeutic agent is an GLP-1 analog or functional variant thereof or mimetic thereof.

In some embodiments, the compound comprises the structure as shown in FIG. 16.

In some embodiments, the compound comprises a

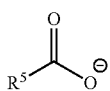

to

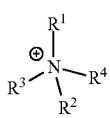

molar ratio of from about 1:1 to about 1:60.

In some embodiments, the compound comprises a

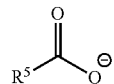

to

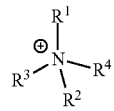

molar ratio of from about 1:1 to about 1:30.

In some embodiments, the compound comprises a

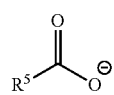

to

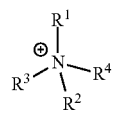

molar ratio of about 1:1.

In some embodiments, the compound comprises a

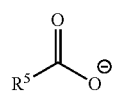

to

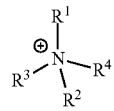

molar ratio of about 1:3.

In some embodiments, the compound comprises a

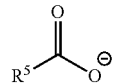

to

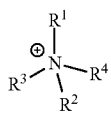

molar ratio of about 1:4.

In some embodiments, the compound comprises a

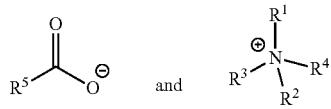

molar ratio of about 1:7.

In some embodiments, the compound comprises a

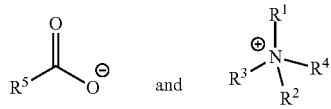

molar ratio of about 1:12.

In some embodiments, the compound comprises a

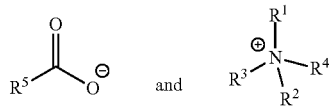

molar ratio of about 1:14.

In some embodiments, the compound comprises a

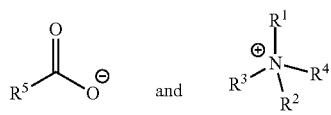

molar ratio of about 1:28.

In some embodiments, the compound comprises a

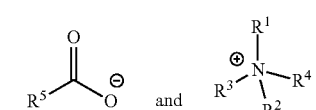

molar ratio of about 1:56.

In some embodiments, the therapeutic agent is an amylin or mimetic or analog thereof, or an amylin analog or functional variant thereof or mimetic or analog thereof.

In some embodiments, the therapeutic agent is an amylin analog or functional variant thereof or mimetic or analog thereof.

In some embodiments, the therapeutic agent is an amylin analog or functional variant thereof or mimetic or analog thereof having the sequence of: [diacid]-[linker]-KCNTAT-CATQRLANFLVHSSNNFGPILPPTNVGSNTY-amide (SEQ ID NO: 21).

In some embodiments, the therapeutic agent is an amylin analog or functional variant thereof or mimetic or analog thereof having the structure as shown in FIGS. 2A, 2B, and 2C, FIG. 3A and FIG. 3B, or FIG. 4A and FIG. 4B.

In some embodiments, the therapeutic agent is an amylin analog or functional variant thereof or mimetic or analog thereof comprising an amino acid substitution of N14E, V17R, Y37P, F15E, L16E, V17E, or any combination thereof.

In some embodiments, the therapeutic agent is an amylin analog or functional variant thereof or mimetic or analog thereof comprising an amino acid substitution of N14E.

In some embodiments, the compound comprises a

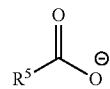

to

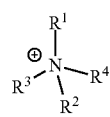

molar ratio of from about 1:1 to about 1:30.

In some embodiments, the compound comprises a

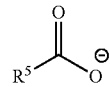

to

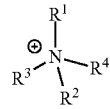

molar ratio of about 1:1.

In some embodiments, the compound comprises a

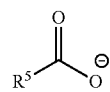

to

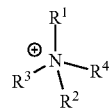

molar ratio of about 1:3.

In some embodiments, the compound comprises a

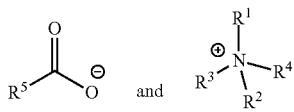

molar ratio of about 1:7.

In some embodiments, the compound comprises a

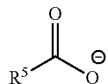

to

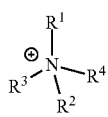

molar ratio of about 1:12.

In some embodiments, the compound comprises a

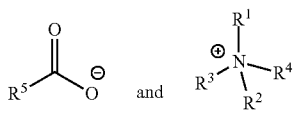

molar ratio of about 1:28.

In some embodiments, the therapeutic agent is an antibody or an antibody fragment thereof.

In some embodiments, the therapeutic agent is any one selected from the group consisting of infliximab or an antibody fragment thereof, adalimumab or an antibody fragment thereof, ustekinumab or an antibody fragment thereof, golimumab or an antibody fragment thereof, natalizumab or an antibody fragment thereof, vedolizumab or an antibody fragment thereof, and certolizumab pegol or an antibody fragment thereof.

In some embodiments, the therapeutic agent comprises:
(i) a sequence with at least 75% sequence identity to the sequence of SEQ ID NO: 1 or SEQ ID NO: 24, a sequence with at least 75% sequence identity to the sequence of SEQ ID NO: 2, or a combination thereof;
(ii) a sequence with at least 75% sequence identity to the sequence of SEQ ID NO: 3, SEQ ID NO: 4, or SEQ ID NO: 5, a sequence with at least 75% sequence identity to the sequence of SEQ ID NO: 6 or SEQ ID NO: 7, or any combination thereof;
(iii) a sequence with at least 75% sequence identity to the sequence of SEQ ID NO: 8, a sequence with at least 75% sequence identity to the sequence of SEQ ID NO: 9, or a combination thereof;
(iv) a sequence with at least 75% sequence identity to the sequence of SEQ ID NO: 10, a sequence with at least 75% sequence identity to the sequence of SEQ ID NO: 11, or a combination thereof;
(v) a sequence with at least 75% sequence identity to the sequence of SEQ ID NO: 12 or SEQ ID NO: 13, a sequence with at least 75% sequence identity to the sequence of SEQ ID NO: 14 or SEQ ID NO: 15, or any combination thereof;
(vi) a sequence with at least 75% sequence identity to the sequence of SEQ ID NO: 16, a sequence with at least 75% sequence identity to the sequence of SEQ ID NO: 17, or a combination thereof; or
(vii) a sequence with at least 75% sequence identity to the sequence of SEQ ID NO: 18, a sequence with at least 75% sequence identity to the sequence of SEQ ID NO: 19, or a combination thereof.

In some embodiments, the therapeutic agent comprises:
(i) the sequence of SEQ ID NO: 1 or SEQ ID NO: 24, the sequence of SEQ ID NO: 2, or a combination thereof;
(ii) the sequence of SEQ ID NO: 3, SEQ ID NO: 4, or SEQ ID NO: 5, the sequence of SEQ ID NO: 6 or SEQ ID NO: 7, or any combination thereof;
(iii) the sequence of SEQ ID NO: 8, the sequence of SEQ ID NO: 9, or a combination thereof;
(iv) the sequence of SEQ ID NO: 10, the sequence of SEQ ID NO: 11, or a combination thereof;
(v) the sequence of SEQ ID NO: 12 or SEQ ID NO: 13, the sequence of SEQ ID NO: 14 or SEQ ID NO: 15, or any combination thereof;
(vi) the sequence of SEQ ID NO: 16, the sequence of SEQ ID NO: 17, or a combination thereof, or
(vii) the sequence of SEQ ID NO: 18, the sequence of SEQ ID NO: 19, or a combination thereof.

In some embodiments, the therapeutic agent comprises:
(i) the sequence of SEQ ID NO: 1 or SEQ ID NO: 24, and the sequence of SEQ ID NO: 2;
(ii) the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7;
(iii) the sequence of SEQ ID NO: 8 and the sequence of SEQ ID NO: 9;
(iv) the sequence of SEQ ID NO: 10 and the sequence of SEQ ID NO: 11;
(v) the sequence of SEQ ID NO: 12 and the sequence of SEQ ID NO: 14, or the sequence of SEQ ID NO: 13 and the sequence of SEQ ID NO: 15;
(vi) the sequence of SEQ ID NO: 16 and the sequence of SEQ ID NO: 17; or
(vii) the sequence of SEQ ID NO: 18 and the sequence of SEQ ID NO: 19.

In some embodiments, the therapeutic agent is infliximab or an antibody fragment thereof.

In some embodiments, the therapeutic agent comprises the sequence of SEQ ID NO: 1 or SEQ ID NO: 24, and the sequence of SEQ ID NO: 2.

In some embodiments, the compound comprises a

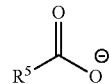

to

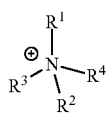

molar ratio of from about 1:1 to about 1:164.

In some embodiments, the compound comprises a

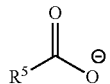

to

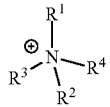

molar ratio of about 1:1.

In some embodiments, the compound comprises a

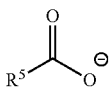

to

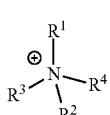

molar ratio of about 1:33.

In some embodiments, the compound comprises a

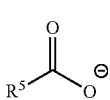

to

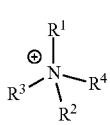

molar ratio of about 1:41.

In some embodiments, the compound comprises a

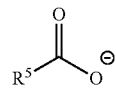

to

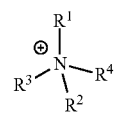

molar ratio of about 1:66.

In some embodiments, the compound comprises a

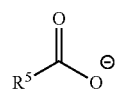

to

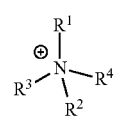

molar ratio of about 1:82.

In some embodiments, the compound comprises a

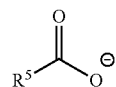

to

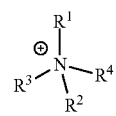

molar ratio of about 1:132.

In some embodiments, the compound comprises a

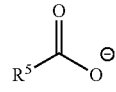

to

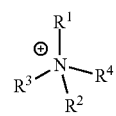

molar ratio of about 1:164.

In some embodiments, the therapeutic agent is adalimumab or an antibody fragment thereof.

In some embodiments, the therapeutic agent comprises the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7.

In some embodiments, the compound comprises a

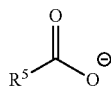

to

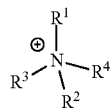

molar ratio of from about 1:1 to about 1:144.

In some embodiments, the therapeutic agent is ustekinumab or an antibody fragment thereof.

In some embodiments, the therapeutic agent comprises the sequence of SEQ ID NO: 8 and the sequence of SEQ ID NO: 9.

In some embodiments, the compound comprises a

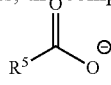

to

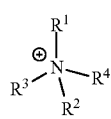

molar ratio of from about 1:1 to about 1:140.

In some embodiments, the therapeutic agent is golimumab or an antibody fragment thereof.

In some embodiments, the therapeutic agent comprises the sequence of SEQ ID NO: 10 and the sequence of SEQ ID NO: 11.

In some embodiments, the compound comprises a

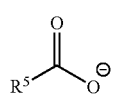

to

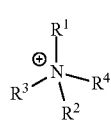

molar ratio of from about 1:1 to about 1:80.

In some embodiments, the therapeutic agent is natalizumab or an antibody fragment thereof.

In some embodiments, the therapeutic agent comprises the sequence of SEQ ID NO: 12 and the sequence of SEQ ID NO: 14, or the sequence of SEQ ID NO: 13 and the sequence of SEQ ID NO: 15.

In some embodiments, the compound comprises a

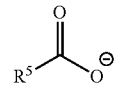

to

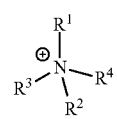

molar ratio of from about 1:1 to about 1:156.

In some embodiments, the therapeutic agent is vedolizumab or an antibody fragment thereof.

In some embodiments, the therapeutic agent comprises the sequence of SEQ ID NO: 16 and the sequence of SEQ ID NO: 17.

In some embodiments, the compound comprises a

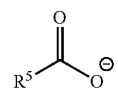

to

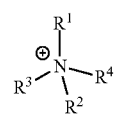

molar ratio of from about 1:1 to about 1:256.

In some embodiments, the therapeutic agent is certolizumab pegol or an antibody fragment thereof.

In some embodiments, the therapeutic agent comprises the sequence of SEQ ID NO: 18 and the sequence of SEQ ID NO: 19.

In some embodiments, the compound comprises a

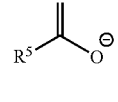

to

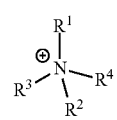

molar ratio of from about 1:1 to about 1:70.

In some embodiments, the therapeutic agent is an antibody or an antibody fragment thereof comprising one or more choline or choline derivative-peptide salt formed on the C-terminus of a light chain, the C-terminus of a heavy chain or a combination thereof.

In some embodiments, the therapeutic agent is a dual GIP/GLP-1 receptor agonist or functional variant thereof.

In some embodiments, the therapeutic agent comprises a sequence with at least 75% sequence identity to the sequence of SEQ ID NO: 25.

In some embodiments, the therapeutic agent comprises the sequence of SEQ ID NO: 25.

In some embodiments, the therapeutic agent comprises C20 diacid-γ-Glu-(AEEA)2 attached to a residue of a sequence with at least 75% sequence identity to the sequence of SEQ ID NO: 25.

In some embodiments, the therapeutic agent comprises C20 diacid-γ-Glu-(AEEA)2 attached to a residue of the sequence of SEQ ID NO: 25.

In some embodiments, the therapeutic agent comprises C20 diacid-γ-Glu-(AEEA)2 attached to the Lys residue at the position 20 from the N-terminus of the sequence of SEQ ID NO: 25.

In some embodiments, the compound comprises a

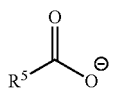

to

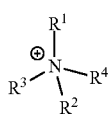

molar ratio of from about 1:1 to about 1:20.

In some embodiments, the compound comprises a

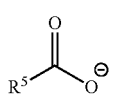

to

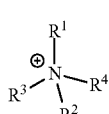

molar ratio of about 1:1.

In some embodiments, the compound comprises a

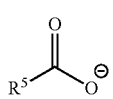

to

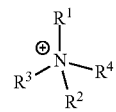

molar ratio of about 1:2.

In some embodiments, the compound comprises a

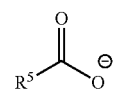

to

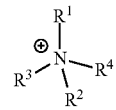

molar ratio of about 1:3.

In some embodiments, the compound comprises a

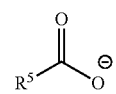

to

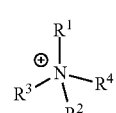

molar ratio of about 1:4.

In some embodiments, the compound comprises a

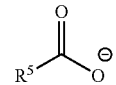

to

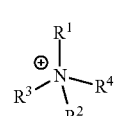

molar ratio of about 1:5.

In some embodiments, the compound comprises a

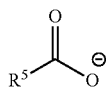

to

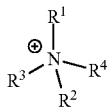

molar ratio of about 1:10.

In some embodiments, the compound comprises a

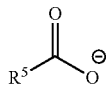

to

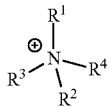

molar ratio of about 1:20.

In some embodiments, the compound comprises the therapeutic agent having a modified structure.

In some embodiments, the compound comprises the therapeutic agent having a choline or choline derivative-modified structure.

In some embodiments, the compound comprises the therapeutic agent having a cation moiety comprising choline or choline derivative.

In some embodiments, the compound comprises the therapeutic agent having a cation moiety comprising a choline or choline derivative-like residue.

In some embodiments, the compound comprises the therapeutic agent comprising one or more choline or choline derivative-peptide derivative formed on a Glu residue, an Asp residue, or a combination thereof.

In some embodiments, the compound comprises the therapeutic agent comprising a linker comprising one or more gamma glutamate (γGlu) residues, one or more 8-amino-3,6-dioxaoctanoic acid (OEG) residues, or a combination thereof.

In some embodiments, the compound comprises the therapeutic agent comprising a linker comprising one or more gamma glutamate (γGlu) residues.

In some embodiments, the compound comprises the therapeutic agent comprising a choline or choline derivative-peptide salt that is formed on the carboxylic acid of the one or more gamma glutamate residues of the linker.

In some embodiments, the compound comprises the therapeutic agent comprising a choline or choline derivative-peptide ester that is formed on the carboxylic acid of the one or more gamma glutamate residues of the linker.

In some embodiments, the compound comprises the therapeutic agent comprising a diacid consisting of 10, 12, 14, 16, 18, or 20 carbons in length.

In some embodiments, the diacid comprises a C10, C12, C14, C16, C18, or C20 fatty diacid.

In some embodiments, the diacid comprises 1,20-icosanedioic acid.

In another aspect, provided herein is a compound according to Formula II:

Formula II

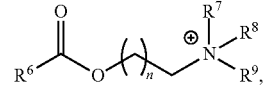

wherein:

$R^6$ is a therapeutic agent.

$R^7$, $R^8$, and $R^9$ are independently $C_1$-$C_5$ alkyl; and n is 1, 2, 3, 4, or 5.

In some embodiments, $R^7$, $R^8$, and $R^9$ are methyl.

In some embodiments, $R^7$, $R^8$, and $R^9$ are ethyl.

In some embodiments, $R^7$, $R^8$, and $R^9$ are propyl.

In some embodiments, $R^7$ and $R^8$ are methyl, and $R^9$ is ethyl.

In some embodiments, $R^7$ and $R^9$ are methyl, and $R^8$ is ethyl.

In some embodiments, $R^7$ and $R^8$ are ethyl, and $R^9$ is methyl.

In some embodiments, $R^7$ and $R^9$ are ethyl, and $R^8$ is methyl.

In some embodiments, $R^7$ and $R^8$ are propyl, and $R^9$ is methyl.

In some embodiments, $R^7$ and $R^9$ are propyl, and $R^8$ is methyl.

In some embodiments, n is 1.

In some embodiments, the compound is according to Formula IIa:

Formula IIa

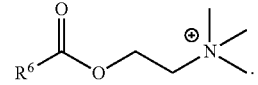

In some embodiments, the compound is according to Formula IIb:

Formula IIb

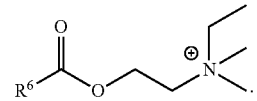

In some embodiments, the compound is according to Formula IIc:

Formula IIc

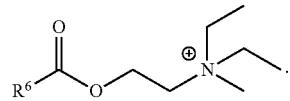

In some embodiments, the therapeutic agent is an GLP-1 analog or functional variant thereof or mimetic thereof, Liraglutide, Exenatide, Peptide tyrosine tyrosine (YY), glucagon, gastric inhibitory polypeptide (GIP), or amylin.

In some embodiments, the therapeutic agent is an GLP-1 analog or functional variant thereof or mimetic thereof.

In some embodiments, the compound comprises the structure as shown in FIG. 17B.

In some embodiments, the therapeutic agent is an amylin or mimetic or analog thereof, or an amylin analog or functional variant thereof or mimetic or analog thereof.

In some embodiments, the therapeutic agent is an amylin analog or functional variant thereof or mimetic or analog thereof.

In some embodiments, the therapeutic agent is an amylin analog or functional variant thereof or mimetic or analog thereof having the sequence of: [diacid]-[linker]-KCNTAT-CATQRLANFLVHSSNNFGPILPPTNVGSNTY-amide (SEQ ID NO: 21).

In some embodiments, the therapeutic agent is an amylin analog or functional variant thereof or mimetic or analog thereof having the structure as shown in FIGS. 2A, 2B, and 2C, FIG. 3A and FIG. 3B, or FIG. 4A and FIG. 4B.

In some embodiments, the therapeutic agent is an amylin analog or functional variant thereof or mimetic or analog thereof comprising an amino acid substitution of N14E, V17R, Y37P, F15E, L16E, V17E, or any combination thereof.

In some embodiments, the therapeutic agent is an amylin analog or functional variant thereof or mimetic or analog thereof comprising an amino acid substitution of N14E.

In some embodiments, the therapeutic agent is an antibody or an antibody fragment thereof.

In some embodiments, the therapeutic agent is any one selected from the group consisting of infliximab or an antibody fragment thereof, adalimumab or an antibody fragment thereof, ustekinumab or an antibody fragment thereof, golimumab or an antibody fragment thereof, natalizumab or an antibody fragment thereof, vedolizumab or an antibody fragment thereof, and certolizumab pegol or an antibody fragment thereof.

In some embodiments, the therapeutic agent comprises:
(i) a sequence with at least 75% sequence identity to the sequence of SEQ ID NO: 1 or SEQ ID NO: 24, a sequence with at least 75% sequence identity to the sequence of SEQ ID NO: 2, or a combination thereof;
(ii) a sequence with at least 75% sequence identity to the sequence of SEQ ID NO: 3, SEQ ID NO: 4, or SEQ ID NO: 5, a sequence with at least 75% sequence identity to the sequence of SEQ ID NO: 6 or SEQ ID NO: 7, or any combination thereof;
(iii) a sequence with at least 75% sequence identity to the sequence of SEQ ID NO: 8, a sequence with at least 75% sequence identity to the sequence of SEQ ID NO: 9, or a combination thereof;
(iv) a sequence with at least 75% sequence identity to the sequence of SEQ ID NO: 10, a sequence with at least 75% sequence identity to the sequence of SEQ ID NO: 11, or a combination thereof;
(v) a sequence with at least 75% sequence identity to the sequence of SEQ ID NO: 12 or SEQ ID NO: 13, a sequence with at least 75% sequence identity to the sequence of SEQ ID NO: 14 or SEQ ID NO: 15, or any combination thereof;
(vi) a sequence with at least 75% sequence identity to the sequence of SEQ ID NO: 16, a sequence with at least 75% sequence identity to the sequence of SEQ ID NO: 17, or a combination thereof; or
(vii) a sequence with at least 75% sequence identity to the sequence of SEQ ID NO: 18, a sequence with at least 75% sequence identity to the sequence of SEQ ID NO: 19, or a combination thereof.

In some embodiments, the therapeutic agent comprises:
(i) the sequence of SEQ ID NO: 1 or SEQ ID NO: 24, the sequence of SEQ ID NO: 2, or a combination thereof;
(ii) the sequence of SEQ ID NO: 3, SEQ ID NO: 4, or SEQ ID NO: 5, the sequence of SEQ ID NO: 6 or SEQ ID NO: 7, or any combination thereof;
(iii) the sequence of SEQ ID NO: 8, the sequence of SEQ ID NO: 9, or a combination thereof;
(iv) the sequence of SEQ ID NO: 10, the sequence of SEQ ID NO: 11, or a combination thereof;
(v) the sequence of SEQ ID NO: 12 or SEQ ID NO: 13, the sequence of SEQ ID NO: 14 or SEQ ID NO: 15, or any combination thereof;
(vi) the sequence of SEQ ID NO: 16, the sequence of SEQ ID NO: 17, or a combination thereof; or
(vii) the sequence of SEQ ID NO: 18, the sequence of SEQ ID NO: 19, or a combination thereof.

In some embodiments, the therapeutic agent comprises:
(i) the sequence of SEQ ID NO: 1 or SEQ ID NO: 24, and the sequence of SEQ ID NO: 2;
(ii) the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7;
(iii) the sequence of SEQ ID NO: 8 and the sequence of SEQ ID NO: 9;
(iv) the sequence of SEQ ID NO: 10 and the sequence of SEQ ID NO: 11;
(v) the sequence of SEQ ID NO: 12 and the sequence of SEQ ID NO: 14, or the sequence of SEQ ID NO: 13 and the sequence of SEQ ID NO: 15;
(vi) the sequence of SEQ ID NO: 16 and the sequence of SEQ ID NO: 17; or
(vii) the sequence of SEQ ID NO: 18 and the sequence of SEQ ID NO: 19.

In some embodiments, the therapeutic agent is infliximab or an antibody fragment thereof.

In some embodiments, the therapeutic agent comprises the sequence of SEQ ID NO: 1 or SEQ ID NO: 24, and the sequence of SEQ ID NO: 2.

In some embodiments, the therapeutic agent is adalimumab or an antibody fragment thereof.

In some embodiments, the therapeutic agent comprises the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7.

In some embodiments, the therapeutic agent is ustekinumab or an antibody fragment thereof.

In some embodiments, the therapeutic agent comprises the sequence of SEQ ID NO: 8 and the sequence of SEQ ID NO: 9.

In some embodiments, the therapeutic agent is golimumab or an antibody fragment thereof.

In some embodiments, the therapeutic agent comprises the sequence of SEQ ID NO: 10 and the sequence of SEQ ID NO: 11.

In some embodiments, the therapeutic agent is natalizumab or an antibody fragment thereof.

In some embodiments, the therapeutic agent comprises the sequence of SEQ ID NO: 12 and the sequence of SEQ ID NO: 14, or the sequence of SEQ ID NO: 13 and the sequence of SEQ ID NO: 15.

In some embodiments, the therapeutic agent is vedolizumab or an antibody fragment thereof.

In some embodiments, the therapeutic agent comprises the sequence of SEQ ID NO: 16 and the sequence of SEQ ID NO: 17.

In some embodiments, the therapeutic agent is certolizumab pegol or an antibody fragment thereof.

In some embodiments, the therapeutic agent comprises the sequence of SEQ ID NO: 18 and the sequence of SEQ ID NO: 19.

In some embodiments, the therapeutic agent is an antibody or an antibody fragment thereof comprising one or more choline or choline derivative-peptide ester formed on the C-terminus of a light chain, the C-terminus of a heavy chain or a combination thereof.

In some embodiments, the therapeutic agent is an antibody or an antibody fragment thereof comprising one or more choline or choline derivative-peptide ester formed on a Cys residue, a Lys residue, or any combination thereof.

In some embodiments, the one or more choline or choline derivative-peptide ester formed on the Cys residue comprises a linker-to-antibody ratio of 2-8, the one or more choline or choline derivative-peptide ester formed on the Lys residue comprises a linker-to-antibody ratio of 2-4, or a combination thereof.

In some embodiments, the therapeutic agent is a dual GIP/GLP-1 receptor agonist or functional variant thereof.

In some embodiments, the therapeutic agent comprises a sequence with at least 75% sequence identity to the sequence of SEQ ID NO: 25.

In some embodiments, the therapeutic agent comprises the sequence of SEQ ID NO: 25.

In some embodiments, the therapeutic agent comprises $C_{20}$ diacid-γ-Glu-(AEEA)2 attached to a residue of a sequence with at least 75% sequence identity to the sequence of SEQ ID NO: 25.

In some embodiments, the therapeutic agent comprises $C_{20}$ diacid-γ-Glu-(AEEA)2 attached to a residue of the sequence of SEQ ID NO: 25.

In some embodiments, the therapeutic agent comprises $C_{20}$ diacid-γ-Glu-(AEEA)2 attached to the Lys residue at the position 20 from the N-terminus of the sequence of SEQ ID NO: 25.

In some embodiments, the compound comprises the therapeutic agent having a choline or choline derivative-modified structure.

In some embodiments, the compound comprises the therapeutic agent having a choline or choline derivative-modified salt structure.

In some embodiments, the compound comprises the therapeutic agent having a cation moiety comprising choline or choline derivative.

In some embodiments, the compound comprises the therapeutic agent having a choline or choline derivative-modified ester structure.

In some embodiments, the compound comprises the therapeutic agent having a cation moiety comprising a choline or choline derivative-like residue.

In some embodiments, the compound comprises the therapeutic agent comprising one or more choline or choline derivative-peptide ester formed on a Cys residue, a Lys residue, or any combination thereof.

In some embodiments, the one or more choline or choline derivative-peptide ester formed on the Cys residue comprises a linker-to-the therapeutic agent ratio of 2-8, the one or more choline or choline derivative-peptide ester formed on the Lys residue comprises a linker-to-the therapeutic agent ratio of 2-4, or a combination thereof.

In some embodiments, the compound comprises the therapeutic agent comprising a linker comprising one or more gamma glutamate (γGlu) residues, one or more 8-amino-3,6-dioxaoctanoic acid (OEG) residues, or a combination thereof.

In some embodiments, the compound comprises the therapeutic agent comprising a linker comprising one or more gamma glutamate (γGlu) residues.

In some embodiments, the compound comprises the therapeutic agent comprising a choline or choline derivative-peptide salt that is formed on the carboxylic acid of the one or more gamma glutamate residues of the linker.

In some embodiments, the compound comprises the therapeutic agent comprising a choline or choline derivative-peptide ester that is formed on the carboxylic acid of the one or more gamma glutamate residues of the linker.

In some embodiments, the compound comprises the therapeutic agent comprising a diacid consisting of 10, 12, 14, 16, 18, or 20 carbons in length.

In some embodiments, the diacid comprises a $C_{10}$, $C_{12}$, $C_{14}$, $C_{16}$, $C_{18}$, or $C_{20}$ fatty diacid.

In some embodiments, the diacid comprises 1,20-icosanedioic acid.

In another aspect, provided herein is a compound according to Formula III:

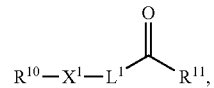

Formula III wherein:

$R^{10}$ is a therapeutic agent;

$R^{11}$ is substituted or unsubstituted $C_5$-$C_{10}$;

$X^1$ is

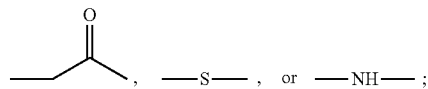

and $L^1$ is a covalent bond or a linker.

In some embodiments, $L^1$ is a non-cleavable linker.

In some embodiments, $L^1$ comprises a maleimide alkane linker or a maleimide cyclohexane linker.

In some embodiments, $L^1$ comprises

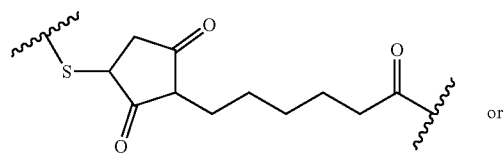

-continued

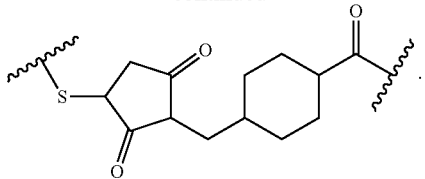

In some embodiments, $L^1$ is a chemically cleavable linker.
In some embodiments, $L^1$ comprises a hydrazone linker or a disulfide linker.
In some embodiments, $L^1$ comprises

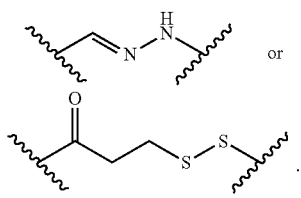

In some embodiments, $R^{11}$ is substituted or unsubstituted $C_{10}$.

In some embodiments, the therapeutic agent is an GLP-1 analog or functional variant thereof or mimetic thereof, Liraglutide, Exenatide, Peptide tyrosine tyrosine (YY), glucagon, gastric inhibitory polypeptide (GIP), or amylin.

In some embodiments, the therapeutic agent is an GLP-1 analog or functional variant thereof or mimetic thereof.

In some embodiments, the therapeutic agent is an amylin or mimetic or analog thereof, or an amylin analog or functional variant thereof or mimetic or analog thereof.

In some embodiments, the therapeutic agent is an amylin analog or functional variant thereof or mimetic or analog thereof.

In some embodiments, the therapeutic agent is an amylin analog or functional variant thereof or mimetic or analog thereof having the sequence of: [diacid]-[linker]-KCNTAT-CATQRLANFLVHSSNNFGPILPPTNVGSNTY-amide (SEQ ID NO: 21).

In some embodiments, the therapeutic agent is an amylin analog or functional variant thereof or mimetic or analog thereof comprising an amino acid substitution of N14E, V17R, Y37P, F15E, L16E, V17E, or any combination thereof.

In some embodiments, the therapeutic agent is an amylin analog or functional variant thereof or mimetic or analog thereof comprising an amino acid substitution of N14E.

In some embodiments, the therapeutic agent is an antibody or an antibody fragment thereof.

In some embodiments, the therapeutic agent is any one selected from the group consisting of infliximab or an antibody fragment thereof, adalimumab or an antibody fragment thereof, ustekinumab or an antibody fragment thereof, golimumab or an antibody fragment thereof, natalizumab or an antibody fragment thereof, vedolizumab or an antibody fragment thereof, and certolizumab pegol or an antibody fragment thereof.

In some embodiments, the therapeutic agent comprises:
(i) a sequence with at least 75% sequence identity to the sequence of SEQ ID NO: 1 or SEQ ID NO: 24, a sequence with at least 75% sequence identity to the sequence of SEQ ID NO: 2, or a combination thereof;
(ii) a sequence with at least 75% sequence identity to the sequence of SEQ ID NO: 3, SEQ ID NO: 4, or SEQ ID NO: 5, a sequence with at least 75% sequence identity to the sequence of SEQ ID NO: 6 or SEQ ID NO: 7, or any combination thereof;
(iii) a sequence with at least 75% sequence identity to the sequence of SEQ ID NO: 8, a sequence with at least 75% sequence identity to the sequence of SEQ ID NO: 9, or a combination thereof;
(iv) a sequence with at least 75% sequence identity to the sequence of SEQ ID NO: 10, a sequence with at least 75% sequence identity to the sequence of SEQ ID NO: 11, or a combination thereof;
(v) a sequence with at least 75% sequence identity to the sequence of SEQ ID NO: 12 or SEQ ID NO: 13, a sequence with at least 75% sequence identity to the sequence of SEQ ID NO: 14 or SEQ ID NO: 15, or any combination thereof;
(vi) a sequence with at least 75% sequence identity to the sequence of SEQ ID NO: 16, a sequence with at least 75% sequence identity to the sequence of SEQ ID NO: 17, or a combination thereof; or
(vii) a sequence with at least 75% sequence identity to the sequence of SEQ ID NO: 18, a sequence with at least 75% sequence identity to the sequence of SEQ ID NO: 19, or a combination thereof.

In some embodiments, the therapeutic agent comprises:
(i) the sequence of SEQ ID NO: 1 or SEQ ID NO: 24, the sequence of SEQ ID NO: 2, or a combination thereof;
(ii) the sequence of SEQ ID NO: 3, SEQ ID NO: 4, or SEQ ID NO: 5, the sequence of SEQ ID NO: 6 or SEQ ID NO: 7, or any combination thereof;
(iii) the sequence of SEQ ID NO: 8, the sequence of SEQ ID NO: 9, or a combination thereof;
(iv) the sequence of SEQ ID NO: 10, the sequence of SEQ ID NO: 11, or a combination thereof;
(v) the sequence of SEQ ID NO: 12 or SEQ ID NO: 13, the sequence of SEQ ID NO: 14 or SEQ ID NO: 15, or any combination thereof;
(vi) the sequence of SEQ ID NO: 16, the sequence of SEQ ID NO: 17, or a combination thereof; or
(vii) the sequence of SEQ ID NO: 18, the sequence of SEQ ID NO: 19, or a combination thereof.

In some embodiments, the therapeutic agent comprises:
(i) the sequence of SEQ ID NO: 1 or SEQ ID NO: 24, and the sequence of SEQ ID NO: 2;
(ii) the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7;
(iii) the sequence of SEQ ID NO: 8 and the sequence of SEQ ID NO: 9;
(iv) the sequence of SEQ ID NO: 10 and the sequence of SEQ ID NO: 11;
(v) the sequence of SEQ ID NO: 12 and the sequence of SEQ ID NO: 14, or the sequence of SEQ ID NO: 13 and the sequence of SEQ ID NO: 15;
(vi) the sequence of SEQ ID NO: 16 and the sequence of SEQ ID NO: 17; or
(vii) the sequence of SEQ ID NO: 18 and the sequence of SEQ ID NO: 19.

In some embodiments, the therapeutic agent is infliximab or an antibody fragment thereof.

In some embodiments, the therapeutic agent comprises the sequence of SEQ ID NO: 1 or SEQ ID NO: 24, and the sequence of SEQ ID NO: 2.

In some embodiments, the therapeutic agent is adalimumab or an antibody fragment thereof.

In some embodiments, the therapeutic agent comprises the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7.

In some embodiments, the therapeutic agent is ustekinumab or an antibody fragment thereof.

In some embodiments, the therapeutic agent comprises the sequence of SEQ ID NO: 8 and the sequence of SEQ ID NO: 9.

In some embodiments, the therapeutic agent is golimumab or an antibody fragment thereof.

In some embodiments, the therapeutic agent comprises the sequence of SEQ ID NO: 10 and the sequence of SEQ ID NO: 11.

In some embodiments, the therapeutic agent is natalizumab or an antibody fragment thereof.

In some embodiments, the therapeutic agent comprises the sequence of SEQ ID NO: 12 and the sequence of SEQ ID NO: 14, or the sequence of SEQ ID NO: 13 and the sequence of SEQ ID NO: 15.

In some embodiments, the therapeutic agent is vedolizumab or an antibody fragment thereof.

In some embodiments, the therapeutic agent comprises the sequence of SEQ ID NO: 16 and the sequence of SEQ ID NO: 17.

In some embodiments, the therapeutic agent is certolizumab pegol or an antibody fragment thereof.

In some embodiments, the therapeutic agent comprises the sequence of SEQ ID NO: 18 and the sequence of SEQ ID NO: 19.

In some embodiments, the therapeutic agent is an antibody or an antibody fragment thereof comprising one or more $R^{11}$ linked to the C-terminus of a light chain, the C-terminus of a heavy chain or a combination thereof.

In some embodiments, the therapeutic agent is a dual GIP/GLP-1 receptor agonist or functional variant thereof.

In some embodiments, the therapeutic agent comprises a sequence with at least 75% sequence identity to the sequence of SEQ ID NO: 25.

In some embodiments, the therapeutic agent comprises the sequence of SEQ ID NO: 25.

In some embodiments, the therapeutic agent comprises C20 diacid-γ-Glu-(AEEA)2 attached to a residue of a sequence with at least 75% sequence identity to the sequence of SEQ ID NO: 25.

In some embodiments, the therapeutic agent comprises C20 diacid-γ-Glu-(AEEA)2 attached to a residue of the sequence of SEQ ID NO: 25.

In some embodiments, the therapeutic agent comprises C20 diacid-γ-Glu-(AEEA)2 attached to the Lys residue at the position 20 from the N-terminus of the sequence of SEQ ID NO: 25.

In some embodiments, the compound comprises the therapeutic agent having a choline or choline derivative-modified structure.

In some embodiments, the compound comprises the therapeutic agent having a choline or choline derivative-modified salt structure.

In some embodiments, the compound comprises the therapeutic agent having a cation moiety comprising choline or choline derivative.

In some embodiments, the compound comprises the therapeutic agent having a choline or choline derivative-modified ester structure.

In some embodiments, the compound comprises the therapeutic agent having a cation moiety comprising a choline or choline derivative-like residue.

In some embodiments, the compound comprises the therapeutic agent comprising one or more $R^{11}$ linked to a Lys residue, a Cys residue, or any combination thereof.

In some embodiments, $R^{11}$ is linked to the Lys residue with a linker-to-the therapeutic agent ratio of 2-4, $R^{11}$ is linked to the Cys residue with a linker-to-the therapeutic agent ratio of 2-8 or with a linker-to-the therapeutic agent ratio of 4, or a combination thereof.

In some embodiments, the compound comprises the therapeutic agent comprising a dual conjugation.

In some embodiments, the dual conjugation comprises a linker-to-the therapeutic agent ratio of 1-2.

In some embodiments, the compound comprises the therapeutic agent comprising a linker comprising one or more gamma glutamate (γGlu) residues, one or more 8-amino-3,6-dioxaoctanoic acid (OEG) residues, or a combination thereof.

In some embodiments, the compound comprises the therapeutic agent comprising a linker comprising one or more gamma glutamate (γGlu) residues.

In some embodiments, the compound comprises the therapeutic agent comprising a choline or choline derivative-peptide salt that is formed on the carboxylic acid of the one or more gamma glutamate residues of the linker.

In some embodiments, the compound comprises the therapeutic agent comprising a choline or choline derivative-peptide ester that is formed on the carboxylic acid of the one or more gamma glutamate residues of the linker.

In some embodiments, the compound comprises the therapeutic agent comprising a diacid consisting of 10, 12, 14, 16, 18, or 20 carbons in length.

In some embodiments, the diacid comprises a $C_{10}$, $C_{12}$, $C_{14}$, $C_{16}$, $C_{18}$, or $C_{20}$ fatty diacid.

In some embodiments, the diacid comprises 1,20-icosanedioic acid.

In another aspect, provided herein is a composition comprising the compound as provided herein, and one or more ionic liquid.

In some embodiments, the one or more ionic liquid independently comprises a cation selected from the group consisting of aminoguanidine, choline or choline derivative, carnitine, acetylcholine, ammonium, tetramethyl ammonium, tetraethyl ammonium, tetrabutyl ammonium, and guanidine derivatives.

In some embodiments, the one or more ionic liquid independently comprises choline or choline derivative, carnitine, or acetylcholine.

In some embodiments, the one or more ionic liquid independently comprises an anion selected from the group consisting of (R)-ax-Lipoic Acid, 12-Hydroxystearic Acid, 2-(4-Isobutylphenyl)propionic Acid, 2-(4,4-Dimethyl-2-pentanyl)-5,7,7-trimethyloctanoic Acid, 2-Aminoethanesulfonic Acid (Taurine Acid), 2-Hexyldecanoic Acid, 2-Hydroxyhippuric Acid, 3-(4-Hydroxyphenyl)propionic Acid, 3-Methylcrotonic Acid, 3,3-Diphenylpropionic Acid, 3,4-Dihydroxbenzoic Acid (Protocatechuic Acid), 3,7-Dimethyloctanoic Acid, 4-Hydroxybenzenesulfonic Acid, 4-Hydroxybenzoic Acid, 4-Methylhexanoic Acid, 4-Methyloctanoic Acid, 4-Methylvaleric Acid, 5-Norbornene-2-carboxylic Acid, 8-[(2-hydroxybenzoyl)amino] octanoic acid, Abietic Acid, Acetic Acid, Acetylcysteine, Aconitic Acid, Arachidonic Acid, Behenic Acid, Benzoic Acid, Caffeic Acid, Chenodeoxycholic Acid, Cis-Cinnamic acid, Citric Acid, Citronellic Acid, Crotonic Acid, D-(+)-

Galactonic Acid, Decanoic Acid, Deoxycholic Acid, Dihydrocaffeic Acid, DL-2-Phenylpropionic (Hydratropic) Acid, DL-Tartaric Acid, DL-Tropic Acid, Eicosanedioic Acid, Eicosapentanoic Acid (EPA), Elaidic Acid, Ellagic Acid, Erucic Acid, Ethylenediaminetetraacetic Acid (EDTA), Formic Acid, Fumaric Acid, Geranic Acid, Glutaric Acid, Glycolic Acid, Heptanoic Acid, Hexanoic Acid, Hydrocinnamic Acid (3-Phenylpropionic Acid), Isobutyric Acid, Isovaleric Acid, L-(+)-Tartaric Acid, L-Ascorbic Acid, L-Aspartic Acid, L-Glutamic Acid, L-Glutathione reduced, Lactic Acid, Lauric Acid, Levulinic Acid, Linoleic Acid, Linolenic Acid, Lithocholic Acid, Maleic Acid, Malic Acid, Malonic Acid, Mandelic acid, Mesaconic Acid, Nicotinic Acid, Nonanoic Acid, Octanoic Acid, Oleic Acid, Oxalic Acid, p-Coumaric Acid, p-Toluenesulfonic Acid, Palmitic Acid, Perillic Acid, Phosphoric Acid, Pimelic Acid, Pivalic Acid, Propionic Acid, Pyroglutamic Acid, Pyruvic Acid, Ricinoleic Acid, Salicylic Acid (2-Hydroxybenzoic Acid), Sinapinic Acid (3,5-Dimethoxy-4-Hydroxycinnamic Acid), Sorbic Acid, Stearic acid, Succinic Acid, Syringic Acid, Tiglic Acid, Trans-2-Decenoic Acid, Trans-2-Hexenoic Acid, Trans-2-Octenoic Acid, Trans-3-Octenoic Acid, Trans-γ-Octenoic Acid, Trans-Cinnamic Acid, Trans-Ferulic Acid, Undecanoic Acid, Valeric Acid, Vanillic Acid, and α-Ketoglutaric Acid.

In some embodiments, the one or more ionic liquid independently comprises an anion selected from the group consisting of glycolic acid, tartaric acid, malic acid, hydrocinnamic acid, citric acid, cinnamic acid, mandelic acid, mesaconic acid, ricinoleic acid, linoleic acid, and tiglic acid.

In some embodiments, the one or more ionic liquid independently comprises an anion selected from the group consisting of cinnamic acid, mandelic acid, citric acid, ricinoleic acid, linoleic acid, and tiglic acid.

In some embodiments, the one or more ionic liquid independently comprises choline or choline derivative-cinnamic acid, choline or choline derivative-mandelic acid, choline or choline derivative-citric acid, choline or choline derivative-ricinoleic acid, choline or choline derivative-linoleic acid, or choline or choline derivative-tiglic acid.

In some embodiments, the one or more ionic liquid independently comprises carnitine-cinnamic acid, carnitine-mandelic acid, carnitine-citric acid, carnitine-ricinoleic acid, carnitine-linoleic acid, or carnitine-tiglic acid.

In some embodiments, the one or more ionic liquid independently comprises acetylcholine-cinnamic acid, acetylcholine-mandelic acid, acetylcholine-citric acid, acetylcholine-ricinoleic acid, acetylcholine-linoleic acid, or acetylcholine-tiglic acid.

In some embodiments, the composition as provided herein further comprises at least one permeation enhancer.

In some embodiments, the at least one permeation enhancer is selected from the group consisting of salcaprozate sodium (SNAC), sodium caprylate, sodium caprate, a bile salt, ethylenediaminetetraacetic acid (EDTA), ethylene glycol-bis-(2-aminoethylether)-N,N,N',N'-tetraacetic acid (EGTA), and 3-[N,N-Dimethyl(3-palmitoylaminopropyl)-ammonio]-propanesulfonate (PPS), and any combination thereof.

In some embodiments, the bile salt is selected from the group consisting of sodium deoxycholate, sodium chenodeoxycholate, sodium taurodeoxycholate, and a combination thereof.

In some embodiments, the composition as provided herein further comprises at least one pharmaceutically acceptable excipient.

In another aspect, provided herein is a composition comprising a therapeutic agent, and one or more ionic liquid, wherein the therapeutic agent is:
(i) an GLP-1 analog or functional variant thereof or mimetic thereof, Liraglutide, Exenatide, Peptide tyrosine tyrosine (YY), glucagon, gastric inhibitory polypeptide (GIP), or amylin;
(ii) an amylin or mimetic or analog thereof, or an amylin analog or functional variant thereof or mimetic or analog thereof;
(iii) wherein the therapeutic agent is an antibody or an antibody fragment thereof; or
(iv) a dual GIP/GLP-1 receptor agonist or functional variant thereof.

In some embodiments, the one or more ionic liquid independently comprises a cation selected from the group consisting of aminoguanidine, choline or choline derivative, carnitine, acetylcholine, ammonium, tetramethyl ammonium, tetraethyl ammonium, tetrabutyl ammonium, and guanidine derivatives.

In some embodiments, the one or more ionic liquid independently comprises choline or choline derivative, carnitine, or acetylcholine.

In some embodiments, the one or more ionic liquid independently comprises an anion selected from the group consisting of (R)-ax-Lipoic Acid, 12-Hydroxystearic Acid, 2-(4-Isobutylphenyl)propionic Acid, 2-(4,4-Dimethyl-2-pentanyl)-5,7,7-trimethyloctanoic Acid, 2-Aminoethanesulfonic Acid (Taurine Acid), 2-Hexyldecanoic Acid, 2-Hydroxyhippuric Acid, 3-(4-Hydroxyphenyl)propionic Acid, 3-Methylcrotonic Acid, 3,3-Diphenylpropionic Acid, 3,4-Dihydroxbenzoic Acid (Protocatechuic Acid), 3,7-Dimethyloctanoic Acid, 4-Hydroxybenzenesulfonic Acid, 4-Hydroxybenzoic Acid, 4-Methylhexanoic Acid, 4-Methyloctanoic Acid, 4-Methylvaleric Acid, 5-Norbornene-2-carboxylic Acid, 8-[(2-hydroxybenzoyl)amino]octanoic acid, Abietic Acid, Acetic Acid, Acetylcysteine, Aconitic Acid, Arachidonic Acid, Behenic Acid, Benzoic Acid, Caffeic Acid, Chenodeoxycholic Acid, Cis-Cinnamic acid, Citric Acid, Citronellic Acid, Crotonic Acid, D-(+)-Galactonic Acid, Decanoic Acid, Deoxycholic Acid, Dihydrocaffeic Acid, DL-2-Phenylpropionic (Hydratropic) Acid, DL-Tartaric Acid, DL-Tropic Acid, Eicosanedioic Acid, Eicosapentanoic Acid (EPA), Elaidic Acid, Ellagic Acid, Erucic Acid, Ethylenediaminetetraacetic Acid (EDTA), Formic Acid, Fumaric Acid, Geranic Acid, Glutaric Acid, Glycolic Acid, Heptanoic Acid, Hexanoic Acid, Hydrocinnamic Acid (3-Phenylpropionic Acid), Isobutyric Acid, Isovaleric Acid, L-(+)-Tartaric Acid, L-Ascorbic Acid, L-Aspartic Acid, L-Glutamic Acid, L-Glutathione reduced, Lactic Acid, Lauric Acid, Levulinic Acid, Linoleic Acid, Linolenic Acid, Lithocholic Acid, Maleic Acid, Malic Acid, Malonic Acid, Mandelic acid, Mesaconic Acid, Nicotinic Acid, Nonanoic Acid, Octanoic Acid, Oleic Acid, Oxalic Acid, p-Coumaric Acid, p-Toluenesulfonic Acid, Palmitic Acid, Perillic Acid, Phosphoric Acid, Pimelic Acid, Pivalic Acid, Propionic Acid, Pyroglutamic Acid, Pyruvic Acid, Ricinoleic Acid, Salicylic Acid (2-Hydroxybenzoic Acid), Sinapinic Acid (3,5-Dimethoxy-4-Hydroxycinnamic Acid), Sorbic Acid, Stearic acid, Succinic Acid, Syringic Acid, Tiglic Acid, Trans-2-Decenoic Acid, Trans-2-Hexenoic Acid, Trans-2-Octenoic Acid, Trans-3-Octenoic Acid, Trans-γ-Octenoic Acid, Trans-Cinnamic Acid, Trans-Ferulic Acid, Undecanoic Acid, Valeric Acid, Vanillic Acid, and α-Ketoglutaric Acid.

In some embodiments, the one or more ionic liquid independently comprises an anion selected from the group consisting of glycolic acid, tartaric acid, malic acid, hydrocinnamic acid, citric acid, cinnamic acid, mandelic acid, mesaconic acid, ricinoleic acid, linoleic acid, and tiglic acid.

In some embodiments, the one or more ionic liquid independently comprises an anion selected from the group consisting of cinnamic acid, mandelic acid, citric acid, ricinoleic acid, linoleic acid, and tiglic acid.

In some embodiments, the one or more ionic liquid independently comprises choline or choline derivative-cinnamic acid, choline or choline derivative-mandelic acid, choline or choline derivative-citric acid, choline or choline derivative-ricinoleic acid, choline or choline derivative-linoleic acid, or choline or choline derivative-tiglic acid.

In some embodiments, the one or more ionic liquid independently comprises carnitine-cinnamic acid, carnitine-mandelic acid, carnitine-citric acid, carnitine-ricinoleic acid, carnitine-linoleic acid, or carnitine-tiglic acid.

In some embodiments, the one or more ionic liquid independently comprises acetylcholine-cinnamic acid, acetylcholine-mandelic acid, acetylcholine-citric acid, acetylcholine-ricinoleic acid, acetylcholine-linoleic acid, or acetylcholine-tiglic acid.

In some embodiments, the solubility of the therapeutic agent is increased relative to a therapeutic agent in a composition without a ionic liquid.

In some embodiments, the delivery efficiency of the therapeutic agent in a subject in need thereof is enhanced or improved when administered to the subject, relative to a therapeutic agent in a composition without a ionic liquid.

In some embodiments, the composition as provided herein further comprises at least one permeation enhancer.

In some embodiments, the at least one permeation enhancer is selected from the group consisting of salcaprozate sodium (SNAC), sodium caprylate, sodium caprate, a bile salt, ethylenediaminetetraacetic acid (EDTA), ethylene glycol-bis-(2-aminoethylether)-N,N,N',N'-tetraacetic acid (EGTA), and 3-[N,N-Dimethyl(3-palmitoylaminopropyl)-ammonio]-propanesulfonate (PPS), and any combination thereof.

In some embodiments, the bile salt is selected from the group consisting of sodium deoxycholate, sodium chenodeoxycholate, sodium taurodeoxycholate, and a combination thereof.

In another aspect, provided herein is a pharmaceutical composition comprising the compound as provided herein or the composition as provided herein, and at least one pharmaceutically acceptable excipient.

In some embodiments, the pharmaceutical composition as provided herein further comprises at least one permeation enhancer.

In some embodiments, the at least one permeation enhancer is selected from the group consisting of salcaprozate sodium (SNAC), sodium caprylate, sodium caprate, a bile salt, ethylenediaminetetraacetic acid (EDTA), ethylene glycol-bis-(2-aminoethylether)-N,N,N',N'-tetraacetic acid (EGTA), and 3-[N,N-Dimethyl(3-palmitoylaminopropyl)-ammonio]-propanesulfonate (PPS), and any combination thereof.

In some embodiments, the bile salt is selected from the group consisting of sodium deoxycholate, sodium chenodeoxycholate, sodium taurodeoxycholate, and a combination thereof.

In another aspect, provided herein is a method of treating a disease or disorder in a subject in need thereof, comprising administering to the subject a therapeutically effective amount of the compound as provided herein, the composition as provided herein, or the pharmaceutical composition as provided herein, wherein the administering is effective to treat the disease or disorder in the subject.

In some embodiments, the disease or disorder is a metabolic disease or disorder.

In some embodiments, the disease or disorder is diabetes mellitus.

In some embodiments, the disease or disorder is type 1 diabetes mellitus (T1DM).

In some embodiments, the disease or disorder is type 2 diabetes mellitus (T2DM).

In some embodiments, the disease or disorder is non-alcoholic steatohepatitis (NASH).

In some embodiments, the disease or disorder is obesity or overweight.

In some embodiments, the administration activates GIP receptor signaling, GLP-1 receptor signaling, or a combination thereof.

In some embodiments, the administration increases or improves glucose-dependent insulin secretion, improves glucose tolerance, or a combination thereof.

In some embodiments, the administration increases or improves blood sugar control.

In some embodiments, the administration decreases or reduces fasting serum glucose.

In some embodiments, the administration decreases or reduces body weight, decreases or reduces food intake, or a combination thereof.

In some embodiments, the administration delivers improvement in glycaemic control, body weight, or a combination thereof.

In some embodiments, the disease or disorder is an autoimmune or immunological disease or disorder.

In some embodiments, the disease or disorder is Crohn's disease, ulcerative colitis, rheumatoid arthritis, ankylosing spondylitis, psoriasis, psoriatic arthritis, Behret's disease, plaque psoriasis, hidradenitis suppurativa, uveitis, and juvenile idiopathic arthritis, plaque psoriasis, multiple sclerosis, or eosinophilic esophagitis.

In another aspect, provided herein is a method of treating obesity, preventing weight gain, or reducing weight in a subject in need thereof, comprising administering to the subject a therapeutically effective amount of the compound as provided herein, the composition as provided herein, or the pharmaceutical composition as provided herein, wherein the administering is effective to treat the disease or disorder in the subject.

In some embodiments, the composition, the compound, or the pharmaceutical composition is administered via subcutaneous, intravenous, or oral administration.

In some embodiments, the composition, the compound, or the pharmaceutical composition is administered orally.

In some embodiments, the composition, the compound, or the pharmaceutical composition is administered as a liquid-filled capsule.

In some embodiments, the composition, the compound, or the pharmaceutical composition is administered in multiple doses.

In some embodiments, the composition, the compound, or the pharmaceutical composition is administered in a single dose.

In some embodiments, the composition, the compound, or the pharmaceutical composition is administered to a mucus membrane.

In some embodiments, the composition, the compound, or the pharmaceutical composition is administered via subcutaneous, intravenous, or oral administration.

In some embodiments, the concentration of the compound as provided herein is at least 0.1% weight per volume.

In some embodiments, the concentration of the compound as provided herein is at least 0.05M.

In some embodiments, the composition further comprises one or more additional agents.

In some embodiments, the one or more additional agent is selected from the group consisting of a nucleic acid, a small molecule, and a polypeptide.

In some embodiments, the one or more additional agent is a nucleic acid.

In some embodiments, the one or more additional agent is a small molecule.

In some embodiments, the one or more additional agent is a polypeptide.

In some embodiments, the one or more additional agent is a polypeptide.

In some embodiments, the one or more additional agents is a therapeutic that treats a metabolic disease or disorder.

In some embodiments, the one or more additional agents is a therapeutic that treats diabetes mellitus.

In some embodiments, the one or more additional agents is a therapeutic that treats type 2 diabetes mellitus (T2DM).

In some embodiments, the one or more additional agents is a therapeutic that treats obesity or overweight.

In another aspect, provided herein is a method of increasing the solubility of a therapeutic agent comprising: preparing a composition comprising a compound according to Formula I:

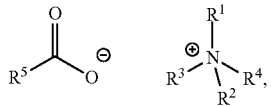

Formula I wherein:
$R^1$, $R^2$, and $R^3$ are independently $C_1$-$C_5$ alkyl;
$R^4$ is $C_2$-$C_5$ alkyl, wherein the $C_2$-$C_5$ alkyl is unsubstituted or substituted with 1 or more hydroxyl; and
$R^5$ is the therapeutic agent;
wherein the therapeutic agent is:
(i) an GLP-1 analog or functional variant thereof or mimetic thereof, Liraglutide, Exenatide, Peptide tyrosine tyrosine (YY), glucagon, gastric inhibitory polypeptide (GIP), or amylin;
(ii) an amylin or mimetic or analog thereof, or an amylin analog or functional variant thereof or mimetic or analog thereof;
(iii) wherein the therapeutic agent is an antibody or an antibody fragment thereof;
(iv) a dual GIP/GLP-1 receptor agonist or functional variant thereof.

In another aspect, provided herein is a method of enhancing or improving the delivery efficiency of a therapeutic agent in a subject in need thereof comprising preparing a composition comprising a compound according to Formula I:

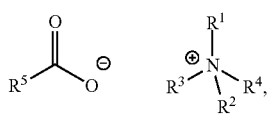

Formula I wherein:
$R^1$, $R^2$, and $R^3$ are independently $C_1$-$C_5$ alkyl;
$R^4$ is $C_2$-$C_5$ alkyl, wherein the $C_2$-$C_5$ alkyl is unsubstituted or substituted with 1 or more hydroxyl; and
$R^5$ is the therapeutic agent;
wherein the therapeutic agent is:
(i) an GLP-1 analog or functional variant thereof or mimetic thereof, Liraglutide, Exenatide, Peptide tyrosine tyrosine (YY), glucagon, gastric inhibitory polypeptide (GIP), or amylin;
(ii) an amylin or mimetic or analog thereof, or an amylin analog or functional variant thereof or mimetic or analog thereof;
(iii) wherein the therapeutic agent is an antibody or an antibody fragment thereof;
(iv) a dual GIP/GLP-1 receptor agonist or functional variant thereof.

In some embodiments, $R^1$, $R^2$, and $R^3$ are methyl.
In some embodiments, $R^1$, $R^2$, and $R^3$ are ethyl.
In some embodiments, $R^1$, $R^2$, and $R^3$ are propyl.
In some embodiments, $R^1$ and $R^2$ are methyl, and $R^3$ is ethyl.
In some embodiments, $R^1$ and $R^3$ are methyl, and $R^2$ is ethyl.
In some embodiments, $R^1$ and $R^2$ are ethyl, and $R^3$ is methyl.
In some embodiments, $R^1$ and $R^3$ are ethyl, and $R^2$ is methyl.
In some embodiments, $R^1$ and $R^2$ are propyl, and $R^3$ is methyl.
In some embodiments, $R^1$ and $R^3$ are propyl, and $R^2$ is methyl.
In some embodiments, $R^4$ is $C_2$-$C_5$ alkyl substituted with a hydroxyl.
In some embodiments, $R^4$ is

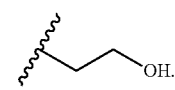

In some embodiments, the compound is according to Formula Ia:

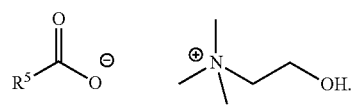

Formula Ia

In some embodiments, in the compound is according to Formula Ib:

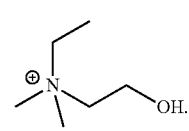

Formula Ib

In some embodiments, the compound is according to Formula Ic:

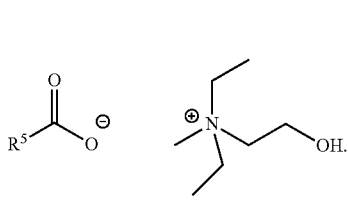

Formula Ic

In some embodiments, the therapeutic agent is the GLP-1 analog or functional variant thereof or mimetic thereof, Liraglutide, Exenatide, Peptide tyrosine tyrosine (YY), glucagon, gastric inhibitory polypeptide (GIP), or amylin.

In some embodiments, the therapeutic agent is an GLP-1 analog or functional variant thereof or mimetic thereof.

In some embodiments, the compound comprises the structure as shown in FIG. 16.

In some embodiments, the compound comprises a

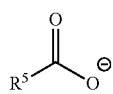

to

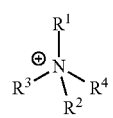

molar ratio of from about 1:1 to about 1:60.

In some embodiments, the compound comprises a

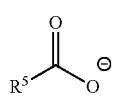

to

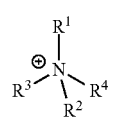

molar ratio of from about 1:1 to about 1:30.

In some embodiments, the compound comprises a

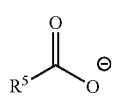

to

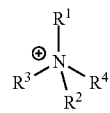

molar ratio of about 1:1.

In some embodiments, the compound comprises a

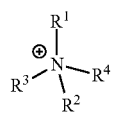

to

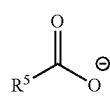

molar ratio of about 1:3.

In some embodiments, the compound comprises a

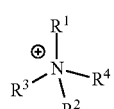

to

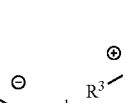

molar ratio of about 1:4.

In some embodiments, the compound comprises a

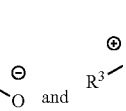

molar ratio of about 1:7.

In some embodiments, the compound comprises a

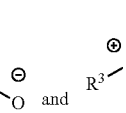

molar ratio of about 1:12.

In some embodiments, the compound comprises a

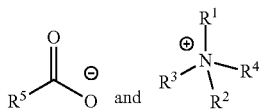

molar ratio of about 1:14.

In some embodiments, the compound comprises a

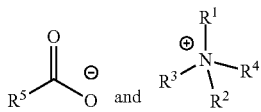

molar ratio of about 1:28.

In some embodiments, the compound comprises a

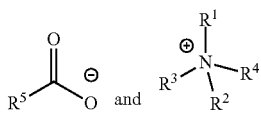

molar ratio of about 1:56.

In some embodiments, the therapeutic agent is an amylin or mimetic or analog thereof, or an amylin analog or functional variant thereof or mimetic or analog thereof.

In some embodiments, the therapeutic agent is an amylin analog or functional variant thereof or mimetic or analog thereof.

In some embodiments, the therapeutic agent is an amylin analog or functional variant thereof or mimetic or analog thereof having the sequence of: [diacid]-[linker]-KCNTAT-CATQRLANFLVHSSNNFGPILPPTNVGSNTY-amide (SEQ ID NO: 21).

In some embodiments, the therapeutic agent is an amylin analog or functional variant thereof or mimetic or analog thereof having the structure as shown in FIGS. 2A, 2B, and 2C, FIG. 3A and FIG. 3B, or FIG. 4A and FIG. 4B.

In some embodiments, the therapeutic agent is an amylin analog or functional variant thereof or mimetic or analog thereof comprising an amino acid substitution of N14E, V17R, Y37P, F15E, L16E, V17E, or any combination thereof.

In some embodiments, the therapeutic agent is an amylin analog or functional variant thereof or mimetic or analog thereof comprising an amino acid substitution of N14E.

In some embodiments, the compound comprises a

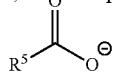

to

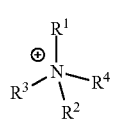

molar ratio of from about 1:1 to about 1:30.

In some embodiments, the compound comprises a

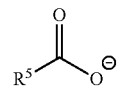

to

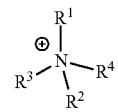

molar ratio of about 1:1.

In some embodiments, the compound comprises a

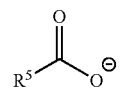

to

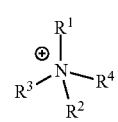

molar ratio of about 1:3.

In some embodiments, the compound comprises a

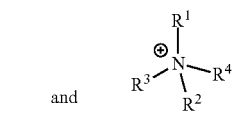

molar ratio of about 1:7.

In some embodiments, the compound comprises a

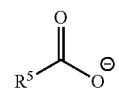

to

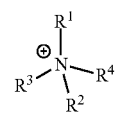

molar ratio of about 1:12.

In some embodiments, the compound comprises a

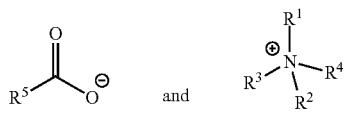

molar ratio of about 1:28.

In some embodiments, the therapeutic agent is an antibody or an antibody fragment thereof.

In some embodiments, the therapeutic agent is any one selected from the group consisting of infliximab or an antibody fragment thereof, adalimumab or an antibody fragment thereof, ustekinumab or an antibody fragment thereof, golimumab or an antibody fragment thereof, natalizumab or an antibody fragment thereof, vedolizumab or an antibody fragment thereof, and certolizumab pegol or an antibody fragment thereof.

In some embodiments, the therapeutic agent comprises:
(i) a sequence with at least 75% sequence identity to the sequence of SEQ ID NO: 1 or SEQ ID NO: 24, a sequence with at least 75% sequence identity to the sequence of SEQ ID NO: 2, or a combination thereof;
(ii) a sequence with at least 75% sequence identity to the sequence of SEQ ID NO: 3, SEQ ID NO: 4, or SEQ ID NO: 5, a sequence with at least 75% sequence identity to the sequence of SEQ ID NO: 6 or SEQ ID NO: 7, or any combination thereof;
(iii) a sequence with at least 75% sequence identity to the sequence of SEQ ID NO: 8, a sequence with at least 75% sequence identity to the sequence of SEQ ID NO: 9, or a combination thereof;
(iv) a sequence with at least 75% sequence identity to the sequence of SEQ ID NO: 10, a sequence with at least 75% sequence identity to the sequence of SEQ ID NO: 11, or a combination thereof;
(v) a sequence with at least 75% sequence identity to the sequence of SEQ ID NO: 12 or SEQ ID NO: 13, a sequence with at least 75% sequence identity to the sequence of SEQ ID NO: 14 or SEQ ID NO: 15, or any combination thereof;
(vi) a sequence with at least 75% sequence identity to the sequence of SEQ ID NO: 16, a sequence with at least 75% sequence identity to the sequence of SEQ ID NO: 17, or a combination thereof, or
(vii) a sequence with at least 75% sequence identity to the sequence of SEQ ID NO: 18, a sequence with at least 75% sequence identity to the sequence of SEQ ID NO: 19, or a combination thereof.

In some embodiments, the therapeutic agent comprises:
(i) the sequence of SEQ ID NO: 1 or SEQ ID NO: 24, the sequence of SEQ ID NO: 2, or a combination thereof;
(ii) the sequence of SEQ ID NO: 3, SEQ ID NO: 4, or SEQ ID NO: 5, the sequence of SEQ ID NO: 6 or SEQ ID NO: 7, or any combination thereof;
(iii) the sequence of SEQ ID NO: 8, the sequence of SEQ ID NO: 9, or a combination thereof;
(iv) the sequence of SEQ ID NO: 10, the sequence of SEQ ID NO: 11, or a combination thereof;
(v) the sequence of SEQ ID NO: 12 or SEQ ID NO: 13, the sequence of SEQ ID NO: 14 or SEQ ID NO: 15, or any combination thereof;
(vi) the sequence of SEQ ID NO: 16, the sequence of SEQ ID NO: 17, or a combination thereof; or
(vii) the sequence of SEQ ID NO: 18, the sequence of SEQ ID NO: 19, or a combination thereof.

In some embodiments, the therapeutic agent comprises:
(i) the sequence of SEQ ID NO: 1 or SEQ ID NO: 24, and the sequence of SEQ ID NO: 2;
(ii) the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7;
(iii) the sequence of SEQ ID NO: 8 and the sequence of SEQ ID NO: 9;
(iv) the sequence of SEQ ID NO: 10 and the sequence of SEQ ID NO: 11;
(v) the sequence of SEQ ID NO: 12 and the sequence of SEQ ID NO: 14, or the sequence of SEQ ID NO: 13 and the sequence of SEQ ID NO: 15;
(vi) the sequence of SEQ ID NO: 16 and the sequence of SEQ ID NO: 17; or
(vii) the sequence of SEQ ID NO: 18 and the sequence of SEQ ID NO: 19.

In some embodiments, the therapeutic agent is infliximab or an antibody fragment thereof.

In some embodiments, the therapeutic agent comprises the sequence of SEQ ID NO: 1 or SEQ ID NO: 24, and the sequence of SEQ ID NO: 2.

In some embodiments, the compound comprises a

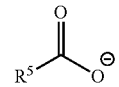

to

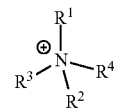

molar ratio of from about 1:1 to about 1:164.

In some embodiments, the compound comprises a

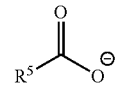

to

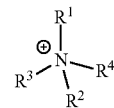

molar ratio of about 1:1.

In some embodiments, the compound comprises a

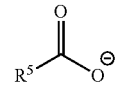

to

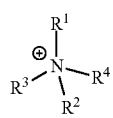

molar ratio of about 1:33.

In some embodiments, the compound comprises a

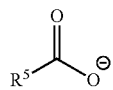

to

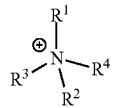

molar ratio of about 1:41.

In some embodiments, the compound comprises a

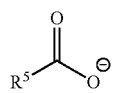

to

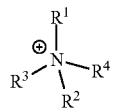

molar ratio of about 1:66.

In some embodiments, the compound comprises a

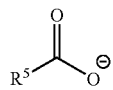

to

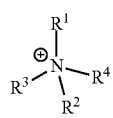

molar ratio of about 1:82.

In some embodiments, the compound comprises a

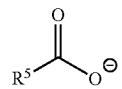

to

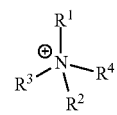

molar ratio of about 1:132.

In some embodiments, the compound comprises a

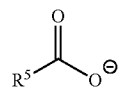

to

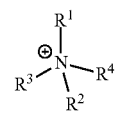

molar ratio of about 1:164.

In some embodiments, the therapeutic agent is adalimumab or an antibody fragment thereof.

In some embodiments, the therapeutic agent comprises the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7.

In some embodiments, the compound comprises a

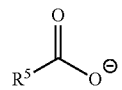

to

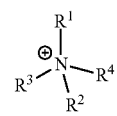

molar ratio of from about 1:1 to about 1:144.

In some embodiments, the therapeutic agent is ustekinumab or an antibody fragment thereof.

In some embodiments, the therapeutic agent comprises the sequence of SEQ ID NO: 8 and the sequence of SEQ ID NO: 9.

In some embodiments, the compound comprises a

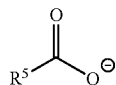

to

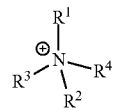

molar ratio of from about 1:1 to about 1:140.

In some embodiments, the therapeutic agent is golimumab or an antibody fragment thereof.

In some embodiments, the therapeutic agent comprises the sequence of SEQ ID NO: 10 and the sequence of SEQ ID NO: 11.

In some embodiments, the compound comprises a

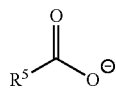

to

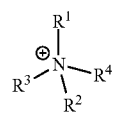

molar ratio of from about 1:1 to about 1:80.

In some embodiments, the therapeutic agent is natalizumab or an antibody fragment thereof.

In some embodiments, the therapeutic agent comprises the sequence of SEQ ID NO: 12 and the sequence of SEQ ID NO: 14, or the sequence of SEQ ID NO: 13 and the sequence of SEQ ID NO: 15.

In some embodiments, the compound comprises a

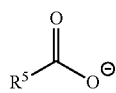

to

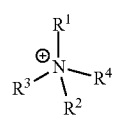

molar ratio of from about 1:1 to about 1:156.

In some embodiments, the therapeutic agent is vedolizumab or an antibody fragment thereof.

In some embodiments, the therapeutic agent comprises the sequence of SEQ ID NO: 16 and the sequence of SEQ ID NO: 17.

In some embodiments, the compound comprises a

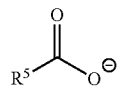

to

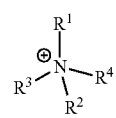

molar ratio of from about 1:1 to about 1:256.

In some embodiments, the therapeutic agent is certolizumab pegol or an antibody fragment thereof.

In some embodiments, the therapeutic agent comprises the sequence of SEQ ID NO: 18 and the sequence of SEQ ID NO: 19.

In some embodiments, the compound comprises a

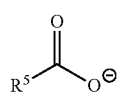

to

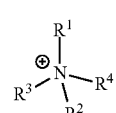

molar ratio of from about 1:1 to about 1:70.

In some embodiments, the therapeutic agent is the dual GIP/GLP-1 receptor agonist or functional variant thereof.

In some embodiments, $R^5$ comprises a sequence with at least 75% sequence identity to the sequence of SEQ ID NO: 25.

In some embodiments, $R^5$ comprises the sequence of SEQ ID NO: 25.

In some embodiments, $R^5$ comprises C20 diacid-γ-Glu-(AEEA)2 attached to a residue of a sequence with at least 75% sequence identity to the sequence of SEQ ID NO: 25.

In some embodiments, $R^5$ comprises C20 diacid-γ-Glu-(AEEA)2 attached to a residue of the sequence of SEQ ID NO: 25.

In some embodiments, $R^5$ comprises C20 diacid-γ-Glu-(AEEA)2 attached to the Lys residue at the position 20 from the N-terminus of the sequence of SEQ ID NO: 25.

In some embodiments, the compound comprises a

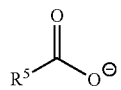

to

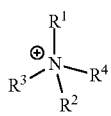

molar ratio of from about 1:1 to about 1:20.

In some embodiments, the compound comprises a

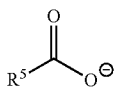

to

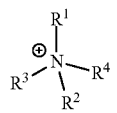

molar ratio of about 1:1.

In some embodiments, the compound comprises a

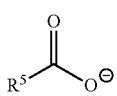

to

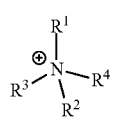

molar ratio of about 1:2.

In some embodiments, the compound comprises a

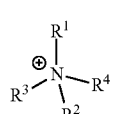

to (structure)

molar ratio of about 1:3.

In some embodiments, the compound comprises a

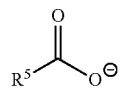

to

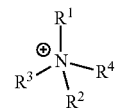

molar ratio of about 1:4.

In some embodiments, the compound comprises a

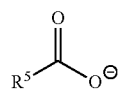

to

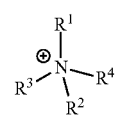

molar ratio of about 1:5.

In some embodiments, the compound comprises a

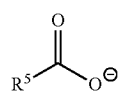

to

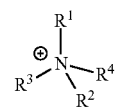

molar ratio of about 1:10.

In some embodiments, the compound comprises a

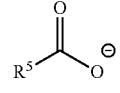

to

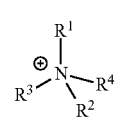

molar ratio of about 1:20.

In another aspect, provided herein is a method of increasing the solubility of a therapeutic agent comprising preparing a composition comprising a compound according to Formula II:

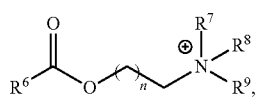

Formula II wherein:
R⁶ is the therapeutic agent, wherein the therapeutic agent is:
(i) an GLP-1 analog or functional variant thereof or mimetic thereof, Liraglutide, Exenatide, Peptide tyrosine tyrosine (YY), glucagon, gastric inhibitory polypeptide (GIP), or amylin;
(ii) an amylin or mimetic or analog thereof, or an amylin analog or functional variant thereof or mimetic or analog thereof;
(iii) an antibody or an antibody fragment thereof; or
(iv) a dual GIP/GLP-1 receptor agonist or functional variant thereof;
R⁷, R⁸, and R⁹ are independently unsubstituted or substituted C₁-C₅ alkyl; and
n is 1, 2, 3, 4, or 5.

In another aspect, provided herein is a method of enhancing or improving the delivery efficiency a therapeutic agent in a subject in need thereof comprising preparing a composition comprising compound according to Formula II:

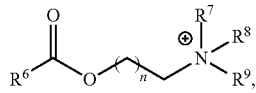

Formula II wherein:
R⁶ is the therapeutic agent, wherein the therapeutic agent is:
(i) an GLP-1 analog or functional variant thereof or mimetic thereof, Liraglutide, Exenatide, Peptide tyrosine tyrosine (YY), glucagon, gastric inhibitory polypeptide (GIP), or amylin;
(ii) an amylin or mimetic or analog thereof, or an amylin analog or functional variant thereof or mimetic or analog thereof;
(iii) an antibody or an antibody fragment thereof; or
(iv) a dual GIP/GLP-1 receptor agonist or functional variant thereof,
R⁷, R⁸, and R⁹ are independently unsubstituted or substituted C₁-C₅ alkyl; and
n is 1, 2, 3, 4, or 5, and
administering the composition to the subject.

In some embodiments, R⁷, R⁸, and R⁹ are methyl.
In some embodiments, R⁷, R⁸, and R⁹ are ethyl.
In some embodiments, R⁷, R⁸, and R⁹ are propyl.
In some embodiments, R⁷ and R⁸ are methyl, and R⁹ is ethyl.
In some embodiments, R⁷ and R⁹ are methyl, and R⁸ is ethyl.
In some embodiments, R⁷ and R⁸ are ethyl, and R⁹ is methyl.
In some embodiments, R⁷ and R⁹ are ethyl, and R⁸ is methyl.
In some embodiments, R⁷ and R⁸ are propyl, and R⁹ is methyl.
In some embodiments, R⁷ and R⁹ are propyl, and R⁸ is methyl.
In some embodiments, n is 1.
In some embodiments, the compound is according to Formula IIa:

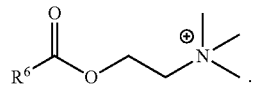

Formula IIa

In some embodiments, the compound is according to Formula IIb:

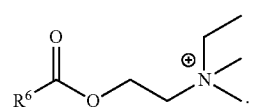

Formula IIb

In some embodiments, the compound is according to Formula IIc:

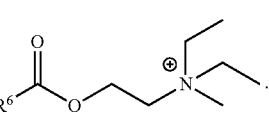

Formula IIc

In some embodiments, the therapeutic agent is the GLP-1 analog or functional variant thereof or mimetic thereof, Liraglutide, Exenatide, Peptide tyrosine tyrosine (YY), glucagon, gastric inhibitory polypeptide (GIP), or amylin.
In some embodiments, the therapeutic agent is the GLP-1 analog or functional variant thereof or mimetic thereof.
In some embodiments, the compound comprises the structure as shown in FIG. 17B.
In some embodiments, the therapeutic agent is an amylin or mimetic or analog thereof, or an amylin analog or functional variant thereof or mimetic or analog thereof.
In some embodiments, the therapeutic agent is an amylin analog or functional variant thereof or mimetic or analog thereof.
In some embodiments, the therapeutic agent is an amylin analog or functional variant thereof or mimetic or analog thereof having the sequence of:

(SEQ ID NO: 21)
[diacid]-[linker]-KCNTATCATQRLANFLVHSSNNFGPILPPTNV
GSNTY-amide.

In some embodiments, the therapeutic agent is an amylin analog or functional variant thereof or mimetic or analog thereof having the structure as shown in FIGS. 2A, 2B, and 2C, FIG. 3A and FIG. 3B, or FIG. 4A and FIG. 4B.
In some embodiments, the therapeutic agent is an amylin analog or functional variant thereof or mimetic or analog thereof comprising an amino acid substitution of N14E, V17R, Y37P, F15E, L16E, V17E, or any combination thereof.

In some embodiments, the therapeutic agent is an amylin analog or functional variant thereof or mimetic or analog thereof comprising an amino acid substitution of N14E.

In some embodiments, the therapeutic agent is an antibody or an antibody fragment thereof.

In some embodiments, the therapeutic agent is any one selected from the group consisting of infliximab or an antibody fragment thereof, adalimumab or an antibody fragment thereof, ustekinumab or an antibody fragment thereof, golimumab or an antibody fragment thereof, natalizumab or an antibody fragment thereof, vedolizumab or an antibody fragment thereof, and certolizumab pegol or an antibody fragment thereof.

In some embodiments, the therapeutic agent comprises:
(i) a sequence with at least 75% sequence identity to the sequence of SEQ ID NO: 1 or SEQ ID NO: 24, a sequence with at least 75% sequence identity to the sequence of SEQ ID NO: 2, or a combination thereof;
(ii) a sequence with at least 75% sequence identity to the sequence of SEQ ID NO: 3, SEQ ID NO: 4, or SEQ ID NO: 5, a sequence with at least 75% sequence identity to the sequence of SEQ ID NO: 6 or SEQ ID NO: 7, or any combination thereof;
(iii) a sequence with at least 75% sequence identity to the sequence of SEQ ID NO: 8, a sequence with at least 75% sequence identity to the sequence of SEQ ID NO: 9, or a combination thereof;
(iv) a sequence with at least 75% sequence identity to the sequence of SEQ ID NO: 10, a sequence with at least 75% sequence identity to the sequence of SEQ ID NO: 11, or a combination thereof;
(v) a sequence with at least 75% sequence identity to the sequence of SEQ ID NO: 12 or SEQ ID NO: 13, a sequence with at least 75% sequence identity to the sequence of SEQ ID NO: 14 or SEQ ID NO: 15, or any combination thereof;
(vi) a sequence with at least 75% sequence identity to the sequence of SEQ ID NO: 16, a sequence with at least 75% sequence identity to the sequence of SEQ ID NO: 17, or a combination thereof; or
(vii) a sequence with at least 75% sequence identity to the sequence of SEQ ID NO: 18, a sequence with at least 75% sequence identity to the sequence of SEQ ID NO: 19, or a combination thereof.

In some embodiments, the therapeutic agent comprises:
(i) the sequence of SEQ ID NO: 1 or SEQ ID NO: 24, the sequence of SEQ ID NO: 2, or a combination thereof;
(ii) the sequence of SEQ ID NO: 3, SEQ ID NO: 4, or SEQ ID NO: 5, the sequence of SEQ ID NO: 6 or SEQ ID NO: 7, or any combination thereof;
(iii) the sequence of SEQ ID NO: 8, the sequence of SEQ ID NO: 9, or a combination thereof;
(iv) the sequence of SEQ ID NO: 10, the sequence of SEQ ID NO: 11, or a combination thereof;
(v) the sequence of SEQ ID NO: 12 or SEQ ID NO: 13, the sequence of SEQ ID NO: 14 or SEQ ID NO: 15, or any combination thereof;
(vi) the sequence of SEQ ID NO: 16, the sequence of SEQ ID NO: 17, or a combination thereof; or
(vii) the sequence of SEQ ID NO: 18, the sequence of SEQ ID NO: 19, or a combination thereof.

In some embodiments, the therapeutic agent comprises:
(i) the sequence of SEQ ID NO: 1 or SEQ ID NO: 24, and the sequence of SEQ ID NO: 2;
(ii) the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7;
(iii) the sequence of SEQ ID NO: 8 and the sequence of SEQ ID NO: 9;
(iv) the sequence of SEQ ID NO: 10 and the sequence of SEQ ID NO: 11;
(v) the sequence of SEQ ID NO: 12 and the sequence of SEQ ID NO: 14, or the sequence of SEQ ID NO: 13 and the sequence of SEQ ID NO: 15;
(vi) the sequence of SEQ ID NO: 16 and the sequence of SEQ ID NO: 17; or
(vii) the sequence of SEQ ID NO: 18 and the sequence of SEQ ID NO: 19.

In some embodiments, the therapeutic agent is infliximab or an antibody fragment thereof.

In some embodiments, the therapeutic agent comprises the sequence of SEQ ID NO: 1 or SEQ ID NO: 24, and the sequence of SEQ ID NO: 2.

In some embodiments, the therapeutic agent is adalimumab or an antibody fragment thereof.

In some embodiments, the therapeutic agent comprises the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7.

In some embodiments, the therapeutic agent is ustekinumab or an antibody fragment thereof.

In some embodiments, the therapeutic agent comprises the sequence of SEQ ID NO: 8 and the sequence of SEQ ID NO: 9.

In some embodiments, the therapeutic agent is golimumab or an antibody fragment thereof.

In some embodiments, the therapeutic agent comprises the sequence of SEQ ID NO: 10 and the sequence of SEQ ID NO: 11.

In some embodiments, the therapeutic agent is natalizumab or an antibody fragment thereof.

In some embodiments, the therapeutic agent comprises the sequence of SEQ ID NO: 12 and the sequence of SEQ ID NO: 14, or the sequence of SEQ ID NO: 13 and the sequence of SEQ ID NO: 15.

In some embodiments, the therapeutic agent is vedolizumab or an antibody fragment thereof.

In some embodiments, the therapeutic agent comprises the sequence of SEQ ID NO: 16 and the sequence of SEQ ID NO: 17.

In some embodiments, the therapeutic agent is certolizumab pegol or an antibody fragment thereof.

In some embodiments, the therapeutic agent comprises the sequence of SEQ ID NO: 18 and the sequence of SEQ ID NO: 19.

In some embodiments, the therapeutic agent the GLP-1 analog or functional variant thereof or mimetic thereof, Liraglutide.

In some embodiments, $R^6$ comprises a sequence with at least 75% sequence identity to the sequence of SEQ ID NO: 25.

In some embodiments, $R^6$ comprises the sequence of SEQ ID NO: 25.

In some embodiments, $R^6$ comprises C20 diacid-$\gamma$-Glu-(AEEA)2 attached to a residue of a sequence with at least 75% sequence identity to the sequence of SEQ ID NO: 25.

In some embodiments, $R^6$ comprises C20 diacid-$\gamma$-Glu-(AEEA)2 attached to a residue of the sequence of SEQ ID NO: 25.

In some embodiments, $R^6$ comprises C20 diacid-γ-Glu-(AEEA)2 attached to the Lys residue at the position 20 from the N-terminus of the sequence of SEQ ID NO: 25.

In some embodiments, the composition further comprises one or more ionic liquid.

In some embodiments, the one or more ionic liquid independently comprises a cation selected from the group consisting of aminoguanidine, choline or choline derivative, carnitine, acetylcholine, ammonium, tetramethyl ammonium, tetraethyl ammonium, tetrabutyl ammonium, and guanidine derivatives.

In some embodiments, the one or more ionic liquid independently comprises choline or choline derivative, carnitine, or acetylcholine.

In some embodiments, the one or more ionic liquid independently comprises an anion selected from the group consisting of (R)-ax-Lipoic Acid, 12-Hydroxystearic Acid, 2-(4-Isobutylphenyl)propionic Acid, 2-(4,4-Dimethyl-2-pentanyl)-5,7,7-trimethyloctanoic Acid, 2-Aminoethanesulfonic Acid (Taurine Acid), 2-Hexyldecanoic Acid, 2-Hydroxyhippuric Acid, 3-(4-Hydroxyphenyl)propionic Acid, 3-Methylcrotonic Acid, 3,3-Diphenylpropionic Acid, 3,4-Dihydroxbenzoic Acid (Protocatechuic Acid), 3,7-Dimethyloctanoic Acid, 4-Hydroxybenzenesulfonic Acid, 4-Hydroxybenzoic Acid, 4-Methylhexanoic Acid, 4-Methyloctanoic Acid, 4-Methylvaleric Acid, 5-Norbornene-2-carboxylic Acid, 8-[(2-hydroxybenzoyl)amino]octanoic acid, Abietic Acid, Acetic Acid, Acetylcysteine, Aconitic Acid, Arachidonic Acid, Behenic Acid, Benzoic Acid, Caffeic Acid, Chenodeoxycholic Acid, Cis-Cinnamic acid, Citric Acid, Citronellic Acid, Crotonic Acid, D-(+)-Galactonic Acid, Decanoic Acid, Deoxycholic Acid, Dihydrocaffeic Acid, DL-2-Phenylpropionic (Hydratropic) Acid, DL-Tartaric Acid, DL-Tropic Acid, Eicosanedioic Acid, Eicosapentanoic Acid (EPA), Elaidic Acid, Ellagic Acid, Erucic Acid, Ethylenediaminetetraacetic Acid (EDTA), Formic Acid, Fumaric Acid, Geranic Acid, Glutaric Acid, Glycolic Acid, Heptanoic Acid, Hexanoic Acid, Hydrocinnamic Acid (3-Phenylpropionic Acid), Isobutyric Acid, Isovaleric Acid, L-(+)-Tartaric Acid, L-Ascorbic Acid, L-Aspartic Acid, L-Glutamic Acid, L-Glutathione reduced, Lactic Acid, Lauric Acid, Levulinic Acid, Linoleic Acid, Linolenic Acid, Lithocholic Acid, Maleic Acid, Malic Acid, Malonic Acid, Mandelic acid, Mesaconic Acid, Nicotinic Acid, Nonanoic Acid, Octanoic Acid, Oleic Acid, Oxalic Acid, p-Coumaric Acid, p-Toluenesulfonic Acid, Palmitic Acid, Perillic Acid, Phosphoric Acid, Pimelic Acid, Pivalic Acid, Propionic Acid, Pyroglutamic Acid, Pyruvic Acid, Ricinoleic Acid, Salicylic Acid (2-Hydroxybenzoic Acid), Sinapinic Acid (3,5-Dimethoxy-4-Hydroxycinnamic Acid), Sorbic Acid, Stearic acid, Succinic Acid, Syringic Acid, Tiglic Acid, Trans-2-Decenoic Acid, Trans-2-Hexenoic Acid, Trans-2-Octenoic Acid, Trans-3-Octenoic Acid, Trans-γ-Octenoic Acid, Trans-Cinnamic Acid, Trans-Ferulic Acid, Undecanoic Acid, Valeric Acid, Vanillic Acid, and α-Ketoglutaric Acid.

In some embodiments, the one or more ionic liquid independently comprises an anion selected from the group consisting of glycolic acid, tartaric acid, malic acid, hydrocinnamic acid, citric acid, cinnamic acid, mandelic acid, mesaconic acid, ricinoleic acid, linoleic acid, and tiglic acid.

In some embodiments, the one or more ionic liquid independently comprises an anion selected from the group consisting of cinnamic acid, mandelic acid, citric acid, ricinoleic acid, linoleic acid, and tiglic acid.

In some embodiments, the one or more ionic liquid independently comprises choline or choline derivative-cinnamic acid, choline or choline derivative-mandelic acid, choline or choline derivative-citric acid, choline or choline derivative-ricinoleic acid, choline or choline derivative-linoleic acid, or choline or choline derivative-tiglic acid.

In some embodiments, the one or more ionic liquid independently comprises carnitine-cinnamic acid, carnitine-mandelic acid, carnitine-citric acid, carnitine-ricinoleic acid, carnitine-linoleic acid, or carnitine-tiglic acid.

In some embodiments, the one or more ionic liquid independently comprises acetylcholine-cinnamic acid, acetylcholine-mandelic acid, acetylcholine-citric acid, acetylcholine-ricinoleic acid, acetylcholine-linoleic acid, or acetylcholine-tiglic acid.

In another aspect, provided herein is a method of increasing the solubility of a therapeutic agent comprising preparing a composition comprising the therapeutic agent and one or more ionic liquid,
wherein the therapeutic agent is:
(i) an GLP-1 analog or functional variant thereof or mimetic thereof, Liraglutide, Exenatide, Peptide tyrosine tyrosine (YY), glucagon, gastric inhibitory polypeptide (GIP), or amylin;
(ii) an amylin or mimetic or analog thereof, or an amylin analog or functional variant thereof or mimetic or analog thereof;
(iii) an antibody or an antibody fragment thereof; or
(iv) a dual GIP/GLP-1 receptor agonist or functional variant thereof.

In another aspect, provided herein is a method of enhancing or improving the delivery efficiency of a therapeutic agent in a subject in need thereof comprising preparing a composition comprising the therapeutic agent and one or more ionic liquid, and
administering the composition to the subject,
wherein the therapeutic agent is:
(i) an GLP-1 analog or functional variant thereof or mimetic thereof, Liraglutide, Exenatide, Peptide tyrosine tyrosine (YY), glucagon, gastric inhibitory polypeptide (GIP), or amylin;
(ii) an amylin or mimetic or analog thereof, or an amylin analog or functional variant thereof or mimetic or analog thereof;
(iii) an antibody or an antibody fragment thereof; or
(iv) a dual GIP/GLP-1 receptor agonist or functional variant thereof.

In some embodiments, the one or more ionic liquid independently comprises a cation selected from the group consisting of aminoguanidine, choline or choline derivative, carnitine, acetylcholine, ammonium, tetramethyl ammonium, tetraethyl ammonium, tetrabutyl ammonium, and guanidine derivatives.

In some embodiments, the one or more ionic liquid independently comprises choline or choline derivative, carnitine, or acetylcholine.

In some embodiments, the one or more ionic liquid independently comprises an anion selected from the group consisting of (R)-ax-Lipoic Acid, 12-Hydroxystearic Acid, 2-(4-Isobutylphenyl)propionic Acid, 2-(4,4-Dimethyl-2-pentanyl)-5,7,7-trimethyloctanoic Acid, 2-Aminoethanesulfonic Acid (Taurine Acid), 2-Hexyldecanoic Acid, 2-Hydroxyhippuric Acid, 3-(4-Hydroxyphenyl)propionic Acid, 3-Methylcrotonic Acid, 3,3-Diphenylpropionic Acid, 3,4-Dihydroxbenzoic Acid (Protocatechuic Acid), 3,7-Dimethyloctanoic Acid, 4-Hydroxybenzenesulfonic Acid, 4-Hydroxybenzoic Acid, 4-Methylhexanoic Acid, 4-Methyloctanoic Acid, 4-Methylvaleric Acid, 5-Norbornene-2-carboxylic Acid, 8-[(2-hydroxybenzoyl)amino]

octanoic acid, Abietic Acid, Acetic Acid, Acetylcysteine, Aconitic Acid, Arachidonic Acid, Behenic Acid, Benzoic Acid, Caffeic Acid, Chenodeoxycholic Acid, Cis-Cinnamic acid, Citric Acid, Citronellic Acid, Crotonic Acid, D-(+)-Galactonic Acid, Decanoic Acid, Deoxycholic Acid, Dihydrocaffeic Acid, DL-2-Phenylpropionic (Hydratropic) Acid, DL-Tartaric Acid, DL-Tropic Acid, Eicosanedioic Acid, Eicosapentanoic Acid (EPA), Elaidic Acid, Ellagic Acid, Erucic Acid, Ethylenediaminetetraacetic Acid (EDTA), Formic Acid, Fumaric Acid, Geranic Acid, Glutaric Acid, Glycolic Acid, Heptanoic Acid, Hexanoic Acid, Hydrocinnamic Acid (3-Phenylpropionic Acid), Isobutyric Acid, Isovaleric Acid, L-(+)-Tartaric Acid, L-Ascorbic Acid, L-Aspartic Acid, L-Glutamic Acid, L-Glutathione reduced, Lactic Acid, Lauric Acid, Levulinic Acid, Linoleic Acid, Linolenic Acid, Lithocholic Acid, Maleic Acid, Malic Acid, Malonic Acid, Mandelic acid, Mesaconic Acid, Nicotinic Acid, Nonanoic Acid, Octanoic Acid, Oleic Acid, Oxalic Acid, p-Coumaric Acid, p-Toluenesulfonic Acid, Palmitic Acid, Perillic Acid, Phosphoric Acid, Pimelic Acid, Pivalic Acid, Propionic Acid, Pyroglutamic Acid, Pyruvic Acid, Ricinoleic Acid, Salicylic Acid (2-Hydroxybenzoic Acid), Sinapinic Acid (3,5-Dimethoxy-4-Hydroxycinnamic Acid), Sorbic Acid, Stearic acid, Succinic Acid, Syringic Acid, Tiglic Acid, Trans-2-Decenoic Acid, Trans-2-Hexenoic Acid, Trans-2-Octenoic Acid, Trans-3-Octenoic Acid, Trans-γ-Octenoic Acid, Trans-Cinnamic Acid, Trans-Ferulic Acid, Undecanoic Acid, Valeric Acid, Vanillic Acid, and α-Ketoglutaric Acid.

In some embodiments, the one or more ionic liquid independently comprises an anion selected from the group consisting of glycolic acid, tartaric acid, malic acid, hydrocinnamic acid, citric acid, cinnamic acid, mandelic acid, mesaconic acid, ricinoleic acid, linoleic acid, and tiglic acid.

In some embodiments, the one or more ionic liquid independently comprises an anion selected from the group consisting of cinnamic acid, mandelic acid, citric acid, ricinoleic acid, linoleic acid, and tiglic acid.

In some embodiments, the one or more ionic liquid independently comprises choline or choline derivative-cinnamic acid, choline or choline derivative-mandelic acid, choline or choline derivative-citric acid, choline or choline derivative-ricinoleic acid, choline or choline derivative-linoleic acid, or choline or choline derivative-tiglic acid.

In some embodiments, the one or more ionic liquid independently comprises carnitine-cinnamic acid, carnitine-mandelic acid, carnitine-citric acid, carnitine-ricinoleic acid, carnitine-linoleic acid, or carnitine-tiglic acid.

In some embodiments, the one or more ionic liquid independently comprises acetylcholine-cinnamic acid, acetylcholine-mandelic acid, acetylcholine-citric acid, acetylcholine-ricinoleic acid, acetylcholine-linoleic acid, or acetylcholine-tiglic acid.

In another aspect, provided herein is a method of enhancing the hydrophobicity of a therapeutic agent, comprising linking $R^{12}$ to a therapeutic agent,
wherein $R^{12}$ is substituted or unsubstituted $C_5$-$C_{10}$; and
wherein the therapeutic agent is:
(i) an GLP-1 analog or functional variant thereof or mimetic thereof, Liraglutide, Exenatide, Peptide tyrosine tyrosine (YY), glucagon, gastric inhibitory polypeptide (GIP), or amylin;
(ii) an amylin or mimetic or analog thereof, or an amylin analog or functional variant thereof or mimetic or analog thereof;
(iii) an antibody or an antibody fragment thereof; or
(iv) a dual GIP/GLP-1 receptor agonist or functional variant thereof.

In some embodiments, $R^{12}$ is linked to

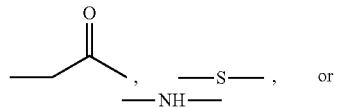

of the therapeutic agent.

In some embodiments, $R^{12}$ is linked to the therapeutic agent via a covalent bond or a linker.

In some embodiments, the linker is a non-cleavable linker.

In some embodiments, the linker comprises a maleimide alkane linker or a maleimide cyclohexane linker.

In some embodiments, the linker comprises

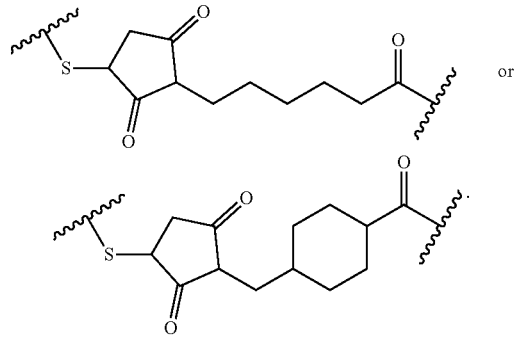

In some embodiments, the linker is a chemically cleavable linker.

In some embodiments, the linker comprises a hydrazone linker or a disulfide linker.

In some embodiments, the linker comprises or.

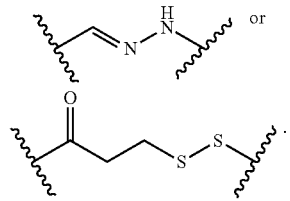

In some embodiments, $R^{12}$ is substituted or unsubstituted $C_{10}$.

In some embodiments, the therapeutic agent is the GLP-1 analog or functional variant thereof or mimetic thereof, Liraglutide, Exenatide, Peptide tyrosine tyrosine (YY), glucagon, gastric inhibitory polypeptide (GIP), or amylin.

In some embodiments, the therapeutic agent is the GLP-1 analog or functional variant thereof or mimetic thereof.

In some embodiments, the therapeutic agent is an amylin or mimetic or analog thereof, or an amylin analog or functional variant thereof or mimetic or analog thereof.

In some embodiments, the therapeutic agent is an amylin analog or functional variant thereof or mimetic or analog thereof.

In some embodiments, the therapeutic agent is an amylin analog or functional variant thereof or mimetic or analog thereof having the sequence of: [diacid]-[linker]-KCNTAT-CATQRLANFLVHSSNNFGPILPPTNVGSNTY-amide (SEQ ID NO: 21).

In some embodiments, the therapeutic agent is an amylin analog or functional variant thereof or mimetic or analog thereof having the structure as shown in FIGS. 2A, 2B, and 2C, FIG. 3A and FIG. 3B, or FIG. 4A and FIG. 4B.

In some embodiments, the therapeutic agent is an amylin analog or functional variant thereof or mimetic or analog thereof comprising an amino acid substitution of N14E, V17R, Y37P, F15E, L16E, V17E, or any combination thereof.

In some embodiments, the therapeutic agent is an amylin analog or functional variant thereof or mimetic or analog thereof comprising an amino acid substitution of N14E.

In some embodiments, the therapeutic agent is an antibody or an antibody fragment thereof.

In some embodiments, the therapeutic agent is any one selected from the group consisting of infliximab or an antibody fragment thereof, adalimumab or an antibody fragment thereof, ustekinumab or an antibody fragment thereof, golimumab or an antibody fragment thereof, natalizumab or an antibody fragment thereof, vedolizumab or an antibody fragment thereof, and certolizumab pegol or an antibody fragment thereof.

In some embodiments, the therapeutic agent comprises:
(i) a sequence with at least 75% sequence identity to the sequence of SEQ ID NO: 1 or SEQ ID NO: 24, a sequence with at least 75% sequence identity to the sequence of SEQ ID NO: 2, or a combination thereof;
(ii) a sequence with at least 75% sequence identity to the sequence of SEQ ID NO: 3, SEQ ID NO: 4, or SEQ ID NO: 5, a sequence with at least 75% sequence identity to the sequence of SEQ ID NO: 6 or SEQ ID NO: 7, or any combination thereof;
(iii) a sequence with at least 75% sequence identity to the sequence of SEQ ID NO: 8, a sequence with at least 75% sequence identity to the sequence of SEQ ID NO: 9, or a combination thereof;
(iv) a sequence with at least 75% sequence identity to the sequence of SEQ ID NO: 10, a sequence with at least 75% sequence identity to the sequence of SEQ ID NO: 11, or a combination thereof;
(v) a sequence with at least 75% sequence identity to the sequence of SEQ ID NO: 12 or SEQ ID NO: 13, a sequence with at least 75% sequence identity to the sequence of SEQ ID NO: 14 or SEQ ID NO: 15, or any combination thereof;
(vi) a sequence with at least 75% sequence identity to the sequence of SEQ ID NO: 16, a sequence with at least 75% sequence identity to the sequence of SEQ ID NO: 17, or a combination thereof; or
(vii) a sequence with at least 75% sequence identity to the sequence of SEQ ID NO: 18, a sequence with at least 75% sequence identity to the sequence of SEQ ID NO: 19, or a combination thereof.

In some embodiments, the therapeutic agent comprises:
(i) the sequence of SEQ ID NO: 1 or SEQ ID NO: 24, the sequence of SEQ ID NO: 2, or a combination thereof;
(ii) the sequence of SEQ ID NO: 3, SEQ ID NO: 4, or SEQ ID NO: 5, the sequence of SEQ ID NO: 6 or SEQ ID NO: 7, or any combination thereof;
(iii) the sequence of SEQ ID NO: 8, the sequence of SEQ ID NO: 9, or a combination thereof;
(iv) the sequence of SEQ ID NO: 10, the sequence of SEQ ID NO: 11, or a combination thereof;
(v) the sequence of SEQ ID NO: 12 or SEQ ID NO: 13, the sequence of SEQ ID NO: 14 or SEQ ID NO: 15, or any combination thereof;
(vi) the sequence of SEQ ID NO: 16, the sequence of SEQ ID NO: 17, or a combination thereof; or
(vii) the sequence of SEQ ID NO: 18, the sequence of SEQ ID NO: 19, or a combination thereof.

In some embodiments, the therapeutic agent comprises:
(i) the sequence of SEQ ID NO: 1 or SEQ ID NO: 24, and the sequence of SEQ ID NO: 2;
(ii) the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7;
(iii) the sequence of SEQ ID NO: 8 and the sequence of SEQ ID NO: 9;
(iv) the sequence of SEQ ID NO: 10 and the sequence of SEQ ID NO: 11;
(v) the sequence of SEQ ID NO: 12 and the sequence of SEQ ID NO: 14, or the sequence of SEQ ID NO: 13 and the sequence of SEQ ID NO: 15;
(vi) the sequence of SEQ ID NO: 16 and the sequence of SEQ ID NO: 17; or
(vii) the sequence of SEQ ID NO: 18 and the sequence of SEQ ID NO: 19.

In some embodiments, the therapeutic agent is infliximab or an antibody fragment thereof.

In some embodiments, the therapeutic agent comprises the sequence of SEQ ID NO: 1 or SEQ ID NO: 24, and the sequence of SEQ ID NO: 2.

In some embodiments, the therapeutic agent is adalimumab or an antibody fragment thereof.

In some embodiments, the therapeutic agent comprises the sequence of SEQ ID NO: 3 and the sequence of SEQ ID NO: 6, the sequence of SEQ ID NO: 4 and the sequence of SEQ ID NO: 6, or the sequence of SEQ ID NO: 5 and SEQ ID NO: 7.

In some embodiments, the therapeutic agent is ustekinumab or an antibody fragment thereof.

In some embodiments, the therapeutic agent comprises the sequence of SEQ ID NO: 8 and the sequence of SEQ ID NO: 9.

In some embodiments, the therapeutic agent is golimumab or an antibody fragment thereof.

In some embodiments, the therapeutic agent comprises the sequence of SEQ ID NO: 10 and the sequence of SEQ ID NO: 11.

In some embodiments, the therapeutic agent is natalizumab or an antibody fragment thereof.

In some embodiments, the therapeutic agent comprises the sequence of SEQ ID NO: 12 and the sequence of SEQ ID NO: 14, or the sequence of SEQ ID NO: 13 and the sequence of SEQ ID NO: 15.

In some embodiments, the therapeutic agent is vedolizumab or an antibody fragment thereof.

In some embodiments, the therapeutic agent comprises the sequence of SEQ ID NO: 16 and the sequence of SEQ ID NO: 17.

In some embodiments, the therapeutic agent is certolizumab pegol or an antibody fragment thereof.

In some embodiments, the therapeutic agent comprises the sequence of SEQ ID NO: 18 and the sequence of SEQ ID NO: 19.

In some embodiments, the therapeutic agent is the dual GIP/GLP-1 receptor agonist or functional variant thereof.

In some embodiments, the therapeutic agent comprises a sequence with at least 75% sequence identity to the sequence of SEQ ID NO: 25.

In some embodiments, the therapeutic agent comprises the sequence of SEQ ID NO: 25.

In some embodiments, the therapeutic agent comprises C20 diacid-γ-Glu-(AEEA)2 attached to a residue of a sequence with at least 75% sequence identity to the sequence of SEQ ID NO: 25.

In some embodiments, the therapeutic agent comprises C20 diacid-γ-Glu-(AEEA)2 attached to a residue of the sequence of SEQ ID NO: 25.

In some embodiments, the therapeutic agent comprises C20 diacid-γ-Glu-(AEEA)2 attached to the Lys residue at the position 20 from the N-terminus of the sequence of SEQ ID NO: 25.

In some embodiments, the therapeutic agent is linked to one or more fatty acids or carboxylic acid-containing molecules.

In some embodiments, the therapeutic agent is linked to the one or more fatty acids or carboxylic acid-containing molecules via a dual conjugation.

In some embodiments, the one or more fatty acids or carboxylic acid-containing molecules comprise cinnamic acid.

In some embodiments, the one or more fatty acids or carboxylic acid-containing molecules are non-covalently associated with a free amine of the therapeutic agent.

In some embodiments, the one or more fatty acids or carboxylic acid-containing molecules are non-covalently associated with the N-terminal amine in the peptide backbone of the therapeutic agent.

In some embodiments, the one or more fatty acids or carboxylic acid-containing molecules are non-covalently associated with the amine group of a Gln residue, the amine group of an Asn residue, the amine group of an Arg residue, the amine group of a Lys residue, the amine group of a His residue, or a combination thereof of the therapeutic agent.

In some embodiments, the one or more fatty acids or carboxylic acid-containing molecules are covalently conjugated to a free amine of the therapeutic agent.

In some embodiments, the one or more fatty acids or carboxylic acid-containing molecules are covalently conjugated to the N-terminal amine in the peptide backbone of the therapeutic agent.

In some embodiments, the one or more fatty acids or carboxylic acid-containing molecules are covalently conjugated to the amine group of a Gln residue, the amine group of an Asn residue, the amine group of an Arg residue, the amine group of a Lys residue, the amine group of a His residue, or a combination thereof of the therapeutic agent.

In another aspect, provided herein is a method of enhancing or improving a delivery efficiency of a therapeutic agent in a subject in need thereof comprising adding at least one permeation enhancer to the compound as provided herein, the composition as provided herein, or the pharmaceutical composition as provided herein, and administering the composition, the compound, or the pharmaceutical composition to the subject.

In some embodiments, the at least one permeation enhancer is selected from the group consisting of salcaprozate sodium (SNAC), sodium caprylate, sodium caprate, a bile salt, ethylenediaminetetraacetic acid (EDTA), ethylene glycol-bis-(2-aminoethylether)-N,N,N',N'-tetraacetic acid (EGTA), and 3-[N,N-Dimethyl(3-palmitoylaminopropyl)-ammonio]-propanesulfonate (PPS), and any combination thereof.

In some embodiments, the bile salt is selected from the group consisting of sodium deoxycholate, sodium chenodeoxycholate, sodium taurodeoxycholate, and a combination thereof.

What is claimed is:
1. A compound having the structure of Formula Ia:
Formula Ia
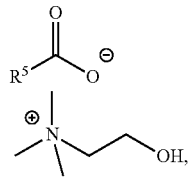
wherein
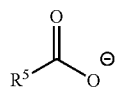
is a therapeutic agent,
wherein the therapeutic agent has the sequence of SEQ ID NO: 35, and
wherein the compound has a
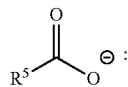
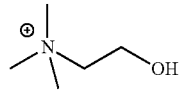
molar ratio of from about 1:1 to about 1:7.
2. The compound of claim 1, wherein the sequence of SEQ ID NO: 35 has the following structure:

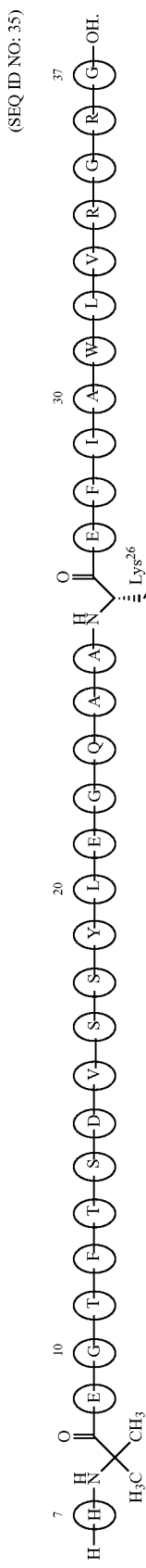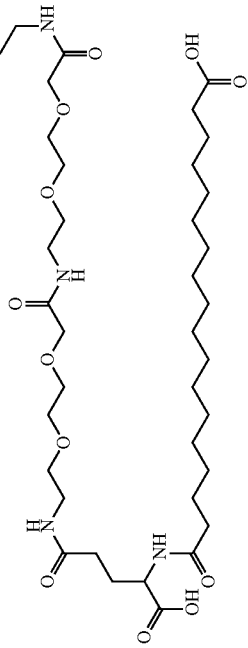
(SEQ ID NO: 35)

3. The compound of claim 1, wherein the compound consists of

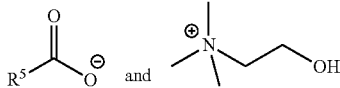

having a

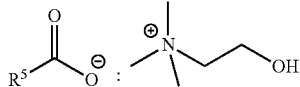

molar ratio of about 1:1.

4. The compound of claim 1, wherein the compound consists of

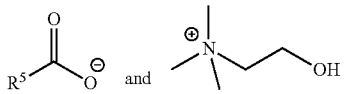

having a

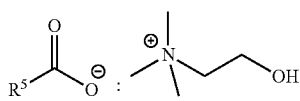

molar ratio of about 1:2.

5. The compound of claim 1, wherein the compound consists of

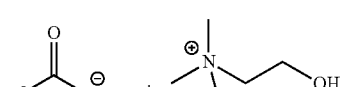

having a

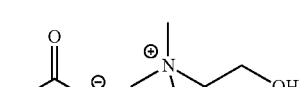

molar ratio of about 1:3.

6. The compound of claim 1, wherein the compound consists of

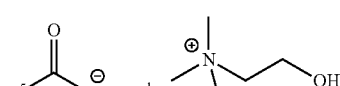

having a

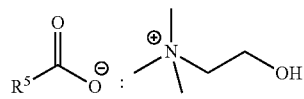

molar ratio of about 1:4.

7. The compound of claim 1, wherein the compound consists of

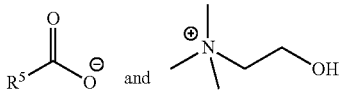

having a

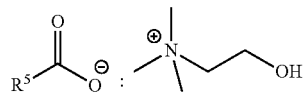

molar ratio of about 1:5.

8. The compound of claim 1, wherein the compound consists of

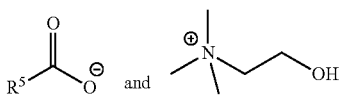

having a

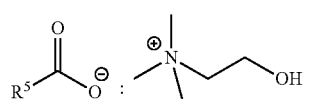

molar ratio of about 1:6.

9. A method of treating a disease or disorder in a subject in need thereof, comprising administering to the subject a therapeutically effective amount of the compound of claim 1,
wherein the administering is effective to treat the disease or disorder in the subject, and
wherein the disease or disorder is a metabolic disease or disorder.

10. The method of claim 9, wherein the metabolic disease or disorder is selected from the group consisting of type 1 diabetes, type 2 diabetes, obesity, overweight, and nonalcoholic steatohepatitis (NASH).

11. The method of claim 9, wherein the metabolic disease or disorder is type 2 diabetes.

12. The method of claim 9, wherein the metabolic disease or disorder is obesity.

13. The method of claim 9, wherein the metabolic disease or disorder is overweight.

14. The method of claim 9, wherein the metabolic disease or disorder is nonalcoholic steatohepatitis (NASH).

15. The method of claim 9, wherein the compound is administered via subcutaneous administration or intravenous administration.

16. The method of claim 9, wherein the compound is administered via oral administration.

17. A method of reducing weight in a subject in need thereof, comprising administering to the subject a therapeutically effective amount of the compound of claim 1,
wherein the administering is effective to reduce weight in the subject.

18. The compound of claim 1, wherein the compound consists of

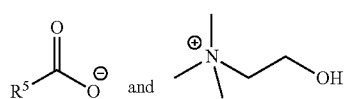

having a

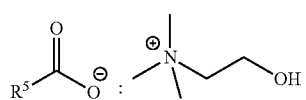

molar ratio of about 1:7.

19. A compound having the following structure:

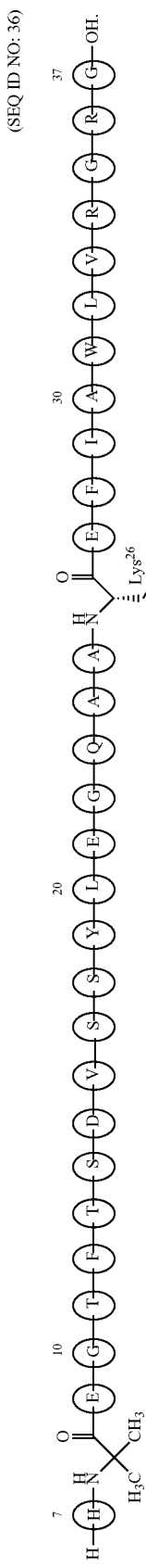
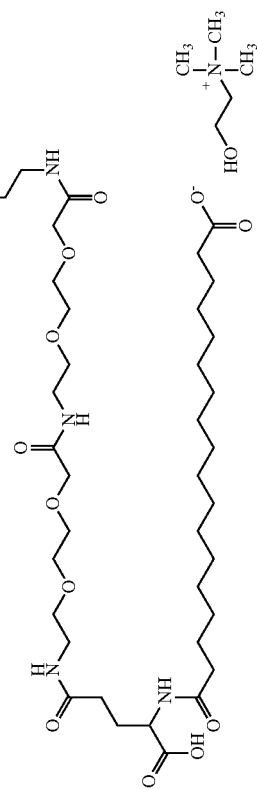

20. A method of treating a disease or disorder in a subject in need thereof, comprising administering to the subject a therapeutically effective amount of the compound of claim 19,
- wherein the administering is effective to treat the disease or disorder in the subject, and
- wherein the disease or disorder is a metabolic disease or disorder.

21. The method of claim 20, wherein the metabolic disease or disorder is selected from the group consisting of type 1 diabetes, type 2 diabetes, obesity, overweight, and nonalcoholic steatohepatitis (NASH).

22. The method of claim 20, wherein the metabolic disease or disorder is type 2 diabetes.

23. The method of claim 20, wherein the metabolic disease or disorder is obesity.

24. The method of claim 20, wherein the metabolic disease or disorder is overweight.

25. The method of claim 20, wherein the metabolic disease or disorder is nonalcoholic steatohepatitis (NASH).

26. The method of claim 20, wherein the compound is administered via subcutaneous administration or intravenous administration.

27. The method of claim 20, wherein the compound is administered via oral administration.

28. A method of reducing weight in a subject in need thereof, comprising administering to the subject a therapeutically effective amount of the compound of claim 19,
- wherein the administering is effective to reduce weight in the subject.

* * * * *